United States Patent
Liu et al.

(10) Patent No.: US 9,771,568 B2
(45) Date of Patent: Sep. 26, 2017

(54) POLYPEPTIDES HAVING BETA-GLUCOSIDASE ACTIVITY AND POLYNUCLEOTIDES ENCODING SAME

(71) Applicant: Novozymes Inc., Davis, CA (US)

(72) Inventors: Ye Liu, Beijing (CN); Junxin Duan, Beijing (CN); Yu Zhang, Beijing (CN); Lan Tang, Beijing (CN)

(73) Assignee: Novozymes, Inc., Davis, CA (US)

( * ) Notice: Subject to any disclaimer, the term of this patent is extended or adjusted under 35 U.S.C. 154(b) by 93 days.

(21) Appl. No.: 14/358,865

(22) PCT Filed: Dec. 19, 2012

(86) PCT No.: PCT/CN2012/086938
§ 371 (c)(1),
(2) Date: May 16, 2014

(87) PCT Pub. No.: WO2013/091544
PCT Pub. Date: Jun. 27, 2013

(65) Prior Publication Data
US 2014/0331364 A1  Nov. 6, 2014

Related U.S. Application Data

(60) Provisional application No. 61/582,885, filed on Jan. 4, 2012, provisional application No. 61/610,028, filed on Mar. 13, 2012.

(30) Foreign Application Priority Data

Dec. 19, 2011 (WO) ................ PCT/CN2011/084228

(51) Int. Cl.
| | | |
|---|---|---|
| *C12N 15/82* | (2006.01) | |
| *C12P 19/14* | (2006.01) | |
| *C12N 9/24* | (2006.01) | |
| *C12N 9/42* | (2006.01) | |
| *C12N 15/113* | (2010.01) | |
| *C12P 19/02* | (2006.01) | |

(52) U.S. Cl.
CPC ........ *C12N 9/2445* (2013.01); *C12N 15/1137* (2013.01); *C12N 15/8246* (2013.01); *C12N 15/8257* (2013.01); *C12P 19/02* (2013.01); *C12P 19/14* (2013.01); *C12Y 302/01021* (2013.01)

(58) Field of Classification Search
None
See application file for complete search history.

(56) References Cited

U.S. PATENT DOCUMENTS

2009/0148903 A1* 6/2009 Lopez de Leon . C12N 15/8245
435/69.1

FOREIGN PATENT DOCUMENTS

| WO | 2011/035029 A1 | 3/2011 |
| WO | 2011/066457 A2 | 6/2011 |
| WO | 2014/059541 A1 | 4/2014 |
| WO | 2014/060379 A1 | 4/2014 |

OTHER PUBLICATIONS

Collins et al 2002, GenBank Accession AF529167, sequence alignment included in action.*
Collins et al., Genbank Accession No. Q8J261 (2003).
Fedorova et al., Genbank Accession No. B8MR59 (2009).
Rouxel et al., Genbank Accession No. E4ZPY2 (2011).
Banerjee et al., Biofuels, Bioproducts & Biorefining, vol. 4, No. 1, pp. 77-93 (2010).
Collins et al., Mycological Research, vol. 111, No. 7, pp. 840-849 (2007).
Gurgu et al., Bioresource Technology, vol. 102, pp. 5229-5236 (2011).
Krogh et al., Appl. Microbiol. Biotechnol., vol. 86, pp. 143-154 (2010).
Kumar et al., J. Ind. Microbiol. Biotechnol., vol. 35, No. 5, pp. 377-391 (2008).
Rosgaard et al., Biotechnol. Prog., vol. 22, No. 2, pp. 493-498 (2006).

* cited by examiner

*Primary Examiner* — Brent Page
(74) *Attorney, Agent, or Firm* — Robert Starnes

(57) ABSTRACT

Provided are isolated polypeptides having beta-glucosidase activity and polynucleotides encoding the polypeptides. Also provided are nucleic acid constructs, vectors and host cells comprising the polynucleotides as well as methods of producing and using the polypeptides.

44 Claims, 19 Drawing Sheets

US 9,771,568 B2

POLYPEPTIDES HAVING BETA-GLUCOSIDASE ACTIVITY AND POLYNUCLEOTIDES ENCODING SAME

CROSS-REFERENCE TO RELATED APPLICATIONS

This application is a 35 U.S.C. 371 national application of PCT/CN2012/086938 filed Dec. 19, 2012, which claims priority or the benefit under 35 U.S.C. 119 of PCT application no. PCT/CN2011/084228 filed Dec. 19, 2011 and U.S. provisional application Nos. 61/582,885 and 61/610,028 filed Jan. 4, 2012 and Mar. 13, 2012, respectively, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having beta-glucosidase activity and polynucleotides encoding the polypeptides. The present invention also relates to nucleic acid constructs, vectors, and host cells comprising the polynucleotides as well as methods of producing and using the polypeptides.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars are easily fermented by yeast into ethanol.

There is a need in the art to improve cellulolytic enzyme compositions through supplementation with additional enzymes to increase efficiency and to provide cost-effective enzyme solutions for degradation of lignocellulose.

The present invention provides polypeptides having beta-glucosidase activity and polynucleotides encoding the polypeptides.

SUMMARY OF THE INVENTION

The present invention relates to isolated polypeptides having beta-glucosidase activity selected from:
(a) a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2, 4, 6, 8, 10, 12, 14, 16, 18, 20, 22, 24, 26, 28, 30, 32, 34, 36, or 38;
(b) a polypeptide encoded by a polynucleotide that hybridizes under at least very low stringency conditions, low stringency conditions, medium stringency conditions, medium-high stringency conditions, high stringency conditions, or very high stringency conditions with (i) the mature polypeptide coding sequence of SEQ ID NO: 1, 3, 5, 7, 9, 11, 13, 15, 17, 19, 21, 23, 25, 27, 29, 31, 33, 35, or 37, (ii) the cDNA sequence thereof, or (iii) the full-length complement of (i) or (ii);
(c) a polypeptide encoded by a polynucleotide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1, 3, 5, 7, 9, 11, 13, 15, 17, 19, 21, 23, 25, 27, 29, 31, 33, 35, or 37, or the cDNA sequences thereof;
(d) a variant of the mature polypeptide of SEQ ID NO: 2, 4, 6, 8, 10, 12, 14, 16, 18, 20, 22, 24, 26, 28, 30, 32, 34, 36, or 38 comprising a substitution, deletion, and/or insertion at one or more (e.g., several) positions; and
(e) a fragment of the polypeptide of (a), (b), (c), or (d) that has beta-glucosidase activity.

The present invention also relates to isolated polynucleotides encoding the polypeptides of the present invention; nucleic acid constructs, recombinant expression vectors, and recombinant host cells comprising the polynucleotides; and methods of producing the polypeptides.

The present invention also relates to processes for degrading or converting a cellulosic material, comprising: treating the cellulosic material with an enzyme composition in the presence of a polypeptide having beta-glucosidase activity of the present invention. In one aspect, the processes further comprise recovering the degraded or converted cellulosic material.

The present invention also relates to processes of producing a fermentation product, comprising: (a) saccharifying a cellulosic material with an enzyme composition in the presence of a polypeptide having beta-glucosidase activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having beta-glucosidase activity of the present invention. In one aspect, the fermenting of the cellulosic material produces a fermentation product. In another aspect, the processes further comprise recovering the fermentation product from the fermentation.

The present invention also relates to a polynucleotide encoding a signal peptide comprising or consisting of amino acids 1 to 23 of SEQ ID NO: 2, amino acids 1 to 21 of SEQ ID NO: 4, amino acids 1 to 23 of SEQ ID NO: 6, amino acids 1 to 23 of SEQ ID NO: 8, amino acids 1 to 21 of SEQ ID NO: 10, amino acids 1 to 19 of SEQ ID NO: 12, amino acids 1 to 20 of SEQ ID NO: 14, amino acids 1 to 21 of SEQ ID NO: 16, amino acids 1 to 23 of SEQ ID NO: 18, amino acids 1 to 22 of SEQ ID NO: 20, amino acids 1 to 23 of SEQ ID NO: 22, amino acids 1 to 23 of SEQ ID NO: 24, amino acids 1 to 23 of SEQ ID NO: 26, amino acids 1 to 15 of SEQ ID NO: 28, amino acids 1 to 17 of SEQ ID NO: 30, amino acids 1 to 17 of SEQ ID NO: 32, amino acids 1 to 19 of SEQ ID NO: 34, amino acids 1 to 22 of SEQ ID NO: 36, or amino acids 1 to 21 of SEQ ID NO: 38, which is operably linked to a gene encoding a protein, wherein the protein is foreign to the signal peptide; nucleic acid constructs, expression vectors, and recombinant host cells comprising the polynucleotides; and methods of producing a protein.

DEFINITIONS

Figure 1:
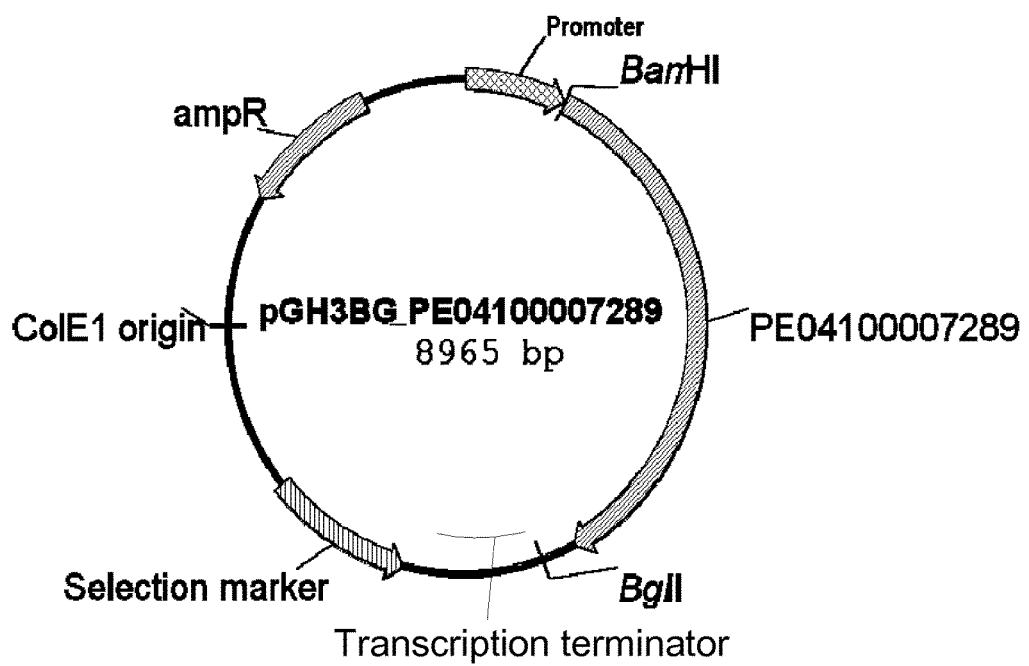
FIG. 1 shows a restriction map of plasmid pGH3BG_PE04100007289.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, J. Bacteriol. 180: 243-249. One unit of alpha-glucuronidase equals the amount of enzyme capable of releasing 1 μmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, J. Basic Microbiol. 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20 or at 50° C., pH 5.0 from 2 mM p-nitrophenyl-beta-D-glucopyranoside as substrate in 100 mM sodium acetate pH 5.0 containing 0.01% TWEEN® 20 (see Example 28 herein).

The polypeptides of the present invention may have at least 20%, e.g., at least 40%, at least 50%, at least 60%, at least 70%, at least 80%, at least 90%, at least 95%, and at least 100% of the beta-glucosidase activity of the mature polypeptide of any one of SEQ ID NOs: 2, 4, 6, 8, 10, 12, 14, 16, 18, 20, 22, 24, 26, 28, 30, 32, 34, 36, or 38.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No. 1 filter paper, microcrystalline cellulose, bacterial cellulose, algal cellulose, cotton, pretreated lignocellulose, etc. The most common total cellulolytic activity assay is the filter paper assay using Whatman No, 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity may be determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide main; wherein the fragment has beta-glucosidase activity. In one aspect, a fragment contains at least 75%, e.g., at least 80%, 85%, 90%, or 95% of the number of amino acid residues in any one of SEQ ID NOs: 2, 4, 6, 8, 10, 12, 14, 16, 18, 20, 22, 24, 26, 28, 30, 32, 34, 36, or 38.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl.*

*Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 24 to 806 of SEQ ID NO: 2 based on the SignalP program (Nielsen et al., 1997, *Protein Engineering* 10:1-6) that predicts amino acids 1 to 23 of SEQ ID NO: 2 are a signal peptide. In another aspect, the mature polypeptide is amino acids 22 to 980 of SEQ ID NO: 4 based on the SignalP program that predicts amino acids 1 to 21 of SEQ ID NO: 4 are a signal peptide. In another aspect, the mature polypeptide is amino acids 24 to 870 of SEQ ID NO: 6 based on the SignalP program that predicts amino acids 1 to 23 of SEQ ID NO: 6 are a signal peptide. In another aspect, the mature polypeptide is amino acids 24 to 865 of SEQ ID NO: 8 based on the SignalP program that predicts amino acids 1 to 23 of SEQ ID NO: 8 are a signal peptide. In another aspect, the mature polypeptide is amino acids 22 to 779 of SEQ ID NO: 10 based on the SignalP program that predicts amino acids 1 to 21 of SEQ ID NO: 10 are a signal peptide. In another aspect, the mature polypeptide is amino acids 20 to 776 of SEQ ID NO: 12 based on the SignalP program that predicts amino acids 1 to 19 of SEQ ID NO: 12 are a signal peptide. In another aspect, the mature polypeptide is amino acids 21 to 773 of SEQ ID NO: 14 based on the SignalP program that predicts amino acids 1 to 20 of SEQ ID NO: 14 are a signal peptide. In another aspect, the mature polypeptide is amino acids 22 to 793 of SEQ ID NO: 16 based on the SignalP program that predicts amino acids 1 to 21 of SEQ ID NO: 16 are a signal peptide. In another aspect, the mature polypeptide is amino acids 24 to 784 of SEQ ID NO: 18 based on the SignalP program that predicts amino acids 1 to 23 of SEQ ID NO: 18 are a signal peptide. In another aspect, the mature polypeptide is amino acids 23 to 774 of SEQ ID NO: 20 based on the SignalP program that predicts amino acids 1 to 22 of SEQ ID NO: 20 are a signal peptide. In another aspect, the mature polypeptide is amino acids 24 to 887 of SEQ ID NO: 22 based on the SignalP program that predicts amino acids 1 to 23 of SEQ ID NO: 22 are a signal peptide. In another aspect, the mature polypeptide is amino acids 24 to 733 of SEQ ID NO: 24 based on the SignalP program that predicts amino acids 1 to 23 of SEQ ID NO: 24 are a signal peptide. In another aspect, the mature polypeptide is amino acids 24 to 728 of SEQ ID NO: 26 based on the SignalP program that predicts amino acids 1 to 23 of SEQ ID NO: 26 are a signal peptide. In another aspect, the mature polypeptide is amino acids 16 to 870 of SEQ ID NO: 28 based on the SignalP program that predicts amino acids 1 to 15 of SEQ ID NO: 28 are a signal peptide. In another aspect, the mature polypeptide is amino acids 18 to 733 of SEQ ID NO: 30 based on the SignalP program that predicts amino acids 1 to 17 of SEQ ID NO: 30 are a signal peptide. In another aspect, the mature polypeptide is amino acids 18 to 777 of SEQ ID NO: 32 based on the SignalP program that predicts amino acids 1 to 17 of SEQ ID NO: 32 are a signal peptide. In another aspect, the mature polypeptide is amino acids 20 to 873 of SEQ ID NO: 34 based on the SignalP program that predicts amino acids 1 to 19 of SEQ ID NO: 34 are a signal peptide. In another aspect, the mature polypeptide is amino acids 23 to 800 of SEQ ID NO: 36 based on the SignalP program that predicts amino acids 1 to 22 of SEQ ID NO: 36 are a signal peptide. In another aspect, the mature polypeptide is amino acids 22 to 778 of SEQ ID NO: 38 based on the SignalP program that predicts amino acids 1 to 21 of SEQ ID NO: 38 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having beta-glucosidase activity. In one aspect, the mature polypeptide coding sequence is nucleotides 70 to 3150 of SEQ ID NO: 1 or the cDNA sequence thereof based on the SignalP program (Nielsen et al., 1997, supra) that predicts nucleotides 1 to 69 of SEQ ID NO: 1 encode a signal peptide. In another aspect, the mature polypeptide coding sequence is nucleotides 64 to 3197 of SEQ ID NO: 3 or the cDNA sequence thereof based on the SignalP program that predicts nucleotides 1 to 63 of SEQ ID NO: 3 encode a signal peptide. In another aspect, the mature polypeptide coding sequence is nucleotides 70 to 2757 of SEQ ID NO: 5 or the cDNA sequence thereof based on the SignalP program that predicts nucleotides 1 to 69 of SEQ ID NO: 5 encode a signal peptide. In another aspect, the mature polypeptide coding sequence is nucleotides 70 to 3042 of SEQ ID NO: 7 or the cDNA sequence thereof based on the SignalP program that predicts nucleotides 1 to 69 of SEQ ID NO: 7 encode a signal peptide. In another aspect, the mature polypeptide coding sequence is nucleotides 64 to 2975 of SEQ ID NO: 9 or the cDNA sequence thereof based on the SignalP program that predicts nucleotides 1 to 63 of SEQ ID NO: 9 encode a signal peptide. In another aspect, the mature polypeptide coding sequence is nucleotides 58 to 2470 of SEQ ID NO: 11 or the cDNA sequence thereof based on the SignalP program that predicts nucleotides 1 to 57 of SEQ ID NO: 11 encode a signal peptide. In another aspect, the mature polypeptide coding sequence is nucleotides 61 to 2478 of SEQ ID NO: 13 or the cDNA sequence thereof based on the SignalP program that predicts nucleotides 1 to 60 of SEQ ID NO: 13 encode a signal peptide. In another aspect, the mature polypeptide coding sequence is nucleotides 64 to 2553 of SEQ ID NO: 15 or the cDNA sequence thereof based on the SignalP program that predicts nucleotides 1 to 63 of SEQ ID NO: 15 encode a signal peptide. In another aspect, the mature polypeptide coding sequence is nucleotides 70 to 3012 of SEQ ID NO: 17 or the cDNA sequence thereof based on the SignalP program that predicts nucleotides 1 to 69 of SEQ ID NO: 17 encode a signal peptide. In another aspect, the mature polypeptide coding sequence is nucleotides 67 to 2771 of SEQ ID NO: 19 or the cDNA sequence thereof based on the SignalP program that predicts nucleotides 1 to 66 of SEQ ID NO: 19 encode a signal peptide. In another aspect, the mature polypeptide coding sequence is nucleotides 70 to 2874 of SEQ ID NO: 21 or the cDNA sequence thereof based on the SignalP program that predicts nucleotides 1 to 69 of SEQ ID NO: 21 encode a signal peptide. In another aspect, the mature polypeptide coding sequence is nucleotides 70 to 2932 of SEQ ID NO: 23 or the cDNA sequence thereof based on the SignalP program that predicts nucleotides 1 to 69 of SEQ ID NO: 23 encode a signal peptide. In another aspect, the mature polypeptide coding sequence is nucleotides 70 to 2747 of SEQ ID NO: 25 or the cDNA sequence thereof based on the SignalP program that predicts nucleotides 1 to 69 of SEQ ID NO: 25 encode a signal peptide. In another aspect, the mature polypeptide coding sequence is nucleotides 46 to 2858 of SEQ ID NO: 27 or the cDNA sequence thereof based on the SignalP program that predicts nucleotides 1 to 45 of SEQ ID NO: 27 encode a signal peptide. In another aspect, the mature polypeptide coding sequence is nucleotides 52 to 2320 of SEQ ID NO: 29 or the cDNA sequence thereof based on the SignalP program that predicts nucleotides 1 to 51 of SEQ ID NO: 29 encode a signal peptide. In another aspect, the mature polypeptide coding sequence is nucleotides 52 to 2397 of SEQ ID NO: 31 or the cDNA sequence thereof based on the SignalP program that predicts nucleotides 1 to 51 of SEQ ID NO: 31 encode a signal peptide. In another aspect, the mature polypeptide coding sequence is nucleotides 58 to 2760 of SEQ ID NO: 33 or the cDNA sequence thereof based on the SignalP program that predicts nucleotides 1 to 57 of SEQ ID NO: 33 encode a signal peptide. In another aspect, the mature polypeptide coding sequence is nucleotides 67 to 2777 of SEQ ID NO: 35 or the cDNA sequence thereof based on the SignalP program that predicts nucleotides 1 to 66 of SEQ ID NO: 35 encode a signal peptide. In another aspect, the mature polypeptide coding sequence is nucleotides 64 to 2969 of SEQ ID NO: 37 or the cDNA sequence thereof based on the SignalP program that predicts nucleotides 1 to 63 of SEQ ID NO: 37 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration wherein a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having beta-glucosidase activity. In one aspect, the number of nucleotides residues in the subsequence is at least 75%, e.g., at least 80%, 85%, 90%, or 95% of the number of nucleotide residues in SEQ ID NOs: 1, 3, 5, 7, 9, 11, 13, 15, 17, 19, 21, 23, 25, 27, 29, 31, 33, 35, or 37.

Variant: The term "variant" means a polypeptide having beta-glucosidase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, Adv. Polym. Sci. 186: 1-67.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, Journal of the Science of Food and Agriculture 86(11): 1636-1647; Spanikova and Biely, 2006, Glucuronoyl esterase—Novel carbohydrate esterase produced by Schizophyllum commune, FEBS Letters 580(19): 4597-4601; Herrmann, Vrsanska, Jurickova, Hirsch, Biely, and Kubicek, 1997, The beta-D-xylosidase of Trichoderma reesei is a multifunctional beta-D-xylan xylohydrolase, Biochemical Journal 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, Journal of Biotechnology 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, Anal. Biochem 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

DETAILED DESCRIPTION OF THE INVENTION

Polypeptides Having Beta-Glucosidase Activity

In an embodiment, the present invention relates to isolated polypeptides having a sequence identity to the mature polypeptide of any one of SEQ ID NOs: 2, 4, 6, 8, 10, 12, 14, 16, 18, 20, 22, 24, 26, 28, 30, 32, 34, 36, and 38 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which have activity. In one aspect, the polypeptides differ by up to 10 amino acids, e.g., 1, 2, 3, 4, 5, 6, 7, 8, 9, or 10, from the mature polypeptide of SEQ ID NO: 2, 4, 6, 8, 10, 12, 14, 16, 18, 20, 22, 24, 26, 28, 30, 32, 34, 36, or 38.

A polypeptide of the present invention may comprise or consist of the amino acid sequence of SEQ ID NO: 2, 4, 6, 8, 10, 12, 14, 16, 18, 20, 22, 24, 26, 28, 30, 32, 34, 36, or 38; or an allelic variant thereof; or is a fragment thereof having beta-glucosidase activity. In another aspect, the polypeptide comprises or consists of the mature polypeptide of SEQ ID NO: 2, 4, 6, 8, 10, 12, 14, 16, 18, 20, 22, 24, 26, 28, 30, 32, 34, 36, or 38. In another aspect, the polypeptide comprises or consists of amino acids 24 to 806 of SEQ ID NO: 2, amino acids 22 to 980 of SEQ ID NO: 4, amino acids 24 to 870 of SEQ ID NO: 6, amino acids 24 to 865 of SEQ ID NO: 8, amino acids 22 to 779 of SEQ ID NO: 10, amino acids 20 to 776 of SEQ ID NO: 12, amino acids 21 to 773 of SEQ ID NO: 14, amino acids 22 to 793 of SEQ ID NO: 16, amino acids 24 to 784 of SEQ ID NO: 18, amino acids 23 to 774 of SEQ ID NO: 20, amino acids 24 to 887 of SEQ ID NO: 22, amino acids 24 to 733 of SEQ ID NO: 24, amino acids 24 to 728 of SEQ ID NO: 26, amino acids 16 to 870 of SEQ ID NO: 28, amino acids 18 to 733 of SEQ ID NO: 30, amino acids 18 to 777 of SEQ ID NO: 32, amino acids 20 to 873 of SEQ ID NO: 34, amino acids 23 to 800 of SEQ ID NO: 36, or amino acids 22 to 778 of SEQ ID NO: 38.

In another embodiment, the present invention relates to isolated polypeptides having beta-glucosidase activity encoded by polynucleotides that hybridize under very low stringency conditions, low stringency conditions, medium stringency conditions, medium-high stringency conditions, high stringency conditions, or very high stringency conditions with (i) the mature polypeptide coding sequence of SEQ ID NO: 1, 3, 5, 7, 9, 11, 13, 15, 17, 19, 21, 23, 25, 27, 29, 31, 33, 35, or 37, (ii) the cDNA sequence of SEQ ID NO: 1, 3, 5, 7, 9, 11, 13, 15, 17, 19, 21, 23, 25, 27, 29, 31, 33, 35, or 37, or (iii) the full-length complement of (i) or (ii) (Sambrook et al., 1989, *Molecular Cloning, A Laboratory Manual,* 2d edition, Cold Spring Harbor, N.Y.).

The polynucleotide of SEQ ID NO: 1, 3, 5, 7, 9, 11, 13, 15, 17, 19, 21, 23, 25, 27, 29, 31, 33, 35, or 37, or a subsequence thereof, as well as the polypeptide of SEQ ID NO: 2, 4, 6, 8, 10, 12, 14, 16, 18, 20, 22, 24, 26, 28, 30, 32, 34, 36, or 38, the mature polypeptide thereof, or a fragment thereof, may be used to design nucleic acid probes to identify and clone DNA encoding polypeptides having beta-glucosidase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having beta-glucosidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, 3, 5, 7, 9, 11, 13, 15, 17, 19, 21, 23, 25, 27, 29, 31, 33, 35, or 37, the mature polypeptide coding sequences thereof, or subsequences thereof, the carrier material is used in a Southern blot.

For purposes of the present invention, hybridization indicates that the polynucleotide hybridizes to a labeled nucleic acid probe corresponding to (i) SEQ ID NO: 1, 3, 5, 7, 9, 11, 13, 15, 17, 19, 21, 23, 25, 27, 29, 31, 33, 35, or 37; (ii) the mature polypeptide coding sequence of SEQ ID NO: 1, 3, 5, 7, 9, 11, 13, 15, 17, 19, 21, 23, 25, 27, 29, 31, 33, 35, or 37; (iii) the cDNA sequence of SEQ ID NO: 1, 3, 5, 7, 9, 11, 13, 15, 17, 19, 21, 23, 25, 27, 29, 31, 33, 35, or 37; (iv) the full-length complement thereof; or (v) a subsequence of the foregoing; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2, 4, 6, 8, 10, 12, 14, 16, 18, 20, 22, 24, 26, 28, 30, 32, 34, 36, or 38; the mature polypeptide thereof; or a fragment of the foregoing. In another aspect, the nucleic acid probe is SEQ ID NO: 1, 3, 5, 7, 9, 11, 13, 15, 17, 19, 21, 23, 25, 27, 29, 31, 33, 35, or 37; the mature polypeptide coding sequences thereof; or the cDNA sequence of SEQ ID NO: 1, 3, 5, 7, 9, 11, 13, 15, 17, 19, 21, 23, 25, 27, 29, 31, 33, 35, or 37, or the mature polypeptide coding sequences thereof.

In another embodiment, the present invention relates to isolated polypeptides having beta-glucosidase activity encoded by polynucleotides having a sequence identity to the mature polypeptide coding sequence of SEQ ID NO: 1, 3, 5, 7, 9, 11, 13, 15, 17, 19, 21, 23, 25, 27, 29, 31, 33, 35, or 37 or the cDNA sequences thereof of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, 4, 6, 8, 10, 12, 14, 16, 18, 20, 22, 24, 26, 28, 30, 32, 34, 36, or 38 comprising a substitution, deletion, and/or insertion at one or more (e.g., several) positions. In an embodiment, the number of amino acid substitutions, deletions and/or insertions introduced into the mature polypeptide of SEQ ID NO: 2, 4, 6, 8, 10, 12, 14, 16, 18, 20, 22, 24, 26, 28, 30, 32, 34, 36, or 38 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for beta-glucosidase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Beta-Glucosidase Activity

A polypeptide having beta-glucosidase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one aspect, the polypeptide is a *Thermoascus* polypeptide. In another aspect, the polypeptide is a *Thermoascus aurantiacus* polypeptide. In another aspect, the polypeptide is a *Penicillium* polypeptide. In another aspect, the polypeptide is a *Penicillium oxalicum* polypeptide. In another aspect, the polypeptide is a *Penicillium emersonii* polypeptide. In another aspect, the polypeptide is a *Malbranchea* polypeptide. In another aspect, the polypeptide is a *Malbranchea cinnamomea* polypeptide. In another aspect, the polypeptide is a *Scytalidium* polypeptide. In another aspect, the polypeptide is a *Scytalidium thermophilum* polypeptide. In another aspect, the polypeptide is a *Rhizomucor* polypeptide. In another aspect, the polypeptide is a *Rhizomucor pusillus* polypeptide. In another aspect, the polypeptide is a *Corynascus* polypeptide. In another aspect, the polypeptide is a *Corynascus thermophilus* polypeptide. It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Corynascus, Malbranchea, Penicillium, Rhizomucor*, or *Thermoascus*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, 3, 5, 7, 9, 11, 13, 15, 17, 19, 21, 23, 25, 27, 29, 31, 33, 35, or 37, or the cDNA sequence of the mature polypeptide coding sequence of SEQ ID NO: 1, 3, 5, 7, 9, 11, 13, 15, 17, 19, 21, 23, 25, 27, 29, 31, 33, 35, or 37, by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more (e.g., several) control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (e.g., several) convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (e.g., several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (e.g., several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces,*

*Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In one aspect, the cell is of the genus *Penicillium* (e.g., a *Penicillium oxalicum* cell). In another aspect, the cell is of the genus *Thermoascus* (e.g., a *Thermoascus aurantiacus* cell). In another aspect, the cell is of the genus *Malbranchea* (e.g., a *Malbranchea cinnamomea* cell). In another aspect, the cell is of the genus *Scytalidium* (e.g., a *Scytalidium thermophilum* cell). In another aspect, the cell is of the genus *Rhizomucor* (e.g., a *Rhizomucor pusillus* cell). In another aspect, the cell is of the genus *Corynascus* (e.g., a *Corynascus thermophilus* cell).

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a whole fermentation broth comprising a polypeptide of the present invention is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide may be constructed in accordance with methods known in the art. In short, the plant or plant cell is constructed by incorporating one or more expression constructs encoding the polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberelic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising (a) cultivating a transgenic plant or a plant cell comprising a polynucleotide encoding the polypeptide under conditions conducive for production of the polypeptide; and (b) recovering the polypeptide.

Removal or Reduction of Beta-Glucosidase Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having beta-glucosidase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 1, 3, 5, 7, 9, 11, 13, 15, 17, 19, 21, 23, 25, 27, 29, 31, 33, 35, or 37 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially beta-glucosidase-free product is of particular interest in the production of eukaryotic polypeptides, in particular fungal proteins such as enzymes. The beta-glucosidase-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from beta-glucosidase activity that is produced by a method of the present invention.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, GH61 polypeptide having cellulolytic enhancing activity, an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Enzyme Compositions

The present invention also relates to compositions comprising a polypeptide of the present invention. Preferably, the compositions are enriched in such a polypeptide. The term "enriched" indicates that the beta-glucosidase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, GH61 polypeptide having cellulolytic enhancing activity, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase. The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The present invention is also directed to the following processes for using the polypeptides having beta-glucosidase activity, or compositions thereof.

The present invention also relates to processes for degrading or converting a cellulosic material, comprising: treating the cellulosic material with an enzyme composition in the presence of a polypeptide having beta-glucosidase activity of the present invention. In one aspect, the processes further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition in the presence of a polypeptide having beta-glucosidase activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having beta-glucosidase activity of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bio-ethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment:

The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition as described herein in the presence of a polypeptide having beta-glucosidase activity of the present invention. The enzyme components of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme components, i.e., optimal for the enzyme components. The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading or converting the cellulosic material.

In one aspect, the enzyme composition comprises or further comprises one or more (e.g., several) proteins selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin In the processes of the present invention, the enzyme(s) can be added prior to or during saccharification, saccharification and fermentation, or fermentation.

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptides having beta-glucosidase activity depend on several factors including, but not limited to, the mixture of cellulolytic and/or hemicellulolytic enzyme components, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a polypeptide having beta-glucosidase activity to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a polypeptide having beta-glucosidase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a Gram-positive bacterial polypeptide such as a *Bacillus*, *Streptococcus*, *Streptomyces*, *Staphylococcus*, *Enterococcus*, *Lactobacillus*, *Lactococcus*, *Clostridium*, *Geobacillus*, *Caldicellulosiruptor*, *Acidothermus*, *Thermobifidia*, or *Oceanobacillus* polypeptide having enzyme activity, or a Gram-negative bacterial polypeptide such as an *E. coli*, *Pseudomonas*, *Salmonella*, *Campylobacter*, *Helicobacter*, *Flavobacterium*, *Fusobacterium*, *Ilyobacter*, *Neisseria*, or *Ureaplasma* polypeptide having enzyme activity.

In one aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide having enzyme activity.

In another aspect, the polypeptide is a *Streptococcus equisimilis*, *Streptococcus pyogenes*, *Streptococcus uberis*, or *Streptococcus* equi subsp. *Zooepidemicus* polypeptide having enzyme activity.

In another aspect, the polypeptide is a *Streptomyces achromogenes*, *Streptomyces* avermitilis, *Streptomyces coelicolor*, *Streptomyces griseus*, or *Streptomyces lividans* polypeptide having enzyme activity.

The polypeptide having enzyme activity may also be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having enzyme activity; or more preferably a filamentous fungal polypeptide such as an *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptosphaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide having enzyme activity.

In one aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide having enzyme activity.

In another aspect, the polypeptide is an *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia spededonium*, *Thielavia setosa*, *Thielavia subthermophila*, *Thielavia terrestris*, *Trichoderma harzianum*, *Trichoderma koningii*, *Trichoderma longibrachiatum*, *Trichoderma reesei*, *Trichoderma viride*, or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In the processes of the present invention, any GH61 polypeptide having cellulolytic enhancing activity can be used as a component of the enzyme composition.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese or copper.

In another aspect, the GH61 polypeptide having cellulolytic enhancing activity is used in the presence of a dioxy compound, a bicyclic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1, 2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thionaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP: AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8X212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number Q0CJP9), *Humicola insolens* (WO 2010/014706), *Penicillium aurantiogriseum* (WO 2009/068565), *Talaromyces emersonii* (UniProt accession number Q8×211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi, Academic Press, CA,* 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals,* McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida*, *Kluyveromyces*, and *Saccharomyces*, e.g., *Candida sonorensis*, *Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans*, *Clostridium acetobutylicum*, *Clostridium thermocellum*, *Clostridium phytofermentans*, *Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis*, *C. methanosorbosa*, *C. diddensiae*, *C. parapsilosis*, *C. naedodendra*, *C. blankii*, *C. entomophilia*, *C. brassicae*, *C. pseudotropicalis*, *C. boidinii*, *C. utilis*, and *C. scehatae*; *Clostridium*, such as *C. acetobutylicum*, *C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus*, *K. lactis*, *K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida* blankii. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another more preferred aspect, the yeast is a *Saccharomyces* spp. In another more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium* phytofermentans. In another more preferred aspect, the bacterium is *Clostridium thermocellum*. In another more preferred aspect, the bacterium is *Geobacilus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptide

The present invention also relates to an isolated polynucleotide encoding a signal peptide comprising or consisting of amino acids 1 to 23 of SEQ ID NO: 2, amino acids 1 to 21 of SEQ ID NO: 4, amino acids 1 to 23 of SEQ ID NO: 6, amino acids 1 to 23 of SEQ ID NO: 8, amino acids 1 to 21 of SEQ ID NO: 10, amino acids 1 to 19 of SEQ ID NO: 12, amino acids 1 to 20 of SEQ ID NO: 14, amino acids 1 to 21 of SEQ ID NO: 16, amino acids 1 to 23 of SEQ ID NO: 18, amino acids 1 to 22 of SEQ ID NO: 20, amino acids 1 to 23 of SEQ ID NO: 22, amino acids 1 to 23 of SEQ ID NO: 24, amino acids 1 to 23 of SEQ ID NO: 26, amino acids 1 to 15 of SEQ ID NO: 28, amino acids 1 to 17 of SEQ ID NO: 30, amino acids 1 to 17 of SEQ ID NO: 32, amino acids 1 to 19 of SEQ ID NO: 34, amino acids 1 to 22 of SEQ ID NO: 36, or amino acids 1 to 21 of SEQ ID NO: 38.

The polynucleotide may further comprise a gene encoding a protein, which is operably linked to the signal peptide. The protein is preferably foreign to the signal peptide. In one aspect, the polynucleotide encoding the signal peptide is nucleotides 1 to 69 of SEQ ID NO: 1. In another aspect, the polynucleotide encoding the signal peptide is nucleotides 1 to 63 of SEQ ID NO: 3. In another aspect, the polynucleotide encoding the signal peptide is nucleotides 1 to 69 of SEQ ID NO: 5. In another aspect, the polynucleotide encoding the signal peptide is nucleotides 1 to 69 of SEQ ID NO: 7. In another aspect, the polynucleotide encoding the signal peptide is nucleotides 1 to 63 of SEQ ID NO: 9. In another aspect, the polynucleotide encoding the signal peptide is nucleotides 1 to 57 of SEQ ID NO: 11. In another aspect, the polynucleotide encoding the signal peptide is nucleotides 1 to 60 of SEQ ID NO: 13. In another aspect, the polynucleotide encoding the signal peptide is nucleotides 1 to 63 of SEQ ID NO: 15. In another aspect, the polynucleotide encoding the signal peptide is nucleotides 1 to 69 of SEQ ID NO: 17. In another aspect, the polynucleotide encoding the signal peptide is nucleotides 1 to 66 of SEQ ID NO: 19. In another aspect, the polynucleotide encoding the signal peptide is nucleotides 1 to 69 of SEQ ID NO: 21. In another aspect, the polynucleotide encoding the signal peptide is nucleotides 1 to 69 of SEQ ID NO: 23. In another aspect, the polynucleotide encoding the signal peptide is nucleotides 1 to 69 of SEQ ID NO: 25. In another aspect, the polynucleotide encoding the signal peptide is nucleotides 1 to 45 of SEQ ID NO: 27. In another aspect, the polynucleotide encoding the signal peptide is nucleotides 1 to 51 of SEQ ID NO: 29. In another aspect, the polynucleotide encoding the signal peptide is nucleotides 1 to 51 of SEQ ID NO: 31. In another aspect, the polynucleotide encoding the signal peptide is nucleotides 1 to 57 of SEQ ID NO: 33. In another aspect, the polynucleotide encoding the signal peptide is nucleotides 1 to 66 of SEQ ID NO: 35. In another aspect, the polynucleotide encoding the signal peptide is nucleotides 1 to 63 of SEQ ID NO: 37.

The present invention also relates to nucleic acid constructs, expression vectors and recombinant host cells comprising such polynucleotides.

The present invention also relates to methods of producing a protein, comprising (a) cultivating a recombinant host cell comprising such a polynucleotide operably linked to a gene encoding the protein; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The gene may be obtained from any prokaryotic, eukaryotic, or other source.

The present invention is further described by the following examples that should not be construed as limiting the scope of the invention.

EXAMPLES

Strains

The fungal strain NN044936 was isolated from a soil sample collected from Yunnan Province, China, by dilution on PDA plates at 45° C. and then purified by transferring a single conidium onto a YG agar plate. The strain NN044936 was identified as *Thermoascus aurantiacus*, based on both morphological characteristics and ITS rDNA sequence.

The fungal strain NN044758 was isolated from a soil sample collected from China by the dilution on PDA plates at 45° C. and then purified by transferring a single conidium onto a YG agar plate. The strain NN044758 was identified as *Malbranchea cinnamomea*, based on both morphological characteristics and ITS rDNA sequence.

The fungal strain NN051602 was isolated from a compost sample collected from China by dilution on PDA plates at 45° C. and then purified by transferring a single conidium onto a YG agar plate. The strain NN051602 was identified as *Penicillium emersonii*, based on both morphological characteristics and ITS rDNA sequence.

The fungal strain NN047338 was isolated from a soil sample collected from Hunan Province, China, by dilution on PDA plates at 45° C. and then purified by transferring a single conidium onto a YG agar plate. The strain NN047338 was identified as *Humicola insolens*, based on both morphological characteristics and ITS rDNA sequence.

The fungal strain NN046782 was isolated from a soil sample collected from China by dilution on PDA plates at 45° C. and then purified by transferring a single conidium onto a YG agar plate. The strain NN046872 was identified as *Rhizomucor pusillus*, based on both morphological characteristics and ITS rDNA sequence.

The fungal strain NN000308 was purchased from Centraalbureau voor Schimmelcultures named as CBS174.70. The strain NN000308 was identified as *Corynascus thermophilus* (previously identified as *Thielavia thermophila*, -syn. *Myceliophthora fergusii*), based on both morphological characteristics and ITS rDNA sequence.

The fungal strain NN051380 was isolated from a soil sample collected from China, by dilution on PDA plates at 25° C. and then purified by transferring a single conidium onto a PDA plate. The strain NN051380 was identified as *Penicillium oxalicum*, based on both morphological characteristics and ITS rDNA sequence.

Media

PDA plates were composed of 39 grams of potato dextrose agar and deionized water to 1 liter.

YG agar plates were composed of 5 g of yeast extract, 10 g of glucose, 20 g of agar, and deionized water to 1 liter.

YPG medium was composed of 0.4% yeast extract, 0.1% $KH_2PO_4$, 0.05% $MgSO_4.7H_2O$, and 1.5% glucose in deionized water.

YPM medium was composed of 1% of yeast extract, 2% of peptone, and 2% of maltose in deionized water.

Czapek's medium was composed of 30 g of sucrose, 3 g of $NaNO_3$, 0.5 g of $MgSO_4.7H_2O$, 0.01 g of $FeSO_4.7H_2O$, 1 g of $K_2HPO_4$, 0.5 g of KCl, and deionized water to 1 liter. The pH was adjusted to pH 4 with 1 M HCl.

Minimal medium plates were composed of 342 g of sucrose, 20 ml of salt solution, 20 g of agar, and deionized water to 1 liter. The salt solution was composed of 2.6% KCl, 2.6% $MgSO_4.7H_2O$, 7.6% $KH_2PO_4$, 2 ppm $Na_2B_4O_7.10H_2O$, 20 ppm $CuSO_4.5H_2O$, 40 ppm $FeSO_4.7H_2O$, 40 ppm $MnSO_4.2H_2O$, 40 ppm $Na_2MoO_4.2H_2O$, and 400 ppm $ZnSO_4.7H_2O$.

COVE-N-gly slants were composed of 218 g of sorbitol, 10 g of glycerol, 2.02 g of $KNO_3$, 50 ml of COVE salt solution, 25 g of agar powder, and deionized water to 1 liter.

COVE plates for protoplast regeneration were composed of 342 g of sucrose, 20 g of agar powder, 20 ml of COVE salt solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, 15 mM CsCl, were added.

COVE top agarose were composed of 342.3 g of sucrose, 20 ml of COVE salt solution, 6 g of GTG agarose (SeaKem, Cat#50070), and deionized water to 1 liter. The medium was sterilized by autoclaving at 15 psi for 15 minutes (Bacteriological Analytical Manual, 8th Edition, Revision A, 1998). The medium was cooled to 60° C., and 10 mM acetamide and 15 mM CsCl were added.

COVE-2 plate for isolation were composed of 30 g of sucrose, 20 ml of COVE salt solution, 30 g of agar powder, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide was added.

COVE salt solution was composed of 26 g of $MgSO_4.7H_2O$, 26 g of KCl, 26 g of $KH_2PO_4$, 50 ml of COVE trace metal solution, and deionized water to 1 liter.

COVE trace metal solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionized water to 1 liter.

NNCYP-PCS medium was composed per liter of 5.0 g of $NaNO_3$, 3.0 g of $NH_4Cl$, 2.0 g of MES, 2.5 g of citric acid, 0.2 g of $CaCl_2$ $2H_2O$, 1.0 g of Bacto Peptone, 5.0 g of yeast extract, 0.2 g of $MgSO_4$ $7H_2O$, 4.0 g of $K_2HPO_4$, 1.0 ml of COVE trace elements solution, 2.5 g of glucose, and 25.0 g of PCS.

FG4 medium was composed of 30 g of soymeal, 15 g of maltose, 5 g of peptone, and deionized water to 1 liter.

Example 1: Genomic DNA Extraction

*Thermoascus aurantiacus* strain NN044936 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using a DNEASY® Plant Maxi Kit (QIAGEN GmbH, Hilden, Germany) following the manufacturer's instructions.

*Malbranchea cinnamomea* strain NN044758 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using a Large-Scale Column Fungal DNAout Kit (BAOMAN BIOTECHNOLOGY, Shanghai, China) following the manufacturer's instructions.

*Penicillium emersonii* strain NN051602 was inoculated onto a PDA plate and incubated for 3 days at 45° C. in the darkness. The mycelia were collected directly from the agar plate and frozen in liquid nitrogen. Frozen mycelia were ground, by a mortar and a pestle, to a fine powder, and genomic DNA was isolated using a DNEASY® Plant Maxi Kit following the manufacturer's instructions.

*Scytalidium thermophilum* strain NN047338 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® and frozen in liquid nitrogen. Frozen mycelia were ground, by a mortar and a pestle, to a fine powder, and genomic DNA was isolated using a DNEASY® Plant Maxi Kit following the manufacturer's instructions.

*Rhizomucor pusillus* strain NN046782 was inoculated onto a PDA plate and incubated for 3 days at 45° C. in the darkness. Several mycelia-PDA plugs were inoculated into 500 ml shake flasks containing 100 ml of FG4 medium. The flasks were incubated for 3 days at 45° C. with shaking at 160 rpm. The mycelia were collected by filtration through MIRACLOTH® and frozen in liquid nitrogen. Frozen mycelia were ground, by a mortar and a pestle, to a fine powder, and genomic DNA was isolated using DNEASY® Plant Maxi Kit following the manufacturer's instructions.

*Corynascus thermophilus* strain NN000308 was inoculated onto a PDA plate and incubated for 3 days at 45° C. in the darkness. Several mycelia-PDA plugs were inoculated into 500 ml shake flasks containing 100 ml of YPG medium. The flasks were incubated for 4 days at 45° C. with shaking at 160 rpm. The mycelia were collected by filtration through MIRACLOTH® and frozen in liquid nitrogen. Frozen mycelia were ground, by a mortar and a pestle, to a fine powder, and genomic DNA was isolated using a DNEASY® Plant Maxi Kit.

*Penicillium oxalicum* strain NN051380 was inoculated onto a PDA plate and incubated for 5 days at 25° C. in the darkness. Several mycelia-PDA plugs were inoculated into 500 ml shake flasks containing 100 ml of Czapek's medium. The flasks were incubated for 3 days at 30° C. with shaking at 160 rpm. The mycelia were collected by filtration through MIRACLOTH® and frozen in liquid nitrogen. Frozen mycelia were ground, by a mortar and a pestle, to a fine powder, and the genomic DNA was isolated using a DNEASY® Plant Maxi Kit following the manufacturer's instructions.

Example 2: Genome Sequencing, Assembly and Annotation

The extracted genomic DNA samples were delivered to Beijing Genome Institute (BGI, Shenzhen, China) for genome sequencing using an ILLUMINA® GA2 System (Illumina, Inc., San Diego, Calif., USA). The raw reads were assembled at BGI using program SOAPdenovo (Li et al., 2010, *Genome Research* 20(2): 265-72). The assembled sequences were analyzed using standard bioinformatics methods for gene finding and functional prediction. Briefly, geneID (Parra et al., 2000, *Genome Research* 10(4): 511-515) was used for gene prediction. Blastall version 2.2.10 (Altschul et al., 1990, *J. Mol. Biol.* 215 (3): 403-410, National Center for Biotechnology Information (NCBI), Bethesda, Md., USA) and HMMER version 2.1.1 (National Center for Biotechnology Information (NCBI), Bethesda, Md., USA) were used to predict function based on structural homology. The beta-glucosidases were identified directly by analysis of the Blast results. The Agene program (Munch and Krogh, 2006, *BMC Bioinformatics* 7: 263) and SignalP program (Nielsen et al., 1997, *Protein Engineering* 10:1-6) were used to identify start codons. The SignalP program was further used to predict signal peptides. Pepstats (Rice et al., 2000, *Trends Genet.* 16(6): 276-277) was used to predict the isoelectric points and molecular weights of the deduced amino acid sequences.

Example 3: Cloning of *Thermoascus aurantiacus* GH3 Beta-Glucosidase Coding Sequences from Genomic DNA Based on the DNA information obtained from genome sequencing in Example 2, the oligonucleotide primers shown below were designed to amplify GH3 beta-glucosidase genes from the genomic DNA of *Thermoascus aurantiacus* NN044936: PE04100007289 (SEQ ID NOs: 1) and PE04100003654 (SEQ ID NOs: 3). Primers were synthesized by Invitrogen, Beijing, China.
SEQ ID 1 forward primer:
5'-ACACAACTGGGGATCCACCatgcttccccactcgttactact-attactcct-3' (SEQ ID NO: 40)
SEQ ID 1 reverse primer:
5'-GTCACCCTCTAGATCTctacccaacaacctcaaacgacg-3' (SEQ ID NO: 41)
SEQ ID 3 forward primer:
5'-ACACAACTGGGGATCC ACC atgccagggcagacat-caacg-3' (SEQ ID NO: 42)
SEQ ID 3 reverse primer:
5'-GTCACCCTCTAGATCTttaatactctccaaccaacggtag-gtctcg-3' (SEQ ID NO: 43)

Lowercase characters of the forward primer represent the coding regions of the gene and lowercase characters of the reverse primer represent the coding region of the gene, while capitalized characters represent regions homologous to the insertion sites of plasmid pPFJO355 (WO2011005867).

For the GH3 beta-glucosidase genes, PE04100007289 and PE04100003654, 20 picomoles of each forward and reverse primer pair above were used in a PCR reaction composed of 2 µl of *Thermoascus aurantiacus* NN044936 genomic DNA, 10 µl of 5×GC Buffer (Finnzymes Oy, Espoo, Finland), 1.5 µl of DMSO, 2.5 mM each of dATP, dTTP, dGTP, and dCTP, and 0.6 unit of PHUSION™ High-Fidelity DNA Polymerase (Finnzymes Oy, Espoo, Finland) in a final volume of 50 µl. The amplifications were performed using a Peltier Thermal Cycler (MJ Research Inc., South San Francisco, Calif., USA) programmed for denaturing at 98° C. for 1 minute; 8 cycles of denaturing at 98° C. for 15 seconds, annealing at 65° C. for 30 seconds, with a 1° C. decrease per cycle, and elongation at 72° C. for 3.25 minutes; 22 cycles each at 98° C. for 15 seconds, 58°

C. for 30 seconds, and 72° C. for 3.25 minutes; and a final extension at 72° C. for 10 minutes. The heat block then went to a 4° C. soak cycle.

The PCR products were isolated by 1.0% agarose gel electrophoresis using 90 mM Tris-borate and 1 mM EDTA (TBE) buffer where product bands of 3.1 kb and 3.2 kb for the GH3 beta-glucosidase genes, PE04100007289 and PE04100003654, respectively, were visualized under UV light. The PCR products were then excised from the gel and purified using an ILLUSTRA® GFX® PCR DNA and Gel Band Purification Kit (GE Healthcare, Buckinghamshire, UK) according to the manufacturer's instructions.

Plasmid pPFJO355 was digested with Bam HI and Bgl II, isolated by 1.0% agarose gel electrophoresis using TBE buffer, and purified using an ILLUSTRA® GFX® PCR and Gel Band Purification Kit according to the manufacturer's instructions.

An IN-FUSION® CF Dry-down Cloning Kit (Clontech Laboratories, Inc., Mountain View, Calif., USA) was used to clone each of the PCR fragments directly into the expression vector pPFJO355, without the need for restriction digestion and ligation.

TABLE 1

Plasmids

Figure 2:
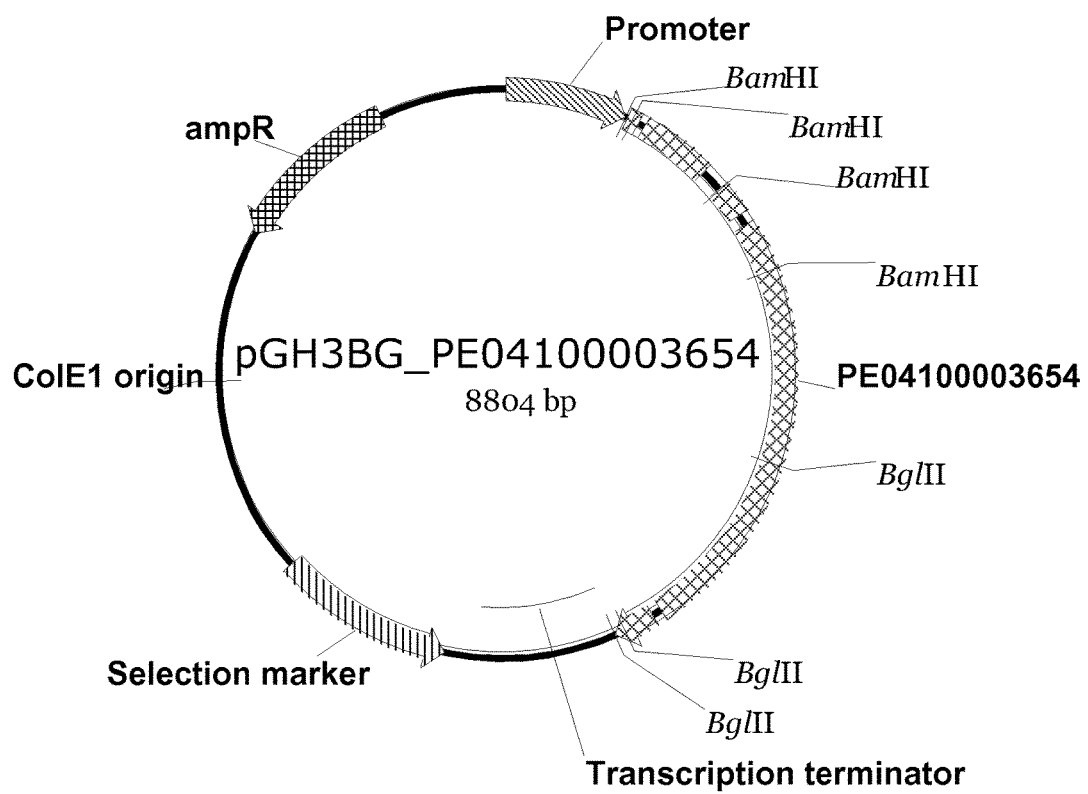
FIG. 2 shows a restriction map of plasmid pGH3BG_PE04100003654.

| Gene name | Plasmid | DNA map |
|---|---|---|
| PE04100007289 | pGH3BG_PE04100007289 | FIG. 1 |
| PE04100003654 | pGH3BG_PE04100003654 | FIG. 2 |

Each PCR product and the digested vector were ligated together using an IN-FUSION® CF Dry-down Cloning Kit resulting in the plasmids shown in Table 1, wherein transcription of the Thermoascus aurantiacus GH3 beta-glucosidase coding sequences were under the control of an Aspergillus oryzae alpha-amylase gene promoter. In brief, 30 ng of pPFJO355, digested with Bam HI and Bgl II, and 60 ng of each purified Thermoascus aurantiacus GH3 beta-glucosidase PCR product were added to reaction vials and resuspended in a final volume of 10 µl by addition of deionized water. The reactions were incubated at 37° C. for 15 minutes and then 50° C. for 15 minutes. Three µl of the reactions were used to transform E. coli TOP10 competent cells (TIANGEN Biotech (Beijing) Co. Ltd., Beijing, China). E. coli transformants containing expression constructs were detected by colony PCR. Colony PCR is a method for quick screening of plasmid inserts directly from E. coli colonies. Briefly, in a premixed PCR solution aliquot in each PCR tube, including PCR buffer, $MgCl_2$, dNTPs, and primer pairs from which the PCR fragment was generated, a single colony was added by picking with a sterile tip and twirling the tip in the reaction solution. Normally 7-10 colonies were screened. After the PCR, reactions were analyzed by 1.0% agarose gel electrophoresis using TBE buffer. Plasmid DNA was prepared from colonies showing inserts with the expected sizes using a QIAPREP® Spin Miniprep Kit (QIAGEN GmbH, Hilden, Germany). The Thermoascus aurantiacus GH3 beta-glucosidase coding sequence inserts of plasmids pGH3BG_PE04100007289 and pGH3BG_PE04100003654 were confirmed by DNA sequencing using a 3730XL DNA Analyzer (Applied Biosystems Inc, Foster City, Calif., USA).

Characterization of the Genomic DNAs Encoding the Thermoascus aurantiacus GH3 Beta-Glucosidases The genomic DNA sequence and deduced amino acid sequence of the Thermoascus aurantiacus GH3 beta-glucosidase gene PE04100007289 are shown in SEQ ID NO: 1 and SEQ ID NO: 2, respectively. The coding sequence is 3150 bp (including the stop codon), which is interrupted by ten introns (nucleotides 212-335, 429-507, 616-673, 738-787, 921-1000, 1180-1243, 1313-1375, 1592-1653, 1952-2013, and 2253-2339). The encoded predicted protein is 806 amino acids. Using the SignalP program (Nielsen et al., 1997, Protein Engineering 10:1-6), a signal peptide of 23 residues was predicted, resulting in a mature polypeptide having 783 amino acids with a predicted molecular mass of 84.63 kDa and a predicted isoelectric point of 5.38.

A comparative pairwise global alignment of amino acid sequences was determined using the Needleman and Wunsch algorithm (Needleman and Wunsch, 1970, J. Mol. Biol. 48: 443-453) with gap open penalty of 10, gap extension penalty of 0.5, and the EBLOSUM62 matrix. The alignment showed that the mature polypeptide of the Thermoascus aurantiacus GH3 beta-glucosidase gene PE04100007289 shares 75.6% sequence identity (excluding gaps) to the deduced amino acid sequence of a gene from Aspergillus oryzae (UNIPROT: Q2U8V9) and 76.1% sequence identity (excluding gaps) to the deduced amino acid sequence of a gene from Aspergillus fumigatus (GENESEQP: AYB85731).

The genomic DNA sequence and deduced amino acid sequence of the Thermoascus aurantiacus GH3 beta-glucosidase gene PE04100003654 are shown in SEQ ID NO: 3 and SEQ ID NO: 4, respectively. The coding sequence is 3197 bp (including the stop codon), which is interrupted by four introns (nucleotides 61-95, 462-575, 739-795, and 2940-2987). The encoded predicted protein is 980 amino acids. Using the SignalP program (Nielsen et al., 1997, supra), a signal peptide of 21 residues was predicted, resulting in a mature polypeptide having 959 amino acids with a predicted molecular mass of 105.71 kDa and a predicted isoelectric point of 7.32.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the Thermoascus aurantiacus GH3 beta-glucosidase gene PE04100003654 shares 65.5% identity (excluding gaps) to the deduced amino acid sequence of a gene from Coccidioides posadasii (UNIPROT: E9D4H8).

Example 4: Expression of Thermoascus aurantiacus a GH3 Beta-Glucosidase Coding Sequence in Aspergillus oryzae Aspergillus oryzae HowB101 (WO 95/035385) protoplasts prepared according to the method of Christensen et al., 1988, Bio/Technology 6: 1419-1422, were separately transformed with 3 µg of pGH3BG_PE04100007289. The transformation yielded about 50 transformants. Four transformants from the transformation were isolated to individual Minimal medium plates.

The four transformants from each transformation were inoculated separately into 3 ml of YPM medium in a 24-well plate and incubated at 30° C. with agitation at 150 rpm. After 3 days incubation, 20 µl of supernatant from each culture were analyzed by SDS-PAGE using a NUPAGE® NOVEX® 4-12% Bis-Tris Gel with 50 mM 2-(N-morpholino)ethanesulfonic acid (MES) (Invitrogen Corporation, Carlsbad, Calif., USA) according to the manufacturer's instructions. The resulting gel was stained with INSTANT-BLUE® (Expedeon Ltd., Babraham Cambridge, UK). SDS- PAGE profiles of the cultures showed transformants of pGH3BG_PE04100007289 had a major protein band at about 98 kDa. One transformant was selected as an expression strain and designated *Aspergillus oryzae* O6YKP.

A slant of expression strain *Aspergillus oryzae* O6YKP was washed with 10 ml of YPM and inoculated into 2-liter flasks containing 400 ml of YPM medium. The culture was harvested on day 3 and filtered using a 0.45 µm DURAPORE® Membrane (Millipore, Bedford, Mass., USA).

Example 5: Cloning of *Malbranchea cinnamomea* GH3 Beta-Glucosidase Coding Sequences from Genomic DNA Based on the DNA information obtained from genome sequencing in Example 2, the oligonucleotide primers shown below were designed to amplify four beta-glucosidase genes from the genomic DNA of *Malbranchea cinnamomea*: GH3_ZY582284_160 (SEQ ID NO: 5), GH3_ZY582296_454 (SEQ ID NO: 7), GH3_ZY582328_115 (SEQ ID NO: 9), and GH3_ZY582278_384 (SEQ ID NO: 11). Primers were synthesized by Invitrogen, Beijing, China.

```
SEQ ID 5 forward primer:
                                       (SEQ ID NO: 44)
5'-ACACAACTGGGGATCC ACC atgtctttcttcaactttctttttga gcgttc-3'

SEQ ID 5 reverse primer:
                                       (SEQ ID NO: 45)
5'-GTCACCCTCTAGATCTcgctgtacagtatttgctgatattacggag tac-3'

SEQ ID 7 forward primer:
                                       (SEQ ID NO: 46)
5'-ACACAACTGGGGATCCACCatgcggctcccttggtg-3'

SEQ ID 7 reverse primer:
                                       (SEQ ID NO: 47)
5'-GTCACCCTCTAGATCTcactctctcgaacccgaatctcc-3'

SEQ ID 9 forward primer:
                                       (SEQ ID NO: 48)
5'-ACACAACTGGGGATCCACCatggctcgtcgcacttc-3'

SEQ ID 9 reverse primer:
                                       (SEQ ID NO: 49)
5'-GTCACCCTCTAGATCTgcatcctgtgacgaggacatca-3'

SEQ ID 11 forward primer:
                                       (SEQ ID NO: 50)
5'-ACACAACTGGGGATCCACCatgcgattgcctgcgacg-3'

SEQ ID 11 reverse primer:
                                       (SEQ ID NO: 51)
5'-GTCACCCTCTAGATCTcttggggctctatcgctgctc-3'
```

Lowercase characters of the forward primer represent the coding regions of the gene and lowercase characters of the reverse primer represent the flanking region of the gene, while capitalized characters represent regions homologous to the insertion sites of plasmid pPFJO355.

For each gene, 20 picomoles of each forward and reverse primer pair were used in a PCR reaction composed of 2 µl of *Malbranchea cinnamomea* genomic DNA, 10 µl of 5×GC Buffer, 1.5 µl of DMSO, 2.5 mM each of dATP, dTTP, dGTP, and dCTP, and 0.6 unit of PHUSION™ High-Fidelity DNA Polymerase in a final volume of 50 µl. The amplifications were performed using a Peltier Thermal Cycler programmed for denaturing at 94° C. for 1 minute; 6 cycles of denaturing at 94° C. for 15 seconds, annealing at 68° C. for 30 seconds, with a 1° C. decrease per cycle, and elongation at 72° C. for 3 minutes; 23 cycles each at 94° C. for 15 seconds, 63° C. for 30 seconds, and 72° C. for 3 minutes; and a final extension at 72° C. for 5 minutes. The heat block then went to a 4° C. soak cycle.

The PCR products were isolated by 1.0% agarose gel electrophoresis using TBE buffer where a single product band for each PCR reaction was visualized under UV light (2.8 kb, 3 kb, 3 kb and 2.5 kb for SEQ ID Nos: 5, 7, 9, and 11, respectively). The PCR products were then purified from solution using an ILLUSTRA® GFX® PCR and Gel Band Purification Kit according to the manufacturer's instructions.

Plasmid pPFJO355 was digested with Bam HI and Bgl II, isolated by 1.0% agarose gel electrophoresis using TBE buffer, and purified using ILLUSTRA® GFX® PCR and Gel Band Purification Kit according to the manufacturer's instructions.

TABLE 2

Figure 3:
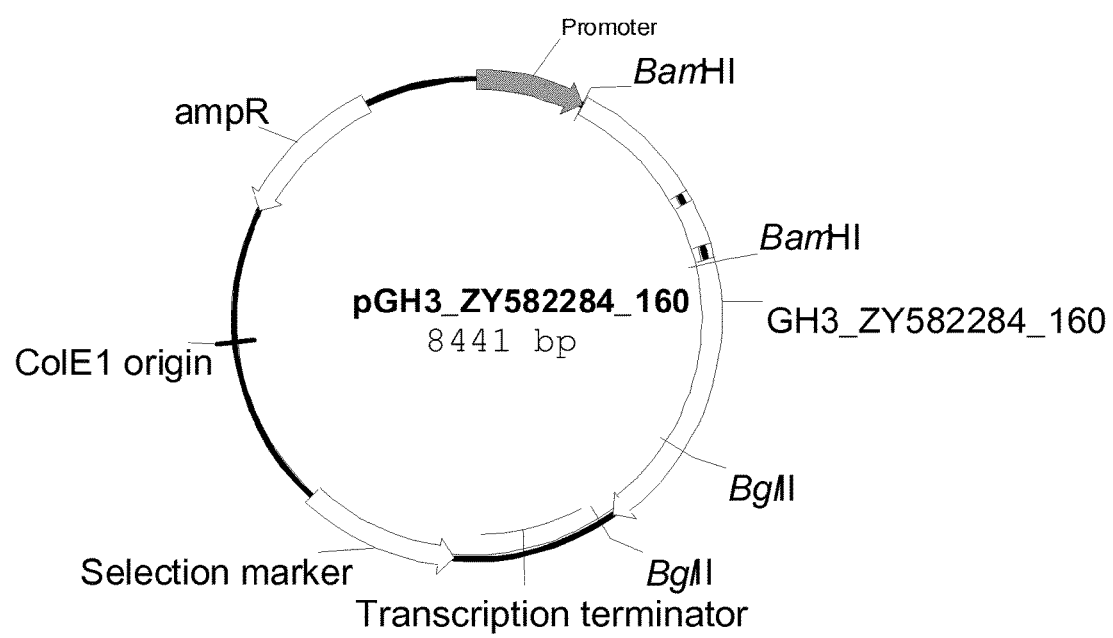
FIG. 3 shows a restriction map of plasmid pGH3_ZY582284_160.
Figure 4:
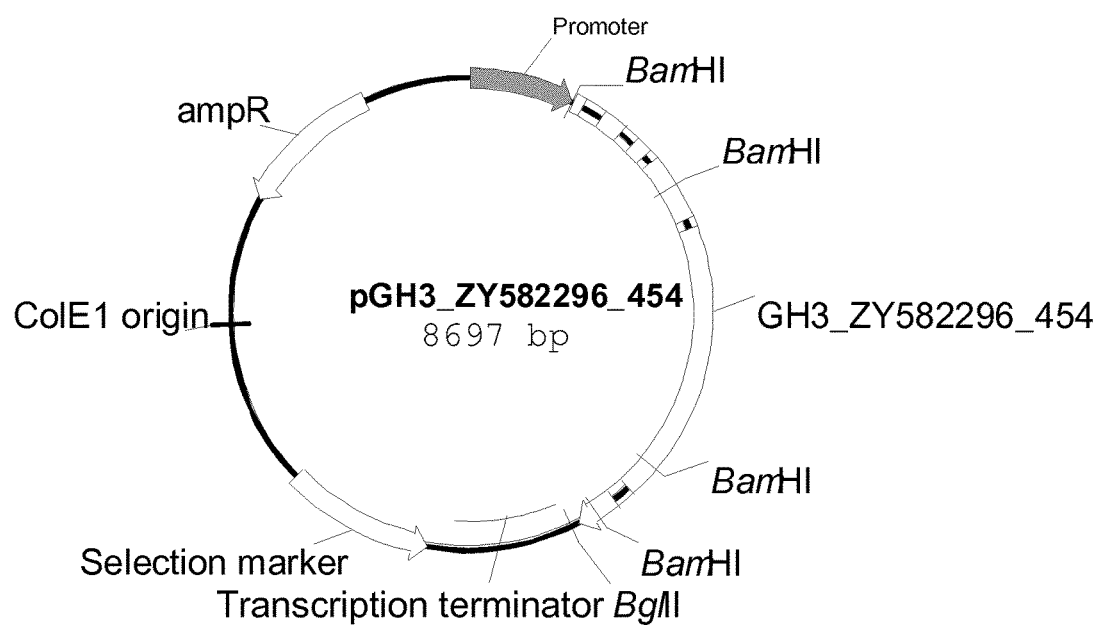
FIG. 4 shows a restriction map of plasmid pGH3_ZY582296_454.
Figure 5:
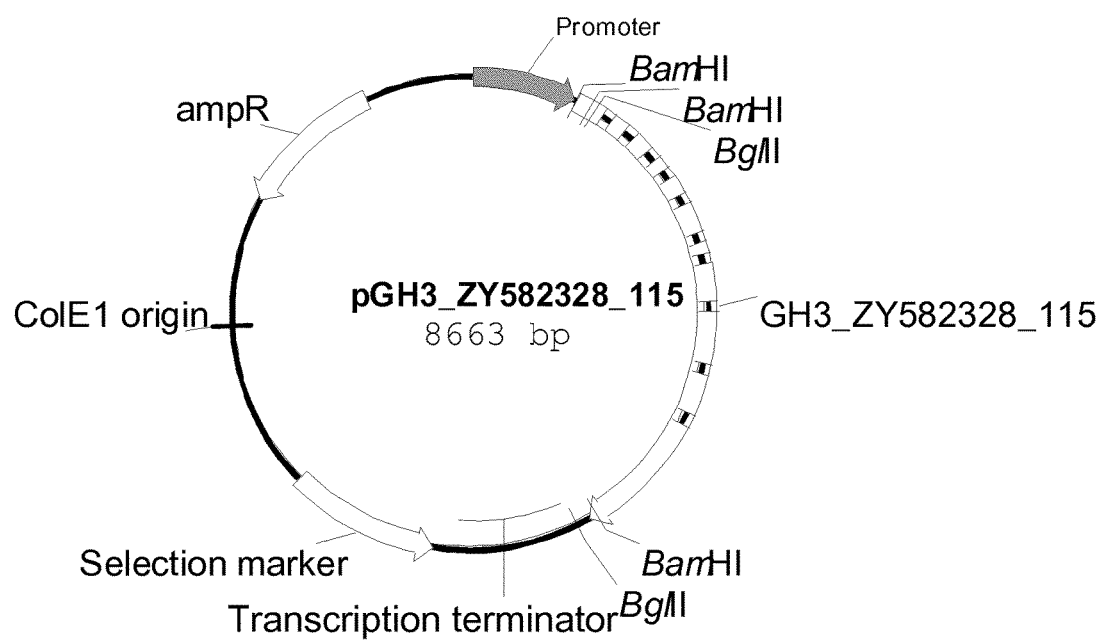
FIG. 5 shows a restriction map of plasmid pGH3_ZY582328_115.
Figure 6:
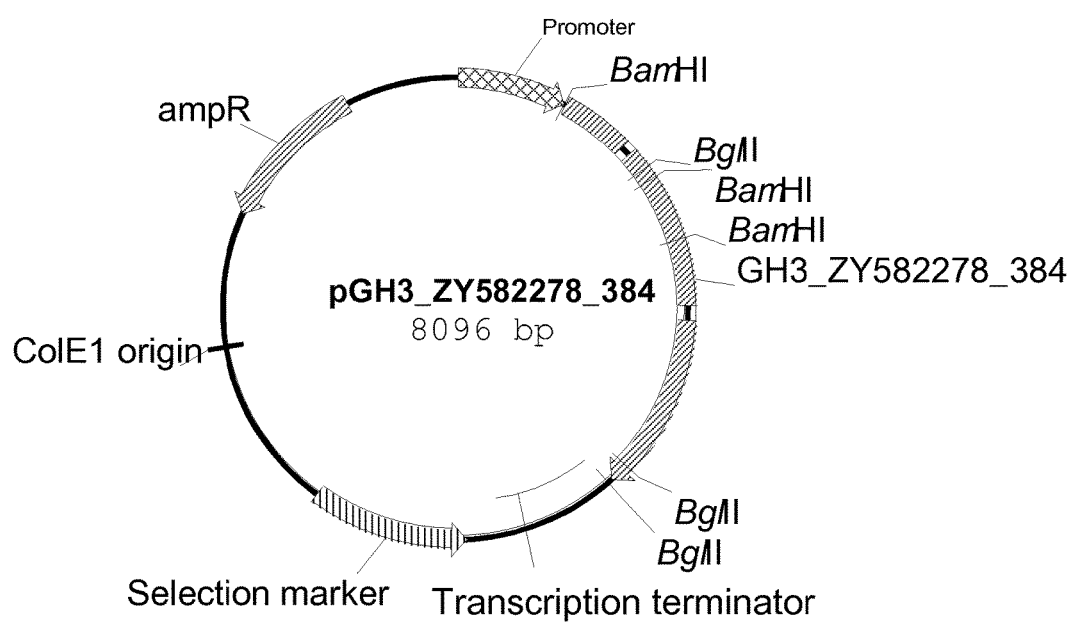
FIG. 6 shows a restriction map of plasmid pGH3_ZY582278_384.

| Plasmids | | |
|---|---|---|
| Gene name | Plasmid | DNA map |
| GH3_ZY582284_160 | pGH3_ZY582284_160 | FIG. 3 |
| GH3_ZY582296_454 | pGH3_ZY582296_454 | FIG. 4 |
| GH3_ZY582328_115 | pGH3_ZY582328_115 | FIG. 5 |
| GH3_ZY582278_384 | pGH3_ZY582278_384 | FIG. 6 |

Each PCR product and the digested vector were ligated together using an IN-FUSION® CF Dry-down Cloning Kit resulting in the plasmids shown in Table 2 wherein transcription of the *Malbranchea cinnamomea* GH3 beta-glucosidase coding sequences were under the control of an *Aspergillus oryzae* alpha-amylase gene promoter. In brief, 30 ng of pPFJO355, digested with Bam HI and Bgl II, and 60 ng of each purified *Malbranchea cinnamomea* GH3 beta-glucosidase PCR product were added to reaction vials and resuspended in a final volume of 10 µl by addition of deionized water. The reactions were incubated at 37° C. for 15 minutes and then 50° C. for 15 minutes. Three µl of the reactions were used to transform *E. coli* TOP10 competent cells. *E. coli* transformants containing expression constructs were detected by colony PCR as described supra. Plasmid DNA was prepared from colonies showing inserts with the expected sizes using a QIAPREP® Spin Miniprep Kit. The *Malbranchea cinnamomea* GH3 beta-glucosidase coding sequence inserts of plasmids pGH3_ZY582284_160, pGH3_ZY582296_454, pGH3_ZY582328_115, and pGH3_ZY582278_384 were confirmed by DNA sequencing using a 3730XL DNA Analyzer.

Characterization of the Genomic DNAs Encoding the *Malbranchea cinnamomea* GH3 Beta-Glucosidases The genomic DNA sequence and deduced amino acid sequence of the *Malbranchea cinnamomea* GH3 beta-glucosidase gene GH3_ZY582284_160 are shown in SEQ ID NO: 5 and SEQ ID NO: 6, respectively. The coding sequence is 2757 bp (including the stop codon), which is interrupted by two introns (nucleotides 742-805, and 1058-1137). The encoded predicted protein is 870 amino acids. Using the SignalP program (Nielsen et al., 1997, supra), a signal peptide of 23 residues was predicted, resulting in a mature polypeptide having 847 amino acids with a predicted molecular mass of 92.77 kDa and a predicted isoelectric point of 5.28.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the *Malbranchea cinnamomea* GH3 beta-glucosidase gene GH3_ZY582284_160 shares 78.4% sequence identity (excluding gaps) to the deduced amino acid sequence of a gene from *T. aurantiacus* (GENESEQP: AYM76612).

The genomic DNA sequence and deduced amino acid sequence of the *Malbranchea cinnamomea* GH3 beta-glucosidase gene GH3_ZY582296_454 are shown in SEQ ID NO: 7 and SEQ ID NO: 8, respectively. The coding sequence is 3042 bp (including the stop codon), which is interrupted by five introns (nucleotides 58-186, 330-424, 523-575, 970-1027, and 2688-2796). The encoded predicted protein is 865 amino acids. Using the SignalP program (Nielsen et al., 1997, supra), a signal peptide of 23 residues was predicted, resulting in a mature polypeptide having 842 amino acids with a predicted molecular mass of 91.09 kDa and a predicted isoelectric point of 4.73.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the *Malbranchea cinnamomea* GH3 beta-glucosidase gene GH3_ZY582296_454 shares 77.7% sequence identity (excluding gaps) to the deduced amino acid sequence of a gene from *Coccidioides posadasii* (UNIPROT: F2TA40).

The genomic DNA sequence and deduced amino acid sequence of the *Malbranchea cinnamomea* GH3 beta-glucosidase gene GH3_ZY582328_115 are shown in SEQ ID NO: 9 and SEQ ID NO: 10, respectively. The coding sequence is 2975 bp (including the stop codon), which is interrupted by ten introns (nucleotides 173-233, 327-393, 502-571, 649-709, 818-880, 1060-1116, 1186-1241, 1458-1522, 1821-1885, and 2125-2194). The encoded predicted protein is 779 amino acids. Using the SignalP program (Nielsen et al., 1997, supra), a signal peptide of 21 residues was predicted, resulting in a mature polypeptide having 758 amino acids with a predicted molecular mass of 83.75 kDa and a predicted isoelectric point of 4.9.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the *Malbranchea cinnamomea* GH3 beta-glucosidase gene GH3_ZY582328_115 shares 74.0% sequence identity (excluding gaps) to the deduced amino acid sequence of a gene from *Neosartorya fischeri* (UNIPROT: A1DFB9).

The genomic DNA sequence and deduced amino acid sequence of the *Malbranchea cinnamomea* GH3 beta-glucosidase gene GH3_ZY582278_384 are shown in SEQ ID NO: 11 and SEQ ID NO: 12, respectively. The coding sequence is 2470 bp (including the stop codon), which is interrupted by two introns (nucleotides 395-450 and 1374-1456). The encoded predicted protein is 776 amino acids. Using the SignalP program (Nielsen et al., 1997, supra), a signal peptide of 19 residues was predicted, resulting in a mature polypeptide having 757 amino acids with a predicted molecular mass of 82.86 kDa and a predicted isoelectric point of 4.7.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the *Malbranchea cinnamomea* GH3 beta-glucosidase gene GH3_ZY582278_384 shares 69.1% sequence identity (excluding gaps) to the deduced amino acid sequence of a putative Beta-glucosidase gene (UNIPROT: A1CA40).

Example 6: Expression of *Malbranchea cinnamomea* GH3 Beta-Glucosidase Coding Sequences in *Aspergillus oryzae*

*Aspergillus oryzae* HowB101 (WO 95/035385) protoplasts prepared according to the method of Christensen et al., 1988, supra, were transformed with 3 µg each of plasmids pGH3_ZY582284_160, pGH3_ZY582296_454, pGH3_ZY582328_115 or pGH3_ZY582278_384. The transformation yielded about 50 transformants. Eight transformants from each transformation were isolated to individual Minimal medium plates.

Four transformants from each transformation were inoculated separately into 3 ml of YPM medium in a 24-well plate and incubated at 30° C. with agitation at 150 rpm. After 3 days incubation, 20 µl of supernatant from each culture were analyzed by SDS-PAGE using a NUPAGE® NOVEX® 4-12% Bis-Tris Gel with 50 mM MES according to the manufacturer's instructions. The resulting gel was stained with INSTANTBLUE®. SDS-PAGE profiles of the cultures showed transformants of pGH3_ZY582284_160, pGH3_ZY582296_454, pGH3_ZY582328_115 and pGH3_ZY582278_384 had the expected major protein bands (98 kDa, 98 kDa, 90 kDa, and 98 kDa, respectively) and one transformant from each transformation was selected as an expression strain (designated *Aspergillus oryzae* O5XGN, O5XGR, O5XGE, and O5XGG, respectively).

A slant of each expression strain was washed with 10 ml of YPM and inoculated into 2-liter flasks containing 400 ml of YPM medium. The cultures were harvested on day 3 and filtered using a 0.45 µm DURAPORE® Membrane.

Example 7: Purification of Recombinant *Malbranchea cinnamomea* GH3 Beta-Glucosidase from *Aspergillus oryzae* Transformants O5XGN, O5XGR, and O5XGE A 3200 ml volume of the filtered broth of *Aspergillus oryzae* O5XGN (Example 6) was precipitated with ammonium sulfate (80% saturation), re-dissolved in 50 ml of 20 mM Tris-HCl pH 6.5, dialyzed against the same buffer, and filtered through a 0.45 µm filter. The final volume was 80 ml. The solution was applied to a 40 ml Q SEPHAROSE® Fast Flow column (GE Healthcare, Buckinghamshire, UK) equilibrated with 20 mM Tris-HCl pH 6.5. The proteins were eluted with a linear 0-0.5 M NaCl gradient and fractions eluted with 0.1-0.35 M NaCl were collected. The collected sample was dialyzed against 20 mM Tris-HCl buffer, pH 6.5, and applied to the same column again. The proteins were eluted with a linear NaCl gradient (0.15-0.32 M) and fractions were evaluated by SDS-PAGE using a NUPAGE®NOVEX® 4-12% Bis-Tris Gel with 50 mM MES. Fractions containing a band of approximately 93 kDa were pooled and then concentrated by ultrafiltration.

A 4000 ml volume of the filtered broth of *Aspergillus oryzae* O5XGR (Example 6) was precipitated with ammonium sulfate (80% saturation), re-dissolved in 50 ml of 20 mM Bis-Tris pH 6.0, dialyzed against the same buffer, and filtered through a 0.45 μm filter. The final volume was 80 ml. The solution was applied to a 40 ml Q SEPHAROSE® Fast Flow column equilibrated with 20 mM Bis-Tris pH 6.0. The proteins were eluted with a linear 0-0.5 M NaCl gradient and fractions checked by SDS-PAGE using a NUPAGE® NOVEX® 4-12% Bis-Tris Gel with 50 mM MES. Fractions containing a band of approximately 98 kDa were pooled and then concentrated by ultrafiltration.

A 2400 ml volume of the filtered broth of *Aspergillus oryzae* O5XGE (Example 6) was precipitated with ammonium sulfate (80% saturation), re-dissolved in 50 ml of 20 mM Bis-Tris pH 6.0, dialyzed against the same buffer, and filtered through a 0.45 μm filter. The final volume was 70 ml. The solution was applied to a 40 ml Q SEPHAROSE® Fast Flow column equilibrated with 20 mM Bis-Tris pH 6.0. The proteins were eluted with a linear 0-0.5 M NaCl gradient and fractions checked by SDS-PAGE using a NUPAGE® NOVEX® 4-12% Bis-Tris Gel with 50 mM MES. Fractions containing a band of approximately 90 kDa were pooled and then concentrated by ultrafiltration.

Example 8: Cloning of *Penicillium emersonii* the GH3 Beta-Glucosidase Coding Sequence PE04230001302 from Genomic DNA Based on the gene information obtained by genome sequencing in Example 2, the oligonucleotide primers shown below were designed to amplify GH3 beta-glucosidase gene PE04230001302 (SEQ ID NO: 13) from the genomic DNA of *Penicillium emersonii*. Primers were synthesized by Invitrogen, Beijing, China.

```
SEQ ID 13 forward primer:
                                    (SEQ ID NO: 52)
5'-ACACAACTGGGGATCCACCatgtttgttcttgctgcgtacctctt-3'

SEQ ID 13 reverse primer:
                                    (SEQ ID NO: 53)
5'-GTCACCCTCTAGATCTcctacagcacctgacaaccct-3'
```

Lowercase characters represent the DNA sequence of the genes, while capitalized characters represent regions homologous to the insertion sites of plasmid pCaHj505 vector. The expression vector pCaHj505 contained the TAKA-amylase promoter derived from *Aspergillus oryzae* and the *Aspergillus niger* glucoamylase terminator elements. Furthermore pCaHj505 had pUC19 derived sequences for selection and propagation in *E. coli*, and an amdS gene, which encoded an acetoamidase gene derived from *Aspergillus nidulans* for selection of an amdS+ *Aspergillus* transformant.

Twenty picomoles of each of primer above were used in a PCR reaction composed of 3.3 μl of *Penicillium emersonii* genomic DNA, 10 μl of 5×GC Buffer, 1.5 μl of DMSO, 2.5 mM each of dATP, dTTP, dGTP, and dCTP, and 0.6 unit of PHUSION™ High-Fidelity DNA Polymerase in a final volume of 50 μl. The amplification was performed using a Peltier Thermal Cycler programmed for denaturing at 98° C. for 1 minute; 8 cycles each at 98° C. for 15 seconds, 65° C. for 30 seconds, with 1° C. decrease per cycle, and 72° C. for 195 seconds; and another 22 cycles each at 98° C. for 15 seconds, 58° C. for 30 seconds and 72° C. for 3 minute 15 seconds; and a final extension at 72° C. for 10 minutes. The heat block then went to a 4° C. soak cycle.

The reaction products were isolated by 1.0% agarose gel electrophoresis using TBE buffer where a product band of 2.5 kb for the GH3 beta-glucosidase gene PE04230001302 was visualized under UV light. The PCR product was then purified from solution using an ILLUSTRA® GFX® PCR and Gel Band Purification Kit according to the manufacturer's instructions.

Plasmid pCaHj505 was digested with Bam HI and Xho I, isolated by 0.7% agarose gel electrophoresis using TBE buffer, and purified using an ILLUSTRA® GFX® PCR and Gel Band Purification Kit according to the manufacturer's instructions.

An IN-FUSION® CF Dry-down Cloning Kit was used to clone the PCR fragment directly into the expression vector pCaHj505, without the need for restriction digestion and ligation.

Figure 7:
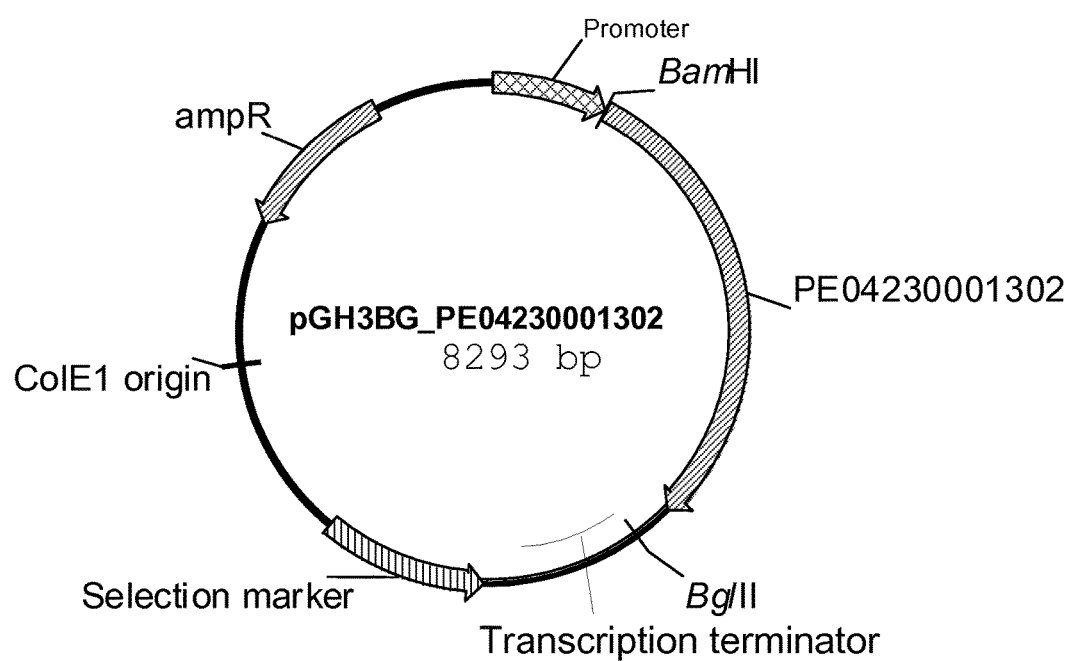
FIG. 7 shows a restriction map of plasmid pGH3BG_PE04230001302.

The PCR product and the digested vector were ligated together using an IN-FUSION® CF Dry-down Cloning Kit resulting in the plasmid pGH3BG_PE04230001302 (FIG. 7) wherein transcription of the *Penicillium emersonii* GH3 beta-glucosidase coding sequence was under the control of a TAKA-amylase promoter from *Aspergillus oryzae*. The cloning operation was according to the manufacturer's instruction. In brief, 30 ng of Bam HI and Xho I digested pCaHj505, and 60 ng of the purified *Penicillium emersonii* GH3 beta-glucosidase gene PCR product were added to the reaction vial and resuspended the powder in a final volume of 10 ul with addition of deionized water. The reaction was incubated at 37° C. for 15 minutes and then 50° C. for 15 minutes. Three μl of the reaction were used to transform *E. coli* TOP10 competent cells An *E. coli* transformant containing pGH3BG_ PE04230001302 was detected by colony PCR as described supra. Plasmid DNA was prepared using a QIAPREP® Spin Miniprep Kit. The *Penicillium emersonii* GH3 beta-glucosidase coding sequence insert of pGH3BG_PE04230001302 was confirmed by DNA sequencing using a 3730XL DNA Analyzer.

Characterization of the Genomic DNA Encoding the PE04230001302 *Penicillium* Emersonii GH3 Beta-Glucosidase The genomic DNA sequence and deduced amino acid sequence of the *Penicillium* emersonii GH3 beta-glucosidase gene PE04230001302 are shown in SEQ ID NO: 13 and SEQ ID NO: 14, respectively. The coding sequence is 2478 bp (including the stop codon), which is interrupted by three introns (nucleotides 89-141, 467-516, and 1832-1884). The encoded predicted protein is 773 amino acids. Using the SignalP program (Nielsen et al., 1997, supra), a signal peptide of 20 residues was predicted, resulting in a mature polypeptide having 753 amino acids with a predicted molecular mass of 80.97 kDa and a predicted isoelectric point of 5.24.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the *Penicillium emersonii* GH3 beta-glucosidase gene PE04230001302 shares 62.7% sequence identity (excluding gaps) to the deduced amino acid sequence of a gene from *Neosartorya fischeri* (UNIPROT: A1DBI2).

Example 9: Expression of a *Penicillium emersonii* GH3 Beta-Glucosidase Coding Sequence PE04230001302 in *Aspergillus niger*

An agar slant (COVE-N-gly) was inoculated with spores of *Aspergillus niger* HowB112, and grown at 32° C. until it was completely sporulated. The spores were resuspended in 5-10 ml of sterile 0.05% TWEEN® 20 in water. About 10⁸ spores were transferred to a 500 ml baffled shake flask containing 100 ml YPG medium with 10 mM NaNO$_3$, and incubated at 32° C. for 16 hours at 99 rpm. Then the mycelia were harvested for protoplasts preparation.

Aspergillus niger HowB112 protoplasts were prepared according to WO 2004/111218 and transformed with 10 μg of pGH3BG_PE04230001302. The Aspergillus niger HowB112 transformants with pGH3BG_PE04230001302 were selected on COVE plates for protoplast regeneration. About 15 transformants were observed on the selective plates and four transformants were isolated on COVE-2 plates for 3-4 days at 32° C.

The four transformants were inoculated separately into 3 ml of YPM medium in 24-well plate and incubated at 30° C. with agitation at 220 rpm. After 3 days incubation, 20 μl of supernatant from each culture were analyzed by SDS-PAGE using a NuPAGE Novex 4-12% Bis-Tris Gel with 50 mM MES. The resulting gel was stained with INSTANTBLUE®. The SDS-PAGE profiles of the cultures showed that the transformants had the expected protein band for expression of pGH3BG_PE04230001302. One transformant was selected as an expression strain and designated Aspergillus oryzae O7MQD.

A slant of the expression strain A. oryzae O7MQD was washed with 10 ml of YPM and inoculated into 2-liter flasks containing 400 ml of YPM medium. The cultures were harvested on day 3 and filtered using a 0.45 μm DURAPORE® Membrane.

Example 10: Cloning of Penicillium emersonii GH3 Beta-Glucosidase Coding Sequences PE04230007249 and PE04230005925 from Genomic DNA Based on the gene information obtained by genome sequencing in Example 2, the oligonucleotide primers shown below were designed to amplify GH3 beta-glucosidase genes PE04230007249 (SEQ ID NO: 15) and PE04230005925 (SEQ ID NO: 17) from the genomic DNA of Penicillium emersonii. Primers were synthesized by Invitrogen, Beijing, China.

```
SEQ ID 15 forward primer:
                                             (SEQ ID NO: 54)
5'-ACACAACTGGGGATCCACCatgaggtggacgagcttcgc-3'

SEQ ID 15 reverse primer:
                                             (SEQ ID NO: 55)
5'-GTCACCCTCTAGATCTacaaggaaagagaatcaggcagca-3'

SEQ ID 17 forward primer:
                                             (SEQ ID NO: 56)
5'-ACACAACTGGGGATCCACCatgacggtcatcacggcagtatct-3'

SEQ ID 17 reverse primer:
                                             (SEQ ID NO: 57)
5'-GTCACCCTCTAGATCTgtactgtgtcgacgtactaggatagct
cct-3'
```

Lowercase characters of the forward primer represent the coding regions of the gene and lowercase characters of the reverse primer represent the flanking region of the gene, while capitalized characters represent regions homologous to the insertion sites of plasmid pPFJO355.

For each GH3 beta-glucosidase gene, 20 picomoles of each of the primer pairs above were used in a PCR reaction composed of 2 μl of Penicillium emersonii genomic DNA, 10 μl of 5×GC Buffer, 1.5 μl DMSO, 2.5 mM each of dATP, dTTP, dGTP, and dCTP, and 0.6 unit of PHUSION™ High-Fidelity DNA Polymerase in a final volume of 50 μl. The amplification was performed using a Peltier Thermal Cycler programmed for denaturing at 98° C. for 1 minute; 8 cycles each at 98° C. for 15 seconds, 65° C. for 30 seconds, with 1° C. decrease per cycle, and 72° C. for 195 seconds; and another 22 cycles each at 98° C. for 15 seconds, 58° C. for 30 seconds and 72° C. for 3 minute 15 seconds; and a final extension at 72° C. for 10 minutes. The heat block then went to a 4° C. soak cycle.

The reaction products were isolated by 1.0% agarose gel electrophoresis using TBE buffer where product bands of 2.5 kb and 3.0 kb for the GH3 beta-glucosidase genes PE04230007249 and PE04230005925, respectively, were visualized under UV light. The PCR products were then purified from solution using an ILLUSTRA® GFX® PCR and Gel Band Purification Kit according to the manufacturer's instructions.

Plasmid pPFJO355 was digested with Bam HI and Bgl II, isolated by 1.0% agarose gel electrophoresis using TBE buffer, and purified using an ILLUSTRA® GFX® PCR and Gel Band Purification Kit according to the manufacturer's instructions.

An IN-FUSION® CF Dry-down Cloning Kit was used to clone each PCR fragment directly into the expression vector pPFJO355, without the need for restriction digestion and ligation.

TABLE 3

Figure 8:
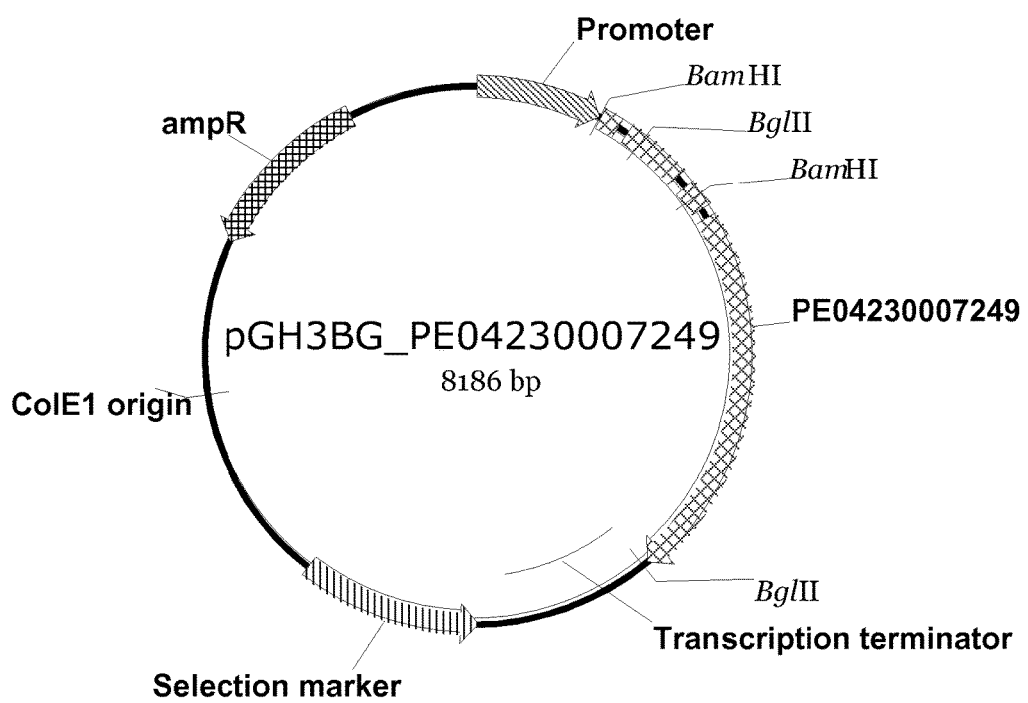
FIG. 8 shows a restriction map of plasmid pGH3BG_PE04230007249.
Figure 9:
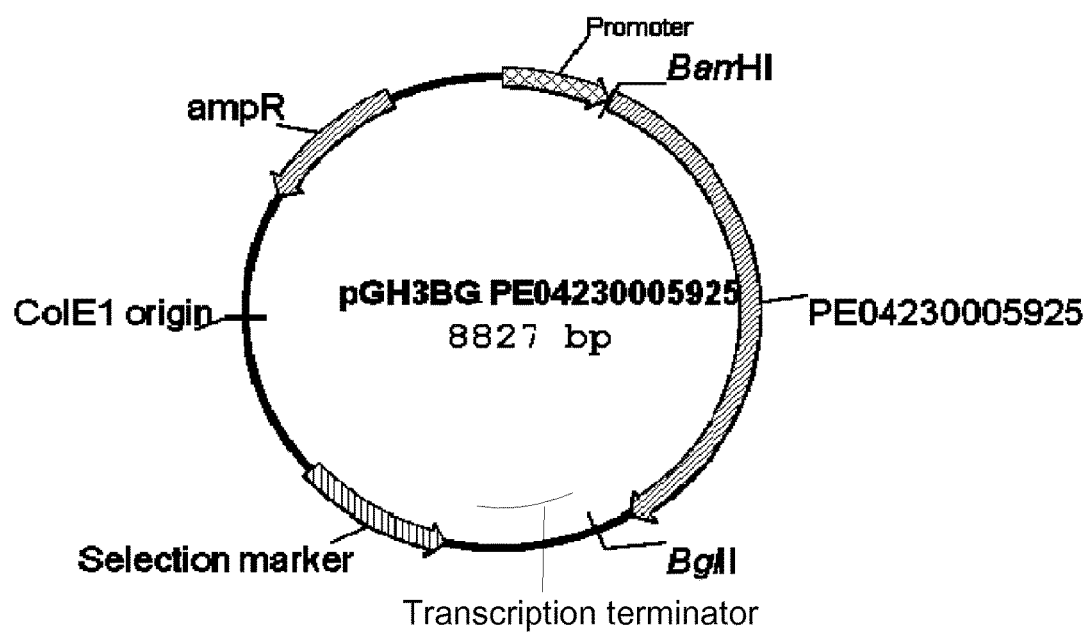
FIG. 9 shows a restriction map of plasmid pGH3BG_PE04230005925.

| Plasmids | | |
|---|---|---|
| Gene name | Plasmid | DNA map |
| PE04230007249 | pGH3BG_PE04230007249 | FIG. 8 |
| PE04230005925 | pGH3BG_PE04230005925 | FIG. 9 |

Each PCR product and the digested vector were ligated together using an IN-FUSION® CF Dry-down Cloning Kit resulting in the plasmids shown in Table 3 wherein transcription of the Penicillium emersonii GH3 beta-glucosidase coding sequences was under the control of an Aspergillus oryzae alpha-amylase gene promoter. In brief, 30 ng of pPFJO355, digested with Bam HI and Bgl II, and 60 ng of each purified Penicillium emersonii GH3 beta-glucosidase gene PCR product were added to reaction vials and resuspended in a final volume of 10 μl by addition of deionized water. The reactions were incubated at 37° C. for 15 minutes and then 50° C. for 15 minutes. Three μl of each reaction were used to transform E. coli TOP10 competent cells. E. coli transformants containing expression constructs were detected by colony PCR as described supra. Plasmid DNA was prepared using a QIAPREP® Spin Miniprep Kit. The Penicillium emersonii GH3 beta-glucosidase coding sequence inserts of pGH3BG_PE04230007249 and pGH3BG_PE04230005925 were confirmed by DNA sequencing using a 3730XL DNA Analyzer.

Characterization of the Genomic DNAs Encoding the PE04230007249 and PE04230005925 Penicillium emersonii GH3 Beta-Glucosidases The genomic DNA sequence and deduced amino acid sequence of the Penicillium emersonii GH3 beta-glucosidase gene PE04230007249 are shown in SEQ ID NO: 15 and SEQ ID NO: 16, respectively. The coding sequence is 2553 bp (including the stop codon), which is interrupted by three introns (nucleotides 95-148, 468-533, and 665-715).

The encoded predicted protein is 793 amino acids. Using the SignalP program (Nielsen et al., 1997, supra), a signal peptide of 21 residues was predicted, resulting in a mature polypeptide having 772 amino acids with a predicted molecular mass of 83.47 kDa and a predicted isoelectric point of 4.70.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the *Penicillium emersonii* GH3 beta-glucosidase gene PE04230007249 shares 68.8% sequence identity (excluding gaps) to the deduced amino acid sequence of a gene from *Penicillium marneffei* (UNIPROT: B6QW86).

The genomic DNA sequence and deduced amino acid sequence of the *Penicillium emersonii* GH3 beta-glucosidase gene PE04230005925 are shown in SEQ ID NO: 17 and SEQ ID NO: 18, respectively. The coding sequence is 3012 bp (including the stop codon), which is interrupted by ten introns (nucleotides 188-250, 344-428, 537-591, 669-718, 827-884, 1064-1133, 1203-1271, 1488-1537, 1836-1902, and 2142-2231). The encoded predicted protein is 784 amino acids. Using the SignalP program (Nielsen et al., 1997, supra), a signal peptide of 23 residues was predicted, resulting in a mature polypeptide having 761 amino acids with a predicted molecular mass of 83.27 kDa and a predicted isoelectric point of 5.22.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the *Penicillium emersonii* GH3 beta-glucosidase gene PE04230005925 shares 76.9% sequence identity (excluding gaps) to the deduced amino acid sequence of a gene from *Aspergillus oryzae* (UNIPROT: Q2U8V9) and 78.4% sequence identity (excluding gaps) to the deduced amino acid sequence of a gene from *Aspergillus fumigatus* (GENESEQP: AWI36254).

Example 11: Expression of *Penicillium emersonii* GH3 Beta-Glucosidase Coding Sequences PE04230007249 and PE04230005925 in *Aspergillus oryzae*

*Aspergillus oryzae* HowB101 (WO 95/035385) protoplasts prepared according to the method of Christensen et al., 1988, supra, were individually transformed with 3 μg of pGH3BG_PE04230005925 or pGH3BG_PE04230007249. Each transformation yielded about 50 transformants. Four transformants from each transformation were isolated to individual Minimal medium plates.

Four transformants from each transformation were inoculated separately into 3 ml of YPM medium in a 24-well plate and incubated at 30° C. with agitation at 150 rpm. After 3 days incubation, 20 μl of supernatant from each culture were analyzed by SDS-PAGE using a NUPAGE® NOVEX® 4-12% Bis-Tris Gel with 50 mM MES. The resulting gel was stained with INSTANTBLUE®. The SDS-PAGE profiles of the cultures showed that the transformants had major bands at approximately 98 kDa and 62 kDa for pGH3BG_PE04230007249 and pGH3BG_PE04230005925, respectively. One transformant from each transformation was selected as an expression strain (designated *Aspergillus oryzae* O7 MP3 and O7 MP4, respectively).

A slant of each expression strain was washed with 10 ml of YPM and inoculated into a 2 liter flask containing 400 ml of YPM medium to generate broth for characterization of the enzyme. The culture was harvested on day 3 and filtered using a 0.45 μm DURAPORE Membrane.

Example 12: *Penicillium emersonii* Strain RNA Preparation, Sequence Assembly, and Mining

*Penicillium emersonii* strain NN051602 was inoculated onto a PDA plate and incubated for 4 days at 45° C. in the darkness. Several mycelia-PDA plugs were inoculated into 500 ml shake flasks containing 100 ml of NNCYP-PCS medium. The flasks were incubated for 6 days at 45° C. with shaking at 160 rpm. The mycelia were collected at days 4, 5, and 6, combined, frozen in liquid nitrogen, and stored in a −80° C. freezer until use.

The frozen mycelia were transferred into a liquid nitrogen prechilled mortar and pestle and ground to a fine powder. Total RNA was prepared from the powdered mycelia by extraction with TRIZOL® reagent (Invitrogen Corporation, Carlsbad, Calif., USA) and purified with a RNEASY® Mini Kit (QIAGEN Inc., Valencia, Calif., USA) by following the standard protocol. Fifty micrograms of total RNA was sent to Fasteris in Switzerland for Illumina sequencing.

Total RNA enriched for polyA sequences with the mRNASeq protocol were sequenced with the Illumina GA2 system. The raw 36 base pair reads were assembled and analyzed using standard bioinformatics methods for gene finding and functional prediction. Briefly, ESTscan 2.0 was used for gene prediction. NCBI blastall version 2.2.10 and HMMER version 2.1.1 were used to predict function based on structural homology. The family GH3 beta-glucosidase candidate was identified directly by analysis of the Blast results.

Total RNA enriched for polyA sequences with the mRNASeq protocol were sequenced with the Illumina GA2 system. The raw 36 base pair reads were assembled with an in-house developed assembler. The assembled sequences were analyzed in-house using standard bioinformatics methods for gene finding and functional prediction. Briefly, ESTscan 2.0 was used for gene prediction. NCBI blastall version 2.2.10 and HMMER version 2.1.1 were used to predict function based on structural homology. The family GH3 beta-glucosidase candidate was identified directly by analysis of the Blast results.

Example 13: Cloning of *Penicillium emersonii* GH3 Beta-Glucosidase Coding Sequence GH3_BG_ZY213882 from Genomic DNA Based on the cDNA sequence information for SEQ ID NO: 39 obtained by RNA experiments in Example 12, the oligonucleotide primers shown below were designed to amplify GH3 beta-glucosidase gene GH3_BG_ZY213882 (SEQ ID NO: 19) from the genomic DNA of *Penicillium emersonii*. Primers were synthesized by Invitrogen, Beijing, China.

```
SEQ ID 39 forward primer:
                                    (SEQ ID NO: 58)
5'-ACACAACTGGGGATCCACCatgtctttcctaatccgtgtactcc
ttt-3'
```

-continued

SEQ ID 39 reverse primer:
(SEQ ID NO: 59)
5'-GTCACCCTCTAGATCTacatatttcaacaagcattgcagcag-3'

Lowercase characters of the forward primer represent the coding regions of the gene and lowercase characters of the reverse primer represent the flanking region of the gene, while capitalized characters represent regions homologous to the insertion sites of plasmid pPFJO355.

Twenty picomoles of each primer above were used in a PCR reaction composed of 4 µl of *Penicillium emersonii* genomic DNA, 10 µl of 5×GC Buffer, 1.5 µl DMSO, 2.5 mM each of dATP, dTTP, dGTP, and dCTP, and 0.6 unit of PHUSION™ High-Fidelity DNA Polymerase in a final volume of 50 µl. The amplification was performed using a Peltier Thermal Cycler programmed for denaturing at 94° C. for 3 minute; 5 cycles each at 94° C. for 40 seconds, 63° C. for 40 seconds, with 1° C. decrease per cycle, and 72° C. for 90 seconds; and another 24 cycles each at 94° C. for 40 seconds, 68° C. for 40 seconds and 72° C. for 90 seconds; and a final extension at 72° C. for 10 minutes. The heat block then went to a 4° C. soak cycle.

The reaction products were isolated by 1.0% agarose gel electrophoresis using TBE buffer where a product band of 2.8 kb for the GH3 beta-glucosidase gene GH3_BG_ZY213882 was visualized under UV light. The PCR products were then purified from solution using an ILLUSTRA® GFX® PCR and Gel Band Purification Kit according to the manufacturer's instructions.

Plasmid pPFJO355 was digested with Bam HI and Bgl II, isolated by 1.0% agarose gel electrophoresis using TBE buffer, and purified using an ILLUSTRA® GFX® PCR and Gel Band Purification Kit according to the manufacturer's instructions.

An IN-FUSION® CF Dry-down Cloning Kit was used to clone the PCR fragment directly into the expression vector pPFJO355, without the need for restriction digestion and ligation.

Figure 10:
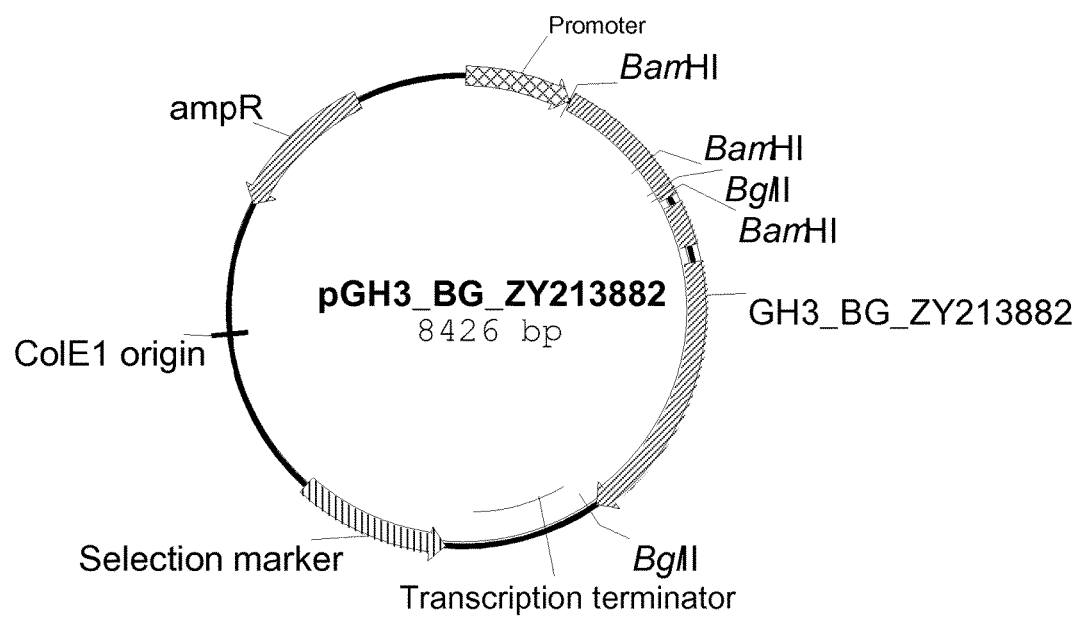
FIG. 10 shows a restriction map of plasmid pGH3_BG_ZY213882.

The PCR product and the digested vector were ligated together using an IN-FUSION® CF Dry-down Cloning Kit resulting in the plasmid pGH3_BG_ZY213882 (FIG. 10) wherein transcription of the *Penicillium emersonii* GH3 beta-glucosidase coding sequence was under the control of an *Aspergillus oryzae* alpha-amylase gene promoter. In brief, 30 ng of pPFJO355, digested with Bam HI and Bgl II, and 60 ng of each purified *Penicillium emersonii* GH3 beta-glucosidase gene PCR product were added to reaction vials and resuspended in a final volume of 10 µl by addition of deionized water. The reactions were incubated at 37° C. for 15 minutes and then 50° C. for 15 minutes. Three µl of each reaction were used to transform *E. coli* TOP10 competent cells. *E. coli* transformants containing expression constructs were detected by colony PCR as described supra. Plasmid DNA was prepared using a QIAPREP® Spin Miniprep Kit. The *Penicillium emersonii* GH3 beta-glucosidase coding sequence insert of pGH3_BG_ZY213882 was confirmed by DNA sequencing using a 3730XL DNA Analyzer.

Characterization of the Genomic DNA Encoding the GH3 BG_ZY213882 *Penicillium* Emersonii GH3 Beta-Glucosidase The genomic DNA sequence and deduced amino acid sequence of the *Malbranchea cinnamomea* GH3 beta-glucosidase gene GH3_BG_ZY213882 are shown in SEQ ID NO: 19 and SEQ ID NO: 20, respectively. The coding sequence is 2771 bp (including the stop codon), which is interrupted by two introns (nucleotides 796-844 and 1097-1193). The encoded predicted protein is 874 amino acids. Using the SignalP program (Nielsen et al., 1997, supra), a signal peptide of 22 residues was predicted, resulting in a mature polypeptide having 852 amino acids with a predicted molecular mass of 91.78 kDa and a predicted isoelectric point of 5.02.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the *Penicillium emersonii* GH3 beta-glucosidase gene GH3_BG_ZY213882 shares 83.14% sequence identity (excluding gaps) to the deduced amino acid sequence of a gene from *Thermoascus aurantiacus* (GENESEQP: AYM76609).

Example 14: Expression of a *Penicillium emersonii* GH3 Beta-Glucosidase Coding Sequence GH3_BG_ZY213882 in *Aspergillus oryzae*

*Aspergillus oryzae* HowB101 (WO 95/035385) protoplasts prepared according to the method of Christensen et al., 1988, supra, were transformed with 3 µg of pGH3_BG_ZY213882. The transformation yielded about 50 transformants. Eight transformants were isolated to individual Minimal medium plates.

Four transformants were inoculated separately into 3 ml of YPM medium in a 24-well plate and incubated at 30° C. with agitation at 150 rpm. After 3 days incubation, 20 µl of supernatant from each culture were analyzed by SDS-PAGE using a NUPAGE® NOVEX® 4-12% Bis-Tris Gel with 50 mM MES. The resulting gel was stained with INSTANT-BLUE®. The SDS-PAGE profiles of the cultures showed that the majority of the transformants had a band at approximately 98 kDa. One transformant was selected as an expression strain and designated *Aspergillus oryzae* O3TMX.

A slant of *A. oryzae* O3TMX was washed with 10 ml of YPM and inoculated into four 2-liter flasks containing 400 ml of YPM medium to generate broth for characterization of the enzyme. The culture was harvested on day 3 and filtered using a 0.45 µm DURAPORE Membrane.

Example 15: Purification of Recombinant *Penicillium emersonii* GH3 Beta-Glucosidase from *Aspergillus oryzae* Transformants O3TMX A 1600 ml volume of the filtered broth of *Aspergillus oryzae* O3TMX (Example 14) was precipitated with ammonium sulfate (80% saturation), re-dissolved in 50 ml of 25 mM Tris-HCl pH 7.0, dialyzed against the same buffer, and filtered through a 0.45 mm filter. The final volume was 60 ml. The solution was applied to a 40 ml Q SEPHAROSE® Fast Flow column equilibrated with 25 mM Tris-HCl pH 7.0. The protein was eluted with a linear 0-0.5 M NaCl gradient and fractions eluted with 0.1-0.5 M NaCl were collected. The collected sample was dialyzed against 25 mM Tris-HCl buffer, pH 7.0, and applied to the same column again. The protein was eluted with a linear NaCl gradient (0.0-0.15M) and fractions were evaluated by SDS-PAGE using a NUPAGE® NOVEX® 4-12% Bis-Tris Gel with 50 mM MES. Fractions containing a band of approximately 92 kDa were pooled and then concentrated by ultrafiltration.

Example 16: Cloning of a *Scytalidium thermophilum* GH3 Beta-Glucosidase Coding Sequence from Genomic DNA Based on the gene information obtained by genome sequencing in Example 2, the oligonucleotide primers shown below were designed to amplify a GH3 beta-glucosidase coding sequence (SEQ ID NO: 21) from the genomic DNA of *Scytalidium thermophilum*. Primers were synthesized by Invitrogen, Beijing, China.

```
SEQ ID 21 forward primer:
                                        (SEQ ID NO: 60)
5'-ACACAACTGGGGATCCACCatgggtcatcacactgccac-3'

SEQ ID 21 reverse primer:
                                        (SEQ ID NO: 61)
5'-GTCACCCTCTAGATCTtcaacgcattctcgccacttc-3'
```

Lowercase characters of the forward primer represent the coding regions of the gene and lowercase characters of the reverse primer represent the flanking region of the gene, while capitalized characters represent regions homologous to the insertion sites of plasmid pPFJO355

Twenty picomoles of each of the primer above was used in a PCR reaction composed of 2.0 µl of *Scytalidium thermophilum* genomic DNA, 10 µl of 5×GC Buffer, 1.5 µl DMSO, 2.5 mM each of dATP, dTTP, dGTP, and dCTP, and 1.0 unit of PHUSION™ High-Fidelity DNA Polymerase in a final volume of 50 µl. The amplification was performed using a Peltier Thermal Cycler programmed for denaturing at 98° C. for 1 minute; 6 cycles each at 98° C. for 15 seconds, 65° C. for 30 seconds, with 1° C. decrease per cycle, and 72° C. for 3 minutes; and another 23 cycles each at 98° C. for 15 seconds, 62° C. for 30 seconds and 72° C. for 3 minutes; and a final extension at 72° C. for 5 minutes. The heat block then went to a 4° C. soak cycle.

The reaction product was isolated by 1.0% agarose gel electrophoresis using TBE buffer where a single product band of 3 kb was visualized under UV light. The PCR product was then purified from solution using an ILLUSTRA® GFX® PCR DNA and Gel Band Purification Kit according to the manufacturer's instructions.

Plasmid pPFJO355 was digested with Bam HI and Bgl II, isolated by 1.0% agarose gel electrophoresis using TBE buffer, and purified using an ILLUSTRA® GFX® PCR and Gel Band Purification Kit according to the manufacturer's instructions.

An IN-FUSION® CF Dry-down Cloning Kit was used to clone each PCR fragment directly into the expression vector pPFJO355, without the need for restriction digestion and ligation.

Figure 11:
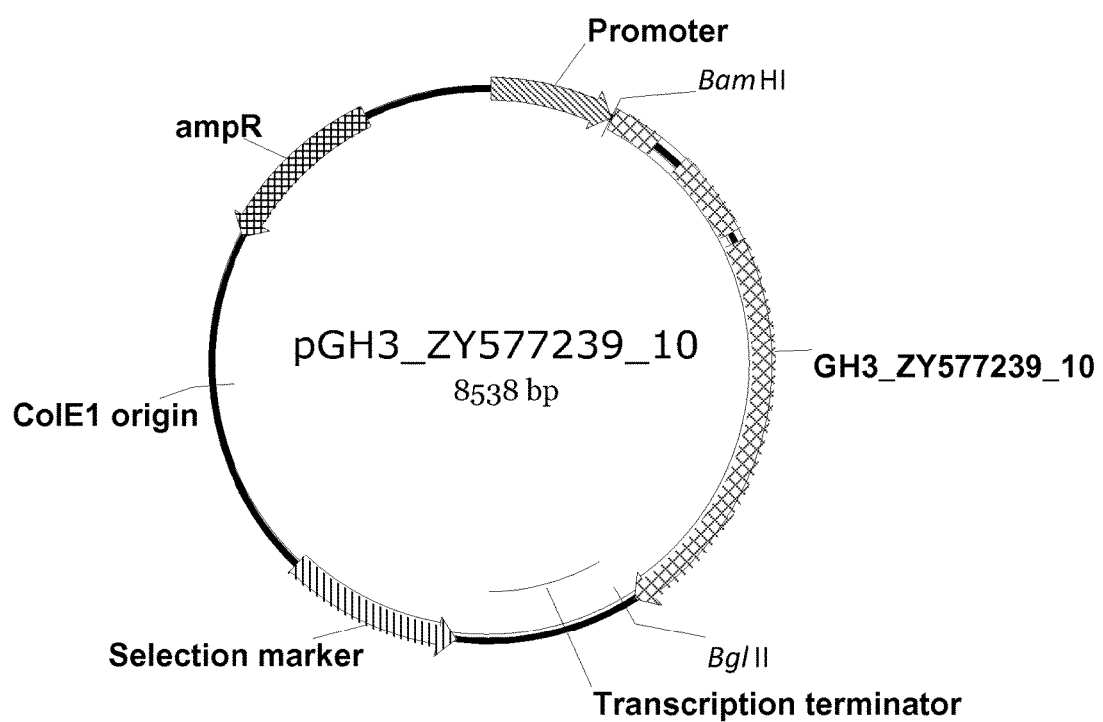
FIG. 11 shows a restriction map of plasmid pGH3_ZY577239_10.

The PCR product and the digested vector were ligated together using an IN-FUSION® CF Dry-down Cloning Kit resulting in plasmid pGH3_ZY577239_10 (FIG. 11) wherein transcription of the *Scytalidium thermophilum* GH3 beta-glucosidase coding sequence was under the control of an *Aspergillus oryzae* alpha-amylase gene promoter. In brief, 30 ng of pPFJO355, digested with Bam HI and Bgl II, and 60 ng of the purified *Scytalidium thermophilum* GH3 beta-glucosidase gene PCR product were added to a reaction vial and resuspended in a final volume of 10 µl by addition of deionized water. The reaction was incubated at 37° C. for 15 minutes and then 50° C. for 15 minutes. Three µl of the reaction were used to transform *E. coli* TOP10 competent cells. *E. coli* transformants containing expression constructs were detected by colony PCR as described supra. Plasmid DNA was prepared using a QIAPREP® Spin Miniprep Kit. The *Scytalidium thermophilum* GH3 beta-glucosidase coding sequence insert of pGH3_ZY577239_10 was confirmed by DNA sequencing using a 3730XL DNA Analyzer. Characterization of the Genomic DNA Encoding the *Scytalidium thermophilum* GH3 Beta-Glucosidase The genomic DNA sequence and deduced amino acid sequence of the *Scytalidium thermophilum* GH3 beta-glucosidase gene GH3_ZY577239_10 are shown in SEQ ID NO: 21 and SEQ ID NO: 22, respectively. The coding sequence is 2874 bp (including the stop codon), which is interrupted by two introns (nucleotides 251-405 and 823-877). The encoded predicted protein is 887 amino acids. Using the SignalP program (Nielsen et al., 1997, supra), a signal peptide of 23 residues was predicted, resulting in a mature polypeptide having 864 amino acids with a predicted molecular mass of 94.11 kDa and a predicted isoelectric point of 6.03.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the *Scytalidium thermophilum* GH3 beta-glucosidase gene GH3_ZY577239_10 shares 79.1% sequence identity (excluding gaps) to the deduced amino acid sequence of a gene from *Chaetomium thermophilum* (UNIPROT: G0SG87).

Example 17: Expression of a *Scytalidium thermophilum* GH3 Beta-Glucosidase Coding Sequence in *Aspergillus oryzae*

*Aspergillus oryzae* HowB101 (WO 95/035385) protoplasts prepared according to the method of Christensen et al., 1988, supra, were transformed with 3 µg of pGH3_ZY577239_10. The transformation yielded about 50 transformants. Eight transformants were isolated to individual Minimal medium plates.

Four transformants were inoculated separately into 3 ml of YPM medium in a 24-well plate and incubated at 30° C. with agitation at 150 rpm. After 3 days incubation, 20 µl of supernatant from each culture were analyzed by SDS-PAGE using a NUPAGE® NOVEX® 4-12% Bis-Tris Gel with 50 mM MES. The resulting gel was stained with INSTANT-BLUE®. The SDS-PAGE profiles of the cultures showed that the majority of the transformants had a band at approximately 94 kDa. One transformant was selected as an expression strain and designated *Aspergillus oryzae* O5JAK.

A slant of *A. oryzae* O5JAK was washed with 10 ml of YPM and inoculated into eight 2-liter flasks containing 400 ml of YPM medium to generate broth for characterization of the enzyme. The culture was harvested on day 3 and filtered using a 0.45 µm DURAPORE Membrane.

Example 18: Purification of a Recombinant *Scytalidium thermophilum* GH3 Beta-Glucosidase from *Aspergillus oryzae* Transformants O5JAK A 3200 ml volume of the filtered broth of *Aspergillus oryzae* O5JAK (Example 17) was precipitated with ammonium sulfate (80% saturation), re-dissolved in 50 ml of 20 mM sodium acetate pH 5.0, dialyzed against the same buffer, and filtered through a 0.45 mm filter. The final volume was 80 ml. The solution was applied to a 40 ml Q SEPHAROSE® Fast Flow column equilibrated with 20 mM sodium acetate pH 5.0. The protein was eluted with a linear 0-0.5 M NaCl gradient and fractions unbound to the column were collected. The collected sample was applied to the same column again. The protein was eluted with a linear NaCl gradient (0.0-0.5M) and fractions were evaluated by SDS-PAGE using a NUPAGE® NOVEX® 4-12% Bis-Tris Gel with 50 mM MES. Fractions containing a band of approximately 92 kDa were pooled and then concentrated by ultrafiltration.

Example 19: Cloning of *Rhizomucor pusillus* GH3 Beta-Glucosidase Coding Sequences from Genomic DNA Based on the gene information obtained by genome sequencing in Example 2, the oligonucleotide primers shown below were designed to amplify GH3 beta-glucosidase genes GH3_ZY654838_321 (SEQ ID NO: 23) and GH3_ZY654973_9450, (SEQ ID NO: 25) from the genomic DNA of *Rhizomucor pusillus*. Primers were synthesized by Invitrogen, Beijing, China.

```
SEQ ID 23 forward primer:
                                    (SEQ ID NO: 62)
5'-ACACAACTGGGGATCCACCatgcgttcgctagcaaatatatctc-3'

SEQ ID 23 reverse primer:
                                    (SEQ ID NO: 63)
5'-GTCACCCTCTAGATCTtgctcatccttaatgtgaccttcag-3'

SEQ ID 25 forward primer:
                                    (SEQ ID NO: 64)
5'-ACACAACTGGGGATCCACCatgtacctaccatcgcttacaacaa cag-3'

SEQ ID 25 reverse primer:
                                    (SEQ ID NO: 65)
5'-GTCACCCTCTAGATCTcagctcgcagatctagataacga-3'
```

Lowercase characters of the forward primer represent the coding regions of the gene and lowercase characters of the reverse primer represent the flanking region of the gene, while capitalized characters represent regions homologous to the insertion sites of plasmid pPFJO355.

For each beta-glucosidase gene, 20 picomoles of each of the primer pairs above were used in a PCR reaction composed of 2 μl of *Rhizomucor pusillus* genomic DNA, 10 μl of 5×GC Buffer, 1.5 μl of DMSO, 2.5 mM each of dATP, dTTP, dGTP, and dCTP, and 0.6 unit of PHUSION™ High-Fidelity DNA Polymerase in a final volume of 50 μl. The amplification was performed using a Peltier Thermal Cycler programmed for denaturing at 98° C. for 1 minute; 6 cycles each at 98° C. for 15 seconds, 65° C. for 30 seconds, with 1° C. decrease per cycle, and 72° C. for 3 minutes; and another 23 cycles each at 98° C. for 15 seconds, 63° C. for 30 seconds and 72° C. for 3 minutes; and a final extension at 72° C. for 5 minutes. The heat block then went to a 4° C. soak cycle.

The reaction products were isolated by 1.0% agarose gel electrophoresis using TBE buffer where product bands of 3 kb and 2.8 kb for the GH3 beta-glucosidase genes GH3_ZY654838_321 and GH3_ZY654973_9450, respectively, were visualized under UV light. The PCR products were then purified from solution using an ILLUSTRA® GFX® PCR and Gel Band Purification Kit according to the manufacturer's instructions.

Plasmid pPFJO355 was digested with Bam HI and Bgl II, isolated by 1.0% agarose gel electrophoresis using TBE buffer, and purified using an ILLUSTRA® GFX® PCR and Gel Band Purification Kit according to the manufacturer's instructions.

An IN-FUSION® CF Dry-down Cloning Kit was used to clone each PCR fragment directly into the expression vector pPFJO355, without the need for restriction digestion and ligation.

TABLE 4

Figure 12:
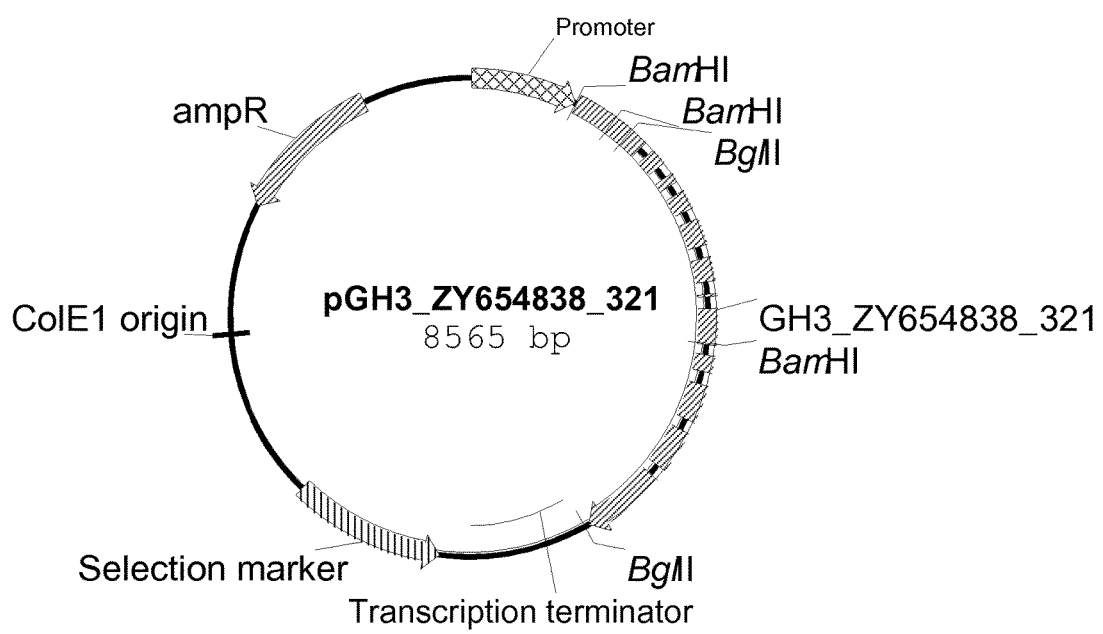
FIG. 12 shows a restriction map of plasmid pGH3_ZY654838_321.
Figure 13:
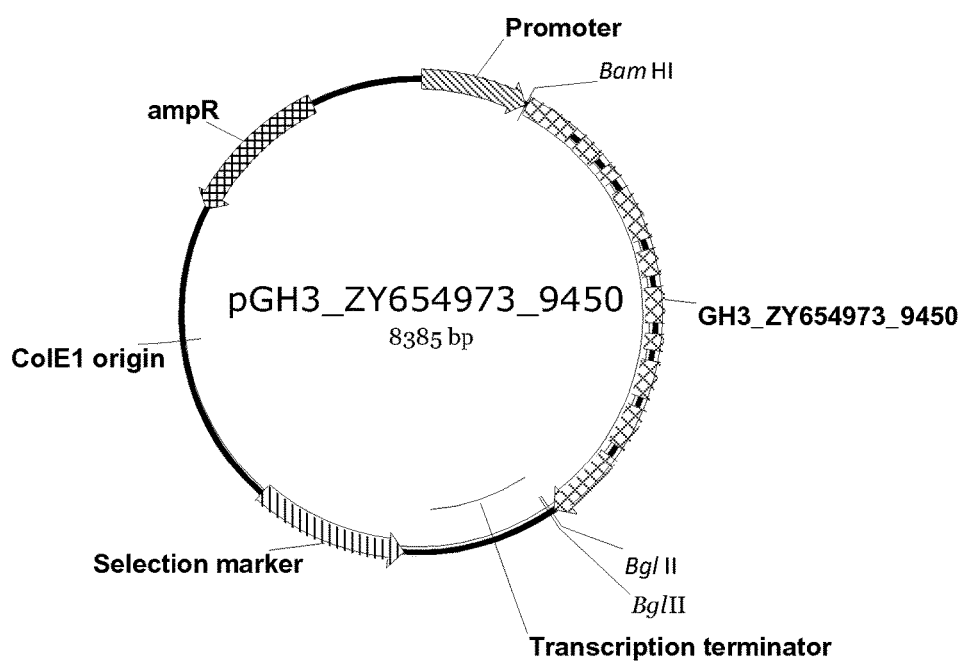
FIG. 13 shows a restriction map of plasmid pGH3_ZY654973_9450.

| | Plasmids | |
|---|---|---|
| Gene name | Plasmid | DNA map |
| GH3_ZY654838_321 | pGH3_ZY654838_321 | FIG. 12 |
| GH3_ZY654973_9450 | pGH3_ZY654973_9450 | FIG. 13 |

Each PCR product and the digested vector were ligated together using an IN-FUSION® CF Dry-down Cloning Kit resulting in the plasmids shown in Table 4 wherein transcription of the *Ruzomucor pusillus* GH3 beta-glucosidase coding sequences was under the control of an *Aspergillus oryzae* alpha-amylase gene promoter. In brief, 30 ng of pPFJO355, digested with Bam HI and Bgl II, and 60 ng of each purified *Ruzomucor pusillus* GH3 beta-glucosidase gene PCR product were added to reaction vials and resuspended in a final volume of 10 μl by addition of deionized water. The reactions were incubated at 37° C. for 15 minutes and then 50° C. for 15 minutes. Three μl of each reaction were used to transform *E. coli* TOP10 competent cells. *E. coli* transformants containing expression constructs were detected by colony PCR as described supra. Plasmid DNA was prepared using a QIAPREP® Spin Miniprep Kit. The *Ruzomucor pusillus* GH3 beta-glucosidase coding sequence inserts of pGH3_ZY654838_321 and pGH3_ZY654973_9450 were confirmed by DNA sequencing using a 3730XL DNA Analyzer.

Characterization of the Genomic DNAs Encoding the *Rhizomucor pusillus* GH3 Beta-Glucosidases The genomic DNA sequence and deduced amino acid sequence of the *Rhizomucor pusillus* GH3 beta-glucosidase gene GH3_ZY654838_321 are shown in SEQ ID NO: 23 and SEQ ID NO: 24, respectively. The coding sequence is 2932 bp (including the stop codon), which is interrupted by 11 introns (nucleotides 443-500, 593-662, 717-777, 884-948, 1099-1167, 1305-1376, 1392-1459, 1663-1723, 1818-1892, 2106-2173, and 2417-2479). The encoded predicted protein is 733 amino acids. Using the SignalP program (Nielsen et al., 1997, supra), a signal peptide of 23 residues was predicted, resulting in a mature polypeptide having 710 amino acids with a predicted molecular mass of 77.46 kDa and a predicted isoelectric point of 4.77.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the *Rhizomucor pusillus* GH3 beta-glucosidase gene GH3_ZY654838_321 shares 55.4% sequence identity (excluding gaps) to the deduced amino acid sequence of a gene from *Rhizomucor miehei* (UNIPROT: B0JE65).

The genomic DNA sequence and deduced amino acid sequence of the *Rhizomucor pusillus* GH3 beta-glucosidase gene GH3_ZY654973_9450 are shown in SEQ ID NO: 25 and SEQ ID NO: 26, respectively. The coding sequence is 2747 bp (including the stop codon), which is interrupted by nine introns (nucleotides 302-359, 500-562, 656-717, 1027-1089, 1237-1301, 1505-1563, 1658-1716, 1930-1990, and 2237-2306). The encoded predicted protein is 728 amino acids. Using the SignalP program (Nielsen et al., 1997, supra), a signal peptide of 23 residues was predicted, resulting in a mature polypeptide having 705 amino acids with a predicted molecular mass of 76.45 kDa and a predicted isoelectric point of 4.96.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the *Rhizomucor pusillus* GH3 beta-glucosidase gene GH3_ZY654973_9450 shares 68.8% sequence identity (excluding gaps) to the deduced amino acid sequence of a gene from *Rhizomucor miehei* (UNI-PROT: B0JE65).

Example 20: Expression of a *Rhizomucor pusillus* GH3 Beta-Glucosidase Coding Sequence in *Aspergillus oryzae*

*Aspergillus oryzae* HowB101 (WO 95/035385) protoplasts prepared according to the method of Christensen et al., 1988, supra, were transformed with 3 µg of pGH3_ZY654973_9450. The transformation yielded about 50 transformants. Eight transformants were isolated to individual Minimal medium plates.

Four transformants were inoculated separately into 3 ml of YPM medium in a 24-well plate and incubated at 30° C. with agitation at 150 rpm. After 3 days incubation, 20 µl of supernatant from each culture were analyzed by SDS-PAGE using a NUPAGE® NOVEX® 4-12% Bis-Tris Gel with 50 mM MES. The resulting gel was stained with INSTANT-BLUE®. The SDS-PAGE profiles of the cultures showed that the majority of the transformants had a band at approximately 80 kDa. One transformant was selected as an expression strain and designated *Aspergillus oryzae* O6QZF.

A slant of *A. oryzae* O6QZF was washed with 10 ml of YPM and inoculated into six 2-liter flasks each containing 400 ml of YPM medium to generate broth for characterization of the enzyme. The culture was harvested on day 3 and filtered using a 0.45 µm DURAPORE Membrane.

Example 21: Purification of Recombinant *Rhizomucor pusillus* GH3 Beta-Glucosidase from *Aspergillus oryzae* O6QZF A 2400 ml volume of filtered supernatant of *Aspergillus oryzae* O6QZF (Example 20) was precipitated with ammonium sulfate (80% saturation), re-dissolved in 50 ml of 20 mM Bis-Tris pH 6.5, dialyzed against the same buffer, and filtered through a 0.45 µm filter. The final volume was 85 ml. The solution was applied to a 40 ml Q SEPHAROSE® Fast Flow column equilibrated with 20 mM Bis-Tris pH 6.5. Proteins were eluted with a linear 0-0.5 M NaCl gradient. Fractions eluted with 0.2-0.4M NaCl were collected and further purified using a 40 ml Phenyl SEPHAROSE® 6 Fast Flow column (GE Healthcare, Buckinghamshire, UK) with a linear 1.2-0 M $(NH_4)_2SO_4$ gradient. Fractions were analyzed by SDS-PAGE using a NUPAGE® NOVEX® 4-12% Bis-Tris Gel with 50 mM MES. The resulting gel was stained with INSTANTBLUE™. Fractions containing a band at approximately 80 kDa were pooled. Then the pooled solution was concentrated by ultrafiltration.

Example 22: Cloning of *Corynascus thermophilus* GH3 Beta-Glucosidase Coding Sequences from Genomic DNA Based on the gene information obtained by genome sequencing in Example 2, the oligonucleotide primers shown below were designed to amplify GH3 beta-glucosidase genes GH3_Mf3898 (SEQ ID NO: 27), GH3_Mf5104 (SEQ ID NO: 29), and GH3_Mf1588 (SEQ ID NO: 31) from the genomic DNA of *Corynascus thermophilus*. Primers were synthesized by Invitrogen, Beijing, China.

```
SEQ ID 27 forward primer:
                                    (SEQ ID NO: 66)
5'-ACACAACTGGGGATCCACCatgaaggctgccgtgc-3'

SEQ ID 27 reverse primer:
                                    (SEQ ID NO: 67)
5'-GTCACCCTCTAGATCTttctgttcgccgaaacctg-3'

SEQ ID 29 forward primer:
                                    (SEQ ID NO: 68)
5'-ACACAACTGGGGATCCACCatgacctttcaagcgctcg-3'

SEQ ID 29 reverse primer:
                                    (SEQ ID NO: 69)
5'-GTCACCCTCTAGATCTactccatccaagaagccgaac-3'

SEQ ID 31 forward primer:
                                    (SEQ ID NO: 70)
5'-ACACAACTGGGGATCCACCatgcggttcctctcc-3'

SEQ ID 31 reverse primer:
                                    (SEQ ID NO: 71)
5'-GTCACCCTCTAGATCTctattgagggttgtctgctcctg-3'
```

Lowercase characters of the forward primer represent the coding regions of the gene and lowercase characters of the reverse primer represent the flanking region of the gene, while capitalized characters represent regions homologous to the insertion sites of plasmid pPFJO355.

For each GH3 beta-glucosidase gene, 20 picomoles of each of the primer pairs above were used in a PCR reaction composed of 2 µl of *Corynascus thermophilus* genomic DNA, 10 µl of 5×GC Buffer, 1.5 µl of 2.5 mM each of dATP, dTTP, dGTP, and dCTP, and 1.0 unit of PHUSION™ High-Fidelity DNA Polymerase in a final volume of 50 µl. The amplification was performed using a Peltier Thermal Cycler programmed for denaturing at 98° C. for 1 minute; 6 cycles each at 98° C. for 15 seconds, 67° C. for 30 seconds, with 1° C. decrease per cycle, and 72° C. for 3 minutes; and another 23 cycles each at 94° C. for 15 seconds, 63° C. for 30 seconds and 72° C. for 3 minutes; and a final extension at 72° C. for 5 minutes. The heat block then went to a 4° C. soak cycle.

The reaction products were isolated by 1.0% agarose gel electrophoresis using TBE buffer where product bands of 3 kb, 3 kb, and 2.5 kb for the GH3 beta-glucosidase genes GH3_Mf3898, GH3_Mf5104, and GH3_Mf1588, respectively, were visualized under UV light. The PCR products were then purified from solution using an ILLUSTRA® GFX® PCR and Gel Band Purification Kit according to the manufacturer's instructions.

Plasmid pPFJO355 was digested with Bam HI and Bgl II, isolated by 1.0% agarose gel electrophoresis using TBE buffer, and purified using an ILLUSTRA® GFX® PCR and Gel Band Purification Kit according to the manufacturer's instructions.

An IN-FUSION® CF Dry-down Cloning Kit was used to clone each PCR fragment directly into the expression vector pPFJO355, without the need for restriction digestion and ligation.

TABLE 5

Figure 14:
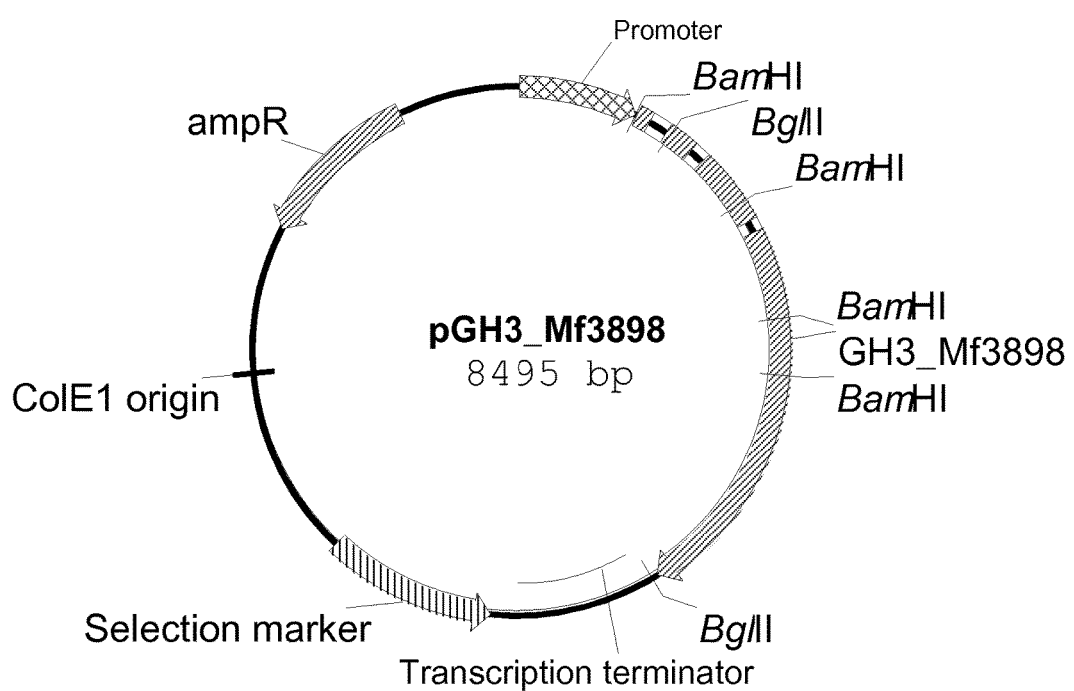
FIG. 14 shows a restriction map of plasmid pGH3_Mf3898.
Figure 15:
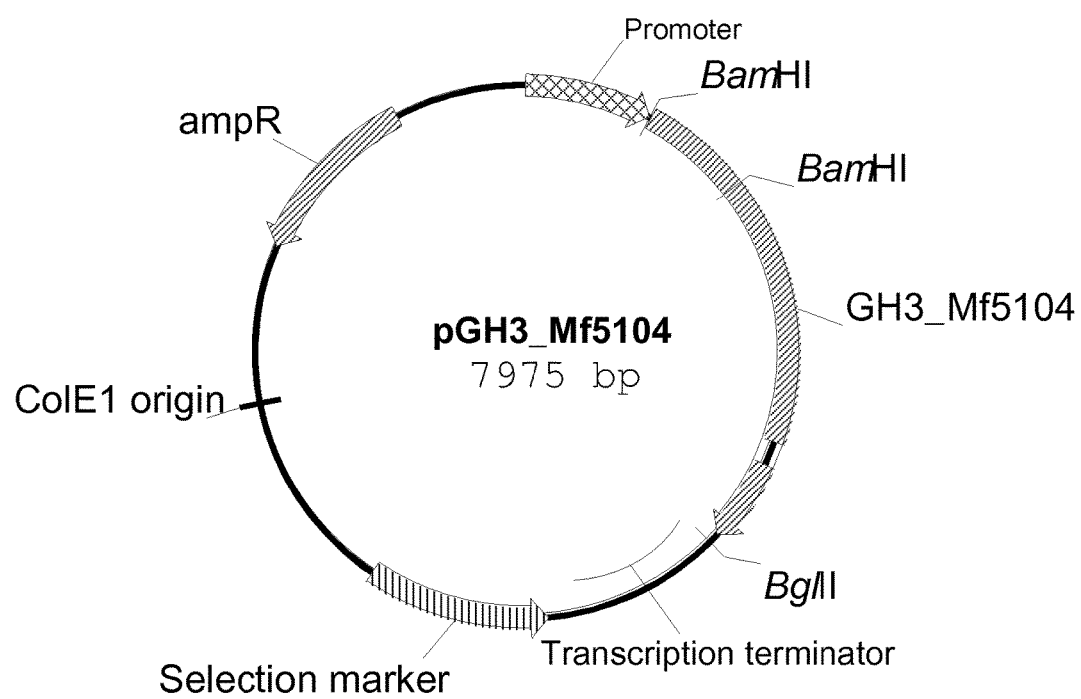
FIG. 15 shows a restriction map of plasmid pGH3_Mf5104.
Figure 16:
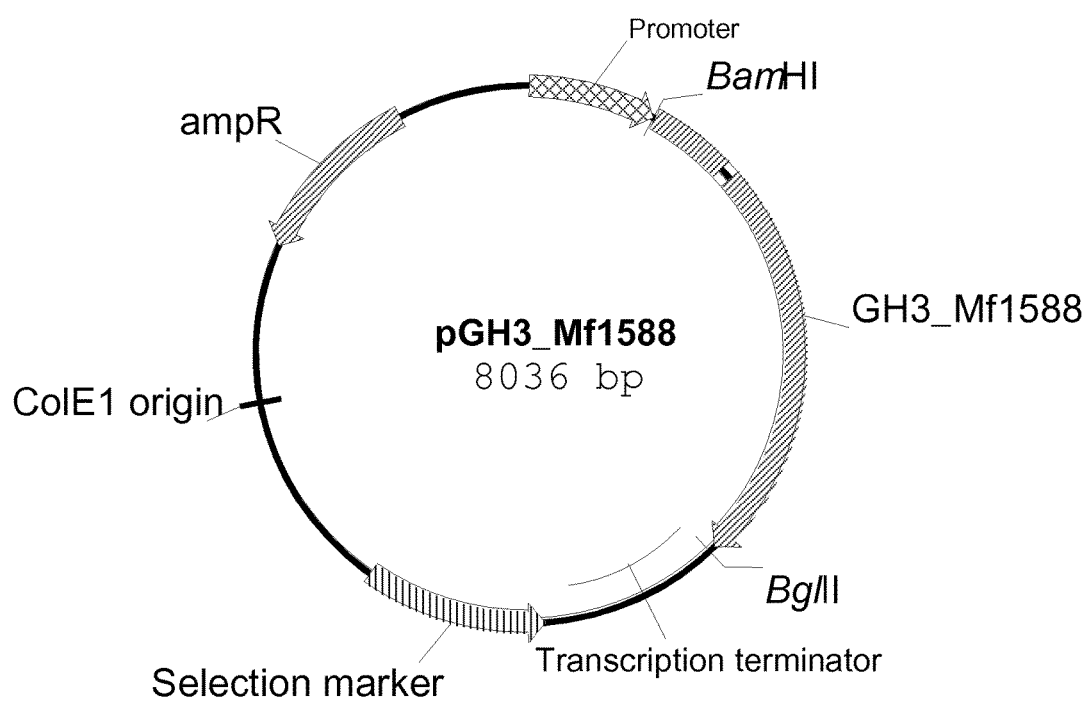
FIG. 16 shows a restriction map of plasmid pGH3_Mf1588.

| Plasmids | | |
|---|---|---|
| Gene name | Plasmid | DNA map |
| GH3_Mf3898 | pGH3_Mf3898 | FIG. 14 |
| GH3_Mf5104 | pGH3_Mf5104 | FIG. 15 |
| GH3_Mf1588 | pGH3_Mf1588 | FIG. 16 |

Each PCR product and the digested vector were ligated together using an IN-FUSION® CF Dry-down Cloning Kit resulting in the plasmids shown in Table 5, wherein transcription of the Corynascus thermophilus GH3 beta-glucosidase coding sequences was under the control of an Aspergillus oryzae alpha-amylase gene promoter. In brief, 30 ng of pPFJO355, digested with Bam HI and Bgl II, and 60 ng of each purified Corynascus thermophilus GH3 beta-glucosidase gene PCR product were added to reaction vials and resuspended in a final volume of 10 μl by addition of deionized water. The reactions were incubated at 37° C. for 15 minutes and then 50° C. for 15 minutes. Three μl of each reaction were used to transform E. coli TOP10 competent cells. E. coli transformants containing expression constructs were detected by colony PCR as described in Example 3. Plasmid DNA was prepared using a QIAPREP® Spin Miniprep Kit. The Corynascus thermophilus GH3 beta-glucosidase coding sequence inserts of pGH3_Mf3898, pGH3_Mf5104, and pGH3_Mf1588 were confirmed by DNA sequencing using a 3730XL DNA Analyzer.

Characterization of the Genomic DNAs Encoding the Corynascus thermophilus GH3 Beta-Glucosidases The genomic DNA sequence and deduced amino acid sequence of the Corynascus thermophilus GH3 beta-glucosidase gene GH3_Mf3898 are shown in SEQ ID NO: 27 and SEQ ID NO: 28, respectively. The coding sequence is 2858 bp (including the stop codon), which is interrupted by three introns (nucleotides 73-175, 331-410, and 800-861). The encoded predicted protein is 870 amino acids. Using the SignalP program (Nielsen et al., 1997, supra), a signal peptide of 15 residues was predicted, resulting in a mature polypeptide having 855 amino acids with a predicted molecular mass of 93.40 kDa and a predicted isoelectric point of 4.79.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the Corynascus thermophilus GH3 beta-glucosidase gene GH3_Mf3898 shares 92.3% sequence identity (excluding gaps) to the deduced amino acid sequence of a gene from Myceliophthora thermophila (GENESEQP: AZJ27053).

The genomic DNA sequence and deduced amino acid sequence of the Corynascus thermophilus GH3 beta-glucosidase gene GH3_Mf5104 are shown in SEQ ID NO: 29 and SEQ ID NO: 30, respectively. The coding sequence is 2320 bp (including the stop codon), which is interrupted by one intron (nucleotides 1796-1913). The encoded predicted protein is 733 amino acids. Using the SignalP program (Nielsen et al., 1997, supra), a signal peptide of 17 residues was predicted, resulting in a mature polypeptide having 716 amino acids with a predicted molecular mass of 76.56 kDa and a predicted isoelectric point of 5.77.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the Corynascus thermophilus GH3 beta-glucosidase gene GH3_Mf5104 shares 87.2% sequence identity (excluding gaps) to the deduced amino acid sequence of a fungal gene (GENESEQP: AWI36371).

The genomic DNA sequence and deduced amino acid sequence of the Corynascus thermophilus GH3 beta-glucosidase gene GH3_Mf1588 are shown in SEQ ID NO: 31 and SEQ ID NO: 32, respectively. The coding sequence is 2397 bp (including the stop codon), which is interrupted by one intron (nucleotides 398-460). The encoded predicted protein is 777 amino acids. Using the SignalP program (Nielsen et al., 1997, supra), a signal peptide of 17 residues was predicted, resulting in a mature polypeptide having 760 amino acids with a predicted molecular mass of 82.51 kDa and a predicted isoelectric point of 5.54.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the Corynascus thermophilus GH3 beta-glucosidase gene GH3_Mf1588 shares 91.7% sequence identity (excluding gaps) to the deduced amino acid sequence of a fungal gene (GENESEQP: AWI36254).

Example 23: Expression of a Corynascus thermophilus GH3 Beta-Glucosidase Coding Sequence in Aspergillus oryzae Aspergillus oryzae HowB101 (WO 95/035385) protoplasts prepared according to the method of Christensen et al., 1988, supra, were individually transformed with 3 μg of pGH3_Mf3898 or pGH3_Mf5104. Each transformation yielded about 50 transformants. Four transformants from each transformation were isolated to individual Minimal medium plates.

Four transformants from each transformation were inoculated separately into 3 ml of YPM medium in a 24-well plate and incubated at 30° C. with agitation at 150 rpm. After 3 days incubation, 20 μl of supernatant from each culture were analyzed by SDS-PAGE using a NUPAGE® NOVEX® 4-12% Bis-Tris Gel with 50 mM MES. The resulting gel was stained with INSTANTBLUE®. The SDS-PAGE profiles of the cultures showed that the transformants had major bands at approximately 100 kDa and 77 kDa for pGH3_Mf3898 and pGH3_Mf5104, respectively. One transformant from each transformation was selected as an expression strain (designated Aspergillus oryzae O8 KV5 and O7J1C, respectively).

A slant of each expression strain was washed with 10 ml of YPM and inoculated into a 2 liter flask containing 400 ml of YPM medium to generate broth for characterization of the enzyme. The cultures were harvested on day 3 and filtered using a 0.45 μm DURAPORE Membrane.

Example 24: Purification of Recombinant Corynascus thermophilus GH3 Beta-Glucosidase from Aspergillus oryzae O8 KV5 and Aspergillus oryzae O7J1C A 3200 ml volume of filtered supernatant of Aspergillus oryzae O8 KV5 (Example 23) was precipitated with ammonium sulfate (80% saturation), re-dissolved in 50 ml of 20 mM Bis-Tris pH 6.0, dialyzed against the same buffer, and filtered through a 0.45 μm filter. The final volume was 80 ml.

The solution was applied to a 40 ml Q SEPHAROSE® Fast Flow column (GE Healthcare, Buckinghamshire, UK) equilibrated with 20 mM Bis-Tris pH 6.0. Proteins were eluted with a linear 0-0.25 M NaCl gradient. Fractions eluted with 0.2-0.25M NaCl were collected and further purified using a 40 ml Phenyl SEPHAROSE® 6 Fast Flow column (GE Healthcare, Buckinghamshire, UK) with a linear 1.2-0 M $(NH_4)_2SO_4$ gradient. Fractions were analyzed by SDS-PAGE using a NUPAGE® NOVEX® 4-12% Bis-Tris Gel with 50 mM MES. The resulting gel was stained with INSTANTBLUE™. Fractions containing a band at approximately 100 kDa were pooled. Then the pooled solution was concentrated by ultrafiltration.

A 3200 ml volume of filtered supernatant of *Aspergillus oryzae* O7J1C (Example 23) was precipitated with ammonium sulfate (80% saturation), re-dissolved in 50 ml of 20 mM Tris-HCl pH 7.5, dialyzed against the same buffer, and filtered through a 0.45 µm filter. The final volume was 100 ml. The solution was applied to a 40 ml Q SEPHAROSE® Fast Flow column equilibrated with 20 mM Tris-HCl pH 7.5. Proteins were eluted with a linear 0-0.5 M NaCl gradient. Fractions unbound to the column were collected and further purified using a 40 ml Phenyl SEPHAROSE® 6 Fast Flow column (GE Healthcare, Buckinghamshire, UK) with a linear 1.2-0 M $(NH_4)_2SO_4$ gradient. Fractions were analyzed by SDS-PAGE using a NUPAGE® NOVEX® 4-12% Bis-Tris Gel with 50 mM MES. The resulting gel was stained with INSTANTBLUE™. Fractions containing a band at approximately 77 kDa were pooled. Then the pooled solution was concentrated by ultrafiltration.

Example 25: Cloning of *Penicillium oxalicum* GH3 Beta-Glucosidase Genes Coding Sequences from Genomic DNA Based on the gene information obtained by genome sequencing in Example 2, the oligonucleotide primers shown below were designed to amplify GH3 beta glucosidase genes GH3_ZY569172_60 (SEQ ID NO: 33), GH3_ZY569163_643 (SEQ ID NO: 35), and GH3_ZY569173_235 (SEQ ID NO: 37) from the genomic DNA of *Penicillium oxalicum*. Primers were synthesized by Invitrogen, Beijing, China.

```
SEQ ID 33 forward primer:
                                        (SEQ ID NO: 72)
5'-ACACAACTGGGGATCCACCatggctgtttggctgc-3'

SEQ ID 33 reverse primer:
                                        (SEQ ID NO: 73)
5'-GTCACCCTCTAGATCTcgctgggctctaccgtgaa-3'

SEQ ID 35 forward primer:
                                        (SEQ ID NO: 74)
5'-ACACAACTGGGGATCCACCatgattgtcaccaaggagttg-3'

SEQ ID 35 reverse primer:
                                        (SEQ ID NO: 75)
5'-ACACAACTGGGGATCCACCgaagagggtcttgggcgatc-3'

SEQ ID 37 forward primer:
                                        (SEQ ID NO: 76)
5'-GTCACCCTCTAGATCTatgttttcaagggtctagctggca-3'

SEQ ID 37 reverse primer:
                                        (SEQ ID NO: 77)
5'-GTCACCCTCTAGATCTatatctccgtcttcaatcggcaca-3'
```

Lowercase characters of the forward primer represent the coding regions of the gene and lowercase characters of the reverse primer represent the flanking region of the gene, while capitalized characters represent regions homologous to the insertion sites of plasmid pPFJO355.

For each GH3 beta-glucosidase gene, 20 picomoles of each of the primer pairs above were used in a PCR reaction composed of 2 µl of *Penicillium oxalicum* genomic DNA, 10 µl of 5×GC Buffer, 1.5 µl of DMSO, 2.5 mM each of dATP, dTTP, dGTP, and dCTP, and 1.0 unit of PHUSION™ High-Fidelity DNA Polymerase in a final volume of 50 µl. The amplification was performed using a Peltier Thermal Cycler programmed for denaturing at 98° C. for 1 minute; 6 cycles each at 98° C. for 15 seconds, 65° C. for 30 seconds, with 1° C. decrease per cycle, and 72° C. for 70 seconds; and another 25 cycles each at 98° C. for 15 seconds, 62° C. for 30 seconds and 72° C. for 70 seconds; and a final extension at 72° C. for 5 minutes. The heat block then went to a 4° C. soak cycle.

The reaction products were isolated by 1.0% agarose gel electrophoresis using TBE buffer where product bands of 2.8 kb, 2.8 kb, and 3.0 kb for the GH3 beta-glucosidase genes GH3_ZY569172_60, GH3_ZY569163_643, and GH3_ZY569173_235, respectively, were visualized under UV light. The PCR products were then purified from solution using an ILLUSTRA® GFX® PCR and Gel Band Purification Kit according to the manufacturer's instructions.

Plasmid pPFJO355 was digested with Bam HI and Bgl II, isolated by 1.0% agarose gel electrophoresis using TBE buffer, and purified using an ILLUSTRA® GFX® PCR and Gel Band Purification Kit according to the manufacturer's instructions.

An IN-FUSION® CF Dry-down Cloning Kit was used to clone each PCR fragment directly into the expression vector pPFJO355, without the need for restriction digestion and ligation.

TABLE 6

Figure 17:
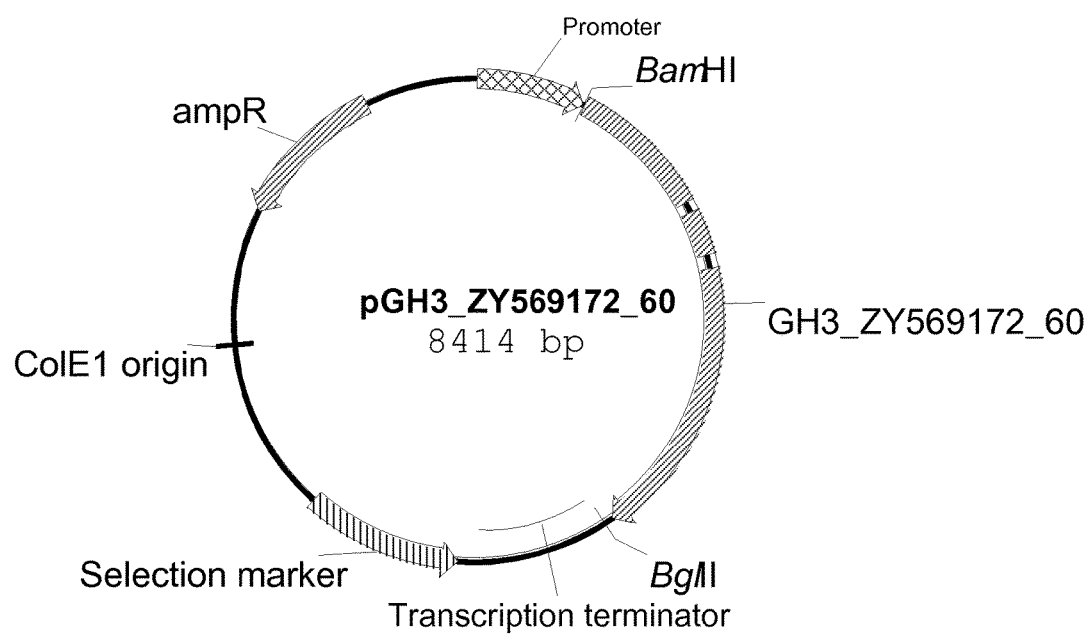
FIG. 17 shows a restriction map of plasmid pGH3_ZY569172_60.
Figure 18:
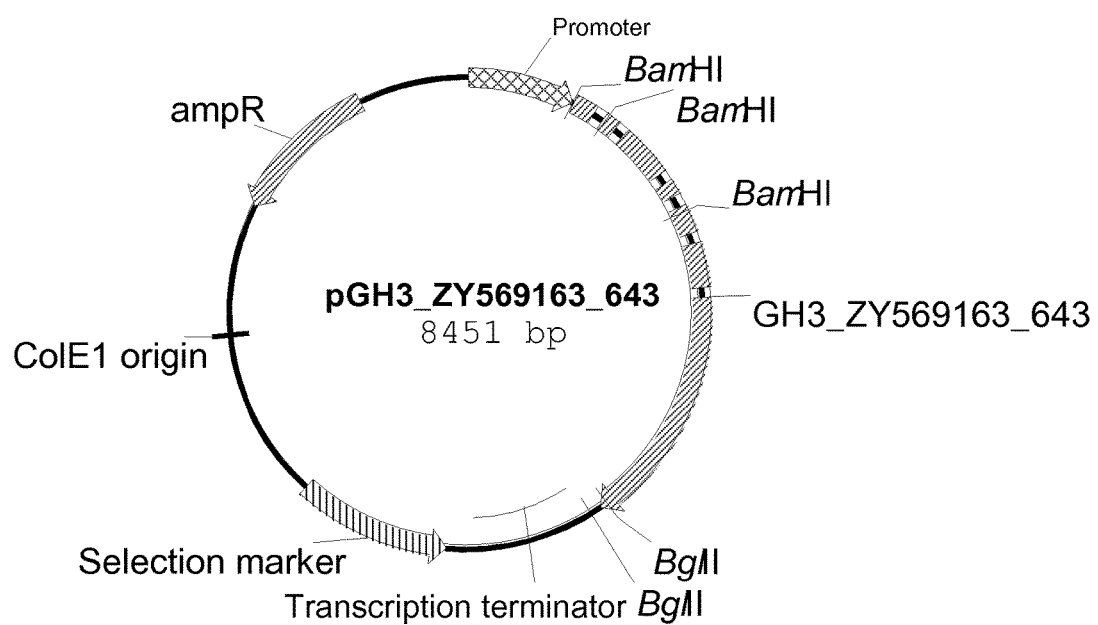
FIG. 18 shows a restriction map of plasmid pGH3_ZY569163_643.
Figure 19:
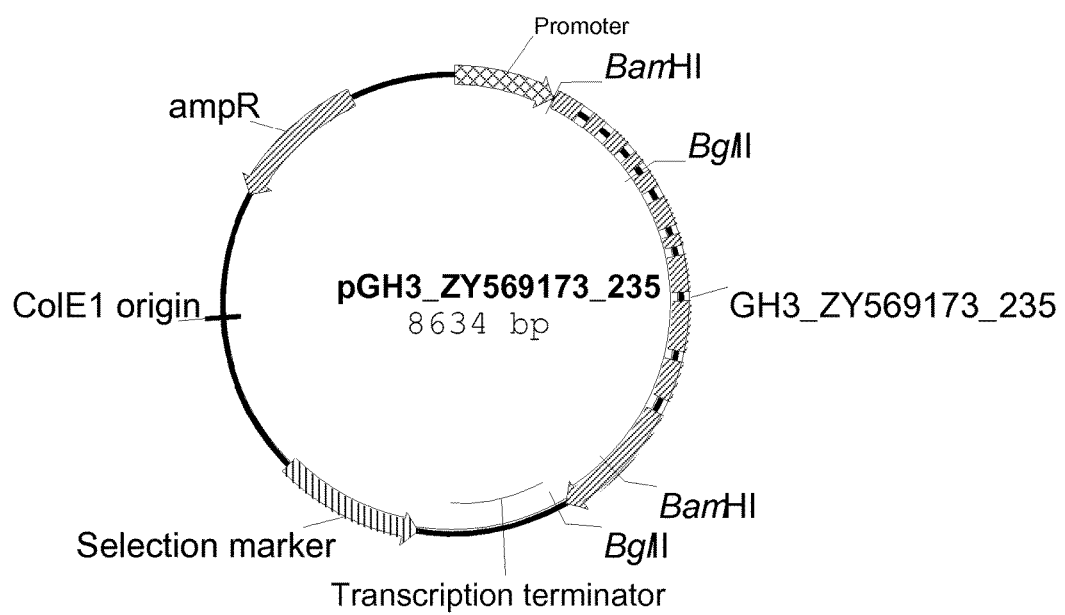
FIG. 19 shows a restriction map of plasmid pGH3_ZY569173_235.

| Plasmids | | |
| --- | --- | --- |
| Gene name | Plasmid | DNA map |
| GH3_ZY569172_60 | pGH3_ZY569172_60 | FIG. 17 |
| GH3_ZY569163_643 | pGH3_ZY569163_643 | FIG. 18 |
| GH3_ZY569173_235 | pGH3_ZY569173_235 | FIG. 19 |

Each PCR product and the digested vector were ligated together using an IN-FUSION® CF Dry-down Cloning Kit resulting in the plasmids shown in Table 6 wherein transcription of the *Penicillium oxalicum* GH3 beta-glucosidase coding sequences was under the control of an *Aspergillus oryzae* alpha-amylase gene promoter. In brief, 30 ng of pPFJO355, digested with Bam HI and Bgl II, and 60 ng of each purified *Penicillium oxalicum* GH3 beta-glucosidase gene PCR product were added to reaction vials and resuspended in a final volume of 10 µl by addition of deionized water. The reactions were incubated at 37° C. for 15 minutes and then 50° C. for 15 minutes. Three µl of each reaction were used to transform *E. coli* TOP10 competent cells. *E. coli* transformants containing expression constructs were detected by colony PCR as described supra. Plasmid DNA was prepared using a QIAPREP® Spin Miniprep Kit. The *Penicillium oxalicum* GH3 beta-glucosidase coding sequence inserts of pGH3_ZY569172_60, pGH3_ZY569163_643, and pGH3_ZY569173_235 were confirmed by DNA sequencing using a 3730XL DNA Analyzer.

Characterization of the Genomic DNAs Encoding the *Penicillium oxalicum* GH3 Beta-Glucosidases The genomic DNA sequence and deduced amino acid sequence of the *Penicillium oxalicum* GH3 beta-glucosidase gene GH3_ZY569172_60 are shown in SEQ ID NO: 33 and SEQ ID NO: 34, respectively. The coding sequence is 2760 bp (including the stop codon), which is interrupted by two introns (nucleotides 790-851 and 1104-1179). The encoded predicted protein is 873 amino acids. Using the SignalP program (Nielsen et al., 1997, supra), a signal peptide of 19 residues was predicted, resulting in a mature polypeptide having 854 amino acids with a predicted molecular mass of 91.38 kDa and a predicted isoelectric point of 5.61.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the *Penicillium oxalicum* GH3 beta-glucosidase gene GH3_ZY569172_60 shares 79.8% sequence identity (excluding gaps) to the deduced amino acid sequence of a gene from *Aspergillus oryzae* (GENESEQP: AXW81304).

The genomic DNA sequence and deduced amino acid sequence of the *Penicillium oxalicum* GH3 beta-glucosidase gene GH3_ZY569163_643 are shown in SEQ ID NO: 35 and SEQ ID NO: 36, respectively. The coding sequence is 2777 bp (including the stop codon), which is interrupted by six introns (nucleotides 128-191, 175-336, 638-697, 787-854, 1016-174, and 1330-1390). The encoded predicted protein is 800 amino acids. Using the SignalP program (Nielsen et al., 1997, supra), a signal peptide of 22 residues was predicted, resulting in a mature polypeptide having 778 amino acids with a predicted molecular mass of 83.79 kDa and a predicted isoelectric point of 5.04.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the *Penicillium oxalicum* GH3 beta-glucosidase gene GH3_ZY569163_643 shares 62.1% sequence identity (excluding gaps) to the deduced amino acid sequence of a gene from *Aspergillus fumigatus* (GENESEQP: AXW81295).

The genomic DNA sequence and deduced amino acid sequence of the *Penicillium oxalicum* GH3 beta-glucosidase gene GH3_ZY569173_235 are shown in SEQ ID NO: 37 and SEQ ID NO: 38, respectively. The coding sequence is 2969 bp (including the stop codon), which is interrupted by ten introns (nucleotides 170-239, 333-398, 507-567, 645-700, 809-875, 1055-1107, 1177-1233, 1450-1504, 1803-1862, and 2102-2188). The encoded predicted protein is 778 amino acids. Using the SignalP program (Nielsen et al., 1997, supra), a signal peptide of 21 residues was predicted, resulting in a mature polypeptide having 757 amino acids with a predicted molecular mass of 82.95 kDa and a predicted isoelectric point of 5.64.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the mature polypeptide of the *Penicillium oxalicum* GH3 beta-glucosidase gene GH3_ZY569173_235 shares 82.7% sequence identity (excluding gaps) to the deduced amino acid sequence of a gene from *Neosartorya fumigata* (UNIPROT: B0Y3L5).

Example 26: Expression of a *Penicillium oxalicum* GH3 Beta-Glucosidase Coding Sequence in *Aspergillus oryzae*

*Aspergillus oryzae* HowB101 (WO 95/035385) protoplasts prepared according to the method of Christensen et al., 1988, supra, were each transformed with 3 µg of pGH3_ZY569172_60 or pGH3_ZY569173_235. The transformation yielded about 50 transformants. Eight transformants were isolated to individual Minimal medium plates.

Four transformants were inoculated separately into 3 ml of YPM medium in a 24-well plate and incubated at 30° C. with agitation at 150 rpm. After 3 days incubation, 20 µl of supernatant from each culture were analyzed by SDS-PAGE using a NUPAGE® NOVEX® 4-12% Bis-Tris Gel with 50 mM MES. The resulting gel was stained with INSTANT-BLUE®. The SDS-PAGE profiles of the cultures showed that the transformants for pGH3_ZY569172_60 and pGH3_ZY569173_235 each had a band at approximately 98 kDa. One transformant for each transformation was selected as an expression strain and designated *Aspergillus oryzae* O4S4U and O4S51 for pGH3_ZY569172_60 and pGH3_ZY569173_235, respectively.

A slant of each expression strain was washed with 10 ml of YPM and inoculated into 2-liter flasks containing 400 ml of YPM medium to generate broth for characterization of the enzyme. The cultures were harvested on day 3 and filtered using a 0.45 µm DURAPORE Membrane.

Example 27: Purification of a Recombinant *Penicillium oxalicum* GH3 Beta-Glucosidase from *Aspergillus oryzae* Transformants O4S4U A 1600 ml volume of the filtered broth of *Aspergillus oryzae* O4S4U (Example 26) was precipitated with ammonium sulfate (80% saturation), re-dissolved in 50 ml of 20 mM Tris-HCl pH 7.5, dialyzed against the same buffer, and filtered through a 0.45 mm filter. The final volume was 80 ml. The solution was applied to a 40 ml Q SEPHAROSE® Fast Flow column equilibrated with 20 mM Tris-HCl pH 7.5. The protein was eluted with a linear 0-0.5 M NaCl gradient and fractions unbound to the column were collected and further purified on a 40 ml Phenyl SEPHAROSE® 6 Fast Flow column with a linear 1.2-0 M $(NH_4)_2SO_4$ gradient. Fractions were evaluated by SDS-PAGE using a NUPAGE® NOVEX® 4-12% Bis-Tris Gel with 50 mM MES and those containing a band of approximately 98 kDa were pooled and concentrated by ultrafiltration.

Example 28: Measurement of Beta-Glucosidase Activity

Beta-glucosidase activity was measured using the following assay procedure. Twenty microliters of protein were mixed with 100 µl of a solution of 2 mM p-nitrophenyl beta-D-glucopyranoside (Sigma-Aldrich, St. Louis, Mo., USA) in 100 mM sodium acetate, 0.01% TWEEN® 20 pH 5.0 buffer in a clear, flat-bottom 96-well plate (Corning, Inc., Oneonta, N.Y., USA) and incubated at 50° C. for 30 minutes. After the 30 minute incubation, 50 µl of 100 mM Borax were added to each reaction mixture in order to stop the reaction. The resulting absorbance at 405 nm was measured using a SPECTRAMAX® 340 pc spectrophotometric plate reader (Molecular Devices, Sunnyvale, Calif., USA) to determine the relative amounts of beta-glucosidase activity in each well. The results are shown in Table 7.

TABLE 7

| Broth | A$_{405}$ |
|---|---|
| O5XGN | 2.0856 |
| O5XGR | 1.7069 |
| O5XGE | 0.3 |
| O3TMX | 0.8706 |
| O5JAK | 1.8759 |
| O6QZF | 0.9548 |
| O8KV5 | 0.3 |
| O7J1C | 0.8594 |
| O4S4U | 2.0153 |

The present invention may be further described by the following numbered paragraphs:

[1] An isolated polypeptide having beta-glucosidase activity, selected from:

(a) a polypeptide having at least 60% sequence identity to the mature polypeptide of SEQ ID NO: 24; at least 65% sequence identity to the mature polypeptide of SEQ ID NO: 14 or 36; at least 70% sequence identity to the mature polypeptide of SEQ ID NO: 4, 12, 16, or 26; at least 75% sequence identity to the mature polypeptide of SEQ ID NO: 10; at least 80% sequence identity to the mature polypeptide of SEQ ID NO: 2, 6, 8, 18, 22, or 34; at least 85% sequence identity to the mature polypeptide of SEQ ID NO: 20 or 38; at least 90% sequence identity to the mature polypeptide of SEQ ID NO: 30; or at least 95% sequence identity to the mature polypeptide of SEQ ID NO: 28 or 32;

(b) a polypeptide encoded by a polynucleotide that hybridizes under at least medium-high stringency conditions with (i) the mature polypeptide coding sequence of SEQ ID NO: 1, 3, 5, 7, 9, 11, 13, 15, 17, 19, 21, 23, 25, 27, 29, 31, 33, 35, or 37, (ii) the cDNA sequence of SEQ ID NO: 1, 3, 5, 7, 9, 11, 13, 15, 17, 19, 21, 23, 25, 27, 29, 31, 33, 35, or 37, or (iii) the full-length complement of (i) or (ii);

(c) a polypeptide encoded by a polynucleotide having at least 60% sequence identity to the mature polypeptide coding sequence of SEQ ID NO: 23; at least 65% sequence identity to the mature polypeptide coding sequence of SEQ ID NO: 13 or 35; at least 70% sequence identity to the mature polypeptide coding sequence of SEQ ID NO: 3, 11, 15, or 25; at least 75% sequence identity to the mature polypeptide coding sequence of SEQ ID NO: 9; at least 80% sequence identity to the mature polypeptide coding sequence of SEQ ID NO: 1, 5, 7, 17, 21, or 33; at least 85% sequence identity to the mature polypeptide coding sequence of SEQ ID NO: 19 or 37; at least 90% sequence identity to the mature polypeptide coding sequence of SEQ ID NO: 29; or at least 95% sequence identity to the mature polypeptide coding sequence of SEQ ID NO: 27 or 31;

(d) a variant of the mature polypeptide of SEQ ID NO: 2, 4, 6, 8, 10, 12, 14, 16, 18, 20, 22, 24, 26, 28, 30, 32, 34, 36, or 38 comprising a substitution, deletion, and/or insertion at one or more (e.g., several) positions; and (e) a fragment of the polypeptide of (a), (b), (c), or (d) that has beta-glucosidase activity.

[2] The polypeptide of paragraph [1], having at least 60%, at least 65%, at least 70%, at least 75%, at least 80%, at least 85%, at least 90%, at least 95%, at least 96%, at least 97%, at least 98%, at least 99%, or 100% sequence identity to the mature polypeptide of SEQ ID NO: 24; at least 65%, at least 70%, at least 75%, at least 80%, at least 85%, at least 90%, at least 95%, at least 96%, at least 97%, at least 98%, at least 99%, or 100% sequence identity to the mature polypeptide of SEQ ID NO: 14 or 36; at least 70%, at least 75%, at least 80%, at least 85%, at least 90%, at least 95%, at least 96%, at least 97%, at least 98%, at least 99%, or 100% sequence identity to the mature polypeptide of SEQ ID NO: 4, 12, 16, or 26; at least 75%, at least 80%, at least 85%, at least 90%, at least 95%, at least 96%, at least 97%, at least 98%, at least 99%, or 100% sequence identity to the mature polypeptide of SEQ ID NO: 10; at least 80%, at least 85%, at least 90%, at least 95%, at least 96%, at least 97%, at least 98%, at least 99%, or 100% sequence identity to the mature polypeptide of SEQ ID NO: 2, 6, 8, 18, 22, or 34; at least 85%, at least 90%, at least 95%, at least 96%, at least 97%, at least 98%, at least 99%, or 100% sequence identity to the mature polypeptide of SEQ ID NO: 20 or 38; at least 90%, at least 95%, at least 96%, at least 97%, at least 98%, at least 99%, or 100% sequence identity to the mature polypeptide of SEQ ID NO: 30; or at least 95%, at least 96%, at least 97%, at least 98%, at least 99%, or 100% sequence identity to the mature polypeptide of SEQ ID NO: 28 or 32.

[3] The polypeptide of paragraph [1], which is encoded by a polynucleotide that hybridizes under medium-high, high, or very high stringency conditions with (i) the mature polypeptide coding sequence of SEQ ID NO: 1, 3, 5, 7, 9, 11, 13, 15, 17, 19, 21, 23, 25, 27, 29, 31, 33, 35, or 37, (ii) the cDNA sequence of SEQ ID NO: 1, 3, 5, 7, 9, 11, 13, 15, 17, 19, 21, 23, 25, 27, 29, 31, 33, 35, or 37, or (iii) the full-length complement of (i) or (ii).

[4] The polypeptide of paragraph [1], which is encoded by a polynucleotide having at least 60%, at least 65%, at least 70%, at least 75%, at least 80%, at least 85%, at least 90%, at least 95%, at least 96%, at least 97%, at least 98%, at least 99%, or 100% sequence identity to the mature polypeptide of SEQ ID NO: 23; at least 65%, at least 70%, at least 75%, at least 80%, at least 85%, at least 90%, at least 95%, at least 96%, at least 97%, at least 98%, at least 99%, or 100% sequence identity to the mature polypeptide of SEQ ID NO: 13 or 35; at least 70%, at least 75%, at least 80%, at least 85%, at least 90%, at least 95%, at least 96%, at least 97%, at least 98%, at least 99%, or 100% sequence identity to the mature polypeptide of SEQ ID NO: 3, 11, 15, or 25; at least 75%, at least 80%, at least 85%, at least 90%, at least 95%, at least 96%, at least 97%, at least 98%, at least 99%, or 100% sequence identity to the mature polypeptide of SEQ ID NO: 9; at least 80%, at least 85%, at least 90%, at least 95%, at least 96%, at least 97%, at least 98%, at least 99%, or 100% sequence identity to the mature polypeptide of SEQ ID NO: 1, 5, 7, 17, 21, or 33; at least 85%, at least 90%, at least 95%, at least 96%, at least 97%, at least 98%, at least 99%, or 100% sequence identity to the mature polypeptide of SEQ ID NO: 19 or 37; at least 90%, at least 95%, at least 96%, at least 97%, at least 98%, at least 99%, or 100% sequence identity to the mature polypeptide of SEQ ID NO: 29; or at least 95%, at least 96%, at least 97%, at least 98%, at least 99%, or 100% sequence identity to the mature polypeptide of SEQ ID NO: 27 or 31.

[5] The polypeptide of any of paragraphs [1]-[4], comprising or consisting of SEQ ID NO: 2, 4, 6, 8, 10, 12, 14, 16, 18, 20, 22, 24, 26, 28, 30, 32, 34, 36, or 38 or the mature polypeptide of SEQ ID NO: 2, 4, 6, 8, 10, 12, 14, 16, 18, 20, 22, 24, 26, 28, 30, 32, 34, 36, or 38.

[6] The polypeptide of paragraph [5], wherein the mature polypeptide is amino acids 24 to 806 of SEQ ID NO: 2, amino acids 22 to 980 of SEQ ID NO: 4, amino acids 24 to 870 of SEQ ID NO: 6, amino acids 24 to 865 of SEQ ID NO: 8, amino acids 22 to 779 of SEQ ID NO: 10, amino acids 20 to 776 of SEQ ID NO: 12, amino acids 21 to 773 of SEQ ID NO: 14, amino acids 22 to 793 of SEQ ID NO: 16, amino acids 24 to 784 of SEQ ID NO: 18, amino acids 23 to 774 of SEQ ID NO: 20, amino acids 24 to 887 of SEQ ID NO: 22, amino acids 24 to 733 of SEQ ID NO: 24, amino acids 24 to 728 of SEQ ID NO: 26, amino acids 16 to 870 of SEQ ID NO: 28, amino acids 18 to 733 of SEQ ID NO: 30, amino acids 18 to 777 of SEQ ID NO: 32, amino acids 20 to 873 of SEQ ID NO: 34, amino acids 23 to 800 of SEQ ID NO: 36, or amino acids 22 to 778 of SEQ ID NO: 38.

[7] The polypeptide of any of paragraphs [1]-[4], which is a variant of the mature polypeptide of SEQ ID NO: 2, 4, 6, 8, 10, 12, 14, 16, 18, 20, 22, 24, 26, 28, 30, 32, 34, 36, or 38 comprising a substitution, deletion, and/or insertion at one or more (e.g., several) positions.

[8] The polypeptide of paragraph [1], which is a fragment of SEQ ID NO: 2, 4, 6, 8, 10, 12, 14, 16, 18, 20, 22, 24, 26, 28, 30, 32, 34, 36, or 38, wherein the fragment has beta-glucosidase activity.

[9] A composition comprising the polypeptide of any of paragraphs [1]-[8].

[10] An isolated polynucleotide encoding the polypeptide of any of paragraphs [1]-[8].

[11] A nucleic acid construct or expression vector comprising the polynucleotide of paragraph [10] operably linked to one or more control sequences that direct the production of the polypeptide in an expression host.

[12] A recombinant host cell comprising the polynucleotide of paragraph [10] operably linked to one or more control sequences that direct the production of the polypeptide.

[13] A method of producing the polypeptide of any of paragraphs [1]-[8], comprising:
(a) cultivating a cell, which in its wild-type form produces the polypeptide, under conditions conducive for production of the polypeptide; and
(b) recovering the polypeptide.

[14] A method of producing a polypeptide having beta-glucosidase activity, comprising:
(a) cultivating the host cell of paragraph [12] under conditions conducive for production of the polypeptide; and
(b) recovering the polypeptide.

[15] A transgenic plant, plant part or plant cell transformed with a polynucleotide encoding the polypeptide of any of paragraphs [1]-[8].

[16] A method of producing a polypeptide having beta-glucosidase activity, comprising:
(a) cultivating the transgenic plant or plant cell of paragraph [15] under conditions conducive for production of the polypeptide; and
(b) recovering the polypeptide.

[17] A method of producing a mutant of a parent cell, comprising inactivating a polynucleotide encoding the polypeptide of any of paragraphs [1]-[8], which results in the mutant producing less of the polypeptide than the parent cell.

[18] A mutant cell produced by the method of paragraph [17].

[19] The mutant cell of paragraph [18], further comprising a gene encoding a native or heterologous protein.

[20] A method of producing a protein, comprising:
(a) cultivating the mutant cell of paragraph [18] or [19] under conditions conducive for production of the protein; and
(b) recovering the protein.

[21] A double-stranded inhibitory RNA (dsRNA) molecule comprising a subsequence of the polynucleotide of paragraph [10], wherein optionally the dsRNA is an siRNA or an miRNA molecule.

[22] The double-stranded inhibitory RNA (dsRNA) molecule of paragraph [21], which is about 15, 16, 17, 18, 19, 20, 21, 22, 23, 24, 25 or more duplex nucleotides in length.

[23] A method of inhibiting the expression of a polypeptide having beta-glucosidase activity in a cell, comprising administering to the cell or expressing in the cell the double-stranded inhibitory RNA (dsRNA) molecule of paragraph [21] or [22].

[24] A cell produced by the method of paragraph [23].

[25] The cell of paragraph [24], further comprising a gene encoding a native or heterologous protein.

[26] A method of producing a protein, comprising:
(a) cultivating the cell of paragraph [24] or [25] under conditions conducive for production of the protein; and
(b) recovering the protein.

[27] An isolated polynucleotide encoding a signal peptide comprising or consisting of amino acids 1 to 23 of SEQ ID NO: 2, amino acids 1 to 21 of SEQ ID NO: 4, amino acids 1 to 23 of SEQ ID NO: 6, amino acids 1 to 23 of SEQ ID NO: 8, amino acids 1 to 21 of SEQ ID NO: 10, amino acids 1 to 19 of SEQ ID NO: 12, amino acids 1 to 20 of SEQ ID NO: 14, amino acids 1 to 21 of SEQ ID NO: 16, amino acids 1 to 23 of SEQ ID NO: 18, amino acids 1 to 22 of SEQ ID NO: 20, amino acids 1 to 23 of SEQ ID NO: 22, amino acids 1 to 23 of SEQ ID NO: 24, amino acids 1 to 23 of SEQ ID NO: 26, amino acids 1 to 15 of SEQ ID NO: 28, amino acids 1 to 17 of SEQ ID NO: 30, amino acids 1 to 17 of SEQ ID NO: 32, amino acids 1 to 19 of SEQ ID NO: 34, amino acids 1 to 22 of SEQ ID NO: 36, or amino acids 1 to 21 of SEQ ID NO: 38.

[28] A nucleic acid construct or expression vector comprising a gene encoding a protein operably linked to the polynucleotide of paragraph [27], wherein the gene is foreign to the polynucleotide encoding the signal peptide.

[29] A recombinant host cell comprising a gene encoding a protein operably linked to the polynucleotide of paragraph [27], wherein the gene is foreign to the polynucleotide encoding the signal peptide.

[30] A method of producing a protein, comprising:
(a) cultivating a recombinant host cell comprising a gene encoding a protein operably linked to the polynucleotide of paragraph [27], wherein the gene is foreign to the polynucleotide encoding the signal peptide, under conditions conducive for production of the protein; and
(b) recovering the protein.

[31] A process for degrading or converting a cellulosic material, comprising: treating the cellulosic material with an enzyme composition in the presence of the polypeptide having beta-glucosidase activity of any of paragraphs [1]-[8].

[32] The process of paragraph [31], wherein the cellulosic material is pretreated.

[33] The process of paragraph [31] or [32], wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[34] The process of paragraph [33], wherein the cellulase is one or more enzymes selected from the group consisting of an endoglucanase, a cellobiohydrolase, and a beta-glucosidase.

[35] The process of paragraph [33], wherein the hemicellulase is one or more enzymes selected from the group consisting of a xylanase, an acetylxylan esterase, a feruloyl esterase, an arabinofuranosidase, a xylosidase, and a glucuronidase.

[36] The process of any of paragraphs [31]-[35], further comprising recovering the degraded cellulosic material.

[37] The process of paragraph [36], wherein the degraded cellulosic material is a sugar.

[38] The process of paragraph [37], wherein the sugar is selected from the group consisting of glucose, xylose, mannose, galactose, and arabinose.

[39] A process for producing a fermentation product, comprising:
(a) saccharifying a cellulosic material with an enzyme composition in the presence of the polypeptide having beta-glucosidase activity of any of paragraphs [1]-[8];
(b) fermenting the saccharified cellulosic material with one or more fermenting microorganisms to produce the fermentation product; and
(c) recovering the fermentation product from the fermentation.

[40] The process of paragraph [39], wherein the cellulosic material is pretreated.

[41] The process of paragraph [39] or [40], wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[42] The process of paragraph 41, wherein the cellulase is one or more enzymes selected from the group consisting of an endoglucanase, a cellobiohydrolase, and a beta-glucosidase.

[43] The process of paragraph [41], wherein the hemicellulase is one or more enzymes selected from the group consisting of a xylanase, an acetylxylan esterase, a feruloyl esterase, an arabinofuranosidase, a xylosidase, and a glucuronidase.

[44] The process of any of paragraphs [39]-[43], wherein steps (a) and (b) are performed simultaneously in a simultaneous saccharification and fermentation.

[45] The process of any of paragraphs [39]-[44], wherein the fermentation product is an alcohol, an alkane, a cycloalkane, an alkene, an amino acid, a gas, isoprene, a ketone, an organic acid, or polyketide.

[46] A process of fermenting a cellulosic material, comprising: fermenting the cellulosic material with one or more fermenting microorganisms, wherein the cellulosic material is saccharified with an enzyme composition in the presence of the polypeptide having beta-glucosidase activity of any of paragraphs [1]-[8].

[47] The process of paragraph [46], wherein the fermenting of the cellulosic material produces a fermentation product.

[48] The process of paragraph [47], further comprising recovering the fermentation product from the fermentation.

[49] The process of any of paragraphs [46]-[48], wherein the cellulosic material is pretreated before saccharification.

[50] The process of any of paragraphs [46]-[49], wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[51] The process of paragraph [50], wherein the cellulase is one or more enzymes selected from the group consisting of an endoglucanase, a cellobiohydrolase, and a beta-glucosidase.

[52] The process of paragraph [50], wherein the hemicellulase is one or more enzymes selected from the group consisting of a xylanase, an acetylxylan esterase, a feruloyl esterase, an arabinofuranosidase, a xylosidase, and a glucuronidase.

[53] The process of any of paragraphs [47]-[52], wherein the fermentation product is an alcohol, an alkane, a cycloalkane, an alkene, an amino acid, a gas, isoprene, a ketone, an organic acid, or polyketide.

[54] A whole broth formulation or cell culture composition comprising the polypeptide of any of paragraphs [1]-[8].

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A process for degrading or converting a cellulosic material, comprising: treating the cellulosic material with an enzyme composition comprising a polypeptide having beta-glucosidase activity, wherein the polypeptide having beta-glucosidase is selected from the group consisting of:
   (a) a polypeptide having at least 95% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38, wherein the polypeptide has beta-glucosidase activity; and
   (b) a polypeptide comprising the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38, wherein the polypeptide has beta-glucosidase activity.

2. A process for producing a fermentation product, comprising:
   (a) saccharifying a cellulosic material with an enzyme composition comprising a polypeptide having beta-glucosidase activity, wherein the polypeptide having beta-glucosidase is selected from the group consisting of:
      (i) a polypeptide having at least 95% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38, wherein the polypeptide has beta-glucosidase activity; and
      (ii) a polypeptide comprising the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38, wherein the polypeptide has beta-glucosidase activity;
   (b) fermenting the saccharified cellulosic material with one or more fermenting microorganisms to produce the fermentation product; and
   (c) recovering the fermentation product from the fermentation.

3. A process of fermenting a cellulosic material, comprising: fermenting the cellulosic material with one or more fermenting microorganisms, wherein the cellulosic material is saccharified with an enzyme composition comprising a polypeptide having beta-glucosidase activity, wherein the polypeptide having beta-glucosidase is selected from the group consisting of:
   (i) a polypeptide having at least 95% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38, wherein the polypeptide has beta-glucosidase activity; and
   (ii) a polypeptide comprising the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38, wherein the polypeptide has beta-glucosidase activity.

4. A nucleic acid construct comprising a polynucleotide encoding a polypeptide having beta-glucosidase activity, wherein the polynucleotide is operably linked to one or more heterologous control sequences that direct the production of the polypeptide in a recombinant host cell, and wherein the polypeptide having beta-glucosidase is selected from the group consisting of:
   (a) a polypeptide having at least 95% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38, wherein the polypeptide has beta-glucosidase activity; and (b) a polypeptide comprising the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38, wherein the polypeptide has beta-glucosidase activity.

5. A recombinant host cell comprising the nucleic acid construct of claim 4.

6. A method of producing a polypeptide having beta-glucosidase activity, comprising:
(a) cultivating the recombinant host cell of claim 5 under conditions conducive for production of the polypeptide; and
(b) recovering the polypeptide.

7. A transgenic plant, plant part or plant cell transformed with the nucleic acid construct of claim 4.

8. A method of producing a polypeptide having beta-glucosidase activity, comprising:
(a) cultivating the transgenic plant or plant cell of claim 7 under conditions conducive for production of the polypeptide; and
(b) recovering the polypeptide.

9. A method of producing a mutant of a parent cell, comprising inactivating a polynucleotide encoding a polypeptide having beta-glucosidase activity, which results in the mutant producing less of the polypeptide than the parent cell, wherein the polypeptide having beta-glucosidase is selected from the group consisting of:
(a) a polypeptide having at least 95% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38, wherein the polypeptide has beta-glucosidase activity; and
(b) a polypeptide comprising the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38, wherein the polypeptide has beta-glucosidase activity.

10. A recombinant host cell comprising a gene encoding a protein operably linked to a polynucleotide encoding a signal peptide, wherein the gene is foreign to the polynucleotide encoding the signal peptide, and wherein the signal peptide comprises amino acids 1 to 23 of SEQ ID NO: 2, amino acids 1 to 21 of SEQ ID NO: 4, amino acids 1 to 23 of SEQ ID NO: 6, amino acids 1 to 23 of SEQ ID NO: 8, amino acids 1 to 21 of SEQ ID NO: 10, amino acids 1 to 19 of SEQ ID NO: 12, amino acids 1 to 20 of SEQ ID NO: 14, amino acids 1 to 23 of SEQ ID NO: 18, amino acids 1 to 22 of SEQ ID NO: 20, amino acids 1 to 23 of SEQ ID NO: 22, amino acids 1 to 23 of SEQ ID NO: 24, amino acids 1 to 23 of SEQ ID NO: 26, amino acids 1 to 15 of SEQ ID NO: 28, amino acids 1 to 17 of SEQ ID NO: 30, amino acids 1 to 17 of SEQ ID NO: 32, amino acids 1 to 19 of SEQ ID NO: 34, amino acids 1 to 22 of SEQ ID NO: 36, or amino acids 1 to 21 of SEQ ID NO: 38.

11. A method of producing a protein, comprising:
(a) cultivating the recombinant host cell of claim 10 under conditions conducive for production of the protein; and
(b) recovering the protein.

12. The process of claim 1, wherein the polypeptide has at least 96% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

13. The process of claim 1, wherein the polypeptide has at least 97% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

14. The process of claim 1, wherein the polypeptide has at least 98% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

15. The process of claim 1, wherein the polypeptide has at least 99% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

16. The process of claim 1, wherein the polypeptide comprises the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

17. The process of claim 1, wherein the cellulosic material is pretreated.

18. The process of claim 1, wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

19. The process of claim 1, further comprising recovering the degraded or converted cellulosic material.

20. The process of claim 18, wherein the degraded cellulosic material is a sugar selected from the group consisting of glucose, xylose, mannose, galactose, and arabinose.

21. The process of claim 2, wherein the polypeptide has at least 96% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

22. The process of claim 2, wherein the polypeptide has at least 97% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO:

24, SEQ ID NO: 26, SEQ ID NO: 28, SEQ ID NO: 30, SEQ ID NO: 32, SEQ ID NO: 34, SEQ ID NO: 36, or SEQ ID NO: 38.

23. The process of claim 2, wherein the polypeptide has at least 98% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

24. The process of claim 2, wherein the polypeptide has at least 99% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

25. The process of claim 2, wherein the polypeptide comprises the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

26. The process of claim 2, wherein the cellulosic material is pretreated.

27. The process of claim 2, wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

28. The process of claim 2, wherein steps (a) and (b) are performed simultaneously in a simultaneous saccharification and fermentation.

29. The process of claim 2, wherein the fermentation product is an alcohol, an alkane, a cycloalkane, an alkene, an amino acid, a gas, isoprene, a ketone, an organic acid, or polyketide.

30. The process of claim 3, wherein the polypeptide has at least 96% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

31. The process of claim 3, wherein the polypeptide has at least 97% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

32. The process of claim 3, wherein the polypeptide has at least 98% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

33. The process of claim 3, wherein the polypeptide has at least 99% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

34. The process of claim 3, wherein the polypeptide comprises the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

35. The process of claim 3, wherein the cellulosic material is pretreated.

36. The process of claim 3, wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

37. The process of claim 3, wherein the fermenting of the cellulosic material produces a fermentation product.

38. The process of claim 36, further comprising recovering the fermentation product from the fermentation.

39. The process of claim 36, wherein the fermentation product is an alcohol, an alkane, a cycloalkane, an alkene, an amino acid, a gas, isoprene, a ketone, an organic acid, or polyketide.

40. The nucleic acid construct of claim 4, wherein the polypeptide has at least 96% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

41. The nucleic acid construct of claim 4, wherein the polypeptide has at least 97% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

42. The nucleic acid construct of claim 4, wherein the polypeptide has at least 98% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

43. The nucleic acid construct of claim 4, wherein the polypeptide has at least 99% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

44. The nucleic acid construct of claim 4, wherein the polypeptide comprises the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38.

* * * * *

SEQUENCE LISTING

```
<160> NUMBER OF SEQ ID NOS: 77

<210> SEQ ID NO 1
<211> LENGTH: 3150
<212> TYPE: DNA
<213> ORGANISM: Thermoascus aurantiacus

<400> SEQUENCE: 1
atgcttcccc actcgttact actattactc ctgcatctct ttgccgtttc tgcagtaagc      60
gcgaatgctg cccgctccag cgatggacat gataaaggca aaggaggaca gagacctccc     120
tacaaggatc ccaatctctc cgtggacgag cgggtcgcgg acctcctggc gcggatgacg     180
atcgaggata gatggctca gttgatgcag ggtatgcata cacccacttg tctggatgga     240
tgaaggatgc agcactgttt ataagcttct agctctatct atcagttttc gacttgaaag     300
```

```
ctatttgaac aaactgtctg atcatgcgtc aacaggagac atcaccaact ggatggaccc    360
gacatccgga gcgttcaact ataccgggct cgtggagaac atggagacga aagcggggat    420
gttttacggt atgtgtcata agactgccac gcttgtgctg gttatgaagg aaatataggc    480
tgactagctg cgattttatt tatccagttg gatacccgt tccctgggac tggatcgcaa    540
cgaacgtgaa acgggcacag gattatcttc tcgagaacac tactctggga attcctgcgc    600
ttattcagac ggaaggtgcc tggccctcgt gagcatatta cacagtatgg ataaaatctg    660
actggaattc taggtatcca cggcttctta attggaaacg cgacaatctt caactcaccc    720
atcggatatg ggtgctcgtg aacataaag gcaagttccg gacatgaatc ccatcggaaa    780
aagaaagaat aaaagtgaca ggtgtaccac agctggtcga aacgatggcc aagataatcg    840
gccaggaagc ccgcgctctc ggtgtcaacc aacttttcgc ccccgttgcc gaccttgctc    900
gggaattgcg gttcggtagg gtaagaacat acatatccag tcacgatcta cctgtcaagc    960
tcgtgtgtag aagcgcctgt ctgactctat tcccacgcag gtcgaagaga caacatctga   1020 ggaccctat ctagcaggag agatcacgta cagttatgtg aaggggctgc agagtacaaa   1080
cgtttccgca acggtcaagc acttcgttgg ctttagcatg ccggagcagg ggctcaatac   1140
tggaccggtg catggagggg agaggagct cgcacaacg tcagtcatct gttttagctc   1200
ctcctgtgct gttcctgtag actgatgaag ttctgatata cagatggatg ccttcattca   1260
aacgagccat catcgacggc ggcgcgtgga gcataatgag cgcttatcat gcgtaagaaa   1320
gtctcgactt tttataaatt acagttgacc ctgactattg attctttcta cctagttacg   1380
acggcattcc cgcagtcgca gaccgccaca ccctcacgga catattgaga gacgaatggg   1440
gttacaagta ctgggtcacc agcgacgcgg gagggacaga caggctctgc acggcgttca   1500
agctctgccg gagcacaccg atcgactcgg aagcagtcac gctgaaggct ctgccagccg   1560
gaaatgacgt cgagatgggt ggcgggtcat tgtgagctat ttattaaata tgaggaacag   1620
ccattgataa agtgatcact gactctgtgg tagcaacttc aagaccatcc cgaagcttgt   1680
caaggacgga aagctcgaca tgaagacggt cgacacggcg gtctcgaggc tcctgagggc   1740
aaagttcgag atgggcctct ttgagaaccc gtacccagct gcaccgaaga gcgagtggtc   1800
cagtctcatc cacaccccg aggcactgca ggtcgcgagg gagctggatc gggaatctat   1860
cgtcctgctg gagaaccaca acggtactct gccctgaag aagagcggca gcatcgcggt   1920
catagggccg atggcgcatg ggttcatgaa tgtgagggaa tcctcatctc cggtttgaat   1980
gctagactcg ctcactcgga actatctatc tagtacggcg actacgtcgt cttcgagagc   2040
cagtgtcgcg gcgtcacccc cctcgacggg atcaaggccg ccgtgggcga caaggccacg   2100
gtgaactatg cccaggggtg caagcgctgg agtaacgacc aatcgggctt tgctgaggca   2160
gtcgaagcag cgaagaagtc ggacgttgcc atcgttgtgg ttgggacatg gtccagagac   2220
cagaaggagc tgtgggaggg atacaacgcg acgtatgtat caacccagtt cctcggatcg   2280
gtccacaaac accaaactac caaaaagaat tcctgactaa aggttatata taccgctaga   2340
accggcgaac acgtcgacgt cgacaccctc aacctcgtcg gcgcccaggg acccctcgtc   2400
aaagccatcg ccgccacggg cgtcccaacc gtcgtcgtct tctcctccgg caagcccatc   2460
tccgagccct ggatcgccaa ctccaccgcc gccctgctgc agcagttcta cccctccgaa   2520
cagggcggac acgccctcgc cgacgttctc ttcggcgact acgacccctc gggcggctc   2580 tccgtcagct ttccccggga cgtgggctcg ctgcccgtct tctacgacta cctcaactcg   2640
```

```
ggccgggcca tcacggattc gggatccatc tacgagaatg gaacgctcag gttcggccac    2700
cagtacgtcc ttggctcgcc gcagccgtgg tacgcgttcg ccacggcct gagctacgcg     2760 accttcgagt acggggccgt caggctggac cggacggccg caagcgtcgg cgacacggtg    2820
acggtgaccg tcgacgtgcg caacacctcc cccgacggcc gcgccggcgc cgaggtcgtg    2880
caggtgtacg tcgccccga cgaaccagca tcctcatcgt cgtcctcccc cggggtagtg     2940
gtcgcgccga accggcagct caaggggttc gagaaggtca cgatcccccgc gggcgcgacg   3000 gtgacggtgg agattccgct acgggtggac gcgctggggc tgtgggacga gcggatgcgg   3060
tatgtggttg cgccggggcg gtacacggtg ctggtgggga ggagcgcggt ggatatcagg   3120
gggagggcgt cgtttgaggt tgttgggtag                                    3150
```

<210> SEQ ID NO 2
<211> LENGTH: 806
<212> TYPE: PRT
<213> ORGANISM: Thermoascus aurantiacus

<400> SEQUENCE: 2

```
Met Leu Pro His Ser Leu Leu Leu Leu Leu His Leu Phe Ala Val
1               5                   10                  15

Ser Ala Val Ser Ala Asn Ala Ala Arg Ser Ser Asp Gly His Asp Lys
                20                  25                  30

Gly Lys Gly Gly Gln Arg Pro Pro Tyr Lys Asp Pro Asn Leu Ser Val
            35                  40                  45

Asp Glu Arg Val Ala Asp Leu Leu Ala Arg Met Thr Ile Glu Asp Lys
        50                  55                  60

Met Ala Gln Leu Met Gln Gly Asp Ile Thr Asn Trp Met Asp Pro Thr
65                  70                  75                  80

Ser Gly Ala Phe Asn Tyr Thr Gly Leu Val Glu Asn Met Glu Thr Lys
                85                  90                  95

Ala Gly Met Phe Tyr Val Gly Tyr Pro Val Pro Trp Asp Trp Ile Ala
            100                 105                 110

Thr Asn Val Lys Arg Ala Gln Asp Tyr Leu Leu Glu Asn Thr Thr Leu
        115                 120                 125

Gly Ile Pro Ala Leu Ile Gln Thr Glu Gly Ile His Gly Phe Leu Ile
    130                 135                 140

Gly Asn Ala Thr Ile Phe Asn Ser Pro Ile Gly Tyr Gly Cys Ser Ile
145                 150                 155                 160

Lys Val Thr Gly Val Pro Gln Leu Val Glu Thr Met Ala Lys Ile Ile
                165                 170                 175

Gly Gln Glu Ala Arg Ala Leu Gly Val Asn Gln Leu Phe Ala Pro Val
            180                 185                 190

Ala Asp Leu Ala Arg Glu Leu Arg Phe Gly Arg Val Glu Thr Thr
        195                 200                 205

Ser Glu Asp Pro Tyr Leu Ala Gly Glu Ile Thr Tyr Ser Tyr Val Lys
    210                 215                 220

Gly Leu Gln Ser Thr Asn Val Ser Ala Thr Val Lys His Phe Val Gly
225                 230                 235                 240

Phe Ser Met Pro Glu Gln Gly Leu Asn Thr Gly Pro Val His Gly Gly
                245                 250                 255

Glu Arg Glu Leu Arg Thr Thr Trp Met Pro Ser Phe Lys Arg Ala Ile
            260                 265                 270

Ile Asp Gly Gly Ala Trp Ser Ile Met Ser Ala Tyr His Ala Tyr Asp
        275                 280                 285
```

-continued

Gly Ile Pro Ala Val Ala Asp Arg His Thr Leu Thr Asp Ile Leu Arg
         290                 295                 300

Asp Glu Trp Gly Tyr Lys Tyr Trp Val Thr Ser Asp Ala Gly Gly Thr
305                 310                 315                 320

Asp Arg Leu Cys Thr Ala Phe Lys Leu Cys Arg Ser Thr Pro Ile Asp
                325                 330                 335

Ser Glu Ala Val Thr Leu Lys Ala Leu Pro Ala Gly Asn Asp Val Glu
            340                 345                 350

Met Gly Gly Gly Ser Phe Asn Phe Lys Thr Ile Pro Lys Leu Val Lys
        355                 360                 365

Asp Gly Lys Leu Asp Met Lys Thr Val Asp Thr Ala Val Ser Arg Leu
370                 375                 380

Leu Arg Ala Lys Phe Glu Met Gly Leu Phe Glu Asn Pro Tyr Pro Ala
385                 390                 395                 400

Ala Pro Lys Ser Glu Trp Ser Ser Leu Ile His Thr Pro Glu Ala Leu
                405                 410                 415

Gln Val Ala Arg Glu Leu Asp Arg Glu Ser Ile Val Leu Leu Glu Asn
            420                 425                 430

His Asn Gly Thr Leu Pro Leu Lys Lys Ser Gly Ser Ile Ala Val Ile
        435                 440                 445

Gly Pro Met Ala His Gly Phe Met Asn Tyr Gly Asp Tyr Val Val Phe
450                 455                 460

Glu Ser Gln Cys Arg Gly Val Thr Pro Leu Asp Gly Ile Lys Ala Ala
465                 470                 475                 480

Val Gly Asp Lys Ala Thr Val Asn Tyr Ala Gln Gly Cys Lys Arg Trp
                485                 490                 495

Ser Asn Asp Gln Ser Gly Phe Ala Glu Ala Val Glu Ala Ala Lys Lys
            500                 505                 510

Ser Asp Val Ala Ile Val Val Gly Thr Trp Ser Arg Asp Gln Lys
        515                 520                 525

Glu Leu Trp Glu Gly Tyr Asn Ala Thr Thr Gly Glu His Val Asp Val
530                 535                 540

Asp Thr Leu Asn Leu Val Gly Ala Gln Gly Pro Leu Val Lys Ala Ile
545                 550                 555                 560

Ala Ala Thr Gly Val Pro Thr Val Val Phe Ser Ser Gly Lys Pro
                565                 570                 575

Ile Ser Glu Pro Trp Ile Ala Asn Ser Thr Ala Ala Leu Leu Gln Gln
            580                 585                 590

Phe Tyr Pro Ser Glu Gln Gly His Ala Leu Ala Asp Val Leu Phe
        595                 600                 605

Gly Asp Tyr Asp Pro Ser Gly Arg Leu Ser Val Ser Phe Pro Arg Asp
610                 615                 620

Val Gly Ser Leu Pro Val Phe Tyr Asp Tyr Leu Asn Ser Gly Arg Ala
625                 630                 635                 640

Ile Thr Asp Ser Gly Ser Ile Tyr Glu Asn Gly Thr Leu Arg Phe Gly
                645                 650                 655

His Gln Tyr Val Leu Gly Ser Pro Gln Pro Trp Tyr Ala Phe Gly His
            660                 665                 670

Gly Leu Ser Tyr Ala Thr Phe Glu Tyr Gly Ala Val Arg Leu Asp Arg
        675                 680                 685

Thr Ala Ala Ser Val Gly Asp Thr Val Thr Val Thr Val Asp Val Arg
690                 695                 700

```
Asn Thr Ser Pro Asp Gly Arg Ala Gly Ala Glu Val Val Gln Val Tyr
705                 710                 715                 720

Val Ala Pro Asp Glu Pro Ala Ser Ser Ser Ser Pro Gly Val
            725                 730                 735

Val Val Ala Pro Asn Arg Gln Leu Lys Gly Phe Glu Lys Val Thr Ile
            740                 745                 750

Pro Ala Gly Ala Thr Val Thr Val Glu Ile Pro Leu Arg Val Asp Ala
            755                 760                 765

Leu Gly Leu Trp Asp Glu Arg Met Arg Tyr Val Val Ala Pro Gly Arg
        770                 775                 780

Tyr Thr Val Leu Val Gly Arg Ser Ala Val Asp Ile Arg Gly Arg Ala
785                 790                 795                 800

Ser Phe Glu Val Val Gly
            805

<210> SEQ ID NO 3
<211> LENGTH: 3197
<212> TYPE: DNA
<213> ORGANISM: Thermoascus aurantiacus

<400> SEQUENCE: 3
atgccagggc agacatcaac gacccggatc ccgctcatca tgtttctgcc tctggtcctg      60
gtgttggaac tggaaacttg ttgaacccct cgcagcagca gcagcagcag caaccttcat     120
cgtctaacat gtaccacgag catggctccg gttcgaaaga acccctgctc accaacacgg     180
agcagtttga gagatacttc gataatgtga acgatgcgca actggacttg ctgtctgctt     240
cttcgctgag ttctgactct gacgatgacg atgaggataa tgagaggact gccgcgctga     300
aaggggggag gaaaagccgt attcgccgcc gcactcgcag gattttcgct tctagaagga     360
ggcggatttg ggcagctgtg gttgcaattg ctgttgtagt tgggttggtg gccggtattg     420
tggggtggtt gacgagcaga cgcccgtcag gaagaaagag ggtgagtatc gacgtgtatt     480
tcaatattca tttctccttt gtctatattc aacgaaggat ctggtgtttc tggtccttct     540
atctgattat gttcaaagct aacttgtgcg accaggaaac ggatccttgg tatcctactc     600
ctcgaggcgg aactactagg cggtgggctg agagctaccg taaggcccag agatggtgg      660 agaagatgac tcttgcagaa aaggtcaata tcacaaccgg cgtcggttgg caaatggggc     720
tttgcgtagg caatacgggt aggaactcca gtgagcagcc tcacttaaac gtttcacatg     780
ctgaacgact cttaggaccg gcaattcatg ttcggtttcc ttccctctgc ttgcaagatg     840
ggcccttggg agtgcgtttc acctccaaca ttactgcttt cccggctggc atcactaccg     900
gcgccacgtg gaatcgagac ctgatgtacg agcgcggttt cgcgctcgga gcgaagctc      960 gcattaaagg cgtaaatgtc attctgggac cttccatggg cccgttgggg aagatgcctg    1020 caggggaag aaactgggaa ggctttggtt cggatcctgt gctacaggct attggagcag     1080
tacaaaccat tcgaggtatc cagcgaaatg gagtaattgc aaccgcaaaa cactacgtca    1140
tgaatgagca agagcatttt cggcagccgt atgaatgggg tataccgact gcactgtcgt    1200
ccaacatcga tgatcgctcg ctgcgtgaag tatttatatg gccatttgct gagagcgttc    1260
gcgctggtgt ggccagcgtc atgtgctcct atcagatggt caataatacc catgcgtgcg    1320
agaatagcaa gatcctcaat ggaattctaa aggatgagtt gggattccaa ggcttcgtcc    1380
aatccgactg gcttgcccaa cgctctggcg tggacagcgc tctcgcgggt ctggatatga    1440
ccatgccggg tgacggcctc cgttgggcca atggagagtc tctctggggt agtcagctga    1500
```

```
cgaaggctgt tctaaacgga actgtaccga tggagcgact caacgatatg gtaactcgca   1560
ttgttgcggc ctggtatcaa atgaggcagg actcctggaa gcagcctccg ccattcggag   1620
atggcggtcc caacttctcc tcatggacgg acgaggagat cggtcgcctg cacgagggta   1680
gtgatgatga tgatgccact ggcgttgtca atcgcttcgt taatgcgcag gggaaaggga   1740
aacacgctca taatatcacg gcccgcaaag tagcatctga gggtacggtg ctggtgaaga   1800
atgtggataa cattttgcca ctttcgagag acgcgccaaa gccagggaag aaatatcgtg   1860
ttggaatata cggtgaagac gccggtccag gtagagggcc caatgcttgt ccggatagag   1920
catgcaacca gggaacactt gggtccggct gggggagtgg agcagtcaac tttccttatc   1980
tgataaaccc ctgggaggct tgcggtccg cctggagatc taaagatgtt gaaacgacaa    2040
gttacctgac gaacaaggtc gaagacacg atctcaagga caaggacctg tgtatagtat     2100
tcgtcaactc ggatggcgga gaaggctttg cctcaagcga cggcatccac ggcgatagga   2160
acgatttgtt cctacagaaa gggggcgatg atcttgtgca gaaagtcgcc aacggctgcg   2220
gtgatggtaa aggaaaaacg gtggtcgttg tgcactccat tggtccggtt attgtggaga   2280
aatggatcga ccttcccggc gttaaagctg tccttttttgc gaatcttccg ggggaagaga   2340 gtggaaaacgc cctagtggat gttcttttcg ggacgtgga cgctagtgga agacttccgt   2400
acacgatcgg caaaagctta gacgattacg gccaggggtc gaaggttctg taccaaccaa   2460
acggccccgt cccacaggtg aatttcactg acggtctcta cgtcgattac cgccatttcg   2520
acaagtataa gattgcacct cgatacgagt tcggctttgg tctgtcgtat acgacatttg   2580
aattcggaga attcaacatt acacgcgtgc gggagaagtc cccctgcct tctcctcgtc    2640 ccgcagacgc agcgctccct ccgtcttacg ctaatgatat tcctgatccc gagtccgcag   2700
tatttccgga gggattcaga aggctgaaga agtatatcta tccgtacatt tcatccgtcg   2760
atgaggctaa aaaacgtggc cattataact atcccgaggg ctacgacacg gtgcagacac   2820
cctcgcctgc gggcggaggt gaaggggca acccgtctct ttatgaagta tttgcgcagg    2880
tgcatgtaca ggtcaagaat accggacccc gcgccggaaa ggaggtggtg cagctctacg   2940
tctcatttcc ggaaaacgtg accgaagtgg acgaaggagc tagagagcag attgaatttc   3000
cggtccgcgt gctccggaat ttcacaaagg tcgagctgca gcccggtcag gtggaaaatg   3060
tagagctgtc tctgacccga aaagacctca gttactggag cacgaggaag cagaactggg   3120
tgatgccggt gaatgggacc tttaagatct gggttggaag gagctcacga gacctaccgt   3180
tggttggaga gtattaa                                                  3197
```

<210> SEQ ID NO 4
<211> LENGTH: 980
<212> TYPE: PRT
<213> ORGANISM: Thermoascus aurantiacus

<400> SEQUENCE: 4

Met Pro Gly Gln Thr Ser Thr Thr Arg Ile Pro Leu Ile Met Phe Leu
1               5                   10                  15

Pro Leu Val Leu Gln Gln Gln Gln Gln Pro Ser Ser Ser Asn Met
            20                  25                  30

Tyr His Glu His Gly Ser Gly Ser Lys Glu Pro Leu Leu Thr Asn Thr
        35                  40                  45

Glu Gln Phe Glu Arg Tyr Phe Asp Asn Val Asn Asp Ala Gln Leu Asp
    50                  55                  60

Leu Leu Ser Ala Ser Ser Leu Ser Ser Asp Ser Asp Asp Asp Asp Glu

```
           65                  70                  75                  80
Asp Asn Glu Arg Thr Ala Ala Leu Lys Gly Gly Arg Lys Ser Arg Ile
                    85                  90                  95
Arg Arg Arg Thr Arg Arg Ile Phe Ala Ser Arg Arg Arg Ile Trp
                100                 105                 110
Ala Ala Val Val Ala Ile Ala Val Val Gly Leu Val Ala Gly Ile
                115                 120                 125
Val Gly Trp Leu Thr Ser Arg Arg Pro Ser Gly Arg Lys Arg Glu Thr
    130                 135                 140
Asp Pro Trp Tyr Pro Thr Pro Arg Gly Gly Thr Thr Arg Arg Trp Ala
145                 150                 155                 160
Glu Ser Tyr Arg Lys Ala Gln Glu Met Val Glu Lys Met Thr Leu Ala
                165                 170                 175
Glu Lys Val Asn Ile Thr Thr Gly Val Gly Trp Gln Met Gly Leu Cys
                180                 185                 190
Val Gly Asn Thr Gly Pro Ala Ile His Val Arg Phe Pro Ser Leu Cys
                195                 200                 205
Leu Gln Asp Gly Pro Leu Gly Val Arg Phe Thr Ser Asn Ile Thr Ala
    210                 215                 220
Phe Pro Ala Gly Ile Thr Thr Gly Ala Thr Trp Asn Arg Asp Leu Met
225                 230                 235                 240
Tyr Glu Arg Gly Phe Ala Leu Gly Arg Glu Ala Arg Ile Lys Gly Val
                245                 250                 255
Asn Val Ile Leu Gly Pro Ser Met Gly Pro Leu Gly Lys Met Pro Ala
                260                 265                 270
Gly Gly Arg Asn Trp Glu Gly Phe Gly Ser Asp Pro Val Leu Gln Ala
                275                 280                 285
Ile Gly Ala Val Gln Thr Ile Arg Gly Ile Gln Arg Asn Gly Val Ile
    290                 295                 300
Ala Thr Ala Lys His Tyr Val Met Asn Glu Gln Glu His Phe Arg Gln
305                 310                 315                 320
Pro Tyr Glu Trp Gly Ile Pro Thr Ala Leu Ser Ser Asn Ile Asp Asp
                325                 330                 335
Arg Ser Leu Arg Glu Val Phe Ile Trp Pro Phe Ala Glu Ser Val Arg
                340                 345                 350
Ala Gly Val Ala Ser Val Met Cys Ser Tyr Gln Met Val Asn Asn Thr
                355                 360                 365
His Ala Cys Glu Asn Ser Lys Ile Leu Asn Gly Ile Leu Lys Asp Glu
    370                 375                 380
Leu Gly Phe Gln Gly Phe Val Gln Ser Asp Trp Leu Ala Gln Arg Ser
385                 390                 395                 400
Gly Val Asp Ser Ala Leu Ala Gly Leu Asp Met Thr Met Pro Gly Asp
                405                 410                 415
Gly Leu Arg Trp Ala Asn Gly Glu Ser Leu Trp Gly Ser Gln Leu Thr
                420                 425                 430
Lys Ala Val Leu Asn Gly Thr Val Pro Met Glu Arg Leu Asn Asp Met
                435                 440                 445
Val Thr Arg Ile Val Ala Ala Trp Tyr Gln Met Arg Gln Asp Ser Trp
    450                 455                 460
Lys Gln Pro Pro Pro Phe Gly Asp Gly Pro Asn Phe Ser Ser Trp
465                 470                 475                 480
Thr Asp Glu Glu Ile Gly Arg Leu His Glu Gly Ser Asp Asp Asp Asp
                485                 490                 495
```

-continued

Ala Thr Gly Val Val Asn Arg Phe Val Asn Ala Gln Gly Lys Gly Lys
            500                 505                 510

His Ala His Asn Ile Thr Ala Arg Lys Val Ala Ser Glu Gly Thr Val
        515                 520                 525

Leu Val Lys Asn Val Asp Asn Ile Leu Pro Leu Ser Arg Asp Ala Pro
    530                 535                 540

Lys Pro Gly Lys Lys Tyr Arg Val Gly Ile Tyr Gly Glu Asp Ala Gly
545                 550                 555                 560

Pro Gly Arg Gly Pro Asn Ala Cys Pro Asp Arg Ala Cys Asn Gln Gly
                565                 570                 575

Thr Leu Gly Ser Gly Trp Gly Ser Gly Ala Val Asn Phe Pro Tyr Leu
            580                 585                 590

Ile Asn Pro Trp Glu Ala Leu Arg Ser Ala Trp Arg Ser Lys Asp Val
        595                 600                 605

Glu Thr Thr Ser Tyr Leu Thr Asn Lys Val Glu Asp Thr Asp Leu Lys
    610                 615                 620

Asp Lys Asp Leu Cys Ile Val Phe Val Asn Ser Asp Gly Gly Glu Gly
625                 630                 635                 640

Phe Ala Ser Ser Asp Gly Ile His Gly Asp Arg Asn Asp Leu Phe Leu
                645                 650                 655

Gln Lys Gly Gly Asp Asp Leu Val Gln Lys Val Ala Asn Gly Cys Gly
            660                 665                 670

Asp Gly Lys Gly Lys Thr Val Val Val His Ser Ile Gly Pro Val
        675                 680                 685

Ile Val Glu Lys Trp Ile Asp Leu Pro Gly Val Lys Ala Val Leu Phe
    690                 695                 700

Ala Asn Leu Pro Gly Glu Glu Ser Gly Asn Ala Leu Val Asp Val Leu
705                 710                 715                 720

Phe Gly Asp Val Asp Ala Ser Gly Arg Leu Pro Tyr Thr Ile Gly Lys
                725                 730                 735

Ser Leu Asp Asp Tyr Gly Gln Gly Ser Lys Val Leu Tyr Gln Pro Asn
            740                 745                 750

Gly Pro Val Pro Gln Val Asn Phe Thr Asp Gly Leu Tyr Val Asp Tyr
        755                 760                 765

Arg His Phe Asp Lys Tyr Lys Ile Ala Pro Arg Tyr Glu Phe Gly Phe
    770                 775                 780

Gly Leu Ser Tyr Thr Thr Phe Glu Phe Gly Glu Phe Asn Ile Thr Arg
785                 790                 795                 800

Val Arg Glu Lys Ser Pro Leu Pro Ser Pro Arg Pro Ala Asp Ala Ala
                805                 810                 815

Leu Pro Pro Ser Tyr Ala Asn Asp Ile Pro Asp Pro Glu Ser Ala Val
            820                 825                 830

Phe Pro Glu Gly Phe Arg Arg Leu Lys Lys Tyr Ile Tyr Pro Tyr Ile
        835                 840                 845

Ser Ser Val Asp Glu Ala Lys Lys Arg Gly His Tyr Asn Tyr Pro Glu
    850                 855                 860

Gly Tyr Asp Thr Val Gln Thr Pro Ser Pro Ala Gly Gly Glu Gly
865                 870                 875                 880

Gly Asn Pro Ser Leu Tyr Glu Val Phe Ala Gln Val His Val Gln Val
                885                 890                 895

Lys Asn Thr Gly Pro Arg Ala Gly Lys Glu Val Val Gln Leu Tyr Gln
            900                 905                 910

```
Ile Glu Phe Pro Val Arg Val Leu Arg Asn Phe Thr Lys Val Glu Leu
            915                 920                 925

Gln Pro Gly Gln Val Glu Asn Val Glu Leu Ser Leu Thr Arg Lys Asp
            930                 935                 940

Leu Ser Tyr Trp Ser Thr Arg Lys Gln Asn Trp Val Met Pro Val Asn
945                 950                 955                 960

Gly Thr Phe Lys Ile Trp Val Gly Arg Ser Ser Arg Asp Leu Pro Leu
                965                 970                 975

Val Gly Glu Tyr
            980

<210> SEQ ID NO 5
<211> LENGTH: 2757
<212> TYPE: DNA
<213> ORGANISM: Malbranchea cinnamomea

<400> SEQUENCE: 5
```

| | | | | | |
|---|---|---|---|---|---|
| atgtctttct | tcaactttct | tttgagcgtt | ctctttctgc | ttctcaacgc | cggtctgctg | 60 |
| gccgacgctg | cccctggata | tgagtcgccc | tcctattatc | cggctcccaa | gggggggctgg | 120 |
| gtccgggaat | gggcggactc | gtacgccagg | gcccaggaga | tcgtctccca | catgaccctc | 180 |
| gcggaaaagg | tcaacctcac | tacaggaacg | ggctacttca | tgggaccctg | cgtgggccag | 240 |
| acggggagtg | cgcttcgttt | tgggattccg | cgcctctgcc | tgcaggacgg | accgctgggt | 300 |
| gtgagaaata | cagatcagag | cactgccttt | cctgctggca | tcacggtcgg | tgcgacattc | 360 |
| gacaagaagc | tgatgtatga | gcggggcgtg | gctatgggcg | aagagttccg | cggcaaaggg | 420 |
| gtcaatatcc | acctgggtcc | gtccgttggt | ccgcttgggc | ggaaaccccg | tggggacgg | 480 |
| aactgggaag | ggtttgggc | cgacccgagc | ttgcagggca | ttgccgcgta | tgagaccatc | 540 |
| aggggcgtgc | agagcacagg | tgtcatagcg | acggtgaaac | accttgttgg | gaatgagcag | 600 |
| gagatgtatc | ggatgaccag | cgtcatccag | cgcgcatatt | ccgccaacat | cgatgatcgt | 660 |
| accttgcatg | agctgtatct | gtggccgttt | gcggaggctg | tgagggcagg | ggtgggcgcc | 720 |
| gtcatgatgg | cctataacga | cgtacgtcac | acgctttcgt | tgacacgact | ttgttttcc | 780 |
| atgatcctga | caatgtgcta | cgtaggtcaa | cgggtctgct | tgtagccaga | acagcaagct | 840 |
| gatcaacggt | atcttgaaag | atgagcttgg | cttccagggg | tttgtcatga | cagattggtt | 900 |
| tggtcacatt | ggtggtgtct | cctccgctct | cgcgggactg | gacatggcga | tgcctggaga | 960 |
| cggggccatc | ccactattag | gatacagttt | ctggggcagt | gagttgtcga | ggtcaattct | 1020 |
| caatggcacc | gtgccgatgg | agcgtttgaa | tgacatggtg | agtagtcaag | aggcccttcc | 1080 |
| gaccaccatt | aataatcgtc | agccacgatc | atgttgcatt | tattaacacg | tcataaggtg | 1140 |
| actcgaatcg | ttgcgacgtg | gatccagctc | gggcaggacg | aagattaccc | cttgcctaat | 1200 |
| ttctcaacaa | acacattgga | cgaaactggg | ctattatatc | ctggagccct | cttctctccg | 1260 |
| cgtgggtcg | tcaaccaatt | cgtcaatgtc | caagacgatc | accataagat | tgcgagagaa | 1320 |
| atcgcaagag | atggaatcac | cctactcaaa | aacgaaaatg | accttctccc | actcgacaag | 1380 |
| aacgcatcct | tgaaaatatt | tggtacggac | gcaggaacca | accccgacgg | catcaactct | 1440 |
| tgtaacgaca | agggctgcaa | caaaggagtt | cttaccatgg | gctggggtag | tggctctgca | 1500 |
| agattgcctt | atctgagcac | tccggaggat | gccatcagag | acatctcaca | gcatgcggaa | 1560 |
| ttccacatca | ctgacaagtt | tccccgccat | attgacgtca | aacccgagga | cattgctatt | 1620 |
| gtcttcctga | gcgctgattc | cggtgaaaac | tacatcacag | tcaagggcaa | cccaggcgac | 1680 |

```
cgtaccgttg ctggcctgtc ggcttggtac gagggagacg aacttgtgca ggccgccgct   1740
gagaagttct caaatgttgt ggtcgttgtc cacacagtgg gcccaataat tctggagcca   1800
tggattgacc ttcctgccgt gaagagcgtg ctcttcgctc atctgccggg acaggaagcc   1860
ggcaacgcag tcacagatat ccttttggga gattacaatc ccagcggcca cctcccttac   1920
tcgatcccca aatccgaatc agactatccc gaatccgtcg gcctcatcaa ccagcctttt   1980
ggtcaaatcc aggacacctt cacagagggc ttgtatattg attaccgcca ctttcaaggc   2040 gccgaaaag ctgtccgcta cccgttcggt cacggactct cgtacacgac cttcagcttc   2100
acaaaacccg ctatctcccc tgtcacagcg ctgacctcat accctcctcc ccgcgaccct   2160
aagggtccga cacccacata tcccagcgac attccgcctg gctcggaggt tgcctggcca   2220
gagaatttcg acaagatctg cgcctacctg taccccctatc tggacaagcc cgaatccatc   2280
catccaaacc cagacaagaa gtaccgtac cctcctggct acagcacaac cccgaaacca   2340
gaccctcggg ccgggggcgg ccaaggagga aatccagccc tctgggacgc ggtcttcacc   2400
gtgtccgtga aggtgacgaa tacggggaag gtgtctgggc gggcggtcgc gcagttctac   2460
gtcgagttgc ctgctgattt tgagcctcat acgccccgct tgcagctaag gcagtttgag   2520
aagacgcggc tgcttgcgcc ggggagagc gaggttttga aggtgcagct cacaaggaaa   2580
gatttgagtg tgtgggatgt tgtggtgcag gactggaggg cgccgaaaga tggacagggg   2640
gtcagggtgt gggtgggaga gagcgtggag gacccgaggg ttgtttgtga ggcggatgga   2700
gagtgttggg agagcattga gcagtttgat atggattggc agaaaagaag acgctaa      2757
```

<210> SEQ ID NO 6  
<211> LENGTH: 870  
<212> TYPE: PRT  
<213> ORGANISM: Malbranchea cinnamomea

<400> SEQUENCE: 6

```
Met Ser Phe Phe Asn Phe Leu Leu Ser Val Leu Phe Leu Leu Leu Asn
1               5                   10                  15

Ala Gly Leu Leu Ala Asp Ala Ala Pro Gly Tyr Glu Ser Pro Ser Tyr
            20                  25                  30

Tyr Pro Ala Pro Lys Gly Gly Trp Val Arg Glu Trp Ala Asp Ser Tyr
        35                  40                  45

Ala Arg Ala Gln Glu Ile Val Ser His Met Thr Leu Ala Glu Lys Val
    50                  55                  60

Asn Leu Thr Thr Gly Thr Gly Tyr Phe Met Gly Pro Cys Val Gly Gln
65                  70                  75                  80

Thr Gly Ser Ala Leu Arg Phe Gly Ile Pro Arg Leu Cys Leu Gln Asp
                85                  90                  95

Gly Pro Leu Gly Val Arg Asn Thr Asp Gln Ser Thr Ala Phe Pro Ala
            100                 105                 110

Gly Ile Thr Val Gly Ala Thr Phe Asp Lys Lys Leu Met Tyr Glu Arg
        115                 120                 125

Gly Val Ala Met Gly Glu Glu Phe Arg Gly Lys Gly Val Asn Ile His
    130                 135                 140

Leu Gly Pro Ser Val Gly Pro Leu Gly Arg Lys Pro Arg Gly Gly Arg
145                 150                 155                 160

Asn Trp Glu Gly Phe Gly Ala Asp Pro Ser Leu Gln Gly Ile Ala Ala
                165                 170                 175

Tyr Glu Thr Ile Arg Gly Val Gln Ser Thr Gly Val Ile Ala Thr Val
            180                 185                 190
```

-continued

```
Lys His Leu Val Gly Asn Glu Gln Glu Met Tyr Arg Met Thr Ser Val
            195                 200                 205
Ile Gln Arg Ala Tyr Ser Ala Asn Ile Asp Asp Arg Thr Leu His Glu
210                 215                 220
Leu Tyr Leu Trp Pro Phe Ala Glu Ala Val Arg Ala Gly Val Gly Ala
225                 230                 235                 240
Val Met Met Ala Tyr Asn Asp Val Asn Gly Ser Ala Cys Ser Gln Asn
                245                 250                 255
Ser Lys Leu Ile Asn Gly Ile Leu Lys Asp Glu Leu Gly Phe Gln Gly
            260                 265                 270
Phe Val Met Thr Asp Trp Phe Gly His Ile Gly Gly Val Ser Ser Ala
                275                 280                 285
Leu Ala Gly Leu Asp Met Ala Met Pro Gly Asp Gly Ala Ile Pro Leu
290                 295                 300
Leu Gly Tyr Ser Phe Trp Gly Ser Glu Leu Ser Arg Ser Ile Leu Asn
305                 310                 315                 320
Gly Thr Val Pro Met Glu Arg Leu Asn Asp Met Val Thr Arg Ile Val
                325                 330                 335
Ala Thr Trp Ile Gln Leu Gly Gln Asp Glu Asp Tyr Pro Leu Pro Asn
            340                 345                 350
Phe Ser Thr Asn Thr Leu Asp Glu Thr Gly Leu Leu Tyr Pro Gly Ala
                355                 360                 365
Leu Phe Ser Pro Arg Gly Val Val Asn Gln Phe Val Asn Val Gln Asp
370                 375                 380
Asp His His Lys Ile Ala Arg Glu Ile Ala Arg Asp Gly Ile Thr Leu
385                 390                 395                 400
Leu Lys Asn Glu Asn Asp Leu Leu Pro Leu Asp Lys Asn Ala Ser Leu
                405                 410                 415
Lys Ile Phe Gly Thr Asp Ala Gly Thr Asn Pro Asp Gly Ile Asn Ser
            420                 425                 430
Cys Asn Asp Lys Gly Cys Asn Lys Gly Val Leu Thr Met Gly Trp Gly
            435                 440                 445
Ser Gly Ser Ala Arg Leu Pro Tyr Leu Ser Thr Pro Glu Asp Ala Ile
    450                 455                 460
Arg Asp Ile Ser Gln His Ala Glu Phe His Ile Thr Asp Lys Phe Pro
465                 470                 475                 480
Arg His Ile Asp Val Lys Pro Glu Asp Ile Ala Ile Val Phe Leu Ser
                485                 490                 495
Ala Asp Ser Gly Glu Asn Tyr Ile Thr Val Lys Gly Asn Pro Gly Asp
            500                 505                 510
Arg Thr Val Ala Gly Leu Ser Trp Tyr Glu Gly Asp Glu Leu Val
            515                 520                 525
Gln Ala Ala Ala Glu Lys Phe Ser Asn Val Val Val Val His Thr
530                 535                 540
Val Gly Pro Ile Ile Leu Glu Pro Trp Ile Asp Leu Pro Ala Val Lys
545                 550                 555                 560
Ser Val Leu Phe Ala His Leu Pro Gly Gln Glu Ala Gly Asn Ala Val
                565                 570                 575
Thr Asp Ile Leu Phe Gly Asp Tyr Asn Pro Ser Gly His Leu Pro Tyr
            580                 585                 590
Ser Ile Pro Lys Ser Glu Ser Asp Tyr Pro Glu Ser Val Gly Leu Ile
            595                 600                 605
```

```
Asn Gln Pro Phe Gly Gln Ile Gln Asp Thr Phe Thr Glu Gly Leu Tyr
    610                 615                 620
Ile Asp Tyr Arg His Phe Gln Gly Ala Gly Lys Ala Val Arg Tyr Pro
625                 630                 635                 640
Phe Gly His Gly Leu Ser Tyr Thr Thr Phe Ser Phe Thr Lys Pro Ala
                645                 650                 655
Ile Ser Pro Val Thr Ala Leu Thr Ser Tyr Pro Pro Arg Asp Pro
                660                 665                 670
Lys Gly Pro Thr Pro Thr Tyr Pro Ser Asp Ile Pro Gly Ser Glu
                675                 680                 685
Val Ala Trp Pro Glu Asn Phe Asp Lys Ile Trp Arg Tyr Leu Tyr Pro
    690                 695                 700
Tyr Leu Asp Lys Pro Glu Ser Ile His Pro Asn Pro Asp Lys Lys Tyr
705                 710                 715                 720
Pro Tyr Pro Pro Gly Tyr Ser Thr Thr Pro Lys Pro Asp Pro Arg Ala
                725                 730                 735
Gly Gly Gly Gln Gly Gly Asn Pro Ala Leu Trp Asp Ala Val Phe Thr
                740                 745                 750
Val Ser Val Lys Val Thr Asn Thr Gly Lys Val Ser Gly Arg Ala Val
                755                 760                 765
Ala Gln Phe Tyr Val Glu Leu Pro Ala Asp Phe Glu Pro His Thr Pro
                770                 775                 780
Arg Leu Gln Leu Arg Gln Phe Glu Lys Thr Arg Leu Leu Ala Pro Gly
785                 790                 795                 800
Glu Ser Glu Val Leu Lys Val Gln Leu Thr Arg Lys Asp Leu Ser Val
                805                 810                 815
Trp Asp Val Val Gln Asp Trp Arg Ala Pro Lys Asp Gly Gln Gly
                820                 825                 830
Val Arg Val Trp Val Gly Glu Ser Val Glu Asp Pro Arg Val Val Cys
                835                 840                 845
Glu Ala Asp Gly Glu Cys Trp Glu Ser Ile Glu Gln Phe Asp Met Asp
    850                 855                 860
Trp Gln Lys Arg Arg Arg
865                 870

<210> SEQ ID NO 7
<211> LENGTH: 3042
<212> TYPE: DNA
<213> ORGANISM: Malbranchea cinnamomea

<400> SEQUENCE: 7
atgcggctcc cttggtggtc cgccatcatc acggcggcta gcgttgcggc cgagcaggta      60
tggtgcagag tcgtctctct cctccacctt taaaaaatga cctccctcga ttagttgttg     120
gccttgaagg tggcgttttc tcctcaattc cccggcgaat gctgactgga aaacgacgta     180
acataggaag tcactgccta ctctcctccg tactacccct tcaccatggc ctccggacaa     240
ggaggctggg aggaagccgt cgccagagct cgggaattcg tatctcagct cacgttggct     300
gagaaagtca atcttacgac cggcgtcggg tatgcctccc cctctccaaa tatgaataat     360
ctccccaagt atattaccgt ttgacgtgtt atgatcgagc gctgctaaag attatatttg     420
gcagatggat gcaggagat tgtgttggca atgccgggtc aatacctcgt ctaggattcc     480
cttcgttatg tctgcaggat gccccttttg gaatccgaat gggtacgttc aatgatcggt     540
cctgatcgaa ttgatttttct gctaactgcg cccagcggat tacgttactg cgttccctgc     600
```

```
gggagtcaat gtcggcgcta cgtttgacaa gtctcttgcc tatctccgtg gaaaggcgat      660
gggagaggag tttcgtgata aggggatcga tgtccagctt ggccccgctg ctggcccatt      720
aggaaggtct cctgacggcg gacggaactg ggagggcttc agtccggatc ccgtactgac      780
ggggttcctc ttcgctgaga cgatcaaggg catccaggat gccggcgtca ttgcttgtgc      840
aaaacattac attgcaaacg aacaggaacg attccgccag gccccagaag cccaaggcta      900
cggatttaat atctccgaaa gctccagctc gaacattgac gatgtcacga tgcacgagct      960
ttacctctgg tgagtacaac agtaatatgc ttcgaagaca tgtcgctgac aacttacgtg     1020
tgaaaaggcc attcgcagat gccgtccgcg ccggagttgg atctatcatg tgctcttata     1080
acctgatcaa caacagttat ggctgccaga acagctacac ccagaacaag ctgctcaagg     1140
gagagcttgg gttccagggg tttatcctga gtgactggca agcgcagcac tcgggcgttg     1200
cagccgcgct cgcaggattg gatatggcga tgcctggtga tacgactttt gggactggcc     1260
gctcgttctg gggaactaac ttgactattg ccgttgcaaa cgggacgatc cccgaatgga     1320 ggggttgatga tatggttgtg cggatcatgg ctgcttacta caaagttgga cgggaccggg     1380
tgtcggtacc caccaacttc aactcctgga cgcgagatga atatggattc caacatgcca     1440
tgtcccagga gcgctatggc ttagtgaacg aacgggtcaa tgtgcgaaac caccatcacc     1500
tcatcgcccg tgaagtggca agccacagca cggtgcttct gaagaacaat ggagcacttc     1560
ccctgactgg aaacgagaag tttacggcca ttattggcga agacgccggt cccaatttcc     1620
gaggcccgaa tagttgccct gatagaggct gtgctgatgg cacgctcgca atgggatggg     1680
gtagtggcac tgctgaattt ccgtacctgg tcacgccagc agagggcatc caaaacgaga     1740
tactatctag aggagttggc aatgtagtcg cggtctttga caattatgcc aaagatcaga     1800
tcaaatcgac tgtgtcacaa gcgtccgtgg ccctggtgtt cgcgaacgca ggtgcgggcg     1860
aaggctacat cagtgtggac gggaatgaag gagatcgcaa gaatctgacc ctgtggaagg     1920
gtggcgacga cctgatcaag accactgctt catactgtaa caacaccatt gtcgtgatac     1980
attccggagg ccctgttctg gtggacgaat ggtatgataa ccagaatgtc actgccatcc     2040
tgtgggcagg gcttcctggc caggagagcg gcaatgcatt ggcagatgtt ctgtacggtc     2100
gagtgaatcc gggcgctaag actcccttta cttggggaaa gactcgagac gactatggtg     2160
caccaattct acgggagccc aatgcgggat cgaatgctcc gcaggtcgac tttgaagagg     2220
gcattttcat cgactaccgc gcgttcgata agaggacat cgagcctatc tatgagtttg     2280
gctttggact gagctacacc gaattttcgt atagtgacct acagattcaa gaggttgccg     2340
ccccgccgta tgctcccact acaggaaaaa cagagcctgc tccagtgttg ggcaactcgt     2400
cgaaggacct ggtagattac cagtttcccg aagcctggga tcacgtctcg ctgtacatct     2460 accccctggct gaactcgacg gacggcgaag aggcatcagg ggatccgtat tacggaatgg     2520
atgctgagga ttatatcccc gaaggagcta cagacagcgg gccacaggag ctactcccag     2580
ctggcggcgg acctggcggc aaccccgtc tgtacgatgt tctgtacaag gtgtcagccg     2640
tgatcaccaa caccggctct gtgccgggcg acgaagtccc tcaattggta aggcgggcca     2700
attggtgatt tttttttagag cccccccccc cacccccctt tttctttttt ttttttttgg     2760
tctctctatc gtttactaac tagatatgct tcacagtacg tgtcgcttgg aggtcccaac     2820
gatgccaaag tcgttttgcg caacttcgac cgcttcaatc ttgcgcctgg tgaaagcaag     2880
acctggcaca cagtcctgac acgacgcgac gtttccaact gggatcccgt ctcgcaggat     2940
tgggtgatca ccgatcatcc caagacagtg tatgtgggca gctcgtcgcg gaagctgcac     3000
```
ttgcaggggc ccctgccacc tcacagcggt agtaatcaat ga          3042

<210> SEQ ID NO 8
<211> LENGTH: 865
<212> TYPE: PRT
<213> ORGANISM: Malbranchea cinnamomea

<400> SEQUENCE: 8

Met Arg Leu Pro Trp Trp Ser Ala Ile Ile Thr Ala Ala Ser Val Ala
1               5                   10                  15

Ala Glu Gln Glu Val Thr Ala Tyr Ser Pro Pro Tyr Tyr Pro Ser Pro
                20                  25                  30

Trp Ala Ser Gly Gln Gly Gly Trp Glu Glu Ala Val Ala Arg Ala Arg
            35                  40                  45

Glu Phe Val Ser Gln Leu Thr Leu Ala Glu Lys Val Asn Leu Thr Thr
    50                  55                  60

Gly Val Gly Trp Met Gln Gly Asp Cys Val Gly Asn Ala Gly Ser Ile
65                  70                  75                  80

Pro Arg Leu Gly Phe Pro Ser Leu Cys Leu Gln Asp Ala Pro Leu Gly
                85                  90                  95

Ile Arg Met Ala Asp Tyr Val Thr Ala Phe Pro Ala Gly Val Asn Val
            100                 105                 110

Gly Ala Thr Phe Asp Lys Ser Leu Ala Tyr Leu Arg Gly Lys Ala Met
        115                 120                 125

Gly Glu Glu Phe Arg Asp Lys Gly Ile Asp Val Gln Leu Gly Pro Ala
130                 135                 140

Ala Gly Pro Leu Gly Arg Ser Pro Asp Gly Gly Arg Asn Trp Glu Gly
145                 150                 155                 160

Phe Ser Pro Asp Pro Val Leu Thr Gly Phe Leu Phe Ala Glu Thr Ile
                165                 170                 175

Lys Gly Ile Gln Asp Ala Gly Val Ile Ala Cys Ala Lys His Tyr Ile
            180                 185                 190

Ala Asn Glu Gln Glu Arg Phe Arg Gln Ala Pro Glu Ala Gln Gly Tyr
        195                 200                 205

Gly Phe Asn Ile Ser Glu Ser Ser Ser Asn Ile Asp Asp Val Thr
210                 215                 220

Met His Glu Leu Tyr Leu Trp Pro Phe Ala Asp Ala Val Arg Ala Gly
225                 230                 235                 240

Val Gly Ser Ile Met Cys Ser Tyr Asn Leu Ile Asn Asn Ser Tyr Gly
                245                 250                 255

Cys Gln Asn Ser Tyr Thr Gln Asn Lys Leu Leu Lys Gly Glu Leu Gly
            260                 265                 270

Phe Gln Gly Phe Ile Leu Ser Asp Trp Gln Ala Gln His Ser Gly Val
        275                 280                 285

Ala Ala Ala Leu Ala Gly Leu Asp Met Ala Met Pro Gly Asp Thr Thr
    290                 295                 300

Phe Gly Thr Gly Arg Ser Phe Trp Gly Thr Asn Leu Thr Ile Ala Val
305                 310                 315                 320

Ala Asn Gly Thr Ile Pro Glu Trp Arg Val Asp Asp Met Val Val Arg
                325                 330                 335

Ile Met Ala Ala Tyr Tyr Lys Val Gly Arg Asp Arg Val Ser Val Pro
            340                 345                 350

Thr Asn Phe Asn Ser Trp Thr Arg Asp Glu Tyr Gly Phe Gln His Ala
        355                 360                 365

```
Met Ser Gln Glu Arg Tyr Gly Leu Val Asn Glu Arg Val Asn Val Arg
    370                 375                 380

Asn His His His Leu Ile Ala Arg Glu Val Ala Ser His Ser Thr Val
385                 390                 395                 400

Leu Leu Lys Asn Asn Gly Ala Leu Pro Leu Thr Gly Asn Glu Lys Phe
                405                 410                 415

Thr Ala Ile Ile Gly Glu Asp Ala Gly Pro Asn Phe Arg Gly Pro Asn
                420                 425                 430

Ser Cys Pro Asp Arg Gly Cys Ala Asp Gly Thr Leu Ala Met Gly Trp
            435                 440                 445

Gly Ser Gly Thr Ala Glu Phe Pro Tyr Leu Val Thr Pro Ala Glu Gly
    450                 455                 460

Ile Gln Asn Glu Ile Leu Ser Arg Gly Val Gly Asn Val Ala Val
465                 470                 475                 480

Phe Asp Asn Tyr Ala Lys Asp Gln Ile Lys Ser Thr Val Ser Gln Ala
                485                 490                 495

Ser Val Ala Leu Val Phe Ala Asn Ala Gly Ala Gly Glu Gly Tyr Ile
                500                 505                 510

Ser Val Asp Gly Asn Glu Gly Asp Arg Lys Asn Leu Thr Leu Trp Lys
            515                 520                 525

Gly Gly Asp Asp Leu Ile Lys Thr Thr Ala Ser Tyr Cys Asn Asn Thr
    530                 535                 540

Ile Val Val Ile His Ser Gly Gly Pro Val Leu Val Asp Glu Trp Tyr
545                 550                 555                 560

Asp Asn Gln Asn Val Thr Ala Ile Leu Trp Ala Gly Leu Pro Gly Gln
                565                 570                 575

Glu Ser Gly Asn Ala Leu Ala Asp Val Leu Tyr Gly Arg Val Asn Pro
            580                 585                 590

Gly Ala Lys Thr Pro Phe Thr Trp Gly Lys Thr Arg Asp Asp Tyr Gly
    595                 600                 605

Ala Pro Ile Leu Arg Glu Pro Asn Ala Gly Ser Asn Ala Pro Gln Val
    610                 615                 620

Asp Phe Glu Glu Gly Ile Phe Ile Asp Tyr Arg Ala Phe Asp Lys Glu
625                 630                 635                 640

Asp Ile Glu Pro Ile Tyr Glu Phe Gly Phe Gly Leu Ser Tyr Thr Glu
                645                 650                 655

Phe Ser Tyr Ser Asp Leu Gln Ile Gln Glu Val Ala Ala Pro Pro Tyr
            660                 665                 670

Ala Pro Thr Thr Gly Lys Thr Glu Pro Ala Pro Val Leu Gly Asn Ser
    675                 680                 685

Ser Lys Asp Leu Val Asp Tyr Gln Phe Pro Glu Ala Trp Asp His Val
    690                 695                 700

Ser Leu Tyr Ile Tyr Pro Trp Leu Asn Ser Thr Asp Gly Glu Ala
705                 710                 715                 720

Ser Gly Asp Pro Tyr Tyr Gly Met Asp Ala Glu Asp Tyr Ile Pro Glu
                725                 730                 735

Gly Ala Thr Asp Ser Gly Pro Gln Glu Leu Leu Pro Ala Gly Gly Gly
            740                 745                 750

Pro Gly Gly Asn Pro Arg Leu Tyr Asp Val Leu Tyr Lys Val Ser Ala
    755                 760                 765

Val Ile Thr Asn Thr Gly Ser Val Pro Gly Asp Glu Val Pro Gln Leu
    770                 775                 780
```

```
Tyr Val Ser Leu Gly Gly Pro Asn Asp Ala Lys Val Val Leu Arg Asn
785                 790                 795                 800

Phe Asp Arg Phe Asn Leu Ala Pro Gly Glu Ser Lys Thr Trp His Thr
            805                 810                 815

Val Leu Thr Arg Arg Asp Val Ser Asn Trp Asp Pro Val Ser Gln Asp
                820                 825                 830

Trp Val Ile Thr Asp His Pro Lys Thr Val Tyr Val Gly Ser Ser Ser
            835                 840                 845

Arg Lys Leu His Leu Gln Gly Pro Leu Pro Pro His Ser Gly Ser Asn
            850                 855                 860

Gln
865

<210> SEQ ID NO 9
<211> LENGTH: 2975
<212> TYPE: DNA
<213> ORGANISM: Malbranchea cinnamomea

<400> SEQUENCE: 9
atggctcgtc gcacttcgaa atgggccttg ctggtcctac aagcatccac actcgcttat     60
ggcgccacca gtgatgcttt gtacaaggat ccaacgcagc ccattgaggt tagagttgaa    120
gatcttcttt caagaatgac aattgaggac aagacagctc agttgatgca aggtaggtcg    180
cccacaacac ctagctctta ggccgctcca ctgtcgaaac tgattctgta aaggcgatat    240
tgccaactgg gtggacctca acgggcgc ctttaattac agcggtttga tcgagaatat     300
gaagtacaag gccggaatgt tcttcggtta gttccacgat cgaggggacc gatatcatgg    360
gcaacgtgtc taagttcttc ttcatctcaa tagctggcca taacctccag tgggatgtac    420
ttgcagagaa tatcaagcgg ggtcaagatt atctactaga aaatactacc cttgggattc    480
cagctcttgt gcattcggaa ggtatgttaa actcttgatc tgtcaactgg ttatggggaa    540
aggaaaagaa aaggctgaga tatccgtgca ggtatccatg gattccttgt gggaaacgca    600
accatcttca attcccccat cggctacggc tgctcttgga atcgggaggt gagatgccca    660
ttgaaatctt gtataccccct gacaaacaca cttgctgacc gttccacagt tggtggaaag    720
aatggcacgg tttattgcgc aggaatccct cacgctcggt gtcaaccagc ttttgccccc    780
cgttgttgac ttggctagag agcttcgatt cggaagagta cgagacgaca tcctgaccat    840
tgcgaataat gtagcacttg ctgaaagtgg gaatttctag gtcgaggagt cgatctccga    900
ggacgcttac ttgaccgcgg aactggcata tcattatgtc aagggattac aagctggcaa    960
tgtctctgcg actgttaagc attttgtcgg cgttagcatg cctgaacagg gcatcaacac   1020
agctcccgtt cacggtggtg agagagagtt gagaacgacg tatgttgacc taccaacgca   1080
cttatgtgac gcgggctaat ggtgaccggg gtatagatgg ctgccaccat tcaaacgtgc   1140
cattattgac gctggggcgt ggagtatcat gactgcttat catgcgtaag tcgacatctt   1200
tccaggctca cttctaactc cactggctga tgcctgctta ggtacgatgg aataccagct   1260
gtggccaaca acacactct cactgacatc ctaagagatg aatggggcta tgagaactgg   1320
gtcatcagcg atgccggtgc tacagatcgt ctctgcaaca gtttcaaaat gtgtcgatct   1380
aatcctattg actcggatgc agtcaccctc aaggtcttga cagctggagg agacgttgaa   1440
atgggaggag ctccttgta tgtgcctacg agcataacat cgaatatgtt tggaaacttc   1500
ctcgctgatt aagagattcc agcaacttcc gatcgatacc ccgtctcgtt gaggaaggaa   1560
aactcgaggt tgaaaatgtt gacagggccg tctcgagagt gctgaaggca aagttcgaaa   1620
```

```
tgggcctgtt tgagaaccca tatcctgcgg cacctgaaga ccagtggaag gaactcatcc    1680
attctaaaga agccgtccag ctagcgagag aactggacag agagtctatc gtgcttcttg    1740
agaaccatga taatactttg cctctgaaga aaagaggctc aattgcggta atcggaccaa    1800
tggctcacgg attcatgaat gtattggcaa ttccgaaccc ttctattaaa cgggctccat    1860
gaaaccacta actctgtctt cgtagtacgg tgactatgtc ccgtatctga gccagtatcg    1920
tggtgtcact cccctcgacg gaatccgtgc tgctgtcggg gataaagcga aaataagata    1980
cgctaaagga tgcgaacgct ggagcaacga caaatctggc ttcgaagagg ccatccaggc    2040
ggccaaaaag tcagatgtcg caatcgtcgt cgtcgggacg tggtcgagag atcagggtga    2100
actgtggcaa ggatacaacg cgacgtaagt ctcttctttc acctgactct tggttgacc    2160 gcgttgggag gttctaattc ctttccctgt atagcactgg cgaaactgtc gatgtcaaca    2220
gccttaacct tgttggcgct cagcgcgaac ttgtgaaggt cattgcagac accggtgttc    2280
cgaccgtcgt cgtttctcc tccggcaagc ccatttccga accgtggatc gccaactcca    2340
cggccgcctt aatccaacaa ttctacccat ccgagcaagg tgggcacgcg ctcgctgacg    2400
ttctcttcgg agactataac ccaagcggta agctgtctgt cagtttcccg cacgacgtcg    2460
gatcaatccc catctactat gactatctca actcggcgcg cgaggtctgg gactctgggt    2520
tcgagtacga gaacggcaca atcgactttg ggcgccagta tgcgattggt acgccgcttc    2580
cgtggtacga gtttggatac ggaaaatcgt attcgacttt caagtatgaa gaggtcaagt    2640
tggataagta tgaggtcagt gcggaagaag acacgcgcgt caaggtgagc gtgtctgtga    2700
cgaacacgag cgagcgtgac ggcacggagg tcgtgcagtt gtacgtctct gacctgattg    2760
catcggtcgc tgtgccgaat cgcgtgctta gagggtttga gaaggtgttc atccctgctg    2820
gagaaagcgt tgccgtggaa atggaagtca aagttcagga tctggggctc tgggatgaga    2880
gtatgaagta cgtcgttgag ccgggagagt ttaacttctt ggttggatcc agttcagcag    2940
acatccgggg aaacgctatt ctcacggttg tctag                              2975
```

<210> SEQ ID NO 10
<211> LENGTH: 779
<212> TYPE: PRT
<213> ORGANISM: Malbranchea cinnamomea

<400> SEQUENCE: 10

```
Met Ala Arg Arg Thr Ser Lys Trp Ala Leu Leu Val Leu Gln Ala Ser
1               5                   10                  15

Thr Leu Ala Tyr Gly Ala Thr Ser Asp Ala Leu Tyr Lys Asp Pro Thr
            20                  25                  30

Gln Pro Ile Glu Val Arg Val Glu Asp Leu Leu Ser Arg Met Thr Ile
        35                  40                  45

Glu Asp Lys Thr Ala Gln Leu Met Gln Gly Asp Ile Ala Asn Trp Val
    50                  55                  60

Asp Leu Thr Thr Gly Ala Phe Asn Tyr Ser Gly Leu Ile Glu Asn Met
65                  70                  75                  80

Lys Tyr Lys Ala Gly Met Phe Phe Ala Gly His Asn Leu Gln Trp Asp
                85                  90                  95

Val Leu Ala Glu Asn Ile Lys Arg Gly Gln Asp Tyr Leu Leu Glu Asn
            100                 105                 110

Thr Thr Leu Gly Ile Pro Ala Leu Val His Ser Glu Gly Ile His Gly
        115                 120                 125
```

-continued

```
Phe Leu Val Gly Asn Ala Thr Ile Phe Asn Ser Pro Ile Gly Tyr Gly
        130                 135                 140
Cys Ser Trp Asn Arg Glu Leu Val Glu Arg Met Ala Arg Phe Ile Ala
145                 150                 155                 160
Gln Glu Ser Leu Thr Leu Gly Val Asn Gln Leu Phe Ala Pro Val Val
                165                 170                 175
Asp Leu Ala Arg Glu Leu Arg Phe Gly Arg Val Glu Glu Ser Ile Ser
                180                 185                 190
Glu Asp Ala Tyr Leu Thr Ala Glu Leu Ala Tyr His Tyr Val Lys Gly
                195                 200                 205
Leu Gln Ala Gly Asn Val Ser Ala Thr Val Lys His Phe Val Gly Val
        210                 215                 220
Ser Met Pro Glu Gln Gly Ile Asn Thr Ala Pro Val His Gly Gly Glu
225                 230                 235                 240
Arg Glu Leu Arg Thr Thr Trp Leu Pro Pro Phe Lys Arg Ala Ile Ile
                245                 250                 255
Asp Ala Gly Ala Trp Ser Ile Met Thr Ala Tyr His Ala Tyr Asp Gly
                260                 265                 270
Ile Pro Ala Val Ala Asn Lys His Thr Leu Thr Asp Ile Leu Arg Asp
        275                 280                 285
Glu Trp Gly Tyr Glu Asn Trp Val Ile Ser Asp Ala Gly Ala Thr Asp
        290                 295                 300
Arg Leu Cys Asn Ser Phe Lys Met Cys Arg Ser Asn Pro Ile Asp Ser
305                 310                 315                 320
Asp Ala Val Thr Leu Lys Val Leu Thr Ala Gly Gly Asp Val Glu Met
                325                 330                 335
Gly Gly Gly Ser Phe Asn Phe Arg Ser Ile Pro Arg Leu Val Glu Glu
                340                 345                 350
Gly Lys Leu Glu Val Glu Asn Val Asp Arg Ala Val Ser Arg Val Leu
        355                 360                 365
Lys Ala Lys Phe Glu Met Gly Leu Phe Glu Asn Pro Tyr Pro Ala Ala
        370                 375                 380
Pro Glu Asp Gln Trp Lys Glu Leu Ile His Ser Lys Glu Ala Val Gln
385                 390                 395                 400
Leu Ala Arg Glu Leu Asp Arg Glu Ser Ile Val Leu Leu Glu Asn His
                405                 410                 415
Asp Asn Thr Leu Pro Leu Lys Lys Arg Gly Ser Ile Ala Val Ile Gly
                420                 425                 430
Pro Met Ala His Gly Phe Met Asn Tyr Gly Asp Tyr Val Pro Tyr Leu
        435                 440                 445
Ser Gln Tyr Arg Gly Val Thr Pro Leu Asp Gly Ile Arg Ala Ala Val
        450                 455                 460
Gly Asp Lys Ala Lys Ile Arg Tyr Ala Lys Gly Cys Glu Arg Trp Ser
465                 470                 475                 480
Asn Asp Lys Ser Gly Phe Glu Glu Ala Ile Gln Ala Ala Lys Lys Ser
                485                 490                 495
Asp Val Ala Ile Val Val Gly Thr Trp Ser Arg Asp Gln Gly Glu
                500                 505                 510
Leu Trp Gln Gly Tyr Asn Ala Thr Thr Gly Glu Thr Val Asp Val Asn
        515                 520                 525
Ser Leu Asn Leu Val Gly Ala Gln Arg Glu Leu Val Lys Val Ile Ala
        530                 535                 540
Asp Thr Gly Val Pro Thr Val Val Val Phe Ser Ser Gly Lys Pro Ile
```

```
                545                 550                 555                 560
Ser Glu Pro Trp Ile Ala Asn Ser Thr Ala Ala Leu Ile Gln Gln Phe
                565                 570                 575

Tyr Pro Ser Glu Gln Gly Gly His Ala Leu Ala Asp Val Leu Phe Gly
                580                 585                 590

Asp Tyr Asn Pro Ser Gly Lys Leu Ser Val Ser Phe Pro His Asp Val
                595                 600                 605

Gly Ser Ile Pro Ile Tyr Tyr Asp Tyr Leu Asn Ser Ala Arg Glu Val
                610                 615                 620

Trp Asp Ser Gly Phe Glu Tyr Glu Asn Gly Thr Ile Asp Phe Gly Arg
625                 630                 635                 640

Gln Tyr Ala Ile Gly Thr Pro Leu Pro Trp Tyr Glu Phe Gly Tyr Gly
                645                 650                 655

Lys Ser Tyr Ser Thr Phe Lys Tyr Glu Glu Val Lys Leu Asp Lys Tyr
                660                 665                 670

Glu Val Ser Ala Glu Glu Asp Thr Arg Val Lys Val Ser Val Ser Val
                675                 680                 685

Thr Asn Thr Ser Glu Arg Asp Gly Thr Glu Val Val Gln Leu Tyr Val
                690                 695                 700

Ser Asp Leu Ile Ala Ser Val Ala Val Pro Asn Arg Val Leu Arg Gly
705                 710                 715                 720

Phe Glu Lys Val Phe Ile Pro Ala Gly Glu Ser Val Ala Val Glu Met
                725                 730                 735

Glu Val Lys Val Gln Asp Leu Gly Leu Trp Asp Glu Ser Met Lys Tyr
                740                 745                 750

Val Val Glu Pro Gly Glu Phe Asn Phe Leu Val Gly Ser Ser Ser Ala
                755                 760                 765

Asp Ile Arg Gly Asn Ala Ile Leu Thr Val Val
                770                 775

<210> SEQ ID NO 11
<211> LENGTH: 2470
<212> TYPE: DNA
<213> ORGANISM: Malbranchea cinnamomea

<400> SEQUENCE: 11
atgcgattgc ctgcgacggt ggtaactctt gcggcaatcg cctctgccgc attgcaaggc    60
agtgacgaat taagccctct gtacaaggac ccgaccgcca gcatcgatga tcgagtcgcc   120
gacctcctct cccggatgac catccaggag aaggccgcgc agttggtgca gggagacctg   180
gccaactgga tcaacacgac aaccaacgag ttcaactata ctgggttggt tgaaaccatg   240
aagaccagag ccagcggatt ctacgtcgga cacccccgtac cccagctgtg gatcgctgaa   300
ggtgtgcgca aggcccagga gtatctggtt gagaacacca cacttgggat tcccgctttt   360
gtacagaccg agggtattca cggtttcctg atcggtgagt gttagcgtcc aaatctcgag   420
gagatggctc tcgaagctga ccttgtgtag gcaacgctac tattttcaac agtcctatcg   480
cgtatgcatg ctctttcaac cgagacctcg tccgcaagat ggctgcagca attgcacagg   540
agtctctggc tctcggtgtc aaccagatct ttgcacctgt cgtggatctt gctcgtgagc   600
tccgtttcgg ccgtgtcgag gaaacctttg gtgaggatcc ttacctggcc ggcgagcttg   660
gctacgagta cgtcgttgga ttgcagagta aaaatgtcag cgccatggtg aagcactttg   720
cgggcttcag tatgcccgag caaggcctca acaccggccc ggtgcacgga ggagagcgcg   780
agctgcggac cacctggctc cctccctccc acagggccat catcgacgct gatgcttgga   840
```

```
gcgtgatggg tgcttaccac tcgtacgacg gtgtccctgc tgtggccgac aagcaccttw   900
tgaccgatat tcttcgcaag gaatggggat atcagtacca tatcatctcg gatgccggcg   960
caaccgacag actctgcaac acattcaaga tgtgccgtga ggatcccatc gattccgagt  1020
cgatcacgtt gctctctcta ccggcgggta acgacattga gatgggcggt ggttcttaca  1080
attttgagac gatcccggaa ctcgtcgagt ctggcaagtt ggatgttctt gccgtcgaca  1140
ccgccgtcgc ccgtgtcctg cgcagcaagt tgtcatggg cctgtttgag aatccaatcc  1200
agtcggcacc tgaggacgaa atcccggatc tgattcacac tccggagatt gtgaagcttg  1260
ctcgtgatct tgatgcagaa tcaattgtgc ttttggaaaa ccatgacaat atccttccgc  1320
tgaaaaagga cacgaacctc gcagtcattg gccaatggc tgatatcctc aacgtgagta  1380
gtaatcttgt cacctagtga gatttttttt tttccccctt gtgaaatgga cgatctaaac  1440
taacgtacta tcaaagttcg gcgactacgt tgtcaaagat tctcaatatc gcgaagacgg  1500
cgtcacgcct ctccaaggca tcaaagccgc gtccaaaggc aaagtgacat acgccaaggg  1560
ctgcgaacgc tggtccaacg acaaatccgg cttccctgaa gccatccagg tcgcagagga  1620
ggctgatgtt gccgtcgtcg tggtcggcac ctggtcccgc gaccagtacg agctctgggc  1680
tggcttgaac gcgacaactg gcgagcacgt cgacgtgtcg tcgctcaacc ttgtcggcgc  1740
ccagggcgcg ctggtgcagg ccatcatcga aacaggcaaa cccaccatcg tcgtctacag  1800
ctctggcaag ccgatcactg aaccgtggat ctccaagtcg gccgccgcgc tgatccagca  1860
gttctacccc tccgagcagg gcggccacgc ccttgccgac gttctctttg gcgacgtcaa  1920
ccccagcggc agactcagcg tcagcttccc ctacgacgtt ggcacgctgc caatctacta  1980
cgactacctc aactctggcc gctacactgc acccggcgag gtcctggcca acggcacgct  2040
gcgctttggc catcagtacg tgctcaacac accacagccg ctctacgagt ttgggttcgg  2100
tcgcagctac tcgaccttcc gctatgggga cacggtgaag ttgtcgcgca cgactgccag  2160
cgcggacgac accgtcacag ccaccgtgtc cgtgaccaac gaatcggagc gcgatggcca  2220
ggaggtcgtg cagctgtacg tgcaggacgt cctcgccagc gttgtcgtgc ccaacaagca  2280
gctgaggggc ttcgagaagg tgtttatcaa agcgggcgag acggtcgatg tcagcatcga  2340
cgtgcggatt aaagatctgg ggttatggga catcaacatg gagtatgtag tggagcccgg  2400
cgagtttgtg ttctggatgg ggaggtccag cttggatctt cctgccaatg cgacgttgac  2460
tgttgtttga                                                         2470
```

<210> SEQ ID NO 12
<211> LENGTH: 776
<212> TYPE: PRT
<213> ORGANISM: Malbranchea cinnamomea

<400> SEQUENCE: 12

```
Met Arg Leu Pro Ala Thr Val Val Thr Leu Ala Ala Ile Ala Ser Ala
1               5                   10                  15

Ala Leu Gln Gly Ser Asp Glu Leu Ser Pro Leu Tyr Lys Asp Pro Thr
                20                  25                  30

Ala Ser Ile Asp Asp Arg Val Ala Asp Leu Leu Ser Arg Met Thr Ile
            35                  40                  45

Gln Glu Lys Ala Ala Gln Leu Val Gln Gly Asp Leu Ala Asn Trp Ile
        50                  55                  60

Asn Thr Thr Thr Asn Glu Phe Asn Tyr Thr Gly Leu Val Glu Thr Met
65                  70                  75                  80
```

```
Lys Thr Arg Ala Ser Gly Phe Tyr Val Gly His Pro Val Pro Gln Leu
                85                  90                  95

Trp Ile Ala Glu Gly Val Arg Lys Ala Gln Glu Tyr Leu Val Glu Asn
               100                 105                 110

Thr Thr Leu Gly Ile Pro Ala Phe Val Gln Thr Glu Gly Ile His Gly
               115                 120                 125

Phe Leu Ile Gly Asn Ala Thr Ile Phe Asn Ser Pro Ile Ala Tyr Ala
           130                 135                 140

Cys Ser Phe Asn Arg Asp Leu Val Arg Lys Met Ala Ala Ile Ala
145                 150                 155                 160

Gln Glu Ser Leu Ala Leu Gly Val Asn Gln Ile Phe Ala Pro Val Val
                165                 170                 175

Asp Leu Ala Arg Glu Leu Arg Phe Gly Arg Val Glu Glu Thr Phe Gly
                180                 185                 190

Glu Asp Pro Tyr Leu Ala Gly Glu Leu Gly Tyr Glu Tyr Val Val Gly
                195                 200                 205

Leu Gln Ser Lys Asn Val Ser Ala Met Val Lys His Phe Ala Gly Phe
            210                 215                 220

Ser Met Pro Glu Gln Gly Leu Asn Thr Gly Pro Val His Gly Gly Glu
225                 230                 235                 240

Arg Glu Leu Arg Thr Thr Trp Leu Pro Pro Phe His Arg Ala Ile Ile
                245                 250                 255

Asp Ala Asp Ala Trp Ser Val Met Gly Ala Tyr His Ser Tyr Asp Gly
                260                 265                 270

Val Pro Ala Val Ala Asp Lys His Leu Met Thr Asp Ile Leu Arg Lys
                275                 280                 285

Glu Trp Gly Tyr Gln Tyr His Ile Ile Ser Asp Ala Gly Ala Thr Asp
            290                 295                 300

Arg Leu Cys Asn Thr Phe Lys Met Cys Arg Glu Asp Pro Ile Asp Ser
305                 310                 315                 320

Glu Ser Ile Thr Leu Leu Ser Leu Pro Ala Gly Asn Asp Ile Glu Met
                325                 330                 335

Gly Gly Gly Ser Tyr Asn Phe Glu Thr Ile Pro Glu Leu Val Glu Ser
                340                 345                 350

Gly Lys Leu Asp Val Ser Ala Val Asp Thr Ala Val Ala Arg Val Leu
            355                 360                 365

Arg Ser Lys Phe Val Met Gly Leu Phe Glu Asn Pro Ile Gln Ser Ala
370                 375                 380

Pro Glu Asp Glu Ile Pro Asp Leu Ile His Thr Pro Glu Ile Val Lys
385                 390                 395                 400

Leu Ala Arg Asp Leu Asp Ala Glu Ser Ile Val Leu Leu Glu Asn His
                405                 410                 415

Asp Asn Ile Leu Pro Leu Lys Lys Asp Thr Asn Leu Ala Val Ile Gly
                420                 425                 430

Pro Met Ala Asp Ile Leu Asn Phe Gly Asp Tyr Val Val Lys Asp Ser
            435                 440                 445

Gln Tyr Arg Glu Asp Gly Val Thr Pro Leu Gln Gly Ile Lys Ala Ala
            450                 455                 460

Ser Lys Gly Lys Val Thr Tyr Ala Lys Gly Cys Glu Arg Trp Ser Asn
465                 470                 475                 480

Asp Lys Ser Gly Phe Pro Glu Ala Ile Gln Val Ala Glu Glu Ala Asp
                485                 490                 495
```

Val Ala Val Val Val Gly Thr Trp Ser Arg Asp Gln Tyr Glu Leu
        500             505             510

Trp Ala Gly Leu Asn Ala Thr Thr Gly Glu His Val Asp Val Ser Ser
    515                 520                 525

Leu Asn Leu Val Gly Ala Gln Gly Ala Leu Val Gln Ala Ile Ile Glu
530                 535                 540

Thr Gly Lys Pro Thr Ile Val Tyr Ser Ser Gly Lys Pro Ile Thr
545             550                 555                 560

Glu Pro Trp Ile Ser Lys Ser Ala Ala Leu Ile Gln Gln Phe Tyr
            565                 570                 575

Pro Ser Glu Gln Gly His Ala Leu Ala Asp Val Leu Phe Gly Asp
                580                 585                 590

Val Asn Pro Ser Gly Arg Leu Ser Val Ser Phe Pro Tyr Asp Val Gly
    595                 600                 605

Thr Leu Pro Ile Tyr Tyr Asp Tyr Leu Asn Ser Gly Arg Tyr Thr Ala
    610                 615                 620

Pro Gly Glu Val Leu Ala Asn Gly Thr Leu Arg Phe Gly His Gln Tyr
625                 630                 635                 640

Val Leu Asn Thr Pro Gln Pro Leu Tyr Glu Phe Gly Phe Gly Arg Ser
                645                 650                 655

Tyr Ser Thr Phe Arg Tyr Gly Asp Thr Val Lys Leu Ser Arg Thr Thr
                660                 665                 670

Ala Ser Ala Asp Asp Thr Val Thr Ala Thr Val Ser Val Thr Asn Glu
        675                 680                 685

Ser Glu Arg Asp Gly Gln Glu Val Val Gln Leu Tyr Val Gln Asp Val
    690                 695                 700

Leu Ala Ser Val Val Pro Asn Lys Gln Leu Arg Gly Phe Glu Lys
705                 710                 715                 720

Val Phe Ile Lys Ala Gly Glu Thr Val Asp Val Ser Ile Asp Val Arg
            725                 730                 735

Ile Lys Asp Leu Gly Leu Trp Asp Ile Asn Met Glu Tyr Val Val Glu
        740                 745                 750

Pro Gly Glu Phe Val Phe Trp Met Gly Arg Ser Ser Leu Asp Leu Pro
            755                 760                 765

Ala Asn Ala Thr Leu Thr Val Val
770                 775

<210> SEQ ID NO 13
<211> LENGTH: 2478
<212> TYPE: DNA
<213> ORGANISM: Penicillium emersonii

<400> SEQUENCE: 13
atgtttgttc ttgctgcgta cctcttgtcc atctcgatgt tcctgacctc aggcatcgct    60
cagaatgtct ccatcggtgc tctccttcgt acgtgacgct ctctccctgt ctatttcgtc   120
ctcagctgat tataatcgta gcccccggca tcaacaccac ccaatggacc atagctgctg   180
cagaggcaga taagttcatt tcgcaactca atctgaccga aaaagcgggc attgtcaccg   240
gcgagcttac cgggacgtgt ctgggatacg tggctccgat agagcgactg ggattccctg   300
gcctttgtct ggccgatggc ccatcggcca tacatctggc tgatgaggcg agtgtctttc   360
ctgcgggatt aactgctgca gccacctggg atagaaatct tctctaccag cgcggcttag   420
cccttggtgc agaattctgt ggcaaaggcg ccaatattgc tctggggtag gtttatacga   480
gcctagtatt caatttcccg aactaaattc agtcagtcca gttgcaggac tctctaggtcg   540

```
caaccctctt ggaggacgca attgggaagt cttctcgccc gatccttacc tcactggcgt     600
ttcgatggac ctcacaatcc gcggcatcca ggacaacggc atccaggcgt gtgcaaaaca     660
ctacatcggg tacgaacaag aaacgcaacg atccaacacg acgactgcag acgggaagaa     720
cgtggacggc tactccgcca acatcgacga ccgcacccct cacgagctct acctgtggcc     780
ctttgccaac gccgtccgcg ctggagtcgc tcagtgatg tgcagctaca accggctcaa      840
ccggacgtac tcatgcgaga attcccatac gctgaacgga attctcaagg gcgagcttgg     900
cttccgcggc ttcgtcgtgt cggatttctt cgccacgcac tccggcgtca cgtcggccct     960
ggcaggcctc gacatggaca tgcccggccc aacggcgcag acaaccatgg agagacctt     1020
ctttggtccg aacatcgtct ccgcagtgca gaatggatca ctgtcggagg cccgcgtggt   1080
cgacatggtc cgccgcgtcc tgacgccgta ctactatctc ggtcaggatg agaattatcc   1140
ctctgtcgac ccgacgaccg agctggtgat tgctgccaac tacggtatgc tgccatcgga   1200
cacacacact ccgtccagcc gaaacgtccg cagcgaccat gcgtggctca tccgccagct   1260
ggccgctgcc ggcaccgtat tgttgaaaaa cgtcaactcg accctgccgt tgcgctctcc   1320
gcgggtcatc ggggtatttg caacgacgc agcggacgtg tcggacggtc tggcctttga    1380
cgggtcaacc ggttccttga ctccgccttt cgggttcgat atcggcacgc tgacgatcgg   1440
cgggggggtca ggaggcggcc gcaatccgta tatagtgtca ccgctggagg cgatcaaagc   1500
gcgggcgagg aaggacgggt cgcgcgtgct atatgtcact gataatagcg tgctcgcgca   1560
ggacgtcttc acgagcgtgt atccctcgcc ggacgtctgt ctggtcttcc tcaaaacgtg   1620
ggcgcgcgag ggagcagacc gcactgcctt cgaggcggac tacgactcga cggctgtcgt   1680
taacaatgtc gcagcgcgat gttctcaacg aaccgtcgtg atcacccgct cgggggggcat   1740
caacactatg ccgtgggcga ccaacccgaa cgtgacggcc atcctcgcgg cgcactatcc   1800
gggacaggag agcgggaatt ccatcatgga tgtgctgtac ggcgacctca atccattggg   1860
cagactgccc tatacgatgc gcagaaggag gcagactaca acacgcagat cctgaacatc   1920
acgggtctgg aggcgaagga gtcgtgggcg tggcaggtca atttcaccga agggcaattc   1980
atcgactacc gccatttcga tgcgaagaac atcacgcagc tgtatgagtt tggctacggg   2040
ttgagctata cgacctttgc gctggagaat ggcctgtccg tgtcgcggac gtcgaatgga   2100
gcagtatcgc catttcccctt ctccaacaac cagacatccg caggcgggaa cccggatctg   2160
tggacgcagc tccttaacgc gacgacgaca gtcgccaaca cgggctcaat cgcgggctcg   2220
accgtcgtcc aactctacgt ctccctgcca caagacgcca tcccatccgg aacaccggtc   2280
cgggtgctca ggggattcga gaagatccat ctcgagccgg gggcacggca gacggtctct   2340
ttcccgctga ccagacggga cgtgagtttc tgggacgtgg agtctcagaa ctggcggatt   2400
ccggaaggcg atatcacggg gcatgttggc ttcagctcgc gggatcttcc atatcgcagg   2460
gttgtcaggg tgctgtag                                                  2478
```

<210> SEQ ID NO 14
<211> LENGTH: 773
<212> TYPE: PRT
<213> ORGANISM: Penicillium emersonii

<400> SEQUENCE: 14

Met Phe Val Leu Ala Ala Tyr Leu Leu Ser Ile Ser Met Phe Leu Thr
1               5                   10                  15

Ser Gly Ile Ala Gln Asn Val Ser Ile Gly Ala Leu Leu Pro Pro Gly

-continued

```
             20                  25                  30
Ile Asn Thr Thr Gln Trp Thr Ile Ala Ala Glu Ala Asp Lys Phe
         35                  40                  45
Ile Ser Gln Leu Asn Leu Thr Glu Lys Ala Gly Ile Val Thr Gly Glu
 50                  55                  60
Leu Thr Gly Thr Cys Leu Gly Tyr Val Ala Pro Ile Glu Arg Leu Gly
 65                  70                  75                  80
Phe Pro Gly Leu Cys Leu Ala Asp Gly Pro Ser Ala Ile His Leu Ala
                 85                  90                  95
Asp Glu Ala Ser Val Phe Pro Ala Gly Leu Thr Ala Ala Thr Trp
                100                 105                 110
Asp Arg Asn Leu Leu Tyr Gln Arg Gly Leu Ala Leu Gly Ala Glu Phe
            115                 120                 125
Cys Gly Lys Gly Ala Asn Ile Ala Leu Gly Pro Val Ala Gly Pro Leu
        130                 135                 140
Gly Arg Asn Pro Leu Gly Gly Arg Asn Trp Glu Val Phe Ser Pro Asp
145                 150                 155                 160
Pro Tyr Leu Thr Gly Val Ser Met Asp Leu Thr Ile Arg Gly Ile Gln
                165                 170                 175
Asp Asn Gly Ile Gln Ala Cys Ala Lys His Tyr Ile Gly Tyr Glu Gln
            180                 185                 190
Glu Thr Gln Arg Ser Asn Thr Thr Thr Ala Asp Gly Lys Asn Val Asp
        195                 200                 205
Gly Tyr Ser Ala Asn Ile Asp Asp Arg Thr Leu His Glu Leu Tyr Leu
    210                 215                 220
Trp Pro Phe Ala Asn Ala Val Arg Ala Gly Val Ala Ser Val Met Cys
225                 230                 235                 240
Ser Tyr Asn Arg Leu Asn Arg Thr Tyr Ser Cys Glu Asn Ser His Thr
                245                 250                 255
Leu Asn Gly Ile Leu Lys Gly Glu Leu Gly Phe Arg Gly Phe Val Val
            260                 265                 270
Ser Asp Phe Phe Ala Thr His Ser Gly Val Thr Ser Ala Leu Ala Gly
        275                 280                 285
Leu Asp Met Asp Met Pro Gly Pro Thr Ala Gln Thr Thr Met Gly Glu
    290                 295                 300
Thr Phe Phe Gly Pro Asn Ile Val Ser Ala Val Gln Asn Gly Ser Leu
305                 310                 315                 320
Ser Glu Ala Arg Val Val Asp Met Val Arg Arg Val Leu Thr Pro Tyr
                325                 330                 335
Tyr Tyr Leu Gly Gln Asp Glu Asn Tyr Pro Ser Val Asp Pro Thr Thr
            340                 345                 350
Glu Leu Val Ile Ala Ala Asn Tyr Gly Met Leu Pro Ser Asp Thr His
        355                 360                 365
Thr Pro Ser Ser Arg Asn Val Arg Ser Asp His Ala Trp Leu Ile Arg
    370                 375                 380
Gln Leu Ala Ala Ala Gly Thr Val Leu Leu Lys Asn Val Asn Ser Thr
385                 390                 395                 400
Leu Pro Leu Arg Ser Pro Arg Val Ile Gly Val Phe Gly Asn Asp Ala
                405                 410                 415
Ala Asp Val Ser Asp Gly Leu Ala Phe Asp Gly Ser Thr Gly Ser Leu
            420                 425                 430
Thr Pro Pro Phe Gly Phe Asp Ile Gly Thr Leu Thr Ile Gly Gly Gly
        435                 440                 445
```

Ser Gly Gly Gly Arg Asn Pro Tyr Ile Val Ser Pro Leu Glu Ala Ile
            450                 455                 460

Lys Ala Arg Ala Arg Lys Asp Gly Ser Arg Val Leu Tyr Val Thr Asp
465                 470                 475                 480

Asn Ser Val Leu Ala Gln Asp Val Phe Thr Ser Val Tyr Pro Ser Pro
                485                 490                 495

Asp Val Cys Leu Val Phe Leu Lys Thr Trp Ala Arg Glu Gly Ala Asp
            500                 505                 510

Arg Thr Ala Phe Glu Ala Asp Tyr Asp Ser Thr Ala Val Val Asn Asn
        515                 520                 525

Val Ala Ala Arg Cys Ser Gln Arg Thr Val Val Ile Thr Arg Ser Gly
530                 535                 540

Gly Ile Asn Thr Met Pro Trp Ala Thr Asn Pro Asn Val Thr Ala Ile
545                 550                 555                 560

Leu Ala Ala His Tyr Pro Gly Gln Glu Ser Gly Asn Ser Ile Met Asp
                565                 570                 575

Lys Glu Ala Asp Tyr Asn Thr Gln Ile Leu Asn Ile Thr Gly Leu Glu
            580                 585                 590

Ala Lys Glu Ser Trp Ala Trp Gln Val Asn Phe Thr Glu Gly Gln Phe
        595                 600                 605

Ile Asp Tyr Arg His Phe Asp Ala Lys Asn Ile Thr Gln Leu Tyr Glu
610                 615                 620

Phe Gly Tyr Gly Leu Ser Tyr Thr Thr Phe Ala Leu Glu Asn Gly Leu
625                 630                 635                 640

Ser Val Ser Arg Thr Ser Asn Gly Ala Val Ser Pro Phe Pro Phe Ser
                645                 650                 655

Asn Asn Gln Thr Ser Ala Gly Gly Asn Pro Asp Leu Trp Thr Gln Leu
            660                 665                 670

Leu Asn Ala Thr Thr Thr Val Ala Asn Thr Gly Ser Ile Ala Gly Ser
        675                 680                 685

Thr Val Val Gln Leu Tyr Val Ser Leu Pro Gln Asp Ala Ile Pro Ser
690                 695                 700

Gly Thr Pro Val Arg Val Leu Arg Gly Phe Glu Lys Ile His Leu Glu
705                 710                 715                 720

Pro Gly Ala Arg Gln Thr Val Ser Phe Pro Leu Thr Arg Arg Asp Val
                725                 730                 735

Ser Phe Trp Asp Val Glu Ser Gln Asn Trp Arg Ile Pro Glu Gly Asp
            740                 745                 750

Ile Thr Val His Val Gly Phe Ser Ser Arg Asp Leu Pro Tyr Arg Arg
        755                 760                 765

Val Val Arg Val Leu
    770

<210> SEQ ID NO 15
<211> LENGTH: 2553
<212> TYPE: DNA
<213> ORGANISM: Penicillium emersonii

<400> SEQUENCE: 15
atgaggtgga cgagcttcgc ggccggcacc tgcgtcttca gcgttgtaca gctggtccag     60
agccagtatg tcgaggaaac ggtctttccc tcacgtaagt gctcctccaa tgcagtgcgt    120
ccaacataca tgctgatgca tttcctagca aatgccaccg gcacaggatg gaagacgca    180 ttcgcgaaag catctgccct cacggcgcaa ttgaacctga cggagaagat cttcatggtc    240

```
acaggcgtca aaggtccctg tgtgggtaat attccagcta ttccacgcgt gggattcaag    300
ggtctctgtc tgcaggatgg ccctctcgcg attcgccaag ctagctatgc gagcgtgttc    360
ccggccggct tgtctgctgc tgcaacgtgg gatagagagt tgatctatca acgcggtgtt    420
gcgctcggag aggagttcag aggcaaaggc gccaatgtca tattagggta ggtcagaaat    480
tctgtatatc ttatcatatc ccaggagtca tgccgctaat gatcatgccg caggccagtt    540
gctgccccac ttggaagatc agtcgaggga ggaagaaatt gggaaggctt ctctccggat    600
ccgtacttga ctggcattgc atttgcaaag acgattgaag gcatccaatc tcagaatgtg    660
cagggtgagt catttcctcg ttggatgtag caagtctcgt cctaatttca accagcatgc    720
ggcaaacact acatcggcta tgaacaagaa acgcagcgca atcccaccgt gaacgaagac    780
ggggtcacaa tagaggccgt gtcgtccaat atcgatgatc gaaccatgca cgagctctat    840
ctctggccct ttgcagacgg tgttaagtca ggccttgcct cgatcatgtg cagttacaat    900
cgtctgaatg agacgtacgc ctgccagaac agcaagactc aaaatggact cttgaaatca    960
gagctgggct tccagggata tgtgacgtca gactggggtg gcacccattc gggcgtcgac   1020
gcgatcctgt caggcgaaga tatgaacatg ccaggaaacc tgggccctgg tgactcgact   1080
gtcagctcct attggggata caacattacc accttcttga caacggaag cgtgccagag    1140 agcaggatcg acgacatggt gcggcgcatt ctgactccgt atttttattt ccaccaggat   1200
gatgactcct ggcccaccat cgatctggat accgtcctac tgaatgaggg tgtcctgcgc   1260
aatcacgtcc ggagtatca acatcccttc aactttggaa atgtgtcaga catgaaccgg    1320
gatgtgcggg ccgaccacgg cgtcttgatt cggcagatcg gttctgcgtc gacagtcctt   1380
ctcaagaacg tgaataacac gttgcctctg cggtcgccca agcgaattgc tgtctttggc   1440
aatgctgctc ccgacttgtc tggggaccg tatgacccgg aaaatgagaa cggacctcag    1500
gcggttggag gcggttctgg aactggtcgg tttacgtatc tgatcccgcc cctggaggcg   1560
atcaaacaac gcaatccatc agccttggta gagtacgtca cagacaatac gcttctcacg   1620
acacagcagt cgtcaaccat cttgaccatt tacccccagc ccgatgtctg tctcgtattc   1680
ttgaagtcgt ttgccaccga aggagaggat cgggcgagtc ttctgtgcga ttttaactcc   1740
acaggggtgg ttaatactgt cacctcgtcc ggattatgcc caaacacaat cgtgatcaca   1800
aattccccgg gccccaacgt gttgccgtgg cagacaacg agaatgtcac gggcgtcatt    1860
gtgggccact accctggcga acagatcgga aactccattg tggacgtctt gttcggcgac   1920
gtgaacccgt caggcaaact gccctacaca attgcctacc aggcgagcga ttataacgca   1980
caaatcgtca acttcacagg cgtggatgac aatgatccca atctctggca gtccaacttc   2040
acggaaggtt tgctgatcga ctaccgccac ttcgactaca acacatcac gccccggtac    2100 gagtttggct ttggcttgtc gtacacgacc ttttcacttt ccaaccttca gatatcaagt   2160
aatgcatcga aggtgagtgc gtacccgcca agcctgggt cgcagatccc gcctccagga    2220
ggaaatccag ccttgtatga catttttggcg actgtcgccg tggacgtgaa aaacaccggc   2280
agcgtcgcag gggcgaccgt cccgcaattg tatctcggct ccctccccga cactccagga   2340
ccaacgccac cgaaagtgct gagagggttc gacaagacca gcgtgctggc cgctggacaa   2400
caggagacga tttggttcag cctgcggaga aaagacgtgt cgttttggga tgtcgtgcgt   2460
caggaatggg ccattccatc ggggccgttt actgtcctcg ttggacaaag cagtcgtgat   2520
ctgccactga gtggcgaatt aactttcttg tag                                2553
```

<210> SEQ ID NO 16
<211> LENGTH: 793
<212> TYPE: PRT
<213> ORGANISM: Penicillium emersonii

<400> SEQUENCE: 16

```
Met Arg Trp Thr Ser Phe Ala Ala Gly Thr Cys Val Phe Ser Val Val
1               5                   10                  15

Gln Leu Val Gln Ser Gln Tyr Val Glu Glu Thr Val Phe Pro Ser Pro
            20                  25                  30

Asn Ala Thr Gly Thr Gly Trp Glu Asp Ala Phe Ala Lys Ala Ser Ala
        35                  40                  45

Leu Thr Ala Gln Leu Asn Leu Thr Glu Lys Ile Phe Met Val Thr Gly
    50                  55                  60

Val Lys Gly Pro Cys Val Gly Asn Ile Pro Ala Ile Pro Arg Val Gly
65                  70                  75                  80

Phe Lys Gly Leu Cys Leu Gln Asp Gly Pro Leu Ala Ile Arg Gln Ala
                85                  90                  95

Ser Tyr Ala Ser Val Phe Pro Ala Gly Leu Ser Ala Ala Thr Trp
            100                 105                 110

Asp Arg Glu Leu Ile Tyr Gln Arg Gly Val Ala Leu Gly Glu Glu Phe
        115                 120                 125

Arg Gly Lys Gly Ala Asn Val Ile Leu Gly Pro Val Ala Gly Pro Leu
    130                 135                 140

Gly Arg Ser Val Glu Gly Gly Arg Asn Trp Glu Gly Phe Ser Pro Asp
145                 150                 155                 160

Pro Tyr Leu Thr Gly Ile Ala Phe Ala Lys Thr Ile Glu Gly Ile Gln
                165                 170                 175

Ser Gln Asn Val Gln Ala Cys Gly Lys His Tyr Ile Gly Tyr Glu Gln
            180                 185                 190

Glu Thr Gln Arg Asn Pro Thr Val Asn Glu Asp Gly Val Thr Ile Glu
        195                 200                 205

Ala Val Ser Ser Asn Ile Asp Asp Arg Thr Met His Glu Leu Tyr Leu
    210                 215                 220

Trp Pro Phe Ala Asp Gly Val Lys Ser Gly Leu Ala Ser Ile Met Cys
225                 230                 235                 240

Ser Tyr Asn Arg Leu Asn Glu Thr Tyr Ala Cys Gln Asn Ser Lys Thr
                245                 250                 255

Gln Asn Gly Leu Leu Lys Ser Glu Leu Gly Phe Gln Gly Tyr Val Thr
            260                 265                 270

Ser Asp Trp Gly Gly Thr His Ser Gly Val Asp Ala Ile Leu Ser Gly
        275                 280                 285

Glu Asp Met Asn Met Pro Gly Asn Leu Gly Pro Gly Ser Thr Val
    290                 295                 300

Ser Ser Tyr Trp Gly Tyr Asn Ile Thr Thr Phe Leu Asn Asn Gly Ser
305                 310                 315                 320

Val Pro Glu Ser Arg Ile Asp Asp Met Val Arg Ile Leu Thr Pro
                325                 330                 335

Tyr Phe Tyr Phe His Gln Asp Asp Ser Trp Pro Thr Ile Asp Leu
            340                 345                 350

Asp Thr Val Leu Leu Asn Glu Gly Val Leu Arg Asn His Val Pro Glu
        355                 360                 365

Tyr Gln His Pro Phe Asn Phe Gly Asn Val Ser Asp Met Asn Arg Asp
    370                 375                 380
```

```
Val Arg Ala Asp His Gly Val Leu Ile Arg Gln Ile Gly Ser Ala Ser
385                 390                 395                 400

Thr Val Leu Leu Lys Asn Val Asn Asn Thr Leu Pro Leu Arg Ser Pro
            405                 410                 415

Lys Arg Ile Ala Val Phe Gly Asn Ala Ala Pro Asp Leu Ser Gly Gly
            420                 425                 430

Pro Tyr Asp Pro Glu Asn Glu Asn Gly Pro Gln Ala Val Gly Gly Gly
            435                 440                 445

Ser Gly Thr Gly Arg Phe Thr Tyr Leu Ile Pro Pro Leu Glu Ala Ile
    450                 455                 460

Lys Gln Arg Asn Pro Ser Ala Leu Val Glu Tyr Val Thr Asp Asn Thr
465                 470                 475                 480

Leu Leu Thr Thr Gln Gln Ser Ser Thr Ile Leu Thr Ile Tyr Pro Gln
                485                 490                 495

Pro Asp Val Cys Leu Val Phe Leu Lys Ser Phe Ala Thr Glu Gly Glu
            500                 505                 510

Asp Arg Ala Ser Leu Leu Cys Asp Phe Asn Ser Thr Gly Val Val Asn
            515                 520                 525

Thr Val Thr Ser Ser Gly Leu Cys Pro Asn Thr Ile Val Ile Thr Asn
530                 535                 540

Ser Pro Gly Pro Asn Val Leu Pro Trp Ala Asp Asn Glu Asn Val Thr
545                 550                 555                 560

Gly Val Ile Val Gly His Tyr Pro Gly Glu Gln Ile Gly Asn Ser Ile
                565                 570                 575

Val Asp Val Leu Phe Gly Asp Val Asn Pro Ser Gly Lys Leu Pro Tyr
            580                 585                 590

Thr Ile Ala Tyr Gln Ala Ser Asp Tyr Asn Ala Gln Ile Val Asn Phe
    595                 600                 605

Thr Gly Val Asp Asp Asn Asp Pro Asn Leu Trp Gln Ser Asn Phe Thr
    610                 615                 620

Glu Gly Leu Leu Ile Asp Tyr Arg His Phe Asp Tyr Asn Asn Ile Thr
625                 630                 635                 640

Pro Arg Tyr Glu Phe Gly Phe Gly Leu Ser Tyr Thr Thr Phe Ser Leu
                645                 650                 655

Ser Asn Leu Gln Ile Ser Ser Asn Ala Ser Lys Val Ser Ala Tyr Pro
            660                 665                 670

Pro Ser Leu Gly Ser Gln Ile Pro Pro Gly Gly Asn Pro Ala Leu
            675                 680                 685

Tyr Asp Ile Leu Ala Thr Val Ala Val Asp Val Lys Asn Thr Gly Ser
    690                 695                 700

Val Ala Gly Ala Thr Val Pro Gln Leu Tyr Leu Gly Phe Pro Pro Asp
705                 710                 715                 720

Thr Pro Gly Pro Thr Pro Lys Val Leu Arg Gly Phe Asp Lys Thr
                725                 730                 735

Ser Val Leu Ala Ala Gly Gln Gln Glu Thr Ile Trp Phe Ser Leu Arg
            740                 745                 750

Arg Lys Asp Val Ser Phe Trp Asp Val Arg Gln Glu Trp Ala Ile
            755                 760                 765

Pro Ser Gly Pro Phe Thr Val Leu Val Gly Gln Ser Ser Arg Asp Leu
    770                 775                 780

Pro Leu Ser Gly Glu Leu Thr Phe Leu
785                 790
```

<210> SEQ ID NO 17
<211> LENGTH: 3012
<212> TYPE: DNA
<213> ORGANISM: Penicillium emersonii

<400> SEQUENCE: 17

| | | | | | |
|---|---|---|---|---|---|
| atgacggtca | tcacggcagt | atctcatgcg | ctcctgcttt | tgactctgtt | tttggcaggt | 60 |
| gtcgaggctc | gcaacaacag | caccgcatta | ccgccgtaca | agaatcctca | tctccccgtg | 120 |
| gagcagagag | ttgcggactt | gctgggccgg | atgaccctcg | aagacaaaat | ggctcaattg | 180 |
| atgcagggtg | cgtatgatgg | acaacagcta | taacctacag | agtagctaac | ctctggttga | 240 |
| acctgcgcag | gtgacatcac | caactggatg | aatgctacga | cgggtgcctt | caactatagc | 300 |
| ggtctcgtgg | agaatatgca | gacgaaggcg | gggatgtttt | acggtacgga | aacactctaa | 360 |
| agacatcact | tgcgcggctc | gaggtgacta | gtgtgctgga | aagactaaca | actgtcacgt | 420 |
| tcttgcagtt | ggatatcctg | ttccttggga | ctggctcaca | atcaacatcc | agagagccca | 480 |
| aaactacctg | ctcgagaaca | caacactagg | cattcctgcc | ctagtgcaaa | cggaaggtac | 540 |
| gtactagcgt | gagaggaata | tatccctgaa | ctcatctgat | aacgcttcca | ggtattcatg | 600 |
| gcttcctaat | cggtaatgga | accatcttca | actccccaat | tggctacgga | tcgtcctgga | 660 |
| accgcgacgt | aagtgggatt | gtctgtcagt | tactcaaaca | aagctaaata | atgatagct | 720 |
| tgtccgtaag | atgggacaga | tcatcgcaca | ggaggctcgt | gcactgggtg | tcactcagct | 780 |
| ttttgctccg | cttgcagatc | ttgctcgcga | gttgcgattt | ggtcgagtaa | gattatctca | 840 |
| ttttcggtct | accgatttta | cgtcaattgc | taataggagg | gcaggttgaa | gagacaacct | 900 |
| ctgaagatcc | atacctggcc | ggcgaaatca | cgtataatta | catcaaggga | ttgcagagcc | 960 |
| tgaatgtttc | cgcaacggtc | aagcatttca | tgggttttag | caatccggag | caaggtctca | 1020 |
| acacggggcc | tgttcatgga | ggcgagcggg | agctgcgaac | gacgtaagtt | ttctttattc | 1080 |
| atatttatct | gggccaaagg | ttctgattat | cagactaatt | tatggatcga | tagatgggcc | 1140 |
| ccatcctaca | aacgagctat | catcgatgct | ggagcgtgga | gtatcatgag | tgcatatcat | 1200 |
| aggtaagctt | atatctactg | tcttttctct | attcttttga | gagtttaagt | tgacttgtca | 1260 |
| cccctgctca | gttacgacgg | tattcctgcg | gttgcagacc | accacactct | cacggacata | 1320 |
| ctgcgagacg | aatggggata | caactactgg | gtcaccagcg | acgcaggcgg | tactgacaga | 1380 |
| ctctgcacgg | ccttcaagct | ctgcaaaagc | tcgcccatcg | actcggaagc | catcacgctg | 1440 |
| aaggccctgc | cggctggaaa | tgatgtggag | atgggaggag | gttcattgtg | agtcttccac | 1500 |
| agcatgaaga | gacagaaact | actaattctt | tttatagcaa | cttcaagaca | atccccgat | 1560 |
| tagttcaatc | aggaaaactc | gacatcaaaa | ccgtagatac | ggctgtctca | agacttctcc | 1620 |
| gcgccaagtt | cgagatgggc | ctcttcgaga | accccatctct | cggagcgccg | cagagtgaat | 1680 |
| ggtgcagtct | catccatacc | cccgaggcac | tgcaggtggc | ccgggaattg | gaccgtgaat | 1740 |
| cgattgtgct | gctcgaaaac | cacaacaaca | cgcttccact | caaaaagggc | gggagcatcg | 1800 |
| cggtcattgg | acctatggct | cacggcttta | tgaacgtagg | tctttcaaga | acgcaatccc | 1860 |
| cgtttcatat | acgatgaatc | aagcttatgg | actgttctct | agtatggaga | ctatgtcgtt | 1920 |
| tacaaaagcc | aataccgtgg | ggtaacgcct | cttgatggca | tcaaagccgc | agtcggcaac | 1980 |
| accacaacca | tcaactacgc | acaaggctgt | gagcgctgga | gcaacgatca | gtcgggattc | 2040 |
| cccgaagcaa | ttgctgctgc | gaagatgtcg | gacgtggcca | tcgtcatcgt | tgggacgtgg | 2100 |
| tcgcgggatc | aaacggagct | gtgggaaggg | ttgaatgcga | cgtaagccag | cgtgtattct | 2160 |

```
ccatgacagt ttctcccaac tggcactgga tagagtacat attggctaat actacatata    2220
ttgtactata gcaccggcga gcacgtcgat gagagcgatc tccgactcgt cggtgcccaa    2280
gcaccactca tcaaagccat cgctgacact ggcgtcccta ccgttgtcgt cttttcgtcc    2340
ggaaagccta tcacggaacc ctggatctcg aactcgaccg ccgctctggt ccagcagttc    2400
tacccgtccg agcaaggtgg tcatgccctc gcggatgttc tcttcggcga ctacaaccca    2460
tccggcaagc tgtcagtgag cttcccacga tccgtcggcg ccctacccat ctactatgat    2520
tacctcaatt ctggccggtc gatcaccgat tccggatata ttattaggga gaacgacact    2580
atagtcttcg gacaccagta cgtgattggg tcgccgctgc catggtatga gtttggctac    2640
gggaagagct actcgacttt cgagtacggt gccgtctcgc tggatcgcac gaatgtgtct    2700
gccagcgaca cagttaccat cagcgttaat gtgaccaata cacatccgtc ccgcgacggc    2760
actgaggtcg tccaggtcta tgtcgtcgac gagtacgcct cggtcgtggt gccgaatcgg    2820
cagctgaagg ggtttgacaa ggtgttcatc cgcgctggtc agacgaagac cgtgcagatc    2880
ccgctgcagg tcggtgacct gggcctgtgg gacgtcaata tgaactacgt cgtcgagccg    2940
ggggcgttta tcgtcctggt tggaagtagt tcggcggata tcaggggcaa tgcgacgttt    3000
tatgtgtctt ga                                                       3012
```

<210> SEQ ID NO 18
<211> LENGTH: 784
<212> TYPE: PRT
<213> ORGANISM: Penicillium emersonii

<400> SEQUENCE: 18

```
Met Thr Val Ile Thr Ala Val Ser His Ala Leu Leu Leu Thr Leu
1               5                   10                  15

Phe Leu Ala Gly Val Glu Ala Arg Asn Asn Ser Thr Ala Leu Pro Pro
                20                  25                  30

Tyr Lys Asn Pro His Leu Pro Val Glu Gln Arg Val Ala Asp Leu Leu
            35                  40                  45

Gly Arg Met Thr Leu Glu Asp Lys Met Ala Gln Leu Met Gln Gly Asp
    50                  55                  60

Ile Thr Asn Trp Met Asn Ala Thr Thr Gly Ala Phe Asn Tyr Ser Gly
65                  70                  75                  80

Leu Val Glu Asn Met Gln Thr Lys Ala Gly Met Phe Tyr Val Gly Tyr
                85                  90                  95

Pro Val Pro Trp Asp Trp Leu Thr Ile Asn Ile Gln Arg Ala Gln Asn
            100                 105                 110

Tyr Leu Leu Glu Asn Thr Thr Leu Gly Ile Pro Ala Leu Val Gln Thr
        115                 120                 125

Glu Gly Ile His Gly Phe Leu Ile Gly Asn Gly Thr Ile Phe Asn Ser
    130                 135                 140

Pro Ile Gly Tyr Gly Ser Ser Trp Asn Arg Asp Leu Val Arg Lys Met
145                 150                 155                 160

Gly Gln Ile Ile Ala Gln Glu Ala Arg Ala Leu Gly Val Thr Gln Leu
                165                 170                 175

Phe Ala Pro Leu Ala Asp Leu Ala Arg Glu Leu Arg Phe Gly Arg Val
            180                 185                 190

Glu Glu Thr Thr Ser Glu Asp Pro Tyr Leu Ala Gly Glu Ile Thr Tyr
        195                 200                 205

Asn Tyr Ile Lys Gly Leu Gln Ser Leu Asn Val Ser Ala Thr Val Lys
```

-continued

```
                210                 215                 220
His Phe Met Gly Phe Ser Asn Pro Glu Gln Gly Leu Asn Thr Gly Pro
225                 230                 235                 240

Val His Gly Gly Glu Arg Glu Leu Arg Thr Thr Trp Ala Pro Ser Tyr
                245                 250                 255

Lys Arg Ala Ile Ile Asp Ala Gly Ala Trp Ser Ile Met Ser Ala Tyr
                260                 265                 270

His Ser Tyr Asp Gly Ile Pro Ala Val Ala Asp His His Thr Leu Thr
                275                 280                 285

Asp Ile Leu Arg Asp Glu Trp Gly Tyr Asn Tyr Trp Val Thr Ser Asp
290                 295                 300

Ala Gly Gly Thr Asp Arg Leu Cys Thr Ala Phe Lys Leu Cys Lys Ser
305                 310                 315                 320

Ser Pro Ile Asp Ser Glu Ala Ile Thr Leu Lys Ala Leu Pro Ala Gly
                325                 330                 335

Asn Asp Val Glu Met Gly Gly Ser Phe Asn Phe Lys Thr Ile Pro
                340                 345                 350

Arg Leu Val Gln Ser Gly Lys Leu Asp Ile Lys Thr Val Asp Thr Ala
                355                 360                 365

Val Ser Arg Leu Leu Arg Ala Lys Phe Glu Met Gly Leu Phe Glu Asn
370                 375                 380

Pro Tyr Leu Gly Ala Pro Gln Ser Glu Trp Cys Ser Leu Ile His Thr
385                 390                 395                 400

Pro Glu Ala Leu Gln Val Ala Arg Glu Leu Asp Arg Glu Ser Ile Val
                405                 410                 415

Leu Leu Glu Asn His Asn Asn Thr Leu Pro Leu Lys Lys Gly Gly Ser
                420                 425                 430

Ile Ala Val Ile Gly Pro Met Ala His Gly Phe Met Asn Tyr Gly Asp
                435                 440                 445

Tyr Val Val Tyr Lys Ser Gln Tyr Arg Gly Val Thr Pro Leu Asp Gly
450                 455                 460

Ile Lys Ala Ala Val Gly Asn Thr Thr Thr Ile Asn Tyr Ala Gln Gly
465                 470                 475                 480

Cys Glu Arg Trp Ser Asn Asp Gln Ser Gly Phe Pro Glu Ala Ile Ala
                485                 490                 495

Ala Ala Lys Met Ser Asp Val Ala Ile Val Ile Val Gly Thr Trp Ser
                500                 505                 510

Arg Asp Gln Thr Glu Leu Trp Glu Gly Leu Asn Ala Thr Thr Gly Glu
                515                 520                 525

His Val Asp Glu Ser Asp Leu Arg Leu Val Gly Ala Gln Ala Pro Leu
                530                 535                 540

Ile Lys Ala Ile Ala Asp Thr Gly Val Pro Thr Val Val Phe Ser
545                 550                 555                 560

Ser Gly Lys Pro Ile Thr Glu Pro Trp Ile Ser Asn Ser Thr Ala Ala
                565                 570                 575

Leu Val Gln Gln Phe Tyr Pro Ser Glu Gln Gly His Ala Leu Ala
                580                 585                 590

Asp Val Leu Phe Gly Asp Tyr Asn Pro Ser Gly Lys Leu Ser Val Ser
                595                 600                 605

Phe Pro Arg Ser Val Gly Ala Leu Pro Ile Tyr Tyr Asp Tyr Leu Asn
                610                 615                 620

Ser Gly Arg Ser Ile Thr Asp Ser Gly Tyr Ile Ile Arg Glu Asn Asp
625                 630                 635                 640
```

```
Thr Ile Val Phe Gly His Gln Tyr Val Ile Gly Ser Pro Leu Pro Trp
                645                 650                 655
Tyr Glu Phe Gly Tyr Gly Lys Ser Tyr Ser Thr Phe Glu Tyr Gly Ala
            660                 665                 670
Val Ser Leu Asp Arg Thr Asn Val Ser Ala Ser Asp Thr Val Thr Ile
        675                 680                 685
Ser Val Asn Val Thr Asn Thr His Pro Ser Arg Asp Gly Thr Glu Val
    690                 695                 700
Val Gln Val Tyr Val Val Asp Glu Tyr Ala Ser Val Val Pro Asn
705                 710                 715                 720
Arg Gln Leu Lys Gly Phe Asp Lys Val Phe Ile Arg Ala Gly Gln Thr
                725                 730                 735
Lys Thr Val Gln Ile Pro Leu Gln Val Gly Asp Leu Gly Leu Trp Asp
            740                 745                 750
Val Asn Met Asn Tyr Val Val Glu Pro Gly Ala Phe Ile Val Leu Val
        755                 760                 765
Gly Ser Ser Ser Ala Asp Ile Arg Gly Asn Ala Thr Phe Tyr Val Ser
    770                 775                 780
```

<210> SEQ ID NO 19
<211> LENGTH: 2771
<212> TYPE: DNA
<213> ORGANISM: Penicillium emersonii

<400> SEQUENCE: 19

```
atgtctttcc taatccgtgt actccttttt gtctccttcc tgttttttccc tactgcggta    60
ctatcatcct cgggatcaga ggataaggaa tctaatcctc acattcgtcg acgcactgat   120
ctccctccgg gatattcgtc gccggactac taccccaccc ccaatggcgg ctgggtgtcg   180
gaatgggcgg atgcctatgc caaggcgcag aaggtcgtga gccagatgac cctggcagaa   240
aaggtcaaca tcacttccgg aacgggctac ttcatgggtc cctgcgtggg aaatactggg   300
agcgccttgc gtttcgggat tcccaatctc tgtctgcaag atggtccctt gggaattcgc   360
aacacggatc acaatacggc attccctgcg ggaatcacca ctggggcaac ctttgacaag   420
gagttgatgt acgctcgtgg ggtggctctg gccaggaag cccgcgggaa aggcatcaac   480
gttcaaatgg ccctgttgt tggaccttta ggacgaaaac ctcgatcagg acgtatctgg   540
gagggctttg agcggatcc ctcgctgcag gcgatcgggg cagcgcaaac gattcagggc   600
atgcagagcg ttggcgtcat cgcgacgctc aagcattata ttggaaatga gcaagagatg   660
taccgcatga ccgatatcct ccagcaaggc tattcgtcca atatcgatga ccgcactctc   720
catgagatct atctctggcc gtttgctgag ggagttcgcg ccggggttgg atccgttatg   780
gcggcttaca atgatgtatg ctttgccttt ttgtcgccat tattgctcac taacctcgca   840
ccaggtcaat ggaacggcat gtacccagaa cagtaaactc atcaatgacc tcttgaaaga   900
tgagctgggt tttcaagggt tgtagtgtc ggactggtac gcccagatcg aggtgtctc   960
ttcagcgctg gctggactgg atatggccat gccaggggat ggcgttgttc cattgttagg  1020
agacagcttc tggaactatg agctatcaac agccatcttg aatgggactg tgccagtgga  1080
gagactgaat gacatggtaa gctttccatc ttggtcgatc atccatcagt gtcattagca  1140
catagatggt agctgttctg tatagtgaga acatctttgc tgacgtcatt taggtcactc  1200
ggattgttgc aacgtggtat aaaatgggcc aggacaagga ctatccgttg cccaactttt  1260
ccacgaatac ccaggacgca gtcggtccac tctatccggg agctctcttc tcgcccactg  1320
```

-continued

```
gagtggtcaa ccaatttgtc aacgtccaag gggatcacaa cgttgtcgcg agagctgtgg      1380
ccagagacgc catcacgctc ctcaagaatg acgataatgc tcttccactc aaacgcaacg      1440
cctcattgaa agtttttggc gccgacgcgg gcccgaatcc ggatggtctc aactcctgca      1500
gcgaccaagg atgcgacaag ggcgtgctga ctatgggatg gggaagtggt agcgccagac      1560
tcccctatct cattacccct caggatgcta ccgcaacgt ctcctccaat gctcaattct       1620
atatctccga ttcatttccg tctgatatct ccgctggccc taatgatatt gctgtcgtct      1680
ttatcaatgc cgactccggc gagaattaca tcactgtgga gggaaacccc ggtgaccggc      1740
tggtagctgg gctgtatgcg tggcacaacg gagacgagtc agtgcaagct gcggcgaaga      1800
aattctccac tgtcgtcgtt gtggtgcaca ctgtaggccc aattatcctt gagaactgga      1860
tcgacctgcc ctcagtcaag gccgtgcttt tgctcatct tccaggtcaa gaagctggtg       1920
actcgcttgt ggatgttctg ttcggtgact acagcccgag tgggcatctg ccatatacaa      1980
ttccgtacaa ggaatccgac tatccatcta gtgtgagtct gatcgaccaa ccgtttgggc      2040
agattcagga tacctataca gagcgcatct acatcgatta ccgccatttc ctccaagcta      2100
acatcacccc gcggtatcca tttggtcacg gtctgtccta caccaccttc aacttttcag      2160
aaccctctct atcagcaatc acgcctctca ctcaatatcc tccgcctcgt cctcccaagg      2220
gccctacgcc cacatacaac aataccattc cgcctgcgtc cgaagtcgcc tggccaaagg      2280
atttcaaccg catctggcgt tatctgtacc catacctgga caatcctgcc gctgcaacgt      2340
cgactgcacc ttatccttac ccaacggggt ataccacgac tccgaagcca ccccgcgag      2400
ctggtggctc ccaaggcgga aactcggcgt tgtgggatgt cgccttcaac gtgagcgtga      2460
aagtcagcaa cacgggttcc cgtcccggcc gtgcggtcgc gcagctgtat gtcgagctgc      2520
ccgcgtcgac tctcggggtt gacttgcccc ctttgcagct gcgccaattc gaaaagaccg      2580
ccattctgcc gcctggagag agtcaggtgt tgacgctctc ggtgacgcgg aaggatttga      2640
gtatctggga cgttgtggca caggactgga aggcgccagt ggacgggcag ggagtgaagt      2700
tttggatagg cgagagcgtg gctgatttga aggttgtgtg tgaagttggt ggacagtgtg      2760
ggagtgtcta g                                                          2771
```

<210> SEQ ID NO 20
<211> LENGTH: 874
<212> TYPE: PRT
<213> ORGANISM: Penicillium emersonii

<400> SEQUENCE: 20

```
Met Ser Phe Leu Ile Arg Val Leu Leu Phe Val Ser Phe Leu Phe Phe
1               5                   10                  15

Pro Thr Ala Val Leu Ser Ser Gly Ser Glu Asp Lys Glu Ser Asn
            20                  25                  30

Pro His Ile Arg Arg Arg Thr Asp Leu Pro Pro Gly Tyr Ser Ser Pro
        35                  40                  45

Asp Tyr Tyr Pro Thr Pro Asn Gly Gly Trp Val Ser Glu Trp Ala Asp
    50                  55                  60

Ala Tyr Ala Lys Ala Gln Lys Val Val Ser Gln Met Thr Leu Ala Glu
65                  70                  75                  80

Lys Val Asn Ile Thr Ser Gly Thr Gly Tyr Phe Met Gly Pro Cys Val
                85                  90                  95

Gly Asn Thr Gly Ser Ala Leu Arg Phe Gly Ile Pro Asn Leu Cys Leu
            100                 105                 110
```

-continued

```
Gln Asp Gly Pro Leu Gly Ile Arg Asn Thr Asp His Asn Thr Ala Phe
        115                 120                 125

Pro Ala Gly Ile Thr Thr Gly Ala Thr Phe Asp Lys Glu Leu Met Tyr
130                 135                 140

Ala Arg Gly Val Ala Leu Gly Gln Glu Ala Arg Gly Lys Gly Ile Asn
145                 150                 155                 160

Val Gln Met Gly Pro Val Val Gly Pro Leu Gly Arg Lys Pro Arg Ser
                165                 170                 175

Gly Arg Ile Trp Glu Gly Phe Gly Ala Asp Pro Ser Leu Gln Ala Ile
                180                 185                 190

Gly Ala Ala Gln Thr Ile Gln Gly Met Gln Ser Val Gly Val Ile Ala
            195                 200                 205

Thr Leu Lys His Tyr Ile Gly Asn Glu Gln Glu Met Tyr Arg Met Thr
210                 215                 220

Asp Ile Leu Gln Gln Gly Tyr Ser Ser Asn Ile Asp Asp Arg Thr Leu
225                 230                 235                 240

His Glu Ile Tyr Leu Trp Pro Phe Ala Glu Gly Val Arg Ala Gly Val
                245                 250                 255

Gly Ser Val Met Ala Ala Tyr Asn Asp Val Asn Gly Thr Ala Cys Thr
                260                 265                 270

Gln Asn Ser Lys Leu Ile Asn Asp Leu Leu Lys Asp Glu Leu Gly Phe
            275                 280                 285

Gln Gly Phe Val Val Ser Asp Trp Tyr Ala Gln Ile Gly Gly Val Ser
        290                 295                 300

Ser Ala Leu Ala Gly Leu Asp Met Ala Met Pro Gly Asp Gly Val Val
305                 310                 315                 320

Pro Leu Leu Gly Asp Ser Phe Trp Asn Tyr Glu Leu Ser Thr Ala Ile
                325                 330                 335

Leu Asn Gly Thr Val Pro Val Glu Arg Leu Asn Asp Met Val Thr Arg
            340                 345                 350

Ile Val Ala Thr Trp Tyr Lys Met Gly Gln Asp Lys Asp Tyr Pro Leu
        355                 360                 365

Pro Asn Phe Ser Thr Asn Thr Gln Asp Ala Val Gly Pro Leu Tyr Pro
370                 375                 380

Gly Ala Leu Phe Ser Pro Thr Gly Val Val Asn Gln Phe Val Asn Val
385                 390                 395                 400

Gln Gly Asp His Asn Val Val Ala Arg Ala Val Ala Arg Asp Ala Ile
                405                 410                 415

Thr Leu Leu Lys Asn Asp Asp Asn Ala Leu Pro Leu Lys Arg Asn Ala
            420                 425                 430

Ser Leu Lys Val Phe Gly Ala Asp Ala Gly Pro Asn Pro Asp Gly Leu
        435                 440                 445

Asn Ser Cys Ser Asp Gln Gly Cys Asp Lys Gly Val Leu Thr Met Gly
450                 455                 460

Trp Gly Ser Gly Ser Ala Arg Leu Pro Tyr Leu Ile Thr Pro Gln Asp
465                 470                 475                 480

Ala Ile Arg Asn Val Ser Ser Asn Ala Gln Phe Tyr Ile Ser Asp Ser
                485                 490                 495

Phe Pro Ser Asp Ile Ser Ala Gly Pro Asn Asp Ile Ala Val Val Phe
            500                 505                 510

Ile Asn Ala Asp Ser Gly Glu Asn Tyr Ile Thr Val Glu Gly Asn Pro
        515                 520                 525
```

```
Gly Asp Arg Leu Val Ala Gly Leu Tyr Ala Trp His Asn Gly Asp Glu
            530                 535                 540
Leu Val Gln Ala Ala Lys Lys Phe Ser Thr Val Val Val Val
545                 550                 555                 560
His Thr Val Gly Pro Ile Ile Leu Glu Asn Trp Ile Asp Leu Pro Ser
                565                 570                 575
Val Lys Ala Val Leu Phe Ala His Leu Pro Gly Gln Glu Ala Gly Asp
            580                 585                 590
Ser Leu Val Asp Val Leu Phe Gly Asp Tyr Ser Pro Ser Gly His Leu
                595                 600                 605
Pro Tyr Thr Ile Pro Tyr Lys Glu Ser Asp Tyr Pro Ser Ser Val Ser
610                 615                 620
Leu Ile Asp Gln Pro Phe Gly Gln Ile Gln Asp Thr Tyr Thr Glu Arg
625                 630                 635                 640
Ile Tyr Ile Asp Tyr Arg His Phe Leu Gln Ala Asn Ile Thr Pro Arg
                645                 650                 655
Tyr Pro Phe Gly His Gly Leu Ser Tyr Thr Thr Phe Asn Phe Ser Glu
                660                 665                 670
Pro Ser Leu Ser Ala Ile Thr Pro Leu Thr Gln Tyr Pro Pro Arg
            675                 680                 685
Pro Pro Lys Gly Pro Thr Pro Thr Tyr Asn Asn Thr Ile Pro Pro Ala
690                 695                 700
Ser Glu Val Ala Trp Pro Lys Asp Phe Asn Arg Ile Trp Arg Tyr Leu
705                 710                 715                 720
Tyr Pro Tyr Leu Asp Asn Pro Ala Ala Ala Thr Ser Thr Ala Pro Tyr
                725                 730                 735
Pro Tyr Pro Thr Gly Tyr Thr Thr Thr Pro Lys Pro Pro Arg Ala
            740                 745                 750
Gly Gly Ser Gln Gly Gly Asn Ser Ala Leu Trp Asp Val Ala Phe Asn
            755                 760                 765
Val Ser Val Lys Val Ser Asn Thr Gly Ser Arg Pro Gly Arg Ala Val
770                 775                 780
Ala Gln Leu Tyr Val Glu Leu Pro Ala Ser Thr Leu Gly Val Asp Leu
785                 790                 795                 800
Pro Pro Leu Gln Leu Arg Gln Phe Glu Lys Thr Ala Ile Leu Pro Pro
                805                 810                 815
Gly Glu Ser Gln Val Leu Thr Leu Ser Val Thr Arg Lys Asp Leu Ser
            820                 825                 830
Ile Trp Asp Val Val Ala Gln Asp Trp Lys Ala Pro Val Asp Gly Gln
            835                 840                 845
Gly Val Lys Phe Trp Ile Gly Glu Ser Val Ala Asp Leu Lys Val Val
850                 855                 860
Cys Glu Val Gly Gly Gln Cys Gly Ser Val
865                 870
```

<210> SEQ ID NO 21
<211> LENGTH: 2874
<212> TYPE: DNA
<213> ORGANISM: Scytalidium thermophilum

<400> SEQUENCE: 21

```
atgggtcatc acactgccac cgtatgcctc tggctcgccc tgggctcctt gacgcccgtc      60
tcctttgccc gcgttgtcga gccccgcgat cctgttcctc aagggtatca tgctgcttcc     120
tactaccccg cgccccatgg cggttgggtc agctcgtggc gcgaggccta cgaaaaagcc     180
```

-continued

```
tatgcactgg tgtcgcagat gacgctggct gagaaggtga acatcacatc gggcgttggc      240
atttatatgg gtacgtactc ctcagaattt ccttttgcgg cgtccgccag ttgcgttctg      300
attactgaca acggcggcag ggtcagtacc gaggagattg catcacccaa ttgtcaattg      360
atattcgaag acagcccgct gacaaaccat gtagaccctg tgtaggaaat accgggagtg      420
tggatcgtct cggcttcccc cagctctgcc tccaagacag cgctctcggc gtcgcctccg      480
ccgacaatgt cacggctttt cccgctggca ttaccaccgg tgccacctgg gacaagcagt      540
tgatgtatgc ccgaggcgtc gcgatcggca aggagttccg cggcaagggc gccaatattc      600
acttgggtcc ttcggttggg cccctcggcc gcaagccctt gggcggccgg aactgggagg      660
gctttggctc cgacccggtg ctccagggca aggccgctgc tctgcacatc cgcggcgttc      720
aggagcaggg cattattgcc accattaagc accttgtcgg caatgagcag agatgtacc       780 gcatgtacca cattttcag gagggttaca cgccaacat tggtgagtat aacctagttc        840
caaccagaag aagcgcctcg gttgacaaag ccttcagacg accgtactct gcatgagctc      900
tacctctggc ccttcgcgga ggcagttcgt gctggagtgg gagccgccat gacggcctac      960
aatgccgtca atggctccgc ttgttcccag aacagttatc tcatcaatgg cattctcaaa     1020
gacgaactcg gcttccaggg attggtcatg tcggactggc tcagtcacat ctcaggcgtg     1080
ggctcggctc tggccggtct tgacctcaac atgccgggcg atacaaacat tcccttgttt     1140
ggtaacagtc tgtggcagta cgagctgact cgtgccgtcc tgaacggctc cgtgcctgta     1200
gacagactga acgacatggc cacgcgcgtt gtggccacct ggtacaagtt tgggcaggat     1260
aagaaccacc cacggcccaa cttctcatcc aacactcgca gccgtgacgg gcccctgtac     1320
cccggcgccc ttttttctcc cagcggtcag gtgaattggt tcgtcaacgt ccaggaggat     1380
cactatcttg tcgcccgcca ggtggctcaa gatgccatca cgctgctcaa gaataacgac     1440
agcctcttgc ctctggacgc tgggatcttc actggcggca agctcagcgt cttcggcact     1500
gacgcccaag tcaaccccga tgggcccaac tcctgcctag cacgggcttg taacaaaggc     1560
actcttggca tgggttgggg ctcgggtatc gcggactatc cgtacatgga cgatcccatc     1620
ggagccatcc gcaagcgcgt ccccgacgtg aagttctaca cacgacagc ctttccgtgg      1680 ttctttggca cgccggagaa tgacgaggtt gctatggtgt tcatcagctc cgactcggga     1740
gagaatacgc tgacagtcga gggcaaccat ggcgaccgcg actcggccaa gctgagggca     1800 tgcacgacg gtgacaagct cgtgcagaag gtggctgaga aattcaagaa cgtaatcgtc       1860
gtcgtgcata cggttggtcc cctgaccctt gagccatgga ttgaacttcc ctcggtcaaa     1920
gccgtcctct ttgcccacct tcccggccaa gaagccggcg agtctctgac caacgtcctc     1980
ttcggcgacg tctcgccgag tggccacctc ccctactcca tcactcgcaa ggcctccgat     2040
ctgcccgaca gcatcgccaa cctgaagggt ttcacctggg gccaagtcca agacacctac     2100
tccgaagggc tctacatcga ctaccgctac ctgcaaaagc actcgatcca gcccgcttc      2160 gccttcggcc acggcttgag ctacaccaac ttctccttca ccaatgccac catccgcgcc     2220
atcactaccc ccctatccgt cacccgcca gccgcc       ccaccaggcc cgcctcagtc       2280
gtcgctaaat actccaccga catccgccc gccagcgaag cctacgagcc tgcaggcttc        2340
tccaggatct ggcgctacct ctaccctgg ctgtccaaat ccgacgccga cgccgccac          2400 gctatcggca cgagcaagtc caaaacctac cctaccctc ccggctattc caccgtgcag        2460
cgcgcgtctt tccctcccgc tggcggcggc gagggcggca accccgcgct ctgggacgtg     2520
```

-continued

```
gcatacgagg tgacggtgcg cgtcaccaac acgggcaaga ggcccgggaa agcctcggcg    2580
cagctgtatc tgcagttccc ggaggggatc gagtacgata cccccgtact gcagctccgg    2640
gatttcgaga agaccaagga gctccagccg gcgagagcc aggagctgaa gctgacattg      2700
acgaggaagg atgtcagcgt gtgggacgtg aggaggcaga actgggttgt tccgacggcg    2760
attgacgaca agaaggggtt cacggcgtgg gtgggcgagg cgagcgataa gttgaaggtg    2820
gcgtgctaca cgggtgaggg gaggtgtgtg gaggggggcga agcagccggt ttga          2874
```

<210> SEQ ID NO 22
<211> LENGTH: 887
<212> TYPE: PRT
<213> ORGANISM: Scytalidium thermophilum

<400> SEQUENCE: 22

```
Met Gly His His Thr Ala Thr Val Cys Leu Trp Leu Ala Leu Gly Ser
1               5                   10                  15

Leu Thr Pro Val Ser Phe Ala Arg Val Val Glu Pro Arg Asp Pro Val
            20                  25                  30

Pro Gln Gly Tyr His Ala Ala Ser Tyr Tyr Pro Ala Pro His Gly Gly
        35                  40                  45

Trp Val Ser Ser Trp Arg Glu Ala Tyr Glu Lys Ala Tyr Ala Leu Val
    50                  55                  60

Ser Gln Met Thr Leu Ala Glu Lys Val Asn Ile Thr Ser Gly Val Gly
65                  70                  75                  80

Ile Tyr Met Gly Asn Thr Gly Ser Val Asp Arg Leu Gly Phe Pro Gln
                85                  90                  95

Leu Cys Leu Gln Asp Ser Ala Leu Gly Val Ala Ser Ala Asp Asn Val
            100                 105                 110

Thr Ala Phe Pro Ala Gly Ile Thr Thr Gly Ala Thr Trp Asp Lys Gln
        115                 120                 125

Leu Met Tyr Ala Arg Gly Val Ala Ile Gly Lys Glu Phe Arg Gly Lys
    130                 135                 140

Gly Ala Asn Ile His Leu Gly Pro Ser Val Gly Pro Leu Gly Arg Lys
145                 150                 155                 160

Pro Leu Gly Gly Arg Asn Trp Glu Gly Phe Gly Ser Asp Pro Val Leu
                165                 170                 175

Gln Gly Lys Ala Ala Leu His Ile Arg Gly Val Gln Glu Gln Gly
            180                 185                 190

Ile Ile Ala Thr Ile Lys His Leu Val Gly Asn Glu Gln Glu Met Tyr
        195                 200                 205

Arg Met Tyr His Ile Phe Gln Glu Gly Tyr Ser Ala Asn Ile Asp Asp
    210                 215                 220

Arg Thr Leu His Glu Leu Tyr Leu Trp Pro Phe Ala Glu Ala Val Arg
225                 230                 235                 240

Ala Gly Val Gly Ala Ala Met Thr Ala Tyr Asn Ala Val Asn Gly Ser
                245                 250                 255

Ala Cys Ser Gln Asn Ser Tyr Leu Ile Asn Gly Ile Leu Lys Asp Glu
            260                 265                 270

Leu Gly Phe Gln Gly Leu Val Met Ser Asp Trp Leu Ser His Ile Ser
        275                 280                 285

Gly Val Gly Ser Ala Leu Ala Gly Leu Asp Leu Asn Met Pro Gly Asp
    290                 295                 300

Thr Asn Ile Pro Leu Phe Gly Asn Ser Leu Trp Gln Tyr Glu Leu Thr
305                 310                 315                 320
```

```
Arg Ala Val Leu Asn Gly Ser Val Pro Val Asp Arg Leu Asn Asp Met
            325                 330                 335

Ala Thr Arg Val Val Ala Thr Trp Tyr Lys Phe Gly Gln Asp Lys Asn
            340                 345                 350

His Pro Arg Pro Asn Phe Ser Ser Asn Thr Arg Ser Arg Asp Gly Pro
            355                 360                 365

Leu Tyr Pro Gly Ala Leu Phe Ser Pro Ser Gly Gln Val Asn Trp Phe
            370                 375                 380

Val Asn Val Gln Glu Asp His Tyr Leu Val Ala Arg Gln Val Ala Gln
385                 390                 395                 400

Asp Ala Ile Thr Leu Leu Lys Asn Asn Asp Ser Leu Leu Pro Leu Asp
                    405                 410                 415

Ala Gly Asp Leu Thr Gly Gly Lys Leu Ser Val Phe Gly Thr Asp Ala
            420                 425                 430

Gln Val Asn Pro Asp Gly Pro Asn Ser Cys Leu Ala Arg Ala Cys Asn
            435                 440                 445

Lys Gly Thr Leu Gly Met Gly Trp Gly Ser Gly Ile Ala Asp Tyr Pro
            450                 455                 460

Tyr Met Asp Asp Pro Ile Gly Ala Ile Arg Lys Arg Val Pro Asp Val
465                 470                 475                 480

Lys Phe Tyr Asn Thr Asp Ser Phe Pro Trp Phe Phe Gly Thr Pro Glu
                    485                 490                 495

Asn Asp Glu Val Ala Met Val Phe Ile Ser Ser Asp Ser Gly Glu Asn
            500                 505                 510

Thr Leu Thr Val Glu Gly Asn His Gly Asp Arg Asp Ser Ala Lys Leu
            515                 520                 525

Arg Ala Trp His Asp Gly Asp Lys Leu Val Gln Lys Val Ala Glu Lys
            530                 535                 540

Phe Lys Asn Val Ile Val Val His Thr Val Gly Pro Leu Asp Leu
545                 550                 555                 560

Glu Pro Trp Ile Glu Leu Pro Ser Val Lys Ala Val Leu Phe Ala His
                    565                 570                 575

Leu Pro Gly Gln Glu Ala Gly Glu Ser Leu Thr Asn Val Leu Phe Gly
            580                 585                 590

Asp Val Ser Pro Ser Gly His Leu Pro Tyr Ser Ile Thr Arg Lys Ala
            595                 600                 605

Ser Asp Leu Pro Asp Ser Ile Ala Asn Leu Lys Gly Phe Thr Trp Gly
            610                 615                 620

Gln Val Gln Asp Thr Tyr Ser Glu Gly Leu Tyr Ile Asp Tyr Arg Tyr
625                 630                 635                 640

Leu Gln Lys His Ser Ile Gln Pro Arg Phe Ala Phe Gly His Gly Leu
                    645                 650                 655

Ser Tyr Thr Asn Phe Ser Phe Thr Asn Ala Thr Ile Arg Ala Ile Thr
            660                 665                 670

Thr Pro Leu Ser Val Thr Pro Pro Ala Pro Ala Thr Arg Pro Ala
            675                 680                 685

Ser Val Val Ala Lys Tyr Ser Thr Asp Ile Pro Pro Ala Ser Glu Ala
            690                 695                 700

Tyr Glu Pro Ala Gly Phe Ser Arg Ile Trp Arg Tyr Leu Tyr Pro Trp
705                 710                 715                 720

Leu Ser Lys Ser Asp Ala Asp Ala Ala His Ala Ile Gly Thr Ser Lys
                    725                 730                 735
```

Ser Lys Thr Tyr Pro Tyr Pro Pro Gly Tyr Ser Thr Val Gln Arg Ala
              740                 745                 750

Ser Phe Pro Pro Ala Gly Gly Glu Gly Gly Asn Pro Ala Leu Trp
        755                 760                 765

Asp Val Ala Tyr Glu Val Thr Val Arg Val Thr Asn Thr Gly Lys Arg
770                 775                 780

Pro Gly Lys Ala Ser Ala Gln Leu Tyr Leu Gln Phe Pro Glu Gly Ile
785                 790                 795                 800

Glu Tyr Asp Thr Pro Val Leu Gln Leu Arg Asp Phe Glu Lys Thr Lys
                805                 810                 815

Glu Leu Gln Pro Gly Glu Ser Gln Glu Leu Lys Leu Thr Leu Thr Arg
            820                 825                 830

Lys Asp Val Ser Val Trp Asp Val Arg Arg Gln Asn Trp Val Val Pro
        835                 840                 845

Thr Ala Ile Asp Asp Lys Lys Gly Phe Thr Ala Trp Val Gly Glu Ala
    850                 855                 860

Ser Asp Lys Leu Lys Val Ala Cys Tyr Thr Gly Glu Gly Arg Cys Val
865                 870                 875                 880

Glu Gly Ala Lys Gln Pro Val
              885

<210> SEQ ID NO 23
<211> LENGTH: 2932
<212> TYPE: DNA
<213> ORGANISM: Rhizomucor pusillus

<400> SEQUENCE: 23
atgcgttcgc tagcaaatat atctctttgg ggcctgatcc tgttaggcac tatccaatca      60
ggacaagcaa ggcctacaga caaaccttac aatgtcttga catgggaaga agcttatgcc     120
aaggctgaga agctgctgtc acaaatgacc ctggagcaaa agtcaatct aacaaccggc      180 actggaaatc agcaaggccc gtgcgaaggc aataccgccc tgtggagga tccgtatttc      240 cctgcgctat gcttgaatga tggacctatt ggtcttcgtg aagcgctgaa cacgagtgcc     300
tttgtgaccg gtatcaactc ttgtgcatca tttgatagag atctcatccg acaacgcggg     360
cagtacatgg gtgccgaatt ccatgataag ggagtcaacg tgcagctagg tcctggtatg     420
aacctcatga gaagtcccag aggtaagagc ctttttcactt gcaataagc atgaatggat     480 tctaaaataa cttcctacag ccggacgcaa ctgggaattt ggtagcgaag atccatatct     540
acttggtata gtctctgcag agacgattct tggtatccag agctctggcg tggtaagact     600 catttagct tctattttac tactcgctaa gcttttaca tatcattaat ggctttacat        660
agatggctac tgccaaacat tatatcggaa atgagcaaga gctcaatcgc tccacggtac     720
gaaggcacta ttctgtttca ctattactac tcaacattga caccatatgg aacgtaggaa     780
tctaccgtta tggatgatcg cacgtatcat gaaatatatc tctggccatt gctcgatca      840 gttgaggccg gcgtcaccgc tgttatgtgc gcttacaata aaggtatcaa tgaattgatg     900
gaaaacacga agcaagttt atggtcaata ctgagctctt tgtgtagtt aatggcactt       960 atgcatgcga aaatgactat actttgaacc atgttctgaa gggagaactt ggtttcaagg    1020
gctttgtcat gagtgactgg tgggctacac attctactgc caccagtgct aacaatggaa    1080
tggatatgag catgccaggt acgttcttta cccaaaaatc cattgctaaa tttgaaattc    1140
ctatttatac aatttatata catgtaggcg atgccaacga tcaaagcatt accggcggtg    1200
gcctttggta tggaaagaac ctcacggatg ccgtcaaaaa tggagaagtc gacgaatcac    1260

```
gagtccatga tatggctctc cgcattgccg ccagctggta taaggtaata atggagacgt   1320
aatgctaatg tctgtcagaa ctttatctga ttatgtatatc gatttacgca aaacaggttg   1380
gacaggataa ggtaaaaaga aaagtttaca gatgtgaaag agtttatcgc ttgcaagagt   1440
cgttaacact gctatgcagg actatccgtc tcttaatttc aatatgtttg atccaagcgt   1500
cggtcaagac cttgacgtcc aaggaaacca caaggaaatt attcgagcga tgggtcgtgc   1560
gtcgctggtt ttacttcgca acgaggatag cattttacct ctgaaggaag atagcctcaa   1620
gaaactggcc attatcggaa gtgatgccgg tccggatcca agtaatact ttatatttt    1680 caaggcccaa tgcgacgtac atctaatctt tcataactgc tagtggcctc aatgcctgca   1740
gcgcaaacag ttgcgataat ggcacccttg ctcaaggctg gggctctggt tcaaccaaat   1800
atccatacat agtgactgta agtgtataag cagctgtaat atatactcca aaaaatgtat   1860
ggtctttgct aatcatcgtt tgatttctac agcctatcga tggtattaaa gctcgagctc   1920
cggaatcttg ggaaatcgta tcgactcttg acgattggaa tcttgataaa gcggcaaagg   1980
tggcagccga aggcgatatt gctatggtgt ttgccaattc ggactctggt gaacaatata   2040
tcaccgtagc tggcaacgtc ggtgaccgaa acaatgtatc cttgtggaat aatggagata   2100
acttggtacg ttaggcaact ttcagcatat gcaaacgttt cccagcgaca ttgactaact   2160
gagtacgtgc tagattaaag cagtcgctga tgcaaatgaa acactatcg ttgtcattca    2220 ctctgtgggt acaattgata tgccgtggct ggaccacccc aatatcaagg cacttgtttg   2280
gccaggactt ccaggtcaag agaccggtaa ctctctcgca gacgtattat tcggtgacta   2340
tgcacccgga ggaaagcttc cgtataccat tgcacctgaa aaagacttcc ctgctgagcc   2400
ttcacctgag gataacgtaa gcagaccta cccattctttg tctttcggac aatggtgtta    2460
acgagatggc attattaagg ttgtctacga ggagaaatta ttgatcggtt atcgctggtt   2520
tgatgccaaa aacattacac ctcagtttga atttggattc ggtctttctt acaccacctt   2580
cgcgattgat gatctcaagg ttaagtcatc tggcaaggga gataagatca aggtatctgc   2640
atctgtaact gtcgagaata caggtgtatat ggaaggcacc gaggttgtcc aagcctatat   2700
ctccttccct gaatccgcag gagagccgcc gaaggtcctt cgcggttttg aaaaggttct   2760
cctcaagccc ggaatgaaga ctaaggtcag cttcgaattc accaagacag agttgagtat   2820
ctgggatacc atgaaacaat cctgggttgt tccttctggc gaattcaaac ttttggttgg   2880
cgctagtagc cgtgatatcc gtcatactgc aactttcaat gtctcagaat ga           2932
```

<210> SEQ ID NO 24
<211> LENGTH: 733
<212> TYPE: PRT
<213> ORGANISM: Rhizomucor pusillus

<400> SEQUENCE: 24

```
Met Arg Ser Leu Ala Asn Ile Ser Leu Trp Gly Leu Ile Leu Leu Gly
1               5                   10                  15

Thr Ile Gln Ser Gly Gln Ala Arg Pro Thr Asp Lys Pro Tyr Asn Val
            20                  25                  30

Leu Thr Trp Glu Glu Ala Tyr Ala Lys Ala Lys Leu Leu Ser Gln
        35                  40                  45

Met Thr Leu Glu Gln Lys Val Asn Leu Thr Thr Gly Thr Gly Asn Gln
    50                  55                  60

Gln Gly Pro Cys Glu Gly Asn Thr Ala Pro Val Glu Asp Pro Tyr Phe
65                  70                  75                  80
```

```
Pro Ala Leu Cys Leu Asn Asp Gly Pro Ile Gly Leu Arg Glu Ala Leu
                85                  90                  95

Asn Thr Ser Ala Phe Val Thr Gly Ile Asn Ser Cys Ala Ser Phe Asp
            100                 105                 110

Arg Asp Leu Ile Arg Gln Arg Gly Gln Tyr Met Gly Ala Glu Phe His
            115                 120                 125

Asp Lys Gly Val Asn Val Gln Leu Gly Pro Gly Met Asn Leu Met Arg
130                 135                 140

Ser Pro Arg Ala Gly Arg Asn Trp Glu Phe Gly Ser Glu Asp Pro Tyr
145                 150                 155                 160

Leu Leu Gly Ile Val Ser Ala Glu Thr Ile Leu Gly Ile Gln Ser Ser
                165                 170                 175

Gly Val Met Ala Thr Ala Lys His Tyr Ile Gly Asn Glu Gln Glu Leu
            180                 185                 190

Asn Arg Ser Thr Glu Ser Thr Val Met Asp Asp Arg Thr Tyr His Glu
            195                 200                 205

Ile Tyr Leu Trp Pro Phe Ala Arg Ser Val Glu Ala Gly Val Thr Ala
210                 215                 220

Val Met Cys Ala Tyr Asn Lys Val Asn Gly Thr Tyr Ala Cys Glu Asn
225                 230                 235                 240

Asp Tyr Thr Leu Asn His Val Leu Lys Gly Glu Leu Gly Phe Lys Gly
                245                 250                 255

Phe Val Met Ser Asp Trp Trp Ala Thr His Ser Thr Ala Thr Ser Ala
            260                 265                 270

Asn Asn Gly Met Asp Met Ser Met Pro Gly Asp Ala Asn Asp Gln Ser
            275                 280                 285

Ile Thr Gly Gly Gly Leu Trp Tyr Gly Lys Asn Leu Thr Asp Ala Val
290                 295                 300

Lys Asn Gly Glu Val Asp Glu Ser Arg Val His Asp Met Ala Leu Arg
305                 310                 315                 320

Ile Ala Ala Ser Trp Tyr Lys Val Gly Gln Asp Lys Asp Tyr Pro Ser
                325                 330                 335

Leu Asn Phe Asn Met Phe Asp Pro Ser Val Gly Gln Asp Leu Asp Val
            340                 345                 350

Gln Gly Asn His Lys Glu Ile Ile Arg Ala Met Gly Arg Ala Ser Leu
            355                 360                 365

Val Leu Leu Arg Asn Glu Asp Ser Ile Leu Pro Leu Lys Glu Asp Ser
370                 375                 380

Leu Lys Lys Leu Ala Ile Ile Gly Ser Asp Ala Gly Pro Asp Pro Asn
385                 390                 395                 400

Gly Leu Asn Ala Cys Ser Ala Asn Ser Cys Asp Asn Gly Thr Leu Ala
                405                 410                 415

Gln Gly Trp Gly Ser Gly Ser Thr Lys Tyr Pro Tyr Ile Val Thr Pro
            420                 425                 430

Ile Asp Gly Ile Lys Ala Arg Ala Pro Glu Ser Trp Glu Ile Val Ser
            435                 440                 445

Thr Leu Asp Asp Trp Asn Leu Asp Lys Ala Ala Lys Val Ala Ala Glu
450                 455                 460

Gly Asp Ile Ala Met Val Phe Ala Asn Ser Asp Ser Gly Glu Gln Tyr
465                 470                 475                 480

Ile Thr Val Ala Gly Asn Val Gly Asp Arg Asn Asn Val Ser Leu Trp
                485                 490                 495
```

```
Asn Asn Gly Asp Asn Leu Ile Lys Ala Val Ala Asp Ala Asn Glu Asn
            500                 505                 510

Thr Ile Val Val Ile His Ser Val Gly Thr Ile Asp Met Pro Trp Leu
            515                 520                 525

Asp His Pro Asn Ile Lys Ala Leu Val Trp Pro Gly Leu Pro Gly Gln
            530                 535                 540

Glu Thr Gly Asn Ser Leu Ala Asp Val Leu Phe Gly Asp Tyr Ala Pro
545                 550                 555                 560

Gly Gly Lys Leu Pro Tyr Thr Ile Ala Pro Glu Lys Asp Phe Pro Ala
                565                 570                 575

Glu Pro Ser Pro Glu Asp Asn Val Val Tyr Glu Glu Lys Leu Leu Ile
            580                 585                 590

Gly Tyr Arg Trp Phe Asp Ala Lys Asn Ile Thr Pro Gln Phe Glu Phe
            595                 600                 605

Gly Phe Gly Leu Ser Tyr Thr Thr Phe Ala Ile Asp Asp Leu Lys Val
            610                 615                 620

Lys Ser Ser Gly Lys Gly Asp Lys Ile Lys Val Ser Ala Ser Val Thr
625                 630                 635                 640

Val Glu Asn Thr Gly Asp Met Glu Gly Thr Glu Val Val Gln Ala Tyr
                645                 650                 655

Ile Ser Phe Pro Glu Ser Ala Gly Glu Pro Pro Lys Val Leu Arg Gly
            660                 665                 670

Phe Glu Lys Val Leu Leu Lys Pro Gly Met Lys Thr Lys Val Ser Phe
            675                 680                 685

Glu Phe Thr Lys Thr Glu Leu Ser Ile Trp Asp Thr Met Lys Gln Ser
            690                 695                 700

Trp Val Val Pro Ser Gly Glu Phe Lys Leu Leu Val Gly Ala Ser Ser
705                 710                 715                 720

Arg Asp Ile Arg His Thr Ala Thr Phe Asn Val Ser Glu
                725                 730

<210> SEQ ID NO 25
<211> LENGTH: 2747
<212> TYPE: DNA
<213> ORGANISM: Rhizomucor pusillus

<400> SEQUENCE: 25
atgtacctac catcgcttac aacaacagca ctggtgctgc tggctgcagt ctcctctgtg     60
tcgcaggctc gaccagcatc caagtacact gacccaattt cttgggatgc cgcctacaag    120
aaggctgaag ccctagtcaa caagatgtct ctcgaccaga agtgggact cgcaacagga     180 atgggctggg aaaagaccaa ctgcgttggt aacacctatg ccagcaccga ccctgacttc    240
ccttcgctct gcttggaaga ctctccctt ggtattcgct ttggaaacaa tgtctctgca     300
ggtttgtata tggatacat agcctctgtc taaaaactca cgcagtttgc atcgtatagg     360
tgtcagtggc atcaacgctg cagcttcctt cgataaagtc caaatccgca agcgtggtga    420
atacattggt gaagaagctt atggtaaagg cgtccatgct attcttggcc cttgcgtcga    480
tgtcatgcgc gcaccttcgg tttgtcttca aagtgctttt acgatatata ctccatacta    540
agatacataa tatcttatta aggcaggacg ggcctgggag gcatttggtg aagatcctta    600
ccttgccggt attgctacga tcgaaactgt caatggtatc cagagccgca atgtggtatg    660
tttggaaatc attaaaacgg gaagatcaag cggaatttaa acttattgtt cgcgtagatt    720
gctactgcaa agcactttat cggtaacaac caggaagaaa accgtactgc ctcgtcctca    780
```

| | |
|---|---|
| aacatcggca agcgtgctct ccatgaaatc tggctctggc cctatgctcg tgcggttgaa | 840 |
| gcaggtgtcg gctccgtcat gtgcgcttac aacctataca acggtaccta cgcttgcgag | 900 |
| aacgaatata ccctcaacac cgtcctcaag ggcgaactcg gcttcagagg tttcgttcag | 960 |
| agtgattggg gcgccaccca ctccactgct ccagctgtca atgctggcct tgacatgaca | 1020 |
| atgcctgtaa gtcttttatg catatattga caaccaagta aatcttacta aatctgggta | 1080 |
| aaatactagg gcgatattaa catgcccgat ggcctcagct attttggtgc caacctcacc | 1140 |
| aaggccgtca agaacggtga agtcagcgaa gaccgtgtta ccgacatggc tgtccgtatc | 1200 |
| gctgccgctt ggtacaagat gggtcaggac aacaaggtag agcttaatta ctccggggct | 1260 |
| ttatgcatgt gcatgctaaa tcgatacccc tattattgca gaacttcccc gaaactacct | 1320 |
| taagagcatt caaccagtct cagtctcctt atgtgcctgt tcaagacgac cacgccaccc | 1380 |
| tgatcagaga aatgggcgcc gcctccaccg tgttgttgac caacaaggat agcatccttc | 1440 |
| ctctgaacgc caagaaactc aagtctgtgg ccatcattgg tagcgatgcc ggtccaaatc | 1500 |
| caaagtgagt ggcacttcca tggcaacgta tattttaaa gctttactaa cttgtggctc | 1560 |
| cagcggcccc aactcttgcc ctgaccgagg atgcgacgaa ggtactcttg cgatgggctg | 1620 |
| gggctccgga actgctgatt tcccctacct tgttacggta agttagagat atatcttgct | 1680 |
| tttggatcat tcgctaacaa gattggaaat ctgcagccca aggaaggtat cgaaaagcgt | 1740 |
| ctcggaaagg atgtcgatct caagtatacc tacgatgact tgacaccga tgctgctgct | 1800 |
| gaattggcca aggatgccga catcgctctc gtttctcca acgctgattc tggtgaaggc | 1860 |
| tacatcactg tcgatggcaa tgaaggcgac cgcaagaact tgactctttg aagaacggt | 1920 |
| gacaacttgg taagaagata gcaacgacat ataagcaaac catgcaatac taatacacgc | 1980 |
| atctatatag atcaaagctg ttgctgatgt taacgaaaac actgttgtcg ttattcacgc | 2040 |
| tgttggtccc gtgttgatgc cctggattga tcatcccaac atcaaggcta ttgtctggcc | 2100 |
| cggtcttcct ggccaggaaa ctggcaactc tctcgctgac gttctctttg gtgatgtcaa | 2160 |
| cccgtctggc cgtcttcctt acaccattgc taagtccgag gaggattatc cagctgaaat | 2220 |
| cagccatgaa ttcgatgtaa gtattatcgt aatccatctc tggagctcct aaggtacaaa | 2280 |
| atctcataca tatctattat aaacaggttg actacactga gggtctctac gttggatacc | 2340 |
| gacactttga tgccaagaac attgaacctc tcttcccctt cggctatggt ctttcctaca | 2400 |
| ccaatttcac ctacagcaag ctcaaggtca agaagggcaa gggtgacaag ttggtttctg | 2460 |
| ctaccatcac tatcaagaac actggcgacg ttgacggtgc agaaattccc caggcctaca | 2520 |
| ttacttttcc cgagtctgcc ggcgagcctt caagaacct tcgtggtttt gaaaaggtct | 2580 |
| tcttgaaggc tggcaaatcc accaaggtca cttttgaatt tagcaagact gaacttagca | 2640 |
| tctgggacga gagctccgag gaatggactg tgccttcagg agaatatacc cttcagatcg | 2700 |
| gtgcttccag tcgtgacatc cgccaaactg ccaagtttac tctataa | 2747 |

<210> SEQ ID NO 26
<211> LENGTH: 728
<212> TYPE: PRT
<213> ORGANISM: Rhizomucor pusillus

<400> SEQUENCE: 26

Met Tyr Leu Pro Ser Leu Thr Thr Thr Ala Leu Val Leu Leu Ala Ala
1               5                   10                  15

Val Ser Ser Val Ser Gln Ala Arg Pro Ala Ser Lys Tyr Thr Asp Pro
            20                  25                  30

```
Ile Ser Trp Asp Ala Ala Tyr Lys Lys Ala Glu Ala Leu Val Asn Lys
         35                  40                  45

Met Ser Leu Asp Gln Lys Val Gly Leu Ala Thr Gly Met Gly Trp Glu
 50                  55                  60

Lys Thr Asn Cys Val Gly Asn Thr Tyr Ala Ser Thr Asp Pro Asp Phe
 65                  70                  75                  80

Pro Ser Leu Cys Leu Glu Asp Ser Pro Leu Gly Ile Arg Phe Gly Asn
                 85                  90                  95

Asn Val Ser Ala Gly Val Ser Gly Ile Asn Ala Ala Ser Phe Asp
                100                 105                 110

Lys Val Gln Ile Arg Lys Arg Gly Glu Tyr Ile Gly Glu Ala Tyr
                115                 120                 125

Gly Lys Gly Val His Ala Ile Leu Gly Pro Cys Val Asp Val Met Arg
130                 135                 140

Ala Pro Ser Ala Gly Arg Ala Trp Glu Ala Phe Gly Glu Asp Pro Tyr
145                 150                 155                 160

Leu Ala Gly Ile Ala Thr Ile Glu Thr Val Asn Gly Ile Gln Ser Arg
                165                 170                 175

Asn Val Ile Ala Thr Ala Lys His Phe Ile Gly Asn Asn Gln Glu Glu
                180                 185                 190

Asn Arg Thr Ala Ser Ser Ser Asn Ile Gly Lys Arg Ala Leu His Glu
                195                 200                 205

Ile Trp Leu Trp Pro Tyr Ala Arg Ala Val Glu Ala Gly Val Gly Ser
210                 215                 220

Val Met Cys Ala Tyr Asn Leu Tyr Asn Gly Thr Tyr Ala Cys Glu Asn
225                 230                 235                 240

Glu Tyr Thr Leu Asn Thr Val Leu Lys Gly Glu Leu Gly Phe Arg Gly
                245                 250                 255

Phe Val Gln Ser Asp Trp Gly Ala Thr His Ser Thr Ala Pro Ala Val
                260                 265                 270

Asn Ala Gly Leu Asp Met Thr Met Pro Gly Asp Ile Asn Met Pro Asp
                275                 280                 285

Gly Leu Ser Tyr Phe Gly Ala Asn Leu Thr Lys Ala Val Lys Asn Gly
                290                 295                 300

Glu Val Ser Glu Asp Arg Val Thr Asp Met Ala Val Arg Ile Ala Ala
305                 310                 315                 320

Ala Trp Tyr Lys Met Gly Gln Asp Asn Lys Asn Phe Pro Glu Thr Thr
                325                 330                 335

Leu Arg Ala Phe Asn Gln Ser Gln Ser Pro Tyr Val Pro Val Gln Asp
                340                 345                 350

Asp His Ala Thr Leu Ile Arg Glu Met Gly Ala Ala Ser Thr Val Leu
                355                 360                 365

Leu Thr Asn Lys Asp Ser Ile Leu Pro Leu Asn Ala Lys Lys Leu Lys
                370                 375                 380

Ser Val Ala Ile Ile Gly Ser Asp Ala Gly Pro Asn Pro Asn Gly Pro
385                 390                 395                 400

Asn Ser Cys Pro Asp Arg Gly Cys Asp Glu Gly Thr Leu Ala Met Gly
                405                 410                 415

Trp Gly Ser Gly Thr Ala Asp Phe Pro Tyr Leu Val Thr Pro Lys Glu
                420                 425                 430

Gly Ile Glu Lys Arg Leu Gly Lys Asp Val Asp Leu Lys Tyr Thr Tyr
                435                 440                 445
```

```
Asp Asp Phe Asp Thr Asp Ala Ala Glu Leu Ala Lys Asp Ala Asp
    450                 455                 460
Ile Ala Leu Val Phe Ser Asn Ala Asp Ser Gly Glu Gly Tyr Ile Thr
465                 470                 475                 480
Val Asp Gly Asn Glu Gly Asp Arg Lys Asn Leu Thr Leu Trp Lys Asn
                    485                 490                 495
Gly Asp Asn Leu Ile Lys Ala Val Ala Asp Val Asn Glu Asn Thr Val
                500                 505                 510
Val Val Ile His Ala Val Gly Pro Val Leu Met Pro Trp Ile Asp His
            515                 520                 525
Pro Asn Ile Lys Ala Ile Val Trp Pro Gly Leu Pro Gly Gln Glu Thr
    530                 535                 540
Gly Asn Ser Leu Ala Asp Val Leu Phe Gly Asp Val Asn Pro Ser Gly
545                 550                 555                 560
Arg Leu Pro Tyr Thr Ile Ala Lys Ser Glu Glu Asp Tyr Pro Ala Glu
                565                 570                 575
Ile Ser His Glu Phe Asp Val Asp Tyr Thr Glu Gly Leu Tyr Val Gly
                580                 585                 590
Tyr Arg His Phe Asp Ala Lys Asn Ile Glu Pro Leu Phe Pro Phe Gly
            595                 600                 605
Tyr Gly Leu Ser Tyr Thr Asn Phe Thr Tyr Ser Lys Leu Lys Val Lys
    610                 615                 620
Lys Gly Lys Gly Asp Lys Leu Val Ser Ala Thr Ile Thr Ile Lys Asn
625                 630                 635                 640
Thr Gly Asp Val Asp Gly Ala Glu Ile Pro Gln Ala Tyr Ile Thr Phe
                645                 650                 655
Pro Glu Ser Ala Gly Glu Pro Phe Lys Asn Leu Arg Gly Phe Glu Lys
                660                 665                 670
Val Phe Leu Lys Ala Gly Lys Ser Thr Lys Val Thr Phe Glu Phe Ser
            675                 680                 685
Lys Thr Glu Leu Ser Ile Trp Asp Glu Ser Ser Glu Gly Trp Thr Val
    690                 695                 700
Pro Ser Gly Glu Tyr Thr Leu Gln Ile Gly Ala Ser Ser Arg Asp Ile
705                 710                 715                 720
Arg Gln Thr Ala Lys Phe Thr Leu
                725
```

<210> SEQ ID NO 27
<211> LENGTH: 2858
<212> TYPE: DNA
<213> ORGANISM: Corynascus thermophilus

<400> SEQUENCE: 27

```
atgaaggctg ccgtgctttc ctgcctctttt ggcagtaccc ttgccgttgc aggcactgct      60
gaatcgagaa aggtatggac caacctcgtc aaaggctcac tcccggatca aactcccctt     120
tcatccagac ccaacccttt ccgcgaggac ctcacttgct gacgatcgtc aacagaccaa     180
tggcaagccc cttgcaagat ctgaaccttt ctaccccgtct ccatggatga ccccaacgc    240 cgacggctgg gtggaggctt acgcccaggc caaggccttt gtctctcaaa tgactttgct     300
agagaaggtc aacttgacca caggagttgg gtaataattt tgataccat ttccccctcc     360 attttgtcca ggcagcccgc agatggatgg tcctgctaac gatatcgaag ctgggcggct     420
gagcagtgcg tcggccaagt gggcgccatc cctcgcctgg gacttcgcag tctgtgcatg     480
cacgactccc ctctcggcat ccggggaacc gactacaact cggccttccc ctccggccag     540
```

| | |
|---|---|
| accgtcgctg ctacctggga ccgcggtctg atgtaccgtc gcggctatgc gatgggccag | 600 |
| gaggccaagg gcaagggcat caatgttctt ctcggaccag tcgccgggcc cctcggccgc | 660 |
| atgcccgcgg ccggccgcaa ttgggaaggt tttgctccgg atcctgtcct gacaggcatc | 720 |
| ggcatgtccg agaccatcaa gggtatccag gatgctggcg tcatcgcttg tgcgaagcac | 780 |
| cttattggga acgagcaggg tgagtggtgg tccaagacgc cgctccggac tggcgccctc | 840 |
| aggctgctga cactgctgca gagcacttca ggcaggcgg agaagcccgg ggctacggct | 900 |
| acaacatcag cgagtccctc tcgtccaaca tcgacgacaa gaccatgcac gaattgtacc | 960 |
| tctggccgtt cgccgatgct gtccgggccg gcgtaggctc tgtcatgtgc gcgtaccagc | 1020 |
| aagtcaacaa ctcgtactcc tgccagaact cgaaactgct gaacgacctc ctcaagaacg | 1080 |
| agctggggtt ccagggcttc gtcatgagcg actggcaggc acagcatacc ggcgtggcaa | 1140 |
| gcgccgtggc cggtcttgat atgaccatgc cgggcgacac cgagttcaac actggcctca | 1200 |
| gcttctgggg cgccaatctc accctcgccg tcctcaatgg cacggtccct gcctaccgca | 1260 |
| tcgatgacat ggccatgcgc atcatggccg ccctcttcaa ggtcaccaag accatcgacc | 1320 |
| tggatccgat caacttctcc ttctggaccg acgacgta tggcccgatc cactgggccg | 1380 |
| cccaggaggg ctatcaggag attaattccc acgtggacgt ccgcgcggac cacggaaacc | 1440 |
| tcatccgcga gattgccgcc aagggcacgg tgctgctgaa gaacaccggc gctctgcccc | 1500 |
| tgaacaagcc aaaattcctc gccgtcatcg gcgaggatgc tggctcgagc cccaacgggc | 1560 |
| ccaacggctg cagcgaccgc ggctgcaaca aaggcacgct cgccatgggc tggggatccg | 1620 |
| gcacagccaa ctatccatac ctcgtctccc cggatgccgc ccttcaggcc caggccatcc | 1680 |
| gggatggtac gaggtacgag agcatcctgt ccaactacgc cgtggaagag acgagagctc | 1740 |
| tggtctcgca gcggatgcc accgccatcg tattcgtgaa tgccgactcg ggcgaaggct | 1800 |
| acatcaacgt ggacggaaac gagggcgacc gccagaacct gactctgtgg aacaatggcg | 1860 |
| atgatctgat caagaacgtc tctcgttggt gcaacaacac catcgtcgtc atccactcgg | 1920 |
| ttggcccggt tctcctgaag gagtggtacg acagccccaa cgtcacggcc atcctctggg | 1980 |
| ccggtcttcc gggccaggag tcgggcaact ccatcaccga cgtgctctac ggcagggtca | 2040 |
| accccgctgc ccgctcaccg ttcacttggg gcaagacccg cgaaagctac ggcgccgacg | 2100 |
| tcctgtacga gccgaataac ggcaacggcg cgccccagca agatttcagc gagggcgtct | 2160 |
| tcatcgacta ccgctacttt gacaaggtcg gcgacgactc ggtcatctac gagttcggcc | 2220 |
| acggcctgag ctacaccact ttcgaataca gcaacatccg cgtcgtcaag tctgacgccg | 2280 |
| gcgagtaccg gcccacgacg ggcaccacgg cccaggcccc gacgtttggc aacttctcca | 2340 |
| ccgacctgga ggactatgtc ttcccggagg acgagtttcc ttacatctac cagtacatct | 2400 |
| acccgtacct caacacgacc gaccccaggg aggcctcggc cgatccccac tacggccaga | 2460 |
| cggccgagga gttcctgccg ccccgcgcga ccgacgacgg gccccagccg ctcctccggt | 2520 |
| cctcgggcgg agactctcct ggcggcaacc gccagctgta cgacgtgctg tacacgatca | 2580 |
| cggccgacat cacgaacacg ggcccgtcg tgggcgagga ggtgccgcag ctctacgtct | 2640 |
| cgctgggcgg gcccgacgat cccaaggtgc agctgcgcga ctttgacagg atgcggatcg | 2700 |
| agcccggcga gacgaggcag ttcaccggcc gcctgacgcg ccgggatctg agcaactggg | 2760 |
| acgtcgtcct gcaggactgg gtcatcagcg agtaccccaa gacggcctac gtcgggagga | 2820 |
| gcagccggaa gctggatctc aagattgagc ttccttga | 2858 |

<210> SEQ ID NO 28
<211> LENGTH: 870
<212> TYPE: PRT
<213> ORGANISM: Corynascus thermophilus

<400> SEQUENCE: 28

Met Lys Ala Ala Val Leu Ser Cys Leu Phe Gly Ser Thr Leu Ala Val
1               5                   10                  15

Ala Gly Thr Ala Glu Ser Arg Lys Thr Asn Gly Lys Pro Leu Ala Arg
            20                  25                  30

Ser Glu Pro Phe Tyr Pro Ser Pro Trp Met Asn Pro Asn Ala Asp Gly
        35                  40                  45

Trp Val Glu Ala Tyr Ala Gln Ala Lys Ala Phe Val Ser Gln Met Thr
    50                  55                  60

Leu Leu Glu Lys Val Asn Leu Thr Thr Gly Val Gly Trp Ala Ala Glu
65                  70                  75                  80

Gln Cys Val Gly Gln Val Gly Ala Ile Pro Arg Leu Gly Leu Arg Ser
                85                  90                  95

Leu Cys Met His Asp Ser Pro Leu Gly Ile Arg Gly Thr Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Ala Ala Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Leu Ile Gly Asn Glu Gln Glu His Phe
        195                 200                 205

Arg Gln Ala Gly Glu Ala Arg Gly Tyr Gly Tyr Asn Ile Ser Glu Ser
    210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ala
                245                 250                 255

Tyr Gln Gln Val Asn Asn Ser Tyr Ser Cys Gln Asn Ser Lys Leu Leu
            260                 265                 270

Asn Asp Leu Leu Lys Asn Glu Leu Gly Phe Gln Gly Phe Val Met Ser
        275                 280                 285

Asp Trp Gln Ala Gln His Thr Gly Val Ala Ser Ala Val Ala Gly Leu
    290                 295                 300

Asp Met Thr Met Pro Gly Asp Thr Glu Phe Asn Thr Gly Leu Ser Phe
305                 310                 315                 320

Trp Gly Ala Asn Leu Thr Leu Ala Val Leu Asn Gly Thr Val Pro Ala
                325                 330                 335

Tyr Arg Ile Asp Asp Met Ala Met Arg Ile Met Ala Ala Leu Phe Lys
            340                 345                 350

Val Thr Lys Thr Ile Asp Leu Asp Pro Ile Asn Phe Ser Phe Trp Thr
        355                 360                 365

Asp Asp Thr Tyr Gly Pro Ile His Trp Ala Ala Gln Glu Gly Tyr Gln
    370                 375                 380

```
Glu Ile Asn Ser His Val Asp Val Arg Ala Asp His Gly Asn Leu Ile
385                 390                 395                 400

Arg Glu Ile Ala Ala Lys Gly Thr Val Leu Leu Lys Asn Thr Gly Ala
            405                 410                 415

Leu Pro Leu Asn Lys Pro Lys Phe Leu Ala Val Ile Gly Glu Asp Ala
            420                 425                 430

Gly Ser Ser Pro Asn Gly Pro Asn Gly Cys Ser Asp Arg Gly Cys Asn
            435                 440                 445

Lys Gly Thr Leu Ala Met Gly Trp Gly Ser Gly Thr Ala Asn Tyr Pro
            450                 455                 460

Tyr Leu Val Ser Pro Asp Ala Ala Leu Gln Ala Gln Ala Ile Arg Asp
465                 470                 475                 480

Gly Thr Arg Tyr Glu Ser Ile Leu Ser Asn Tyr Ala Val Glu Glu Thr
            485                 490                 495

Arg Ala Leu Val Ser Gln Ala Asp Ala Thr Ala Ile Val Phe Val Asn
            500                 505                 510

Ala Asp Ser Gly Glu Gly Tyr Ile Asn Val Asp Gly Asn Glu Gly Asp
            515                 520                 525

Arg Gln Asn Leu Thr Leu Trp Asn Asn Gly Asp Asp Leu Ile Lys Asn
530                 535                 540

Val Ser Arg Trp Cys Asn Asn Thr Ile Val Ile His Ser Val Gly
545                 550                 555                 560

Pro Val Leu Leu Lys Glu Trp Tyr Asp Ser Pro Asn Val Thr Ala Ile
            565                 570                 575

Leu Trp Ala Gly Leu Pro Gly Gln Glu Ser Gly Asn Ser Ile Thr Asp
            580                 585                 590

Val Leu Tyr Gly Arg Val Asn Pro Ala Ala Arg Ser Pro Phe Thr Trp
            595                 600                 605

Gly Lys Thr Arg Glu Ser Tyr Gly Ala Asp Val Leu Tyr Glu Pro Asn
            610                 615                 620

Asn Gly Asn Gly Ala Pro Gln Gln Asp Phe Ser Glu Gly Val Phe Ile
625                 630                 635                 640

Asp Tyr Arg Tyr Phe Asp Lys Val Gly Asp Ser Val Ile Tyr Glu
            645                 650                 655

Phe Gly His Gly Leu Ser Tyr Thr Thr Phe Glu Tyr Ser Asn Ile Arg
            660                 665                 670

Val Val Lys Ser Asp Ala Gly Glu Tyr Arg Pro Thr Thr Gly Thr Thr
            675                 680                 685

Ala Gln Ala Pro Thr Phe Gly Asn Phe Ser Thr Asp Leu Glu Asp Tyr
            690                 695                 700

Val Phe Pro Glu Asp Glu Phe Pro Tyr Ile Tyr Gln Tyr Ile Tyr Pro
705                 710                 715                 720

Tyr Leu Asn Thr Thr Asp Pro Arg Glu Ala Ser Ala Asp Pro His Tyr
            725                 730                 735

Gly Gln Thr Ala Glu Glu Phe Leu Pro Pro Arg Ala Thr Asp Asp Gly
            740                 745                 750

Pro Gln Pro Leu Leu Arg Ser Ser Gly Asp Ser Pro Gly Gly Asn
            755                 760                 765

Arg Gln Leu Tyr Asp Val Leu Tyr Thr Ile Thr Ala Asp Ile Thr Asn
            770                 775                 780

Thr Gly Pro Val Val Gly Glu Glu Val Pro Gln Leu Tyr Val Ser Leu
785                 790                 795                 800
```

Gly Gly Pro Asp Asp Pro Lys Val Gln Leu Arg Asp Phe Asp Arg Met
            805                 810                 815

Arg Ile Glu Pro Gly Glu Thr Arg Gln Phe Thr Gly Arg Leu Thr Arg
        820                 825                 830

Arg Asp Leu Ser Asn Trp Asp Val Val Leu Gln Asp Trp Val Ile Ser
            835                 840                 845

Glu Tyr Pro Lys Thr Ala Tyr Val Gly Arg Ser Ser Arg Lys Leu Asp
        850                 855                 860

Leu Lys Ile Glu Leu Pro
865                 870

<210> SEQ ID NO 29
<211> LENGTH: 2320
<212> TYPE: DNA
<213> ORGANISM: Corynascus thermophilus

<400> SEQUENCE: 29

| | |
|---|---|
| atgaccttc aagcgctcgc gctgctggcg gcggcagcct tcgtacgggc cgaggccccg | 60 |
| accaaggtcc ctcgcgacgc gccggcgaga gctgccgcct gggaagctgc ccactcttcg | 120 |
| gcagctgccg tcctgggaag ctgtcccag caagacaaga tcaacatcgt gacgggcgtc | 180 |
| ggctggaaca aggggccctg cgtgggcaac acgccggcta tcagctccat caactacccg | 240 |
| cagctctgtc tgcaggacgg ccctctgggc gtccgcttca gttccggcaa caccgctttc | 300 |
| actccgggca tccaggccgc gtcgacatgg gacgtcgacc tgatccgcca gcggggcgtg | 360 |
| tacatgggcg aggagttcag ggggagcggc atccacgtcc agctgggccc cgtggccggg | 420 |
| ccgttgggta agattccgca cggcgggcgc aactgggagg gctttggcgt ggaccctac | 480 |
| ctcacgggca tcgccatggc cgagacgatc gaggggatcc agtcggtggg cgtgcaggcc | 540 |
| aacgccaagc actggctcgt caacgagcag gagctcaacc gcgagaccat gagcagcaac | 600 |
| gtcgacgacc gcaccctgca cgagctgtac gtctggccgt cgcggacgc ggtgcactcg | 660 |
| aacgtggcca gcgtcatgtg cagctacaac aagatcaacg gcacgtgggc gtgcgagaac | 720 |
| aaccagttgc tgaacggcat tctgaagaaa gagctcggct ccccgggcta cgtgatgagc | 780 |
| gactggaacg cgcagcactc gaccgacgac gcggccaacc acggcatgga catgacgatg | 840 |
| cccggcagcg acttcaacgg agggactatc ctctggggcc cgcagctcaa caacgcggtc | 900 |
| aacagcggcc gggtgccccg ggagcgcctc gacgacatgg tcaagcgcat cctcgcggca | 960 |
| tggtatcttc tcggccagaa caacggctac ccgcaaatca acctccacgc caacgtgcag | 1020 |
| agcaaccaca aggagaacgt gcgggcggtc gcgcgcgacg gcatcgtgct cctcaagaac | 1080 |
| gacaacggca tcctcccgct caagaggccc tccaagctcg ccctcatcgg ttcggccgcg | 1140 |
| gtcgccaacc gcggggaat caactcgtgc caggatcagg gctgcaacag cggcgccttg | 1200 |
| ggcatgggat ggggctccgg ggcggtcaac tacccgtacc tcgtctcccc gtacgacgcg | 1260 |
| ctcagggccc gcgccgacca ggacgggacc cagctcaacc tgtacagctc ggacaacacg | 1320 |
| ggcgggtttg cgggcgtggc ctcgggcgcg gacgcggcca tcgtggtcat cacggccgac | 1380 |
| tcgggcgagg gctacatcac ggtcgagggc aacgtcgggg accgggtgaa cctgaacccg | 1440 |
| tggcacaacg gcaacgacct tgtgagggcg gtggcggcca ttaacaagaa taccatcgtt | 1500 |
| gtcgtccaca gcgtcgggcc catcatcctc gaggacatct tgtccaacga cggcgtcaag | 1560 |
| gcgatcgtct gggccggcct gccgagccag gagaacggta acgcgctggt ggacatcctg | 1620 |
| tacggcttga cctcgccgtc gggcaagctg gtctacacca tcgccaagcg ggaacaggac | 1680 |

-continued

```
tacggcactt cggtcgttcg cggcgacgac tcgttcccg agggtctgtt tatcgactac   1740
cgccactttg accggcagaa catcgagccg cgctacgagt ttggcttcgg gctgtgtaag   1800
tttttttttt tctttttttc tttctctcaa tgcgccctca cccccagtcc acatcagcgt   1860
ttgctcttct tctcttttta gttcacgtcc taacagcagg gtgaaaccgg cagcatacac   1920
aaacttcacg tatgccaacc tccgcatcac ctcgacggcc acggccggcc cggcgacggg   1980
ccagatcatc cccggcggcg cggccgacct ctgggacgag gtggtcacgg tcacggcgac   2040
catcaccaac agcggcggcg tgcagggcgc cgaggtcgcc cagctctacc tgtcgctgcc   2100
gtcgtcggcg ccggctaccc cgcccaagca gctccgcggc ttcaccaagc tcaagctggc   2160
ccccggcgcc agcggcaccg ccaccttcaa cctgcgccgg cgagacctca gctattggga   2220
caccgtccgc gggcaatggg tcgtgcccca gggcgagttc cgcgtcttgg tcggcgcgag   2280
ctcgcgcgat atccggctca ctggaagctt ccaggtgtga                         2320
```

<210> SEQ ID NO 30
<211> LENGTH: 733
<212> TYPE: PRT
<213> ORGANISM: Corynascus thermophilus

<400> SEQUENCE: 30

```
Met Thr Phe Gln Ala Leu Ala Leu Leu Ala Ala Ala Phe Val Arg
1               5                   10                  15

Ala Glu Ala Pro Thr Lys Val Pro Arg Asp Ala Pro Ala Arg Ala Ala
            20                  25                  30

Ala Trp Glu Ala Ala His Ser Ser Ala Ala Val Leu Gly Arg Leu
        35                  40                  45

Ser Gln Gln Asp Lys Ile Asn Ile Val Thr Gly Val Gly Trp Asn Lys
    50                  55                  60

Gly Pro Cys Val Gly Asn Thr Pro Ala Ile Ser Ser Ile Asn Tyr Pro
65                  70                  75                  80

Gln Leu Cys Leu Gln Asp Gly Pro Leu Gly Val Arg Phe Ser Ser Gly
                85                  90                  95

Asn Thr Ala Phe Thr Pro Gly Ile Gln Ala Ala Ser Thr Trp Asp Val
            100                 105                 110

Asp Leu Ile Arg Gln Arg Gly Val Tyr Met Gly Glu Glu Phe Arg Gly
        115                 120                 125

Ser Gly Ile His Val Gln Leu Gly Pro Val Ala Gly Pro Leu Gly Lys
    130                 135                 140

Ile Pro His Gly Gly Arg Asn Trp Glu Gly Phe Gly Val Asp Pro Tyr
145                 150                 155                 160

Leu Thr Gly Ile Ala Met Ala Glu Thr Ile Glu Gly Ile Gln Ser Val
                165                 170                 175

Gly Val Gln Ala Asn Ala Lys His Trp Leu Val Asn Glu Gln Glu Leu
            180                 185                 190

Asn Arg Glu Thr Met Ser Ser Asn Val Asp Arg Thr Leu His Glu
        195                 200                 205

Leu Tyr Val Trp Pro Phe Ala Asp Ala Val His Ser Asn Val Ala Ser
    210                 215                 220

Val Met Cys Ser Tyr Asn Lys Ile Asn Gly Thr Trp Ala Cys Glu Asn
225                 230                 235                 240

Asn Gln Leu Leu Asn Gly Ile Leu Lys Lys Glu Leu Gly Phe Pro Gly
                245                 250                 255

Tyr Val Met Ser Asp Trp Asn Ala Gln His Ser Thr Asp Asp Ala Ala
```

```
                260                 265                 270
Asn His Gly Met Asp Met Thr Met Pro Gly Ser Asp Phe Asn Gly Gly
            275                 280                 285

Thr Ile Leu Trp Gly Pro Gln Leu Asn Asn Ala Val Asn Ser Gly Arg
        290                 295                 300

Val Pro Arg Glu Arg Leu Asp Asp Met Val Lys Arg Ile Leu Ala Ala
305                 310                 315                 320

Trp Tyr Leu Leu Gly Gln Asn Asn Gly Tyr Pro Gln Ile Asn Leu His
                325                 330                 335

Ala Asn Val Gln Ser Asn His Lys Glu Asn Val Arg Ala Val Ala Arg
            340                 345                 350

Asp Gly Ile Val Leu Leu Lys Asn Asp Asn Gly Ile Leu Pro Leu Lys
        355                 360                 365

Arg Pro Ser Lys Leu Ala Leu Ile Gly Ser Ala Ala Val Ala Asn Pro
    370                 375                 380

Arg Gly Ile Asn Ser Cys Gln Asp Gln Gly Cys Asn Ser Gly Ala Leu
385                 390                 395                 400

Gly Met Gly Trp Gly Ser Gly Ala Val Asn Tyr Pro Tyr Leu Val Ser
                405                 410                 415

Pro Tyr Asp Ala Leu Arg Ala Arg Ala Asp Gln Asp Gly Thr Gln Leu
            420                 425                 430

Asn Leu Tyr Ser Ser Asp Asn Thr Gly Gly Val Ala Gly Val Ala Ser
        435                 440                 445

Gly Ala Asp Ala Ala Ile Val Val Ile Thr Ala Asp Ser Gly Glu Gly
    450                 455                 460

Tyr Ile Thr Val Glu Gly Asn Val Gly Asp Arg Val Asn Leu Asn Pro
465                 470                 475                 480

Trp His Asn Gly Asn Asp Leu Val Arg Ala Val Ala Ala Val Asn Lys
                485                 490                 495

Asn Thr Ile Val Val His Ser Val Gly Pro Ile Ile Leu Glu Asp
            500                 505                 510

Ile Leu Ser Asn Asp Gly Val Lys Ala Ile Val Trp Ala Gly Leu Pro
        515                 520                 525

Ser Gln Glu Asn Gly Asn Ala Leu Val Asp Ile Leu Tyr Gly Leu Thr
    530                 535                 540

Ser Pro Ser Gly Lys Leu Val Tyr Thr Ile Ala Lys Arg Glu Gln Asp
545                 550                 555                 560

Tyr Gly Thr Ser Val Val Arg Gly Asp Asp Ser Phe Pro Glu Gly Leu
                565                 570                 575

Phe Ile Asp Tyr Arg His Phe Asp Arg Gln Asn Ile Glu Pro Arg Tyr
            580                 585                 590

Glu Phe Gly Phe Gly Leu Ser Tyr Thr Asn Phe Thr Tyr Ala Asn Leu
        595                 600                 605

Arg Ile Thr Ser Thr Ala Thr Ala Gly Pro Ala Thr Gly Gln Ile Ile
    610                 615                 620

Pro Gly Gly Ala Ala Asp Leu Trp Asp Glu Val Val Thr Val Thr Ala
625                 630                 635                 640

Thr Ile Thr Asn Ser Gly Gly Val Gln Gly Ala Glu Val Ala Gln Leu
                645                 650                 655

Tyr Leu Ser Leu Pro Ser Ser Ala Pro Ala Thr Pro Pro Lys Gln Leu
            660                 665                 670

Arg Gly Phe Thr Lys Leu Lys Leu Ala Pro Gly Ala Ser Gly Thr Ala
        675                 680                 685
```

```
Thr Phe Asn Leu Arg Arg Arg Asp Leu Ser Tyr Trp Asp Thr Val Arg
    690                 695                 700

Gly Gln Trp Val Val Pro Gln Gly Glu Phe Arg Val Leu Val Gly Ala
705                 710                 715                 720

Ser Ser Arg Asp Ile Arg Leu Thr Gly Ser Phe Gln Val
                725                 730
```

<210> SEQ ID NO 31
<211> LENGTH: 2397
<212> TYPE: DNA
<213> ORGANISM: Corynascus thermophilus

<400> SEQUENCE: 31

| | | | | | |
|---|---|---|---|---|---|
| atgcggttcc | tctccccggc | attgtttctt | gcagcggccg | ctgtggctgc | ggacaagggg | 60 |
| cgtccgagtc | tcaagaatgc | cgtgtacaag | aaccccaaag | cctcggtcga | ggatcgtgtt | 120 |
| gccgatctcc | tcgctcggat | gaccattgag | gagaaggcgt | cccagcttct | ccaaggcgac | 180 |
| atccgcaatt | ggatgaatga | aaaactaac | gcgctcaacc | agaccggcct | ggaatggagc | 240 |
| acaaggtatc | ggggagcgc | cttctacgtg | ggcgttccgg | tcgccaatga | gtggctcaca | 300 |
| aagcacatca | aggccgccca | ggattacatc | agaaggaga | cctacctcgg | tatcccggcc | 360 |
| tttgtgcaga | ctgagggtct | ccacggtttt | cttgctcgtg | ggttcccact | cccagcaccc | 420 |
| ctcgcgagag | catgatggct | gactgtcttc | atggcctcag | acaatgccac | catcttcaat | 480 |
| tcgcccatcg | gacttggctg | ctcatggaac | ccggccctgg | tcgaggagat | ggcggctgtc | 540 |
| attgccaagg | aggcgcgcgc | cctcggtgtc | aaccagctat | cgccccggt | cgccgacctg | 600 |
| gcgcgggaac | tacgccacgg | ccgcgtcgag | gagatgtaca | gcgaggacgg | cctccttgcc | 660 |
| ggcgagctcg | cccgggccta | cgtcaggggc | gcgcagtccg | ccggcgtcag | cgccatggtc | 720 |
| aagcactttg | ccgcctttgg | cgtgccggag | cagggcctga | cacgggcc | cgtccacggc | 780 |
| ggcgagcgag | aactgcgcac | gacctatctt | ccccccgtacc | ggcgcgccat | catggacggg | 840 |
| ggggcctatt | ccatcatgac | ggcctaccat | agctacgacg | gtatcccgc | cgtgtccgac | 900 |
| ccgcacttgc | tcaccgacat | cctccgtgac | gaatgggct | acaaatactt | caccatgacc | 960 |
| gacgccggcg | cctcggaccg | cctctgcaca | gagttcaaga | tgtgcgcctc | gaatcccatc | 1020 |
| gacaaggaag | ccatcgtgag | gtacatcctc | cctgccggcg | gcgacgtgga | gatgggaggc | 1080 |
| ggctcgtact | ccttcgagaa | gatccccgac | ctggtggcca | gcagcaagat | cgaagagggc | 1140 |
| cttgttgatg | ccgccgtcgc | ccgcgtgctg | cgggccaagt | ttgagctcgg | cctcttcgag | 1200 |
| gaaccctcc | cgggcctgcc | tgccgaggag | gcgaacaaag | tgatccacgc | gcccgagcac | 1260 |
| gttgccctcg | ccaggaggct | ggacgaggaa | tccatcgtcc | tcctggagaa | ccacaacaac | 1320 |
| atcctgccgc | tgaggaaaga | tgcgtcggta | gccgtcatcg | gtcccatggc | gcacggattt | 1380 |
| gtgaactacg | cgactacgt | catcgtcaac | tcctcgaccc | gcggagtcac | gcccctcgac | 1440 |
| ggtatcaagg | cggccagccg | gggcaaggtc | acgtacgcga | aaggctgcga | gcgctggtcc | 1500 |
| agctcgcaag | acggcttcgc | cgaggccgtc | gccgccgcgg | aggcggccga | cgtcgccgtc | 1560 |
| gtcgtggtcg | gcacctggtc | ccgggaccag | aacgagctct | ggcagggcct | gaacgccacc | 1620 |
| acgggcgagc | acgtcgacgt | caacagcctc | gacctggtcg | gcgcccagga | ggccctcgtc | 1680 |
| cgcgccatcg | tcgagacggg | caagccgacc | gtggtcgtct | tctcgtccgg | caagcccatc | 1740 |
| actgcccct | ggatctcgga | gcgggctgcc | gccctcgtcc | agcagttcta | cccctccgaa | 1800 |
| cagggaggcg | ccgctctcgc | ctccgtcctc | tttggcgacg | tgaacccgag | cggcaggctg | 1860 |

```
agcgtcagct tcccccgcag cgtcggcgac ctgccggtct actacgacca ctggaactcg    1920
ggacgtagtg cctcgcccga tgccggcgtc gcttacgaga acggcaccct ggtctttggg    1980
caccagtacg tcttgggcga tccgaggcct ctgtacgagt tcggctacgg tctgagctac    2040
tccaggttcg aatacggcga cgtcggcgtt gacaagacga ccgtgggggcc ccaggacacc    2100 gtcaccgtca ccgtcaccgt caagaacgtg tcgagccggg acggtcagga ggtcgtccag    2160
ctttacgtaa aggacctgat cgccagcgtc gtcgttccca acatccgctt gagggggttc    2220
cagaaagtga tgctgagggc tggagagagc aagcgggtga gcatcaaggt caaggtacag    2280
gacttgggcg tctgggatgc taggatgcga tacgtcgttg agcccggcga ctttctgttc    2340
ctcgttggcg catccagtaa cgacttcagg ggaaatgcca ctgttaccgt caaatag      2397
```

<210> SEQ ID NO 32
<211> LENGTH: 777
<212> TYPE: PRT
<213> ORGANISM: Corynascus thermophilus

<400> SEQUENCE: 32

```
Met Arg Phe Leu Ser Pro Ala Leu Phe Leu Ala Ala Ala Val Ala
1               5                   10                  15

Ala Asp Lys Gly Arg Pro Ser Leu Lys Asn Ala Val Tyr Lys Asn Pro
            20                  25                  30

Lys Ala Ser Val Glu Asp Arg Val Ala Asp Leu Leu Ala Arg Met Thr
        35                  40                  45

Ile Glu Glu Lys Ala Ser Gln Leu Leu Gln Gly Asp Ile Arg Asn Trp
50                  55                  60

Met Asn Glu Lys Thr Asn Ala Leu Asn Gln Thr Gly Leu Glu Trp Ser
65                  70                  75                  80

Thr Arg Tyr Arg Gly Ser Ala Phe Tyr Val Gly Val Pro Val Ala Asn
                85                  90                  95

Glu Trp Leu Thr Lys His Ile Lys Ala Ala Gln Asp Tyr Ile Gln Lys
            100                 105                 110

Glu Thr Tyr Leu Gly Ile Pro Ala Phe Val Gln Thr Glu Gly Leu His
        115                 120                 125

Gly Phe Leu Ala His Asn Ala Thr Ile Phe Asn Ser Pro Ile Gly Leu
    130                 135                 140

Gly Cys Ser Trp Asn Pro Ala Leu Val Glu Glu Met Ala Ala Val Ile
145                 150                 155                 160

Ala Lys Glu Ala Arg Ala Leu Gly Val Asn Gln Leu Phe Ala Pro Val
                165                 170                 175

Ala Asp Leu Ala Arg Glu Leu Arg His Gly Arg Val Glu Glu Met Tyr
            180                 185                 190

Ser Glu Asp Gly Leu Leu Ala Gly Glu Leu Ala Arg Ala Tyr Val Arg
        195                 200                 205

Gly Ala Gln Ser Ala Gly Val Ser Ala Met Val Lys His Phe Ala Ala
    210                 215                 220

Phe Gly Val Pro Glu Gln Gly Leu Asn Thr Gly Pro Val His Gly Gly
225                 230                 235                 240

Glu Arg Glu Leu Arg Thr Thr Tyr Leu Pro Pro Tyr Arg Arg Ala Ile
                245                 250                 255

Met Asp Gly Gly Ala Tyr Ser Ile Met Thr Ala Tyr His Ser Tyr Asp
            260                 265                 270

Gly Ile Pro Ala Val Ser Asp Pro His Leu Leu Thr Asp Ile Leu Arg
```

-continued

```
            275                 280                 285
Asp Glu Trp Gly Tyr Lys Tyr Phe Thr Met Thr Asp Ala Gly Ala Ser
290                 295                 300
Asp Arg Leu Cys Thr Glu Phe Lys Met Cys Ala Ser Asn Pro Ile Asp
305                 310                 315                 320
Lys Glu Ala Ile Val Arg Tyr Ile Leu Pro Ala Gly Gly Asp Val Glu
                    325                 330                 335
Met Gly Gly Gly Ser Tyr Ser Phe Glu Lys Ile Pro Asp Leu Val Ala
                340                 345                 350
Ser Ser Lys Ile Glu Glu Gly Leu Val Asp Ala Ala Val Ala Arg Val
            355                 360                 365
Leu Arg Ala Lys Phe Glu Leu Gly Leu Phe Glu Pro Phe Pro Gly
        370                 375                 380
Leu Pro Ala Glu Glu Ala Asn Lys Val Ile His Ala Pro Glu His Val
385                 390                 395                 400
Ala Leu Ala Arg Arg Leu Asp Glu Glu Ser Ile Val Leu Leu Glu Asn
                    405                 410                 415
His Asn Asn Ile Leu Pro Leu Arg Lys Asp Ala Ser Val Ala Val Ile
                420                 425                 430
Gly Pro Met Ala His Gly Phe Val Asn Tyr Gly Asp Tyr Val Ile Val
            435                 440                 445
Asn Ser Ser Thr Arg Gly Val Thr Pro Leu Asp Gly Ile Lys Ala Ala
        450                 455                 460
Ser Arg Gly Lys Val Thr Tyr Ala Lys Gly Cys Glu Arg Trp Ser Ser
465                 470                 475                 480
Ser Gln Asp Gly Phe Ala Glu Ala Val Ala Ala Glu Ala Ala Asp
                    485                 490                 495
Val Ala Val Val Val Gly Thr Trp Ser Arg Asp Gln Asn Glu Leu
                500                 505                 510
Trp Gln Gly Leu Asn Ala Thr Thr Gly Glu His Val Asp Val Asn Ser
            515                 520                 525
Leu Asp Leu Val Gly Ala Gln Glu Ala Leu Val Arg Ala Ile Val Glu
        530                 535                 540
Thr Gly Lys Pro Thr Val Val Phe Ser Ser Gly Lys Pro Ile Thr
545                 550                 555                 560
Ala Pro Trp Ile Ser Glu Arg Ala Ala Ala Leu Val Gln Gln Phe Tyr
                    565                 570                 575
Pro Ser Glu Gln Gly Gly Ala Ala Leu Ala Ser Val Leu Phe Gly Asp
                580                 585                 590
Val Asn Pro Ser Gly Arg Leu Ser Val Ser Phe Pro Arg Ser Val Gly
            595                 600                 605
Asp Leu Pro Val Tyr Tyr Asp His Trp Asn Ser Gly Arg Ser Ala Ser
        610                 615                 620
Pro Asp Ala Gly Val Ala Tyr Glu Asn Gly Thr Leu Val Phe Gly His
625                 630                 635                 640
Gln Tyr Val Leu Gly Asp Pro Arg Pro Leu Tyr Glu Phe Gly Tyr Gly
                    645                 650                 655
Leu Ser Tyr Ser Arg Phe Glu Tyr Gly Asp Val Gly Val Asp Lys Thr
                660                 665                 670
Thr Val Gly Pro Gln Asp Thr Val Thr Val Thr Val Lys Asn
            675                 680                 685
Val Ser Ser Arg Asp Gly Gln Glu Val Val Gln Leu Tyr Val Lys Asp
        690                 695                 700
```

```
Leu Ile Ala Ser Val Val Pro Asn Ile Arg Leu Arg Gly Phe Gln
705                 710                 715                 720

Lys Val Met Leu Arg Ala Gly Glu Ser Lys Arg Val Ser Ile Lys Val
            725                 730                 735

Lys Val Gln Asp Leu Gly Val Trp Asp Ala Arg Met Arg Tyr Val Val
        740                 745                 750

Glu Pro Gly Asp Phe Leu Phe Leu Val Gly Ala Ser Ser Asn Asp Phe
    755                 760                 765

Arg Gly Asn Ala Thr Val Thr Val Lys
    770                 775
```

<210> SEQ ID NO 33
<211> LENGTH: 2760
<212> TYPE: DNA
<213> ORGANISM: Penicillium oxalicum

<400> SEQUENCE: 33

| | | |
|---|---|---|
| atggctgttt ggctgcagct ggtgactgca cttgtcatcg cgcaaaccgc gatcgccaac | 60 |
| ccagtccctg agactcatcc cgatgagctg atgaacctca gcaacgtgg ctcggccgct | 120 |
| cagggctata cttcgcctcc gtactatcca actcctcagg gtgggtggac gtccgactgg | 180 |
| tccgaagcgt acaccaaggc gcaacaggtt gtgagcaaga tgactcttgc cgaaaaggtg | 240 |
| aacttgacca ccggtacggg cttcttcatg ggcccctgcg ttggtcaaac tggtagcgct | 300 |
| tcacgattcg gtattccaaa cctctgtctg caggattccc ctctgggaat acgcaattcg | 360 |
| gaccacaata ccgcctttcc agcgggaatc acggtgggcg caacgttcaa caaagacttg | 420 |
| atgtaccagc gaggcgtggc tattggcgag gaagctcggg gcaaaggtat caacatccag | 480 |
| cttggtccaa ctgtcggccc gcttggtcgc aaacctcgag gaggtcgcaa ctgggagggt | 540 |
| ttcggttcag atcccagtct tcaggccatc ggcggcgccc aaaccatcaa gggtatgcaa | 600 |
| agtaccggta ccattgcaac gatcaaacac ttcatcggaa atgaacagga gattcatcgg | 660 |
| atgagtaatg tggtccagag agggtactca tcaaacattg atgatcgcac gctgcacgag | 720 |
| atatacccttt ggccttttgc cgagggtgtt cgtgcagggg ttgggtcgtt gatggcggca | 780 |
| tataatgatg taggttctgc atctccgtcc gtgaattcat gatttcctcg gctaatctcc | 840 |
| ttccctggca ggtaaatggc tctgcgtgca gtcagaacag catgctcttg aatggcattc | 900 |
| tgaaggatga gctgggcttt caaggcttcg tgatgtcgga ctggagtggc cactacactg | 960 |
| gagtagcatc tgcgttatct ggcctggata tgtccatgcc tggcgatggt gccgtgccgt | 1020 |
| tgcttggtaa tagctattgg gggtccgagc tttcacgctc tattttgaat ggaagcgtcc | 1080 |
| ccgtgtctcg cctgaacgat atggtaagta ataaatacct ttctattctt gcttgtgaca | 1140 |
| caaagaaccg ggcttgaaaa aactgacact gtgcaacagg tgactcgcat gtggctgcg | 1200 |
| tggtataaaa tgggtcagga caagactac cccctgccta atttctcgac aaacaccgaa | 1260 |
| gacgcaaaag ggccactcta tccaggcgct cttttctccc ccagtggagt tgtgaatcaa | 1320 |
| tttgtcaacg ttcagagcga ccataacatc acggcacgtg ctgtggctcg agaagcaatt | 1380 |
| actcttctca gaatgaaga cagcgttctt ccacttgcca gaatgcatc gctgagggtg | 1440 |
| tttggcacag acgcaggtgc taatcctgat ggaatcaatg cttgcgcaga caagggttgt | 1500 |
| gataaaggcg tcttgaccat gggctgggga agtggcactg ccaggttgcc ttatcttatt | 1560 |
| acaccccagg agggcattgc gaacgtgact cagaacgcca gtttatat cacagactcg | 1620 |
| ttcccctctg gcttgactgc gggtgcggat gatattgctg tggttttcat caatgccgac | 1680 |

-continued

```
tcgggcgaga attacatcac cgttgaggga acccccggtg accgcaccgc agccggtctc   1740
tctgcctggc ataacgggga caaacttgtc aaagcggcgg cgcaaaagtt ctcacgggtc   1800
gtggtggtca tccacaccgt tggtccgatc atcatggagg attggattga cctggactcg   1860
gtgaagtccg tgctcgtcgc ccatctgcct ggtcaagaag ctggtaattc cctcgccgac   1920
gttctttcg gggatcacag tcctagcgga catttgccgt acaccattcc tcgtcgcgag   1980
tccgattatc cggatagtgt gagcatcatc gatcagccct ttggtcaaat tcaagacacc   2040
tataccgaag gtatctatgt ggattatcgt cacttcttga acgcgaatat tactccgcgc   2100
tattcctttg gtcacggtct ctcctacacg agcttcaact tcaccaaccc taccgtttct   2160
gtcgtcaccc cactcagctc tgcctatccc ccgcctgcat cctcaaaagg cccacgccc   2220
gtatacagca actccatccc agctgcatcg gaggtcgcct ggtcgtcatt caaattcacg   2280
cggatctggc gttatctcta cccttacctc gataaccccg agaagatcac cgcttcgaac   2340
aactatccct acccagatgg gtacagcact acacagaaac cactgccacg cgccggtgga   2400
ggggaaggtg gcaatcccgc tctctttgat atcgcctttt ctgtccaagt cggtgtgaaa   2460
aacacgggct ctcgacctgg caaggtcgtc gcacaattat acgtgcaact tccttccagc   2520
ctaggcgttg acactcctgc gcttcagctt cgccaattcg agaaaacgaa gacccttgcc   2580
ccgggcgagt ctcaaattct gacgctcgag attacgcgaa gggacgtcag tatctgggac   2640
gttgtcgcgc aggattggaa ggctcccatt aatggggagg gcatcaagct gtatattgga   2700
aacagcgttg ccgatactcc ggtctcgtgc gttgttggtg gagggtgctc cgtccagtag   2760
```

<210> SEQ ID NO 34
<211> LENGTH: 873
<212> TYPE: PRT
<213> ORGANISM: Penicillium oxalicum

<400> SEQUENCE: 34

Met Ala Val Trp Leu Gln Leu Val Thr Ala Leu Val Ile Ala Gln Thr
1               5                   10                  15

Ala Ile Ala Asn Pro Val Pro Glu Thr His Pro Asp Glu Leu Met Asn
            20                  25                  30

Leu Lys Gln Arg Gly Ser Ala Ala Gln Gly Tyr Thr Ser Pro Pro Tyr
        35                  40                  45

Tyr Pro Thr Pro Gln Gly Gly Trp Thr Ser Asp Trp Ser Glu Ala Tyr
    50                  55                  60

Thr Lys Ala Gln Gln Val Val Ser Lys Met Thr Leu Ala Glu Lys Val
65                  70                  75                  80

Asn Leu Thr Thr Gly Thr Gly Phe Phe Met Gly Pro Cys Val Gly Gln
                85                  90                  95

Thr Gly Ser Ala Ser Arg Phe Gly Ile Pro Asn Leu Cys Leu Gln Asp
            100                 105                 110

Ser Pro Leu Gly Ile Arg Asn Ser Asp His Asn Thr Ala Phe Pro Ala
        115                 120                 125

Gly Ile Thr Val Gly Ala Thr Phe Asn Lys Asp Leu Met Tyr Gln Arg
    130                 135                 140

Gly Val Ala Ile Gly Glu Glu Ala Arg Gly Lys Gly Ile Asn Ile Gln
145                 150                 155                 160

Leu Gly Pro Thr Val Gly Pro Leu Gly Arg Lys Pro Arg Gly Gly Arg
                165                 170                 175

Asn Trp Glu Gly Phe Gly Ser Asp Pro Ser Leu Gln Ala Ile Gly Gly

-continued

```
                180                 185                 190
Ala Gln Thr Ile Lys Gly Met Gln Ser Thr Gly Thr Ile Ala Thr Ile
            195                 200                 205

Lys His Phe Ile Gly Asn Glu Gln Glu Ile His Arg Met Ser Asn Val
        210                 215                 220

Val Gln Arg Gly Tyr Ser Ser Asn Ile Asp Asp Arg Thr Leu His Glu
225                 230                 235                 240

Ile Tyr Leu Trp Pro Phe Ala Glu Gly Val Arg Ala Gly Val Gly Ser
                245                 250                 255

Leu Met Ala Ala Tyr Asn Asp Val Asn Gly Ser Ala Cys Ser Gln Asn
            260                 265                 270

Ser Met Leu Leu Asn Gly Ile Leu Lys Asp Glu Leu Gly Phe Gln Gly
        275                 280                 285

Phe Val Met Ser Asp Trp Ser Gly His Tyr Thr Gly Val Ala Ser Ala
    290                 295                 300

Leu Ser Gly Leu Asp Met Ser Met Pro Gly Asp Gly Ala Val Pro Leu
305                 310                 315                 320

Leu Gly Asn Ser Tyr Trp Gly Ser Glu Leu Ser Arg Ser Ile Leu Asn
                325                 330                 335

Gly Ser Val Pro Val Ser Arg Leu Asn Asp Met Val Thr Arg Ile Val
            340                 345                 350

Ala Ala Trp Tyr Lys Met Gly Gln Asp Lys Asp Tyr Pro Leu Pro Asn
        355                 360                 365

Phe Ser Thr Asn Thr Glu Asp Ala Lys Gly Pro Leu Tyr Pro Gly Ala
    370                 375                 380

Leu Phe Ser Pro Ser Gly Val Val Asn Gln Phe Val Asn Val Gln Ser
385                 390                 395                 400

Asp His Asn Ile Thr Ala Arg Ala Val Ala Arg Glu Ala Ile Thr Leu
                405                 410                 415

Leu Lys Asn Glu Asp Ser Val Leu Pro Leu Ala Lys Asn Ala Ser Leu
            420                 425                 430

Arg Val Phe Gly Thr Asp Ala Gly Ala Asn Pro Asp Gly Ile Asn Ala
        435                 440                 445

Cys Ala Asp Lys Gly Cys Asp Lys Gly Val Leu Thr Met Gly Trp Gly
    450                 455                 460

Ser Gly Thr Ala Arg Leu Pro Tyr Leu Ile Thr Pro Gln Glu Gly Ile
465                 470                 475                 480

Ala Asn Val Thr Gln Asn Ala Lys Phe Tyr Ile Thr Asp Ser Phe Pro
                485                 490                 495

Ser Gly Leu Thr Ala Gly Ala Asp Asp Ile Ala Val Val Phe Ile Asn
            500                 505                 510

Ala Asp Ser Gly Glu Asn Tyr Ile Thr Val Glu Gly Asn Pro Gly Asp
        515                 520                 525

Arg Thr Ala Ala Gly Leu Ser Ala Trp His Asn Gly Asp Lys Leu Val
    530                 535                 540

Lys Ala Ala Ala Gln Lys Phe Ser Arg Val Val Val Ile His Thr
545                 550                 555                 560

Val Gly Pro Ile Ile Met Glu Asp Trp Ile Asp Leu Asp Ser Val Lys
                565                 570                 575

Ser Val Leu Val Ala His Leu Pro Gly Gln Glu Ala Gly Asn Ser Leu
            580                 585                 590

Ala Asp Val Leu Phe Gly Asp His Ser Pro Ser Gly His Leu Pro Tyr
        595                 600                 605
```

```
Thr Ile Pro Arg Arg Glu Ser Asp Tyr Pro Asp Ser Val Ser Ile Ile
    610                 615                 620

Asp Gln Pro Phe Gly Gln Ile Gln Asp Thr Tyr Thr Glu Gly Ile Tyr
625                 630                 635                 640

Val Asp Tyr Arg His Phe Leu Asn Ala Asn Ile Thr Pro Arg Tyr Ser
                645                 650                 655

Phe Gly His Gly Leu Ser Tyr Thr Ser Phe Asn Phe Thr Asn Pro Thr
            660                 665                 670

Val Ser Val Val Thr Pro Leu Ser Ser Ala Tyr Pro Pro Pro Ala Ser
            675                 680                 685

Ser Lys Gly Pro Thr Pro Val Tyr Ser Asn Ser Ile Pro Ala Ala Ser
    690                 695                 700

Glu Val Ala Trp Ser Ser Phe Lys Phe Thr Arg Ile Trp Arg Tyr Leu
705                 710                 715                 720

Tyr Pro Tyr Leu Asp Asn Pro Glu Lys Ile Thr Ala Ser Asn Asn Tyr
                725                 730                 735

Pro Tyr Pro Asp Gly Tyr Ser Thr Thr Gln Lys Pro Leu Pro Arg Ala
            740                 745                 750

Gly Gly Gly Glu Gly Gly Asn Pro Ala Leu Phe Asp Ile Ala Phe Ser
            755                 760                 765

Val Gln Val Gly Val Lys Asn Thr Gly Ser Arg Pro Gly Lys Val Val
    770                 775                 780

Ala Gln Leu Tyr Val Gln Leu Pro Ser Ser Leu Gly Val Asp Thr Pro
785                 790                 795                 800

Ala Leu Gln Leu Arg Gln Phe Glu Lys Thr Lys Thr Leu Ala Pro Gly
                805                 810                 815

Glu Ser Gln Ile Leu Thr Leu Glu Ile Thr Arg Arg Asp Val Ser Ile
            820                 825                 830

Trp Asp Val Val Ala Gln Asp Trp Lys Ala Pro Ile Asn Gly Glu Gly
            835                 840                 845

Ile Lys Leu Tyr Ile Gly Asn Ser Val Ala Asp Thr Pro Val Ser Cys
    850                 855                 860

Val Val Gly Gly Gly Cys Ser Val Gln
865                 870

<210> SEQ ID NO 35
<211> LENGTH: 2777
<212> TYPE: DNA
<213> ORGANISM: Penicillium oxalicum

<400> SEQUENCE: 35
```

| | | | | |
|---|---|---|---|---|
| atgattgtca ccaaggagtt ggcattggcg ttggccatgc tttccatgtg cgggttgagt | 60 |
| catgcagaga gtaacatcac ttccgacact tatttctatg ccagtctgaa gccagtgtat | 120 |
| ccctctcgta tgcaggccga ttctgccctc tatgagacct gtgcattgat attttccctt | 180 |
| tggtttcaca gcacagggaa gcggatccgg tggctgggca gctgcgtatg aaaaagccgc | 240 |
| ggccatggtc tcacaaatga cgctggagga aaggtatgt tagatcaaca cgaactatga | 300 |
| agcctgttgc atggactgat gaaagatttg ggatagaaca acctcacgta tggtatcagt | 360 |
| agtgccgaga acgggtgctc tggcaatatt ccgccaattg ctcgccttgg attcactggt | 420 |
| ctctgcctga ctgatgccgg aaatggtgtt cgggcaacag actttgtgaa cagctaccca | 480 |
| agtggaatcc acgttggcgc aagctggaac aaaacgttgg cctatgaacg aggctggcat | 540 |
| atgggtgggg agttcagaaa aaaaggtgat cacgtcgccc tgggtcctct cgttgggcct | 600 |

-continued

```
ctgggcaggg tagttagcgg tggaaggaac tgggaaggta tgcatctggg aggcatgata    660
ctaaatttga tcccacgtgt cgctgattga tccacaggtc cctctaatga cccgtacctt    720
ggaggtgcaa ttgctgctgc tacagtgaaa ggtacccaag agcagggtgt gattactagc    780
gtcaaagttt gtacttccat ccttcccacg aattggataa gatgcagagc taagcgttca    840
accgaactct ttagcatttt attgcgaatg aacaagagct gtaccggatc cccaccctca    900
actcagagaa tcaaacagtc caggccatct ccagcaatct ggacgacaag acaatgcatg    960
agctgtatct ttggccattt caggacgcct tgaaagcggg cgccggtaat atcatgtgag   1020
tcattctatt ttagggcaga caagctccca gagctaacga ttatgatcac gcaggtgctc   1080
atataatcgc atcaacaatt cctatgcttg ccagaacagc aaagcactca acggtcttct   1140
gaaaaccgag ttagggtttc agggatttgt cgtctccgac tggtatggcc agcaagctgg   1200
tgttggagca gctctggctg acttgatat ggccatgcct catggccaaa gtttctgggg    1260
cagcaacttc accgaggctt tcacaaatgg tagcgttcca atgactcgcc tagacgacat   1320
ggccactcgg taagaagtaa tcaaattaaa tggaacatgg tggacagata tgctgatgac   1380
gacggactag tatcatcgcg acctggtatc agatgggaca agacacaaaa ttccctgctc   1440
ttggcgttgg tatgccagca acataagtg cacctcacaa gtttgtgaac gcgctgaccc    1500
ccgatgcgaa gtctgtcttg tttgagggcg cagttgaagg gcacgtactg gttaagaatg   1560
tcaacgacac actgcctctc aaatcacctc aactggtctc cgtatttggg tatgacgcca   1620
aagcacccga cgcctcgatg ccgagtggta agtttacag tgagaacccg tggacgtcgg    1680
gtttagagcc cgcggtcttt caatccgccg aagtctctgt caacgcatca cccaatatcc   1740
ctgactactt ccaagtcgcc ttcaatggta ctctgtccgt tggcggcggc tcaggtgcaa   1800
ataatgggcc ctatctcagt gcacctctcg atgcattaca gcagcgggca tacgaagaca   1860
acacagtgct attctgggac agcgctgttt cctctcgata tcgtgggctg atggaagcat   1920
ccgacgcatg cttagtgttc atcaacgcgt ttgcaatcga aaacatggac cgccctggca   1980
ttcgcgaaga ctactcagac gggttggtcg aacaggtcgc ctcaacctgt gctaacatca   2040
ctgttatcat tcataacgct ggcactcggc tagttgatcg atttgccgat cacgaaaatg   2100
tcactgcaat tgtgtttgcg catttaccgg gccaagagtc tggtcgtgca attgtctctt   2160
tgctttatgg tgatgagaac ttcagtggca agcttcctta taccgttgcc aaaaatgaat   2220
ccgactacac gaccctcatg catgacgggg cagttgctcc ttatgaactc ttccctcagt   2280
caaactttga cgaaggtatc ttgactgact atcgttactt cgacaagcaa acatcaccc    2340
ctcgctacga gtttgggttc ggtctatcat acacgacctt ctctttcaag aacatccaac   2400
tctccgcgcc ccaagccaag ctggctgcct atgctacagg caaaattgaa caaggcggtg   2460
ccgtcgacct ttgggacaac gtcgcgacag tcatcgttga ggtcagcaac actggtcgtc   2520
gttctggtgc tgaagttgcc cagctctacg ttgtcattcc tggcggtcct ccaaagcagc   2580
tgcgcgggtt cgagaaggtg acgatcgccc cgggccagac tgtacaggtg gccttctcct   2640
tgacgcgtcg cgatttgagt acatgggatg tggttgcgca gaaatggaaa ctgcaaagtg   2700
gaaattatac gatctttgcg gggtcttcca gcagagatct tccattgagc atgaacctgg   2760
aactcaacag cgcatga                                                   2777
```

<210> SEQ ID NO 36
<211> LENGTH: 800
<212> TYPE: PRT

<213> ORGANISM: Penicillium oxalicum

<400> SEQUENCE: 36

```
Met Ile Val Thr Lys Glu Leu Ala Leu Ala Leu Ala Met Leu Ser Met
1               5                   10                  15

Cys Gly Leu Ser His Ala Glu Ser Asn Ile Thr Ser Asp Thr Tyr Phe
            20                  25                  30

Tyr Gly Gln Ser Glu Pro Val Tyr Pro Ser Pro Gln Gly Ser Gly Ser
        35                  40                  45

Gly Gly Trp Ala Ala Ala Tyr Glu Lys Ala Ala Met Val Ser Gln
    50                  55                  60

Met Thr Leu Glu Glu Lys Asn Asn Leu Thr Tyr Gly Ile Ser Ser Ala
65                  70                  75                  80

Glu Asn Gly Cys Ser Gly Asn Ile Pro Pro Ile Ala Arg Leu Gly Phe
                85                  90                  95

Thr Gly Leu Cys Leu Thr Asp Ala Gly Asn Gly Val Arg Ala Thr Asp
            100                 105                 110

Phe Val Asn Ser Tyr Pro Ser Gly Ile His Val Gly Ala Ser Trp Asn
            115                 120                 125

Lys Thr Leu Ala Tyr Glu Arg Gly Trp His Met Gly Gly Glu Phe Arg
130                 135                 140

Lys Lys Gly Asp His Val Ala Leu Gly Pro Leu Val Gly Pro Leu Gly
145                 150                 155                 160

Arg Val Val Ser Gly Gly Arg Asn Trp Glu Gly Pro Ser Asn Asp Pro
                165                 170                 175

Tyr Leu Gly Gly Ala Ile Ala Ala Thr Val Lys Gly Thr Gln Glu
            180                 185                 190

Gln Gly Val Ile Thr Ser Val Lys His Phe Ile Ala Asn Glu Gln Glu
            195                 200                 205

Leu Tyr Arg Ile Pro Thr Leu Asn Ser Glu Asn Gln Thr Val Gln Ala
    210                 215                 220

Ile Ser Ser Asn Leu Asp Asp Lys Thr Met His Glu Leu Tyr Leu Trp
225                 230                 235                 240

Pro Phe Gln Asp Ala Leu Lys Ala Gly Ala Gly Asn Ile Met Cys Ser
                245                 250                 255

Tyr Asn Arg Ile Asn Asn Ser Tyr Ala Cys Gln Asn Ser Lys Ala Leu
            260                 265                 270

Asn Gly Leu Leu Lys Thr Glu Leu Gly Phe Gln Gly Phe Val Val Ser
            275                 280                 285

Asp Trp Tyr Gly Gln Gln Ala Gly Val Gly Ala Ala Leu Ala Gly Leu
    290                 295                 300

Asp Met Ala Met Pro His Gly Gln Ser Phe Trp Gly Ser Asn Phe Thr
305                 310                 315                 320

Glu Ala Phe Thr Asn Gly Ser Val Pro Met Thr Arg Leu Asp Asp Met
                325                 330                 335

Ala Thr Arg Ile Ile Ala Thr Trp Tyr Gln Met Gly Gln Asp Thr Lys
            340                 345                 350

Phe Pro Ala Leu Gly Val Gly Met Pro Ala Asn Ile Ser Ala Pro His
            355                 360                 365

Lys Phe Val Asn Ala Leu Thr Pro Asp Ala Lys Ser Val Leu Phe Glu
    370                 375                 380

Gly Ala Val Glu Gly His Val Leu Val Lys Asn Val Asn Asp Thr Leu
385                 390                 395                 400
```

Pro Leu Lys Ser Pro Gln Leu Val Ser Val Phe Gly Tyr Asp Ala Lys
            405                 410                 415

Ala Pro Asp Ala Ser Met Pro Ser Gly Lys Val Tyr Ser Glu Asn Pro
        420                 425                 430

Trp Thr Ser Gly Leu Glu Pro Ala Val Phe Gln Ser Ala Glu Val Ser
        435                 440                 445

Val Asn Ala Ser Pro Asn Ile Pro Asp Tyr Phe Gln Val Ala Phe Asn
    450                 455                 460

Gly Thr Leu Ser Val Gly Gly Ser Gly Ala Asn Asn Gly Pro Tyr
465                 470                 475                 480

Leu Ser Ala Pro Leu Asp Ala Leu Gln Gln Arg Ala Tyr Glu Asp Asn
            485                 490                 495

Thr Val Leu Phe Trp Asp Ser Ala Val Ser Ser Arg Tyr Arg Gly Leu
            500                 505                 510

Met Glu Ala Ser Asp Ala Cys Leu Val Phe Ile Asn Ala Phe Ala Ile
            515                 520                 525

Glu Asn Met Asp Arg Pro Gly Ile Arg Glu Asp Tyr Ser Asp Gly Leu
        530                 535                 540

Val Glu Gln Val Ala Ser Thr Cys Ala Asn Ile Thr Val Ile Ile His
545                 550                 555                 560

Asn Ala Gly Thr Arg Leu Val Asp Arg Phe Ala Asp His Glu Asn Val
            565                 570                 575

Thr Ala Ile Val Phe Ala His Leu Pro Gly Gln Glu Ser Gly Arg Ala
            580                 585                 590

Ile Val Ser Leu Leu Tyr Gly Asp Glu Asn Phe Ser Gly Lys Leu Pro
        595                 600                 605

Tyr Thr Val Ala Lys Asn Glu Ser Asp Tyr Thr Thr Leu Met His Asp
        610                 615                 620

Gly Ala Val Ala Pro Tyr Glu Leu Phe Pro Gln Ser Asn Phe Asp Glu
625                 630                 635                 640

Gly Ile Leu Thr Asp Tyr Arg Tyr Phe Asp Lys Gln Asn Ile Thr Pro
            645                 650                 655

Arg Tyr Glu Phe Gly Phe Gly Leu Ser Tyr Thr Thr Phe Ser Phe Lys
            660                 665                 670

Asn Ile Gln Leu Ser Ala Pro Gln Ala Lys Leu Ala Ala Tyr Ala Thr
        675                 680                 685

Gly Lys Ile Glu Gln Gly Gly Ala Val Asp Leu Trp Asp Asn Val Ala
        690                 695                 700

Thr Val Ile Val Glu Val Ser Asn Thr Gly Arg Arg Ser Gly Ala Glu
705                 710                 715                 720

Val Ala Gln Leu Tyr Val Val Ile Pro Gly Gly Pro Pro Lys Gln Leu
            725                 730                 735

Arg Gly Phe Glu Lys Val Thr Ile Ala Pro Gly Gln Thr Val Gln Val
            740                 745                 750

Ala Phe Ser Leu Thr Arg Arg Asp Leu Ser Thr Trp Asp Val Val Ala
        755                 760                 765

Gln Lys Trp Lys Leu Gln Ser Gly Asn Tyr Thr Ile Phe Ala Gly Ser
    770                 775                 780

Ser Ser Arg Asp Leu Pro Leu Ser Met Asn Leu Glu Leu Asn Ser Ala
785                 790                 795                 800

<210> SEQ ID NO 37
<211> LENGTH: 2969
<212> TYPE: DNA

<213> ORGANISM: Penicillium oxalicum

<400> SEQUENCE: 37

| | |
|---|---:|
| atgttttca agggtctagc tggcagcctg ctgcttgcgc agctggtagc ttctgctaca | 60 |
| agcaaatcaa caccttttgta caaagacccc aaagcttccg tggatgatcg cgtgaaggac | 120 |
| ttgttgggtc gaatgaccat cgaggacaaa atggctcaat tgatgcaggg tgagtattac | 180 |
| cgtgacgtgg caaaaaaaat tgtcactctg dacattgctc atcaagtgcg actctaaagg | 240 |
| tgatattacc aactggatga accagacatc aggcgccttc aactatacgg gccttgttac | 300 |
| caacatggag atgaaagcag ggtccttcta tggtaaactc cggctacgta acttaccacc | 360 |
| agttgatgca aatcaaacta acagattatg aacaaaagtt gggtaccccg tcgcatggga | 420 |
| ttggatcgcg gacaacgtga agagagctca agactacctg gttcacaata caactcttgg | 480 |
| aattccggct cttgtccaat ctgagggtaa gtaaatgagc ggcccaagtc ccgtcgaatt | 540 |
| tggagttgac gtccatgatc ccctaggaa ttcatggctt tttgatcgga acgccacca | 600 |
| tttttcaattc ccccatcgca tacgatctt cctggaatag atgtaagg caattctcgc | 660 |
| tgtcccgcat atggactgag atctaacggc ttcattccag ctcgtggaga aaatggccga | 720 |
| gattgtcgcc caagaagccc aaactctggg tgttaatcaa atcttcgcac cagttgtcga | 780 |
| tttggctcgg gagcttcgct atggacgtgt gggtggtcca acccaaaaaa gaagaaccgt | 840 |
| gacgggactg tttctaactc gctttatctc atcaggtcga agagactttc tccgaagact | 900 |
| cttttcctctc cggagaaatt ggatacagtt acgtcaaggg attgcaaagc aggaatgtct | 960 |
| cggccatggt caagcatttt gtcggcttca gtgaccctga gcaaggtctg aacacgggtc | 1020 |
| cagttcatgg cggcgagaga gagcttcgca ccacgtgaga ctatccgctc caagtggaaa | 1080 |
| tggtgggatt tgctcacaat cgtccagttg gatgccgtcc tttaaacgtg caattattga | 1140 |
| tgcaggcgcc tggtctatta tggccgcata ccactcgtga gtgacacaag tatgccgaac | 1200 |
| atgtctggca tcaagctaat ctattcatgc aagatatgac ggaattccag ctgtctcgga | 1260 |
| ttatcacacc ttgaccgaga ttttgcgcga ggaatggggc tatgactact tcgttatgac | 1320 |
| ggatgctgga ggtagcgacc gagtctgcaa cgctttcaag ctctgcgcaa ccaatcctat | 1380 |
| cgacatggcc tcggttacca cgcagctctt agaggctggt acagacgtgg aaatgggcgg | 1440 |
| tggctccttg ttagtccttt cttgttttt ctgcgatcat gtgtcgtcgc taacatccca | 1500 |
| atagtaactt ccaaaagatc cccgagcttg tcaaatcagg aaagcttgac atgaagaccg | 1560 |
| ttgacacggc cgtttctcga ttccttcgtg ttaagttcga gatggggctc ttcgaaaacc | 1620 |
| cagacctagc tgcgccgaaa gataagtgga agggcttgat caacaattca gcttccaaga | 1680 |
| agcttgctcg ggatcttgac aaggaatcta tcgtgctttt ggagaatcac aacgccacac | 1740 |
| tgccactcaa gaagtccggc aatattgccg tgattgggcc catggctcat ggattcatga | 1800 |
| acgtgagttt ctagtatgtt cctcttttac tcttaatgtc attacttacc aagcgaaatt | 1860 |
| agtacggaga ttacgtcgtc tatcaaagcc agtatcgcgg ggtcaccca ctggacggca | 1920 |
| tcaaggcagc cgttggctca aaagccaaca tccactacgc gcaaggttgt gagcgttgga | 1980 |
| gtaacgatca gtctggcttt gcagaggcag tcgaggcagc caggaagtct gatgtggctg | 2040 |
| tcgtcgtcgt tggcacttgg tcgagggatc agttccagct ctggcaagga ttgaatgcta | 2100 |
| cgtaagtgga accatttggg cctgaacccg gctacgagag taaatttcgg atgcaataat | 2160 |
| ccccgataag gttctgactt tgcaatagaa ctggtgaaca cgttgatgcc gatgatctct | 2220 |
| cgctggttgg cgctcagggc ccgctcatca aagctattgc agagacaggc gtaccaacga | 2280 |

-continued

```
ttgttgtgct ctcgagcgga aagccaatca ccgatacttg gatttcgaat tctacttccg    2340
cccttatcca acaattttac ccgtctgaag agggcggtaa tgccctggcc gatgtcctgt    2400
tcggtgatta caatccctct ggcaagctct ccgtcagctt cccccggtac gtgggtgatc    2460
tcccgatttt ctacgactac ctgaactcag gccgctccat cggagactcg ggtcacattt    2520
atggcaacgg aacccttttca ttcggacacc agtatgtcct cggcagccct cttccatggt    2580
acccattcgg atatggcaag agttactcca acttccacta cggatccgtc cgcgttgacc    2640
gcagcaaggt ctcgtcgcac gataagaagg tcaccatcag cgtcgacgtc accaacacgg    2700
acaagactcg agatggtacc gaagttgtcc aggtatatgt ctccgatgac attgcctcgg    2760
ttgttgttcc caatcgcgcg ctgaagggct ttgagaaggt caagatcccc gctggcaaga    2820
ccaagaccgt aaaaatcccc atcttgatca aggatattgg attgtggaac tcgcgcatga    2880
agtatgtggt tgagccgggc aatttcaccg ttcttgtggg cagcagttcg gaggacattc    2940
ggggaaatgt cacgtttacc gtgcagtaa                                      2969
```

<210> SEQ ID NO 38
<211> LENGTH: 778
<212> TYPE: PRT
<213> ORGANISM: Penicillium oxalicum

<400> SEQUENCE: 38

```
Met Phe Phe Lys Gly Leu Ala Gly Ser Leu Leu Ala Gln Leu Val
1               5                   10                  15

Ala Ser Ala Thr Ser Lys Ser Thr Pro Leu Tyr Lys Asp Pro Lys Ala
            20                  25                  30

Ser Val Asp Asp Arg Val Lys Asp Leu Leu Gly Arg Met Thr Ile Glu
        35                  40                  45

Asp Lys Met Ala Gln Leu Met Gln Gly Asp Ile Thr Asn Trp Met Asn
    50                  55                  60

Gln Thr Ser Gly Ala Phe Asn Tyr Thr Gly Leu Val Thr Asn Met Glu
65                  70                  75                  80

Met Lys Ala Gly Ser Phe Tyr Val Gly Tyr Pro Val Ala Trp Asp Trp
                85                  90                  95

Ile Ala Asp Asn Val Lys Arg Ala Gln Asp Tyr Leu Val His Asn Thr
            100                 105                 110

Thr Leu Gly Ile Pro Ala Leu Val Gln Ser Glu Gly Ile His Gly Phe
        115                 120                 125

Leu Ile Gly Asn Ala Thr Ile Phe Asn Ser Pro Ile Ala Tyr Gly Ser
    130                 135                 140

Ser Trp Asn Arg Asp Leu Val Glu Lys Met Ala Glu Ile Val Ala Gln
145                 150                 155                 160

Glu Ala Gln Thr Leu Gly Val Asn Gln Ile Phe Ala Pro Val Val Asp
                165                 170                 175

Leu Ala Arg Glu Leu Arg Tyr Gly Arg Val Glu Thr Phe Ser Glu
            180                 185                 190

Asp Ser Phe Leu Ser Gly Glu Ile Gly Tyr Ser Tyr Val Lys Gly Leu
        195                 200                 205

Gln Ser Arg Asn Val Ser Ala Met Val Lys His Phe Val Gly Phe Ser
    210                 215                 220

Asp Pro Glu Gln Gly Leu Asn Thr Gly Pro Val His Gly Gly Glu Arg
225                 230                 235                 240

Glu Leu Arg Thr Thr Trp Met Pro Ser Phe Lys Arg Ala Ile Ile Asp
```

-continued

```
                245                 250                 255
Ala Gly Ala Trp Ser Ile Met Ala Ala Tyr His Ser Tyr Asp Gly Ile
            260                 265                 270
Pro Ala Val Ser Asp Tyr His Thr Leu Thr Glu Ile Leu Arg Glu Glu
        275                 280                 285
Trp Gly Tyr Asp Tyr Phe Val Met Thr Asp Ala Gly Gly Ser Asp Arg
    290                 295                 300
Val Cys Asn Ala Phe Lys Leu Cys Ala Thr Asn Pro Ile Asp Met Ala
305                 310                 315                 320
Ser Val Thr Thr Gln Leu Leu Glu Ala Gly Thr Asp Val Glu Met Gly
                325                 330                 335
Gly Gly Ser Phe Asn Phe Gln Lys Ile Pro Glu Leu Val Lys Ser Gly
            340                 345                 350
Lys Leu Asp Met Lys Thr Val Asp Thr Ala Val Ser Arg Phe Leu Arg
        355                 360                 365
Val Lys Phe Glu Met Gly Leu Phe Glu Asn Pro Asp Leu Ala Ala Pro
    370                 375                 380
Lys Asp Lys Trp Lys Gly Leu Ile Asn Asn Ser Ala Ser Lys Lys Leu
385                 390                 395                 400
Ala Arg Asp Leu Asp Lys Glu Ser Ile Val Leu Leu Glu Asn His Asn
                405                 410                 415
Ala Thr Leu Pro Leu Lys Lys Ser Gly Asn Ile Ala Val Ile Gly Pro
            420                 425                 430
Met Ala His Gly Phe Met Asn Tyr Gly Asp Tyr Val Val Tyr Gln Ser
        435                 440                 445
Gln Tyr Arg Gly Val Thr Pro Leu Asp Gly Ile Lys Ala Ala Val Gly
    450                 455                 460
Ser Lys Ala Asn Ile His Tyr Ala Gln Gly Cys Glu Arg Trp Ser Asn
465                 470                 475                 480
Asp Gln Ser Gly Phe Ala Glu Ala Val Glu Ala Ala Arg Lys Ser Asp
                485                 490                 495
Val Ala Val Val Val Gly Thr Trp Ser Arg Asp Gln Phe Gln Leu
            500                 505                 510
Trp Gln Gly Leu Asn Ala Thr Thr Gly Glu His Val Asp Ala Asp Asp
        515                 520                 525
Leu Ser Leu Val Gly Ala Gln Gly Pro Leu Ile Lys Ala Ile Ala Glu
    530                 535                 540
Thr Gly Val Pro Thr Ile Val Val Leu Ser Ser Gly Lys Pro Ile Thr
545                 550                 555                 560
Asp Thr Trp Ile Ser Asn Ser Thr Ser Ala Leu Ile Gln Gln Phe Tyr
                565                 570                 575
Pro Ser Glu Glu Gly Gly Asn Ala Leu Ala Asp Val Leu Phe Gly Asp
            580                 585                 590
Tyr Asn Pro Ser Gly Lys Leu Ser Val Ser Phe Pro Arg Tyr Val Gly
        595                 600                 605
Asp Leu Pro Ile Phe Tyr Asp Tyr Leu Asn Ser Gly Arg Ser Ile Gly
    610                 615                 620
Asp Ser Gly His Ile Tyr Gly Asn Gly Thr Leu Ser Phe Gly His Gln
625                 630                 635                 640
Tyr Val Leu Gly Ser Pro Leu Pro Trp Tyr Pro Phe Gly Tyr Gly Lys
                645                 650                 655
Ser Tyr Ser Asn Phe His Tyr Gly Ser Val Arg Val Asp Arg Ser Lys
            660                 665                 670
```

```
Val Ser Ser His Asp Lys Lys Val Thr Ile Ser Val Asp Val Thr Asn
        675                 680                 685

Thr Asp Lys Thr Arg Asp Gly Thr Glu Val Val Gln Val Tyr Val Ser
    690                 695                 700

Asp Asp Ile Ala Ser Val Val Pro Asn Arg Ala Leu Lys Gly Phe
705                 710                 715                 720

Glu Lys Val Lys Ile Pro Ala Gly Lys Thr Lys Thr Val Lys Ile Pro
                725                 730                 735

Ile Leu Ile Lys Asp Ile Gly Leu Trp Asn Ser Arg Met Lys Tyr Val
            740                 745                 750

Val Glu Pro Gly Asn Phe Thr Val Leu Val Gly Ser Ser Glu Asp
        755                 760                 765

Ile Arg Gly Asn Val Thr Phe Thr Val Gln
    770                 775

<210> SEQ ID NO 39
<211> LENGTH: 2625
<212> TYPE: DNA
<213> ORGANISM: Penicillium emersonii

<400> SEQUENCE: 39
atgtctttcc taatccgtgt actccttttt gtctccttcc tgttttttccc tactgcggta      60 ctatcatcct cgggatcaga ggataaggaa tctaatcctc acattcgtcg acgcactgat     120
ctccctccgg gatattcgtc gccggactac taccccaccc ccaatggcgg ctgggtgtcg     180
gaatgggcgg atgccatgc caaggcgcag aaggtcgtga ccagatgac cctggcagaa      240 aaggtcaaca tcacttccgg aacgggctac ttcatgggtc cctgcgtggg aaatactggg      300
agcgccttgc gtttcgggat tcccaatctc tgtctgcaag atggtccctt gggaattcgc      360
aacacggatc acaatacggc attccctgcg ggaatcacca ctgggcaac ctttgacaag       420 gagttgatgt acgctcgtgg ggtggctctg gccaggaag cccgcgggaa aggcatcaac       480
gttcaaatgg cccctgttgt tggacctta ggacgaaaac ctcgatcagg acgtatctgg       540
gagggctttg agcggatcc ctcgctgcag gcgatcgggg cagcgcaaac gattcagggc       600
atgcagagcg ttggcgtcat cgcgacgctc aagcattata ttggaaatga gcaagagatg      660
taccgcatga ccgatatcct ccagcaaggc tattcgtcca atatcgatga ccgcactctc      720
catgagatct atctctggcc gttgtctgag ggagttcgcg ccggggttgg atccgttatg      780
gcggcttaca atgatgtcaa tggaacggca tgtacccaga acagtaaact catcaatgac      840
ctcttgaaag atgagctggg ttttcaaggg tttgtagtgt cggactggta cgcccagatc      900
ggaggtgtct cttcagcgct ggctggactg gatatggcca tgccaggga tggcgttgtt       960 ccattgttag agacagctt ctggaactat gagctatcaa cagccatctt gaatgggact     1020
gtgccagtgg agagactgaa tgacatggtc actcggattg ttgcaacgtg gtataaatg      1080 ggccaggaca aggactatcc gttgcccaac ttttccacga atacccagga cgcagtcggt     1140
ccactctatc cgggagctct cttctcgccc actggagtgg tcaaccaatt tgtcaacgtc      1200 caagggatc acaacgttgt cgcgagagct gtggccagag acgccatcac gctcctcaag       1260
aatgacgata atgctcttcc actcaaacgc aacgcctcat tgaaagtttt tggcgccgac      1320
gcgggcccga atccggatgg tctcaactcc tgcagcgacc aaggatgcga caagggcgtg     1380
ctgactatgg gatggggaag tggtagcgcc agactcccct atctcattac ccctcaggat     1440
gctatccgca acgtctcctc caatgctcaa ttctatatct ccgattcatt tccgtctgat     1500
```

```
atctccgctg gccctaatga tattgctgtc gtctttatca atgccgactc cggcgagaat    1560
tacatcactg tggagggaaa ccccggtgac cggctggtag ctgggctgta tgcgtggcac    1620
aacggagacg agctagtgca agctgcggcg aagaaattct ccactgtcgt cgttgtggtg    1680
cacactgtag gcccaattat ccttgagaac tggatcgacc tgccctcagt caaggccgtg    1740 cttttgctc atcttccagg tcaagaagct ggtgactcgc ttgtggatgt tctgttcggt    1800
gactacagcc cgagtgggca tctgccatat acaattccgt acaaggaatc cgactatcca    1860
tctagtgtga gtctgatcga ccaaccgttt gggcagattc aggataccta tacagagcgc    1920
atctacatcg attaccgcca tttcctccaa gctaacatca ccccgcggta tccatttggt    1980
cacggtctgt cctacaccac cttcaactt tcagaaccct ctctatcagc aatcacgcct    2040
ctcactcaat atcctccgcc tcgtcctccc aagggcccta cgcccacata caacaatacc    2100
attccgcctg cgtccgaagt cgcctggcca aaggatttca accgcatctg gcgttatctg    2160
tacccatacc tggacaatcc tgccgctgca acgtcgactg cacctatcc ttacccaacg    2220 gggtatacca cgactccgaa gccacccccg cgagctggtg gctcccaagg cggaaactcg    2280
gcgttgtggg atgtcgcctt caacgtgagc gtgaaagtca gcaacacggg ttcccgtccc    2340
ggccgtgcgg tcgcgcagct gtatgtcgag ctgcccgcgt cgactctcgg ggttgacttg    2400
ccccctttgc agctgcgcca attcgaaaag accgccattc tgccgcctgg agagagtcag    2460
gtgttgacgc tctcggtgac gcggaaggat ttgagtatct gggacgttgt ggcacaggac    2520
tggaaggcgc cagtggacgg gcagggagtg aagttttgga taggcgagag cgtggctgat    2580
ttgaaggttg tgtgtgaagt tggtggacag tgtgggagtg tctag                   2625
```

<210> SEQ ID NO 40
<211> LENGTH: 51
<212> TYPE: DNA
<213> ORGANISM: Artificial Sequence
<220> FEATURE:
<223> OTHER INFORMATION: Synthetic Construct

<400> SEQUENCE: 40

```
acacaactgg ggatccacca tgcttcccca ctcgttacta ctattactcc t             51
```

<210> SEQ ID NO 41
<211> LENGTH: 39
<212> TYPE: DNA
<213> ORGANISM: Artificial Sequence
<220> FEATURE:
<223> OTHER INFORMATION: Synthetic Construct

<400> SEQUENCE: 41

```
gtcaccctct agatctctac ccaacaacct caaacgacg                           39
```

<210> SEQ ID NO 42
<211> LENGTH: 40
<212> TYPE: DNA
<213> ORGANISM: Artificial Sequence
<220> FEATURE:
<223> OTHER INFORMATION: Synthetic Construct

<400> SEQUENCE: 42

```
acacaactgg ggatccacca tgccagggca gacatcaacg                          40
```

<210> SEQ ID NO 43
<211> LENGTH: 46
<212> TYPE: DNA

```
<213> ORGANISM: Artificial Sequence
<220> FEATURE:
<223> OTHER INFORMATION: Synthetic Construct

<400> SEQUENCE: 43
gtcaccctct agatctttaa tactctccaa ccaacggtag gtctcg                    46

<210> SEQ ID NO 44
<211> LENGTH: 50
<212> TYPE: DNA
<213> ORGANISM: Artificial Sequence
<220> FEATURE:
<223> OTHER INFORMATION: Synthetic Construct

<400> SEQUENCE: 44
acacaactgg ggatccacca tgtctttctt caactttctt ttgagcgttc                50

<210> SEQ ID NO 45
<211> LENGTH: 49
<212> TYPE: DNA
<213> ORGANISM: Artificial Sequence
<220> FEATURE:
<223> OTHER INFORMATION: Synthetic Construct

<400> SEQUENCE: 45
gtcaccctct agatctcgct gtacagtatt tgctgatatt acggagtac                 49

<210> SEQ ID NO 46
<211> LENGTH: 36
<212> TYPE: DNA
<213> ORGANISM: Artificial Sequence
<220> FEATURE:
<223> OTHER INFORMATION: Synthetic Construct

<400> SEQUENCE: 46
acacaactgg ggatccacca tgcggctccc ttggtg                               36

<210> SEQ ID NO 47
<211> LENGTH: 39
<212> TYPE: DNA
<213> ORGANISM: Artificial Sequence
<220> FEATURE:
<223> OTHER INFORMATION: Synthetic Construct

<400> SEQUENCE: 47
gtcaccctct agatctcact ctctcgaacc cgaatctcc                            39

<210> SEQ ID NO 48
<211> LENGTH: 36
<212> TYPE: DNA
<213> ORGANISM: Artificial Sequence
<220> FEATURE:
<223> OTHER INFORMATION: Synthetic Construct

<400> SEQUENCE: 48
acacaactgg ggatccacca tggctcgtcg cacttc                               36

<210> SEQ ID NO 49
<211> LENGTH: 38
<212> TYPE: DNA
<213> ORGANISM: Artificial Sequence
<220> FEATURE:
<223> OTHER INFORMATION: Synthetic Construct

<400> SEQUENCE: 49
gtcaccctct agatctgcat cctgtgacga ggacatca                             38
```

```
<210> SEQ ID NO 50
<211> LENGTH: 37
<212> TYPE: DNA
<213> ORGANISM: Artificial Sequence
<220> FEATURE:
<223> OTHER INFORMATION: Synthetic Construct

<400> SEQUENCE: 50
acacaactgg ggatccacca tgcgattgcc tgcgacg                              37

<210> SEQ ID NO 51
<211> LENGTH: 37
<212> TYPE: DNA
<213> ORGANISM: Artificial Sequence
<220> FEATURE:
<223> OTHER INFORMATION: Synthetic Construct

<400> SEQUENCE: 51
gtcaccctct agatctcttg gggctctatc gctgctc                              37

<210> SEQ ID NO 52
<211> LENGTH: 45
<212> TYPE: DNA
<213> ORGANISM: Artificial Sequence
<220> FEATURE:
<223> OTHER INFORMATION: Synthetic Construct

<400> SEQUENCE: 52
acacaactgg ggatccacca tgtttgttct tgctgcgtac ctctt                     45

<210> SEQ ID NO 53
<211> LENGTH: 38
<212> TYPE: DNA
<213> ORGANISM: Artificial Sequence
<220> FEATURE:
<223> OTHER INFORMATION: Synthetic Construct

<400> SEQUENCE: 53
gtcaccctct agatctccta cagcaccctg acaaccct                             38

<210> SEQ ID NO 54
<211> LENGTH: 39
<212> TYPE: DNA
<213> ORGANISM: Artificial Sequence
<220> FEATURE:
<223> OTHER INFORMATION: Synthetic Construct

<400> SEQUENCE: 54
acacaactgg ggatccacca tgaggtggac gagcttcgc                            39

<210> SEQ ID NO 55
<211> LENGTH: 40
<212> TYPE: DNA
<213> ORGANISM: Artificial Sequence
<220> FEATURE:
<223> OTHER INFORMATION: Synthetic Construct

<400> SEQUENCE: 55
gtcaccctct agatctacaa ggaaagagaa tcaggcagca                           40

<210> SEQ ID NO 56
<211> LENGTH: 43
<212> TYPE: DNA
<213> ORGANISM: Artificial Sequence
<220> FEATURE:
```

<223> OTHER INFORMATION: Synthetic Construct

<400> SEQUENCE: 56
acacaactgg ggatccacca tgacggtcat cacggcagta tct    43

<210> SEQ ID NO 57
<211> LENGTH: 46
<212> TYPE: DNA
<213> ORGANISM: Artificial Sequence
<220> FEATURE:
<223> OTHER INFORMATION: Synthetic Construct

<400> SEQUENCE: 57
gtcaccctct agatctgtac tgtgtcgacg tactaggata gctcct    46

<210> SEQ ID NO 58
<211> LENGTH: 47
<212> TYPE: DNA
<213> ORGANISM: Artificial Sequence
<220> FEATURE:
<223> OTHER INFORMATION: Synthetic Construct

<400> SEQUENCE: 58
acacaactgg ggatccacca tgtctttcct aatccgtgta ctccttt    47

<210> SEQ ID NO 59
<211> LENGTH: 42
<212> TYPE: DNA
<213> ORGANISM: Artificial Sequence
<220> FEATURE:
<223> OTHER INFORMATION: Synthetic Construct

<400> SEQUENCE: 59
gtcaccctct agatctacat atttcaacaa gcattgcagc ag    42

<210> SEQ ID NO 60
<211> LENGTH: 39
<212> TYPE: DNA
<213> ORGANISM: Artificial Sequence
<220> FEATURE:
<223> OTHER INFORMATION: Synthetic Construct

<400> SEQUENCE: 60
acacaactgg ggatccacca tgggtcatca cactgccac    39

<210> SEQ ID NO 61
<211> LENGTH: 37
<212> TYPE: DNA
<213> ORGANISM: Artificial Sequence
<220> FEATURE:
<223> OTHER INFORMATION: Synthetic Construct

<400> SEQUENCE: 61
gtcaccctct agatcttcaa cgcattctcg ccacttc    37

<210> SEQ ID NO 62
<211> LENGTH: 44
<212> TYPE: DNA
<213> ORGANISM: Artificial Sequence
<220> FEATURE:
<223> OTHER INFORMATION: Synthetic Construct

<400> SEQUENCE: 62
acacaactgg ggatccacca tgcgttcgct agcaaatata tctc    44

```
<210> SEQ ID NO 63
<211> LENGTH: 41
<212> TYPE: DNA
<213> ORGANISM: Artificial Sequence
<220> FEATURE:
<223> OTHER INFORMATION: Synthetic Construct

<400> SEQUENCE: 63
gtcaccctct agatcttgct catccttaat gtgaccttca g        41

<210> SEQ ID NO 64
<211> LENGTH: 47
<212> TYPE: DNA
<213> ORGANISM: Artificial Sequence
<220> FEATURE:
<223> OTHER INFORMATION: Synthetic Construct

<400> SEQUENCE: 64
acacaactgg ggatccacca tgtacctacc atcgcttaca acaacag    47

<210> SEQ ID NO 65
<211> LENGTH: 41
<212> TYPE: DNA
<213> ORGANISM: Artificial Sequence
<220> FEATURE:
<223> OTHER INFORMATION: Synthetic Construct

<400> SEQUENCE: 65
gtcaccctct agatctcagc tcgcagatct agatacaacg a         41

<210> SEQ ID NO 66
<211> LENGTH: 35
<212> TYPE: DNA
<213> ORGANISM: Artificial Sequence
<220> FEATURE:
<223> OTHER INFORMATION: Synthetic Construct

<400> SEQUENCE: 66
acacaactgg ggatccacca tgaaggctgc cgtgc               35

<210> SEQ ID NO 67
<211> LENGTH: 35
<212> TYPE: DNA
<213> ORGANISM: Artificial Sequence
<220> FEATURE:
<223> OTHER INFORMATION: Synthetic Construct

<400> SEQUENCE: 67
gtcaccctct agatctttct gttcgccgaa acctg               35

<210> SEQ ID NO 68
<211> LENGTH: 38
<212> TYPE: DNA
<213> ORGANISM: Artificial Sequence
<220> FEATURE:
<223> OTHER INFORMATION: Synthetic Construct

<400> SEQUENCE: 68
acacaactgg ggatccacca tgacctttca agcgctcg            38

<210> SEQ ID NO 69
<211> LENGTH: 37
<212> TYPE: DNA
<213> ORGANISM: Artificial Sequence
<220> FEATURE:
<223> OTHER INFORMATION: Synthetic Construct
```

```
<400> SEQUENCE: 69
gtcaccctct agatctactc catccaagaa gccgaac                              37

<210> SEQ ID NO 70
<211> LENGTH: 34
<212> TYPE: DNA
<213> ORGANISM: Artificial Sequence
<220> FEATURE:
<223> OTHER INFORMATION: Synthetic Construct

<400> SEQUENCE: 70
acacaactgg ggatccacca tgcggttcct ctcc                                 34

<210> SEQ ID NO 71
<211> LENGTH: 39
<212> TYPE: DNA
<213> ORGANISM: Artificial Sequence
<220> FEATURE:
<223> OTHER INFORMATION: Synthetic Construct

<400> SEQUENCE: 71
gtcaccctct agatctctat tgagggttgt ctgctcctg                            39

<210> SEQ ID NO 72
<211> LENGTH: 35
<212> TYPE: DNA
<213> ORGANISM: Artificial Sequence
<220> FEATURE:
<223> OTHER INFORMATION: Synthetic Construct

<400> SEQUENCE: 72
acacaactgg ggatccacca tgctgtttg gctgc                                 35

<210> SEQ ID NO 73
<211> LENGTH: 35
<212> TYPE: DNA
<213> ORGANISM: Artificial Sequence
<220> FEATURE:
<223> OTHER INFORMATION: Synthetic Construct

<400> SEQUENCE: 73
gtcaccctct agatctcgct gggctctacc gtgaa                                35

<210> SEQ ID NO 74
<211> LENGTH: 40
<212> TYPE: DNA
<213> ORGANISM: Artificial Sequence
<220> FEATURE:
<223> OTHER INFORMATION: Synthetic Construct

<400> SEQUENCE: 74
acacaactgg ggatccacca tgattgtcac caaggagttg                           40

<210> SEQ ID NO 75
<211> LENGTH: 39
<212> TYPE: DNA
<213> ORGANISM: Artificial Sequence
<220> FEATURE:
<223> OTHER INFORMATION: Synthetic Construct

<400> SEQUENCE: 75
acacaactgg ggatccaccg aagagggtct tgggcgatc                            39

<210> SEQ ID NO 76
<211> LENGTH: 41
```

```
<212> TYPE: DNA
<213> ORGANISM: Artificial Sequence
<220> FEATURE:
<223> OTHER INFORMATION: Synthetic Construct

<400> SEQUENCE: 76
gtcaccctct agatctatgt ttttcaaggg tctagctggc a                              41

<210> SEQ ID NO 77
<211> LENGTH: 40
<212> TYPE: DNA
<213> ORGANISM: Artificial Sequence
<220> FEATURE:
<223> OTHER INFORMATION: Synthetic Construct

<400> SEQUENCE: 77
gtcaccctct agatctatat ctccgtcttc aatcggcaca                                40
```